US009095540B2

(12) United States Patent
Schneewind et al.

(10) Patent No.: US 9,095,540 B2
(45) Date of Patent: Aug. 4, 2015

(54) METHODS AND COMPOSITIONS INVOLVING PROTECTIVE STAPHYLOCOCCAL ANTIGENS

(75) Inventors: Olaf Schneewind, Chicago, IL (US); Alice G. Cheng, Boston, MA (US); Dominique M. Missiakas, Chicago, IL (US); Hwan Keun Kim, Naperville, IL (US); Hye-Young Kim, Rancho Cucamonga, CA (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 13/821,943

(22) PCT Filed: Sep. 9, 2011

(86) PCT No.: PCT/US2011/051079
§ 371 (c)(1), (2), (4) Date: May 22, 2013

(87) PCT Pub. No.: WO2012/034067
PCT Pub. Date: Mar. 15, 2012

(65) Prior Publication Data
US 2013/0230550 A1 Sep. 5, 2013

Related U.S. Application Data

(60) Provisional application No. 61/381,372, filed on Sep. 9, 2010, provisional application No. 61/435,617, filed on Jan. 24, 2011.

(51) Int. Cl.
| A61K 39/00 | (2006.01) |
| A61K 39/02 | (2006.01) |
| A61K 39/09 | (2006.01) |
| C07K 1/00 | (2006.01) |
| A61K 39/085 | (2006.01) |
| C07K 14/31 | (2006.01) |

(52) U.S. Cl.
CPC .............. *A61K 39/085* (2013.01); *C07K 14/31* (2013.01); *A61K 2039/522* (2013.01); *A61K 2039/55566* (2013.01)

(58) Field of Classification Search
USPC ............... 424/185.1, 190.1, 243.1, 244.1; 530/350
See application file for complete search history.

(56) References Cited

U.S. PATENT DOCUMENTS

| 3,791,932 A | 2/1974 | Schurrs et al. ............... 435/7.8 |
| 3,949,064 A | 4/1976 | Bornstein et al. ............. 436/527 |
| 4,174,384 A | 11/1979 | Ullman et al. ............... 436/537 |
| 4,338,298 A | 7/1982 | Myers ....................... 424/242.1 |
| 4,356,170 A | 10/1982 | Jennings et al. ........... 424/194.1 |
| 4,372,945 A | 2/1983 | Likhite ....................... 530/405 |
| 4,474,757 A | 10/1984 | Arnon et al. ................ 424/186.1 |
| 4,578,770 A | 3/1986 | Mitani ...................... 250/559.2 |
| 4,596,792 A | 6/1986 | Vyas ........................ 424/185.1 |
| 4,599,230 A | 7/1986 | Milich et al. ............... 424/189.1 |
| 4,599,231 A | 7/1986 | Milch et al. ............... 424/189.1 |
| 4,601,903 A | 7/1986 | Frasch ...................... 424/250.1 |
| 4,748,018 A | 5/1988 | Stolle et al. ............... 424/157.1 |
| 5,512,282 A | 4/1996 | Krivan et al. ............... 424/169.1 |
| 5,548,066 A | 8/1996 | Leneau et al. ............. 530/390.5 |
| 5,620,896 A | 4/1997 | Herrmann et al. .......... 435/320.1 |
| 5,648,240 A | 7/1997 | Hook et al. .................. 435/69.3 |
| 5,801,234 A | 9/1998 | Hodgson et al. ............ 536/23.7 |
| 5,840,846 A | 11/1998 | Hook et al. .................... 530/350 |
| 5,958,895 A | 9/1999 | Pachuk et al. ............... 514/44 R |
| 6,008,341 A | 12/1999 | Foster et al. ................. 536/23.7 |
| 6,288,214 B1 | 9/2001 | Hook et al. ................. 530/387.1 |
| 6,294,177 B1 | 9/2001 | Fattom ...................... 424/243.1 |
| 6,733,754 B2 | 5/2004 | Roberts et al. ............. 424/184.1 |
| 6,756,361 B1 | 6/2004 | Fattom et al. .................. 514/54 |
| 6,770,278 B1 | 8/2004 | Skelly ....................... 424/130.1 |
| 6,793,923 B2 | 9/2004 | Brown et al. .............. 424/184.1 |
| 6,936,258 B1 | 8/2005 | Pavliak et al. ............. 424/243.1 |
| 2002/0169288 A1 | 11/2002 | Hook et al. .................... 530/350 |
| 2003/0153022 A1 | 8/2003 | Patti et al. .................... 435/7.35 |

FOREIGN PATENT DOCUMENTS

| CN | 1884302 | 12/2006 |
| CN | 101983067 | 3/2011 |
| EP | 0 594 610 | 12/1991 |
| EP | 0 786 519 | 7/1997 |
| WO | WO 95/08348 | 3/1995 |
| WO | WO 98/57994 | 12/1998 |
| WO | WO 00/02523 | 1/2000 |
| WO | WO 00/12132 | 3/2000 |
| WO | WO 00/12689 | 3/2000 |
| WO | WO 00/15238 | 3/2000 |
| WO | WO 01/34809 | 5/2001 |
| WO | WO 01/60852 | 8/2001 |
| WO | WO 02/059148 | 8/2002 |
| WO | WO 02/094868 | 11/2002 |
| WO | WO 2006/032472 | 3/2006 |
| WO | WO 2006/032475 | 3/2006 |

(Continued)

OTHER PUBLICATIONS

Greenspan et al (Nature Biotechnology 7: 936-937, 1999).*

(Continued)

*Primary Examiner* — Jennifer Graser
(74) *Attorney, Agent, or Firm* — Norton Rose Fulbright US LLP

(57) ABSTRACT

The present invention concerns methods and compositions for treating or preventing a bacterial infection, particularly infection by a *Staphylococcus* bacterium. The invention provides methods and compositions for stimulating an immune response against the bacteria. In certain embodiments, the methods and compositions involve a non-toxigenic Protein A (SpA) variant. In some embodiments, the methods and compositions involve SdrD, ClfA, and/or FnbpB polypeptides.

15 Claims, 15 Drawing Sheets

(56) References Cited

FOREIGN PATENT DOCUMENTS

| WO | WO 2006/032500 | 3/2006 |
|---|---|---|
| WO | WO2007071692 A2 * | 6/2007 |
| WO | WO 2007/113222 | 10/2007 |
| WO | WO 2007/113223 | 10/2007 |
| WO | WO 2008/019162 | 2/2008 |
| WO | WO 2010/119343 | 10/2010 |

OTHER PUBLICATIONS

Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Abdallah et al., "A specific secretion system mediates PPE41 transport in pathogenic mycobacteria", Mol. Microbiol., 62(3):667-679, 2006.
Abdallah et al., "Type VII secretion—mycobacteria show the way", Nat. Rev. Microbiol., 5 :883-891, 2007.
Anderson et al., "Recall of long-lived immunity to Mycobacterium tuberculosis infecton in mice", J. Immunol., 154 :3359-3372, 1995.
Archer, "Staphylococcus aureus : A Well-Armed Pathogen", Clin. Infect. Dis., 26 :1179-1181, 1998.
Baba et al., "Genome Sequence of Staphylococcus aureus Strain Newman and Comparative Analysis of Staphylococcal Genomes : Polymorphism and Evolution of Two Major Pathogenicity Islands", J. Bacteriol., 190 :300-310, 2007.
Bae and Schneewind, "Allelic replacement in Staphylococcus aureus with inducible counter-selection", Plasmid, 55 :58-63, 2006.
Bae et al., "Staphylococcus aureus virulence genes identified by bursa aureolis mutagenesis and nematode killing", Proc. Natl. Acad. Sci. USA, 101:12312-12317, 2004.
Behring EA. Uber das Zustandekommen der Diphtherie—Immunitat bei Theiren. Deutsche Medzinische Wochenschrift, 16:1145-1148, 1890.
Bjerketorp et al., "The von Willebrand factor-binding protein (vWbp) of Staphylococcus aureus is a coagulase", FEMS Microbiol. Lett., 234 :309-314, 2004.
Brown et al., "Determining Protein-Protein Interactions by Oxidative Cross-Linking of a Glycine-Glycine-Histidine Fusion Protein", Biochemistry, 37:4397-4406, 1998.
Burke et al., "The influence of adjuvant on the therapeutic efficacy of a recombinant genital herpes vaccine", J. Inf. Dis., 170 :1110-1119, 1994.
Burts et al., "EsaC substrate for the ESAT-6 Secretion Pathway and its role in persistent infections of S. aureus", Mol. Microbiol, 69:736-746, 2008.
Burts et al., "EsxA and EsxB are secreted by an ESAT-6-like system that is required for the pathogenesis of Staphylococcus aureus infections", Proc. Natl. Acad. Sci. USA, 102:1169-1174, 2005.
Cedergrene et al., "Mutational analysis of the interaction between staphylococcal protein A and human IgGI", Protein Eng., 6(4):441-448, 1993.
Cespedes et al., "The Clonality of Staphylococcus aureus Nasal Carriage", J. Infect. Dis., 191(3):444-452, 2005.
Chang et al., "Gene expression profiling for the prediction of therapeutic response to docetaxel in patients with breast cancer", Lancet., 362(9381) :362-369, 2003.
Cheng et al., "Genetic requirements for Staphylococcus aureus abscess formation and persistence in host tissue",FASEB J., 23 :3393-3404, 2009.
Dalbey and Wickner, "Leader Peptidase Catalyzes the Release of Experoted Proteins rom the Outer Surface of the Escherichia coli Plamsa Membrane", J. Biol. Chem., 260(29):15925-15931, 1985.
DeDent et al., "Signal peptides direct surface proteins to two distinct envelope locations of Staphylococcus aureus", EMBO J., 37(20):2656-2668, 2008.
DeDent et al., "Distribution of Protein A on the Surface of Staphylococcus", J. Bacteriol., 189(12):4473-4484, 2007.

Deisenhofer et al., "Crystallizaton ,crystal structure analysis and atomic model of the complex formed by a human Fc fragment and fragment B of protein A from Staphylococcus aureus", Hoppe-Seyh Zeitsch. Physiol. Chem, 359(8):975-985, 1978.
Deisenhofer, "Crystallographic refinement and atomic models of a human Fc fragment and its complex with fragment B of protein A from Staphylococcus aureus at 2.9- and 2.8-A resolution", Biochemistry, 20:2361-2370, 1981.
Diep et al., "Roles of 34 virulence genes in the evolution of hospital- and community-associated strains of methicillin-resistant Staphylococcus aureus", J. Infect. Dis., 193 :1495-1503, 2006a.
Diep et al., "Complete genome ssequence of USA300, an epidemic clone of community-acquired methicillin-resistant Staphylococcus aureus", Lancet, 367 :731-739, 2006b.
Dinges et al., "Exotoxins of Staphylococcus aureus", Clin. Microbiol. Rev., 13(1) :16-34, 2000.
Duthie and Lorenz, "Staphylococcal Coagulase: Mode of Action and Antigenicity", J. Gen. Microbiol., 6:95-107, 1952.
Field and Smith, "the Coagulase Test for Staphylococci", J. Comp. Pathol., 55:63, 1945.
Fortune et al., "Mutually dependent secretion of proteins required for mycobacterial virulence", Proc. Natl. Acad. Sci. USA, 102 :10676-10681, 2005.
Foster, "Immune Evasion by Staphylococci", Nat. Rev. Microbiol., 3:948-958, 2005.
Friedrich et al., "Staphylocoagulase is a prototype for the mechanism of cofactor-induced zymogen activation", Nature, 425:535-539, 2003.
Gomez et al., "Staphylococcus aureus protein A activates TACE through EGFR-dependent signaling", EMBO J., 26(3):701-709, 2007.
Gomez et al., J. Biol. Chem., "Staphylococcus aureus Protein A Activates TNFR1 Signaling through Conserved IgG Binding Domains", 281:20190-20196, 2006.
Gomez et al., "Staphylococcus aureus protein A induces airway epithelial inflammatory responses by activating TNFR1", Nature Med., 10(8):842-848, 2004.
Goodyear and Silverman, "Death by a B Cell Superantigen: In Vivo Vh-targed Apoptotic Supraclonal B Cell Deletion by a Staphylococcal Toxin", J. Exp. Med., 197(9):1125-1139, 2003.
Goodyear and Silverman, "Staphylococcal Toxin Induced Preferential and Prolonged in vivo Deletion of Innate-Like B Lymphocytes", Proc. Nat. Acad. Sci. USA, 101(31):11392-11397, 2004.
Gouda et al., "Three-Dimensional Solution Structure of the B Domain of Staphylococcal Protein A: Comparisons of the Solution and Crystal Structures", Biochemistry, 31(40):9665-9672, 1992.
Graille et al., "Crystal Structure of a Staphylococcus aureus Protein A Domain complexed with the Fab Fragment of a Human IgM Antibody: Structural Basis for Recognition of B-Cell Receptors and Superantigen Activity", Proc. Nat. Acad. Sci. USA, 97(10):5399-5404, 2000.
Guss et al., "Region X, the cell-wall-attachment part of staphylococcal protein A", Eur. J. Biochem., 138 :413-420, 1984.
Hartleib et al., "Protein A is the von Willebrand factor binding protein on Staphylococcus aureus", Blood, 96:2149-2156, 2000.
Hsu et al., "The primary mechanism of attenuation of bacillus Calmette-Guerin is a loss of secreted lytic function required for invasion of lung interstitial tissue", Proc. Natl. Acad. Sci. USA, 100 :12420-12425, 2003.
Huston et al., "Protein Engineering of Single-Chain Fv Analogs and Fusion Proteins", In : Methods in Enzymology, Langone (Ed.), Academic Press, NY, 203:46-88, 1991.
Jansson et al., "All individual domains of staphylococcal protein A show Fab binding", FEMS Immunol. Med. Microbiol., 20:69-78, 1998.
Jensen, "A normally occurring staphylococcus antibody in human serum", Acta Path. Microbiol. Scandin., 44:421-428, 1958.
Johnson et al., "Construction of a single-chain Fv derivatives monoclonal antibodies and their production in Escherichia coli." Methods in Enzymol., 203:88-99, 1991.
Jonsson et al., "Current issues in Sjogren's syndrome", Oral Dis., 8(3) :130-140, 2002.

(56) References Cited

OTHER PUBLICATIONS

Kennedy et al., "Epidemic Community-Associated Methicillin-Resistant *Staphylococcus aureus:* Recent Clonal Expansion and Diversification", *Proc. Natl. Acad. Sci. USA,* 105(4):1327-1332, 2008.
Kim et al., "Nontoxigenic protein A vaccine for methicillin-resistant *Staphylococcus aureus* infections in mice", *J. Exp. Med.,* 207(9):1863-1870, 2010.
Kuklin et al., "A Novel *Staphylococcus aureus* Vaccine : Iron Surface Determinant B Induces Rapid Antibody Responses in Rhesus Macaques and Specific Increased Survival in a Murine *S. aureus* Sepsis Model", *Infect. Immun.,* 74(4):2215-2223, 2006.
Lagergard et al., "Determination of neurtralizing antibodies and specific immunoglobulin isotype levels in infants after vaccination against diphtheria", *Eur. J. Clin. Microbiol. Infect. Dis.,* 11(4):341-345, 1992.
Lee et al., "The prospects for developing a vaccine against *Staphylococcus aureus*", *Trends Microbiol.,* 4(4) :162-166, 1996.
MacGurn et al., "A non-RD1 gene cluster is required for Snm secretion in *Mycobacterium tuberculosis"*, *Mol. Microbiol.,* 57:1653-1663, 2005.
Marraffini et al., "Sortases and the Art of Anchoring Proteins to the Envelopes of Gram-Positive Bacteria", *Microbiology and Molecular Biology Review,* 70(1):192-221, 2006.
Mazmanian et al., "Sortase-catalysed anchoring of surface proteins to the cell wall of *Staphylococcus aureus"*, *Mol. Microbiol.,* 40(5):1049-1057, 2001.
Mazmanian et al., "*Staphylococcus aureus* Sortase Mutant Defective in the Display of Surface Proteins and in the Pathogenesis of Animal Infections", *Proc. Natl. Acad. Sci. USA,* 97(10):5510-5515, 2000.
Mazmanian et al., "*Staphylococcus aureus* Sortase, an Enzyme that Anchors Suface Proteins to the Cell Wall", *Science,* 285(5428) :760-763, 1999.
McLaughlin et al., "A *Mycobacterium* ESX-1-Secreted virulence Factor with Unique Requirements for Export", *PLoS Pathog.,* 3(8):e105, 2007.
Mernaugh and Mernaugh, "An Overview of Phage-Displayed Recombinant Antibodies", In: *Molecular methods in Plant Pathology,* Singh et al. (Eds.), CRC Press Inc., Boca Raton, FL, 359-365, 1995.
Moreillon et al., "Role of *Staphylococcus aureus* Coagulase and Clumping Factor in Pathogenesis of Experimental endocarditis", *Inffect. Immun.,* 63:4738-4743, 1995.
Navarre et al., "Multiple Enzymatic Activities of the murein Hydrolase from Staphylococcal p. 11: Identification of a d-Alanyl-Glycine Endopoptidase Activity", *J. Biol. Chem.,* 274(22):15847-15856, 1999.
Novick, "Autoinduction and signal transduction in the regulation of staphylococcal virulence", *Mol. Microbiol.,* 48(6):1429-1449, 2003.
O'Brein et al., "Multiple mechanisms for the activation of human platelet aggregation by *Staphylococcus aureus:* roles for the clumping factors ClfA and ClfB, the serine-aspartate repeat protein SdrE and protein A", *Mol. Microbio.,* 44(4):1033-1044, 2002.
O'Seaghdha et al., "*Staphylococcus aureus* protein A binding to von Willebrand factor A1 domain is mediated by conservative IgG binding regions", *FEBS J.,* 273:4831-4841, 2006.
Pallen, "The ESAT-6/WXG100 superfamily—and a new Gram-positive secretion system?", *Trends Microbiol.,* 10(5):209-212, 2002.
Palmqvist et al., "Bacterial cell wall-expressed protein A triggers supraclonal B-Cell responses upon in vivo infection with *Staphylococcus aureus"*, *Microbes Infect.,* 7(15):1501-1511, 2005.
Panizzi et al., "Fibrinogen Substrate Recognition by Staphylocoagulase-(Pro) thrombin Complexes", *J. Biol. Chem.,* 281(2):1179-1187, 2006.
Phonimdaeng et al., "The coagulase of *Staphylococcus aureus* 8325-4. Sequence analysis and virulence of site-specific coagulase-deficient mutants", *Mol. Microbiol.,* 4(3):393-404, 1990.
Pym et al., "Loss of RD1 contributed to the attenuation of the live tuberculosis vaccines *Mycobacterium bovis* BCG and *Mycobacterium microti"*, *Mol. Microbiol.,* 46(3):709-717, 2002.
Roben et al., "VH3 Family Antibodies Bind Domain D of Staphylococcal Protein A1", *J. Immunol.,* 154:6437-6445, 1995.
Salid-Salim et al., "Community-Acquired Methicillin-Resistant *Staphylococcus aureus* : An Emerging Pathogen", *Infect. Control Hosp. Epidemiol.,* 24 :451-455, 2003.
Schneewind et al., "Sorting of Protein A to the Staphylococcal Cell Wall", *Cell,* 70:267-281, 1992.
Schneewind et al., "Structure of the Cell Wall Anchor of Surface Proteins in *Staphylococcus aureus"*, *Science,* 268(5207):103-106, 1995.
Shaw et al., "The role and regulation of the extracellular proteases of *Staphylococcus aureus"*, *Microbiology,* 150:217-228, 2004.
Shopsin et al., "Evaluation of Protein A Gene Polymorphic Region DNA Sequencing for Typing of *Staphylococcus aureus* Strains", *J. Clin. Microbiol.,* 37:3556-3563, 1999.
Sibbald et al., "Mapping the Pathways to Staphylococcal Pathogenesis by Comparative Secretomics", *Microbiol. Mol. Biol. Rev.,* 70(3):755-788, 2006.
Sjodahl, "Repetitive Sequences in Protein A from *Staphylococcus aureus"*, *Eur. J. Biochem.,* 73:343-351, 1977.
Sjoquist et al., "Localization of protein A in the bacteria", *Eur. J. Biochem.,* 30(1):190-194, 1972.
Smith et al., "The Role of Coagulase in Staphylococcal Infections", *Brit. J. Exp. Pathol.,* 28:57-67, 1947.
Stanley et al., "Acute infection and macrophage subversion by *Mycobacterium tuberculosis* require a specialized secretion system", *Proc. Natl. Acad. Sci. USA,* 100:13001-13006, 2003.
Stranger-Jones et al., "Vaccine assembly from surface proteins of *Staphylococcus aureus"*, *Proc. Nat. Acad. Sci. USA,* 103(45):16942-16947, 2006.
Tiedemann et al., "Isolation of HLA-DR1-(staphylococcal enterotoxin A)2 trimers in solution", *Proc. Natl. Acad. Sci. USA,* 92:12156-12159, 1995.
Tigges et al., "Human herpes simplex virus (HSV)-specific CD8+ CTL clones recognize HSV-2-infected fibroblasts after treatment with IFN-gamma or when virion host shutoff functions are disabled", *J. Immunol.,* 156(10):3901-3910, 1996.
Ton-That et al., "Purification and characterization of sortase, the transpeptidase that cleaves surface proteins from *Staphylococcus aureus* at the LPXTG motif", *Proc. Nat. Acad. Sci. USA,* 96(22) :12424-12429, 1999.
Uhlen et al., "complete Sequence of the Staphylococcal Gene Encoding Protein A", *J. Biol. Chem.,* 259(3):1695-1702, 1984.
van Wely et al., "Translocation of proteins across the cell envelope of Gram-positive bacteria", *FEMS Microbiol. Rev.,* 25(4):437-454, 2001.
Weiss et al., "Effect of srtA and srtB gene expression on the virulence of *Staphylococcus aureus* in animal models of infection", *J. Antimicrob. Chemother.,* 53(3):480-486, 2004.
Xu et al., "A unique *Mycobacterium* ESX-1 protein co-secretes with CFP-10/ESAT-6 and is necessary for inhibiting phagosome maturation", *Mol. Microbiol.,* 66(3):787-800, 2007.
Office Communication in Chinese Patent Application No. 201180051168.X dated May 30, 2014.

* cited by examiner

SEQUENCE LISTING

```
<160> NUMBER OF SEQ ID NOS: 67

<210> SEQ ID NO 1
<211> LENGTH: 150
<212> TYPE: DNA
<213> ORGANISM: Staphylococcus sp.

<400> SEQUENCE: 1
ttcaacaaag atcaacaaag cgccttctat gaaatcttga acatgcctaa cttaaacgaa      60
gcgcaacgta acggcttcat tcaaagtctt aaagacgacc caagccaaag cactaatgtt     120
ttaggtgaag ctaaaaaatt aaacgaatct                                      150

<210> SEQ ID NO 2
<211> LENGTH: 54
<212> TYPE: PRT
<213> ORGANISM: Staphylococcus sp.

<400> SEQUENCE: 2

Gln Gln Asn Asn Phe Asn Lys Asp Gln Gln Ser Ala Phe Tyr Glu Ile
1               5                   10                  15

Leu Asn Met Pro Asn Leu Asn Glu Ala Gln Arg Asn Gly Phe Ile Gln
            20                  25                  30

Ser Leu Lys Asp Asp Pro Ser Gln Ser Thr Asn Val Leu Gly Glu Ala
        35                  40                  45

Lys Lys Leu Asn Glu Ser
    50

<210> SEQ ID NO 3
<211> LENGTH: 51
<212> TYPE: PRT
<213> ORGANISM: Staphylococcus sp.

<400> SEQUENCE: 3

Gln His Asp Glu Ala Gln Gln Asn Ala Phe Tyr Gln Val Leu Asn Met
1               5                   10                  15

Pro Asn Leu Asn Ala Asp Gln Arg Asn Gly Phe Ile Gln Ser Leu Lys
            20                  25                  30

Asp Asp Pro Ser Gln Ser Ala Asn Val Leu Gly Glu Ala Gln Lys Leu
        35                  40                  45

Asn Asp Ser
    50

<210> SEQ ID NO 4
<211> LENGTH: 52
<212> TYPE: PRT
<213> ORGANISM: Staphylococcus sp.

<400> SEQUENCE: 4
```

```
Asn Asn Phe Asn Lys Glu Gln Gln Asn Ala Phe Tyr Glu Ile Leu Asn
1               5                   10                  15

Met Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ser Glu Ala Lys Lys
        35                  40                  45

Leu Asn Glu Ser
    50

<210> SEQ ID NO 5
<211> LENGTH: 52
<212> TYPE: PRT
<213> ORGANISM: Staphylococcus sp.

<400> SEQUENCE: 5

Asn Lys Phe Asn Lys Glu Gln Gln Asn Ala Phe Tyr Glu Ile Leu His
1               5                   10                  15

Leu Pro Asn Leu Thr Glu Glu Gln Arg Asn Gly Phe Ile Gln Ser Leu
            20                  25                  30

Lys Asp Asp Pro Ser Val Ser Lys Glu Ile Leu Ala Glu Ala Lys Lys
        35                  40                  45

Leu Asn Asp Ala
    50

<210> SEQ ID NO 6
<211> LENGTH: 52
<212> TYPE: PRT
<213> ORGANISM: Staphylococcus sp.

<400> SEQUENCE: 6

Asn Lys Phe Asn Lys Glu Gln Gln Asn Ala Phe Tyr Glu Ile Leu His
1               5                   10                  15

Leu Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ala Glu Ala Lys Lys
        35                  40                  45

Leu Asn Asp Ala
    50

<210> SEQ ID NO 7
<211> LENGTH: 52
<212> TYPE: PRT
<213> ORGANISM: Staphylococcus sp.
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid

<400> SEQUENCE: 7

Asn Asn Phe Asn Lys Asp Xaa Xaa Ser Ala Phe Tyr Glu Ile Leu Asn
1               5                   10                  15

Met Pro Asn Leu Asn Glu Ala Gln Arg Asn Gly Phe Ile Gln Ser Leu
            20                  25                  30

Lys Xaa Xaa Pro Ser Gln Ser Thr Asn Val Leu Gly Glu Ala Lys Lys
        35                  40                  45

Leu Asn Glu Ser
```

```
<210> SEQ ID NO 8
<211> LENGTH: 52
<212> TYPE: PRT
<213> ORGANISM: Staphylococcus sp.
<220> FEATURE:
<221> NAME/KEY: MISC_FEATURE
<222> LOCATION: (7)..(8)
<223> OTHER INFORMATION: where X is any amino acid other than Q
<220> FEATURE:
<221> NAME/KEY: MISC_FEATURE
<222> LOCATION: (12)..(35)
<223> OTHER INFORMATION: where Y is any amion acid other than D

<400> SEQUENCE: 8

Asn Asn Phe Asn Lys Asp Xaa Xaa Ser Ala Phe Tyr Glu Ile Leu Asn
1               5                   10                  15

Met Pro Asn Leu Asn Glu Ala Gln Arg Asn Gly Phe Ile Gln Ser Leu
            20                  25                  30

Lys Tyr Tyr Pro Ser Gln Ser Thr Asn Val Leu Gly Glu Ala Lys Lys
        35                  40                  45

Leu Asn Glu Ser
    50

<210> SEQ ID NO 9
<211> LENGTH: 450
<212> TYPE: PRT
<213> ORGANISM: Staphylococcus sp.

<400> SEQUENCE: 9

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220
```

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Val Ser Lys Glu Ile Leu
            245                 250                 255

Ala Glu Ala Lys Lys Leu Asn Asp Ala Gln Ala Pro Lys Glu Glu Asp
        260                 265                 270

Asn Lys Lys Pro Gly Lys Glu Asp Gly Asn Lys Pro Gly Lys Glu Asp
    275                 280                 285

Gly Asn Lys Pro Gly Lys Glu Asp Asn Lys Pro Gly Lys Glu Asp
290                 295                 300

Gly Asn Lys Pro Gly Lys Glu Asp Asn Asn Lys Pro Gly Lys Glu Asp
305                 310                 315                 320

Gly Asn Lys Pro Gly Lys Glu Asp Asn Asn Lys Pro Gly Lys Glu Asp
            325                 330                 335

Gly Asn Lys Pro Gly Lys Glu Asp Gly Asn Lys Pro Gly Lys Glu Asp
        340                 345                 350

Gly Asn Gly Val His Val Val Lys Pro Gly Asp Thr Val Asn Asp Ile
        355                 360                 365

Ala Lys Ala Asn Gly Thr Thr Ala Asp Lys Ile Ala Ala Asp Asn Lys
370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
            405                 410                 415

Pro Glu Thr Gly Glu Asn Pro Phe Ile Gly Thr Thr Val Phe Gly
        420                 425                 430

Gly Leu Ser Leu Ala Leu Gly Ala Ala Leu Leu Ala Gly Arg Arg Arg
            435                 440                 445

Glu Leu
    450

<210> SEQ ID NO 10
<211> LENGTH: 450
<212> TYPE: PRT
<213> ORGANISM: Staphylococcus sp.

<400> SEQUENCE: 10

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys

```
                130                 135                 140
Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Val Ser Lys Glu Ile Leu
                245                 250                 255

Ala Glu Ala Lys Lys Leu Asn Asp Ala Gln Ala Pro Lys Glu Glu Asp
            260                 265                 270

Asn Lys Lys Pro Gly Lys Glu Asp Asn Lys Pro Gly Lys Glu Asp
        275                 280                 285

Gly Asn Lys Pro Gly Lys Glu Asp Asn Lys Pro Gly Lys Glu Asp
    290                 295                 300

Gly Asn Lys Pro Gly Lys Glu Asp Asn Lys Pro Gly Lys Glu Asp
305                 310                 315                 320

Gly Asn Lys Pro Gly Lys Glu Asp Asn Lys Pro Gly Lys Glu Asp
                325                 330                 335

Gly Asn Lys Pro Gly Lys Glu Asp Gly Asn Lys Pro Gly Lys Glu Asp
            340                 345                 350

Gly Asn Gly Val His Val Lys Pro Gly Asp Thr Val Asn Asp Ile
        355                 360                 365

Ala Lys Ala Asn Gly Thr Thr Ala Asp Lys Ile Ala Ala Asp Asn Lys
    370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
                405                 410                 415

Pro Glu Thr Gly Glu Glu Asn Pro Phe Ile Gly Thr Thr Val Phe Gly
            420                 425                 430

Gly Leu Ser Leu Ala Leu Gly Ala Ala Leu Leu Ala Gly Arg Arg Arg
        435                 440                 445

Glu Leu
    450

<210> SEQ ID NO 11
<211> LENGTH: 97
<212> TYPE: PRT
<213> ORGANISM: Staphylococcus sp.

<400> SEQUENCE: 11

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
        35                  40                  45
```

```
Ser Arg Phe Glu Glu Gln Phe Gln Gln Leu Ser Pro Lys Val Glu Lys
    50                  55                  60

Phe Ala Gln Leu Leu Glu Glu Ile Lys Gln Gln Leu Asn Ser Thr Ala
 65                  70                  75                  80

Asp Ala Val Gln Glu Gln Asp Gln Gln Leu Ser Asn Asn Phe Gly Leu
                 85                  90                  95

Gln

<210> SEQ ID NO 12
<211> LENGTH: 102
<212> TYPE: PRT
<213> ORGANISM: Staphylococcus sp.

<400> SEQUENCE: 12

Met Gly Gly Tyr Lys Gly Ile Lys Ala Asp Gly Gly Lys Val Asn Gln
 1               5                  10                  15

Ala Lys Gln Leu Ala Ala Lys Ile Ala Lys Asp Ile Glu Ala Cys Gln
                20                  25                  30

Lys Gln Thr Gln Gln Leu Ala Glu Tyr Ile Glu Gly Ser Asp Trp Glu
            35                  40                  45

Gly Gln Phe Ala Asn Lys Val Lys Asp Val Leu Leu Ile Met Ala Lys
    50                  55                  60

Phe Gln Glu Glu Leu Val Gln Pro Met Ala Asp His Gln Lys Ala Ile
 65                  70                  75                  80

Asp Asn Leu Ser Gln Asn Leu Ala Lys Tyr Asp Thr Leu Ser Ile Lys
                 85                  90                  95

Gln Gly Leu Asp Arg Val
            100

<210> SEQ ID NO 13
<211> LENGTH: 1385
<212> TYPE: PRT
<213> ORGANISM: Staphylococcus sp.

<400> SEQUENCE: 13

Met Leu Asn Arg Glu Asn Lys Thr Ala Ile Thr Arg Lys Gly Met Val
 1               5                  10                  15

Ser Asn Arg Leu Asn Lys Phe Ser Ile Arg Lys Tyr Thr Val Gly Thr
                20                  25                  30

Ala Ser Ile Leu Val Gly Thr Thr Leu Ile Phe Gly Leu Gly Asn Gln
            35                  40                  45

Glu Ala Lys Ala Ala Glu Ser Thr Asn Lys Glu Leu Asn Glu Ala Thr
    50                  55                  60

Thr Ser Ala Ser Asp Asn Gln Ser Ser Asp Lys Val Asp Met Gln Gln
 65                  70                  75                  80

Leu Asn Gln Glu Asp Asn Thr Lys Asn Asp Gln Lys Glu Met Val
                 85                  90                  95

Ser Ser Gln Gly Asn Glu Thr Ser Asn Gly Asn Lys Ser Ile Glu
            100                 105                 110

Lys Glu Ser Val Gln Ser Thr Thr Gly Asn Lys Val Glu Val Ser Thr
            115                 120                 125

Ala Lys Ser Asp Glu Gln Ala Ser Pro Lys Ser Thr Asn Glu Asp Leu
        130                 135                 140

Asn Thr Lys Gln Thr Ile Ser Asn Gln Glu Gly Leu Gln Pro Asp Leu
145                 150                 155                 160

Leu Glu Asn Lys Ser Val Val Asn Val Gln Pro Thr Asn Glu Glu Asn
```

```
            165                 170                 175
Lys Lys Val Asp Ala Lys Thr Glu Ser Thr Thr Leu Asn Val Lys Ser
            180                 185                 190

Asp Ala Ile Lys Ser Asn Ala Glu Thr Leu Val Asp Asn Asn Ser Asn
            195                 200                 205

Ser Asn Asn Glu Asn Asn Ala Asp Ile Ile Leu Pro Lys Ser Thr Ala
            210                 215                 220

Pro Lys Ser Leu Asn Thr Arg Met Arg Met Ala Ala Ile Gln Pro Asn
225                 230                 235                 240

Ser Thr Asp Ser Lys Asn Val Asn Asp Leu Ile Thr Ser Asn Thr Thr
                245                 250                 255

Leu Thr Val Val Asp Ala Asp Asn Ser Lys Thr Ile Val Pro Ala Gln
                260                 265                 270

Asp Tyr Leu Ser Leu Lys Ser Gln Ile Thr Val Asp Asp Lys Val Lys
                275                 280                 285

Ser Gly Asp Tyr Phe Thr Ile Lys Tyr Ser Asp Thr Val Gln Val Tyr
            290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
                340                 345                 350

Lys Met Gly Ile Asn Tyr Ser Ile Tyr Met Asp Ala Asp Thr Ile Pro
                355                 360                 365

Val Asp Lys Lys Asp Val Pro Phe Ser Val Thr Ile Gly Asn Gln Ile
            370                 375                 380

Thr Thr Thr Thr Ala Asp Ile Thr Tyr Pro Ala Tyr Lys Glu Ala Asp
385                 390                 395                 400

Asn Asn Ser Ile Gly Ser Ala Phe Thr Glu Thr Val Ser His Val Gly
                405                 410                 415

Asn Val Glu Asp Pro Gly Tyr Tyr Asn Gln Val Val Tyr Val Asn Pro
            420                 425                 430

Met Asp Lys Asp Leu Lys Gly Ala Lys Leu Lys Val Glu Ala Tyr His
            435                 440                 445

Pro Lys Tyr Pro Thr Asn Ile Gly Gln Ile Asn Gln Asn Val Thr Asn
            450                 455                 460

Ile Lys Ile Tyr Arg Val Pro Glu Gly Tyr Thr Leu Asn Lys Gly Tyr
465                 470                 475                 480

Asp Val Asn Thr Asn Asp Leu Val Asp Val Thr Asp Glu Phe Lys Asn
                485                 490                 495

Lys Met Thr Tyr Gly Ser Asn Gln Ser Val Asn Leu Asp Phe Gly Asp
            500                 505                 510

Ile Thr Ser Ala Tyr Val Val Met Val Asn Thr Lys Phe Gln Tyr Thr
            515                 520                 525

Asn Ser Glu Ser Pro Thr Leu Val Gln Met Ala Thr Leu Ser Ser Thr
            530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
            580                 585                 590
```

```
Val Gly Asn Val Thr Val Thr Val Phe Asp Asn Asn Thr Asn Thr Lys
        595                 600                 605

Val Gly Glu Ala Val Thr Lys Glu Asp Gly Ser Tyr Leu Ile Pro Asn
610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
                660                 665                 670

Ala Asp Leu Gly Ile Tyr Lys Pro Lys Tyr Asn Leu Gly Asp Tyr Val
                675                 680                 685

Trp Glu Asp Thr Asn Lys Asn Gly Ile Gln Asp Gln Asp Glu Lys Gly
        690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
                740                 745                 750

Pro Thr Thr Val Thr Ser Gly Ser Asp Ile Glu Lys Asp Ser Asn Gly
                755                 760                 765

Leu Thr Thr Thr Gly Val Ile Asn Gly Ala Asp Asn Met Thr Leu Asp
        770                 775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                805                 810                 815

Ser Gly Val Thr Val Thr Leu Lys Asn Glu Asn Gly Glu Val Leu Gln
                820                 825                 830

Thr Thr Lys Thr Asp Lys Asp Gly Lys Tyr Gln Phe Thr Gly Leu Glu
        835                 840                 845

Asn Gly Thr Tyr Lys Val Glu Phe Glu Thr Pro Ser Gly Tyr Thr Pro
        850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
                885                 890                 895

Gly Phe Tyr Lys Pro Thr Tyr Asn Leu Gly Asp Tyr Val Trp Glu Asp
                900                 905                 910

Thr Asn Lys Asn Gly Val Gln Asp Lys Asp Glu Lys Gly Ile Ser Gly
        915                 920                 925

Val Thr Val Thr Leu Lys Asp Glu Asn Asp Lys Val Leu Lys Thr Val
        930                 935                 940

Thr Thr Asp Glu Asn Gly Lys Tyr Gln Phe Thr Asp Leu Asn Asn Gly
945                 950                 955                 960

Thr Tyr Lys Val Glu Phe Glu Thr Pro Ser Gly Tyr Thr Pro Thr Ser
                965                 970                 975

Val Thr Ser Gly Asn Asp Thr Glu Lys Asp Ser Asn Gly Leu Thr Thr
                980                 985                 990

Thr Gly Val Ile Lys Asp Ala Asp  Asn Met Thr Leu Asp  Ser Gly Phe
        995                 1000                1005
```

```
Tyr Lys Thr Pro Lys Tyr Ser Leu Gly Asp Tyr Val Trp Tyr Asp
    1010                1015                1020

Ser Asn Lys Asp Gly Lys Gln Asp Ser Thr Glu Lys Gly Ile Lys
    1025                1030                1035

Asp Val Lys Val Ile Leu Leu Asn Glu Lys Gly Glu Val Ile Gly
    1040                1045                1050

Thr Thr Lys Thr Asp Glu Asn Gly Lys Tyr Arg Phe Asp Asn Leu
    1055                1060                1065

Asp Ser Gly Lys Tyr Lys Val Ile Phe Glu Lys Pro Thr Gly Leu
    1070                1075                1080

Thr Gln Thr Gly Thr Asn Thr Thr Glu Asp Asp Lys Asp Ala Asp
    1085                1090                1095

Gly Gly Glu Val Asp Val Thr Ile Thr Asp His Asp Asp Phe Thr
    1100                1105                1110

Leu Asp Asn Gly Tyr Tyr Glu Glu Glu Thr Ser Asp Ser Asp Ser
    1115                1120                1125

Asp Ser Asp Ser Asp Ser Asp Ser Asp Ser Asp Ser Asp Ser Asp
    1130                1135                1140

Ser Asp Ser Asp Ser Asp Ser Asp Ser Asp Ser Asp Ser Asp Ser
    1145                1150                1155

Asp Ser Asp Ser Asp Ser Asp Ser Asp Ser Asp Ser Asp Ser Asp
    1160                1165                1170

Ser Asp Ser Asp Ser Asp Ser Asp Ser Asp Ser Asp Ser Asp Ser
    1175                1180                1185

Asp Ser Asp Ser Asp Ser Asp Ser Asp Ser Asp Ser Asp Ser Asp
    1190                1195                1200

Ser Asp Ser Asp Ser Asp Ser Asp Ser Asp Ser Asp Ser Asp Ser
    1205                1210                1215

Asp Ser Asp Ser Asp Ser Asp Ser Asp Ser Asp Ser Asp Ser Asp
    1220                1225                1230

Ser Asp Ser Asp Ser Asp Ser Asp Ser Asp Ser Asp Ser Asp Ser
    1235                1240                1245

Asp Ser Asp Ser Asp Ser Asp Ser Asp Ser Asp Ser Asp Ser Asp
    1250                1255                1260

Ser Asp Ser Asp Ser Asp Ser Asp Ser Asp Ser Asp Ser Asp Ser
    1265                1270                1275

Asp Ser Asp Ser Asp Ser Asp Ser Asp Ser Asp Ser Asp Ser Asp
    1280                1285                1290

Ser Asp Ser Asp Ser Asp Ser Asp Ser Asp Ser Asp Ser Asp Ser
    1295                1300                1305

Asp Ser Asp Ser Asp Ser Asp Ser Asp Ser Asp Ser Asp Ser Asp
    1310                1315                1320

Ser Asp Ala Gly Lys His Thr Pro Val Lys Pro Met Ser Thr Thr
    1325                1330                1335

Lys Asp His His Asn Lys Ala Lys Ala Leu Pro Glu Thr Gly Asn
    1340                1345                1350

Glu Asn Ser Gly Ser Asn Asn Ala Thr Leu Phe Gly Gly Leu Phe
    1355                1360                1365

Ala Ala Leu Gly Ser Leu Leu Leu Phe Gly Arg Arg Lys Lys Gln
    1370                1375                1380

Asn Lys
    1385
```

-continued

```
<210> SEQ ID NO 14
<211> LENGTH: 1141
<212> TYPE: PRT
<213> ORGANISM: Staphylococcus sp.

<400> SEQUENCE: 14
```

Met Ile Asn Arg Asp Asn Lys Lys Ala Ile Thr Lys Lys Gly Met Ile
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Asn Thr Ser Thr Glu Asn Ala Lys Gln Asp
    50                  55                  60

Asp Ala Thr Thr Ser Asp Asn Lys Glu Val Val Ser Glu Thr Glu Asn
65                  70                  75                  80

Asn Ser Thr Thr Glu Asn Asp Ser Thr Asn Pro Ile Lys Lys Glu Thr
                85                  90                  95

Asn Thr Asp Ser Gln Pro Glu Ala Lys Glu Ser Thr Thr Ser Ser
            100                 105                 110

Thr Gln Gln Gln Gln Asn Asn Val Thr Ala Thr Thr Gly Thr Lys Pro
        115                 120                 125

Gln Asn Ile Glu Lys Glu Asn Val Lys Pro Ser Thr Asp Lys Thr Ala
    130                 135                 140

Thr Glu Asp Thr Ser Val Ile Leu Glu Glu Lys Lys Ala Pro Asn Tyr
145                 150                 155                 160

Thr Asn Asn Asp Val Thr Thr Lys Pro Ser Thr Ser Glu Ile Gln Thr
                165                 170                 175

Lys Pro Thr Thr Pro Gln Glu Ser Thr Asn Ile Glu Asn Ser Gln Pro
            180                 185                 190

Gln Pro Thr Pro Ser Lys Val Asp Asn Gln Val Thr Asp Ala Thr Asn
        195                 200                 205

Pro Lys Glu Pro Val Asn Val Ser Lys Glu Glu Leu Lys Asn Asn Pro
    210                 215                 220

Glu Lys Leu Lys Glu Leu Val Arg Asn Asp Asn Asn Thr Asp Arg Ser
225                 230                 235                 240

Thr Lys Pro Val Ala Thr Ala Pro Thr Ser Val Ala Pro Lys Arg Leu
                245                 250                 255

Asn Ala Lys Met Arg Phe Ala Val Ala Gln Pro Ala Ala Val Ala Ser
            260                 265                 270

Asn Asn Val Asn Asp Leu Ile Thr Val Thr Lys Gln Thr Ile Lys Val
        275                 280                 285

Gly Asp Gly Lys Asp Asn Val Ala Ala Ala His Asp Gly Lys Asp Ile
    290                 295                 300

Glu Tyr Asp Thr Glu Phe Thr Ile Asp Asn Lys Val Lys Lys Gly Asp
305                 310                 315                 320

Thr Met Thr Ile Asn Tyr Asp Lys Asn Val Ile Pro Ser Asp Leu Thr
                325                 330                 335

Asp Lys Asn Asp Pro Ile Asp Ile Thr Asp Pro Ser Gly Glu Val Ile
            340                 345                 350

Ala Lys Gly Thr Phe Asp Lys Ala Thr Lys Gln Ile Thr Tyr Thr Phe
        355                 360                 365

Thr Asp Tyr Val Asp Lys Tyr Glu Asp Ile Lys Ala Arg Leu Thr Leu
    370                 375                 380

-continued

Tyr Ser Tyr Ile Asp Lys Gln Ala Val Pro Asn Glu Thr Ser Leu Asn
385                 390                 395                 400

Leu Thr Phe Ala Thr Ala Gly Lys Glu Thr Ser Gln Asn Val Ser Val
            405                 410                 415

Asp Tyr Gln Asp Pro Met Val His Gly Asp Ser Asn Ile Gln Ser Ile
        420                 425                 430

Phe Thr Lys Leu Asp Glu Asn Lys Gln Thr Ile Glu Gln Gln Ile Tyr
    435                 440                 445

Val Asn Pro Leu Lys Lys Thr Ala Thr Asn Thr Lys Val Asp Ile Ala
450                 455                 460

Gly Ser Gln Val Asp Asp Tyr Gly Asn Ile Lys Leu Gly Asn Gly Ser
465                 470                 475                 480

Thr Ile Ile Asp Gln Asn Thr Glu Ile Lys Val Tyr Lys Val Asn Pro
                485                 490                 495

Asn Gln Gln Leu Pro Gln Ser Asn Arg Ile Tyr Asp Phe Ser Gln Tyr
            500                 505                 510

Glu Asp Val Thr Ser Gln Phe Asp Asn Lys Ser Phe Ser Asn Asn
        515                 520                 525

Val Ala Thr Leu Asp Phe Gly Asp Ile Asn Ser Ala Tyr Ile Ile Lys
530                 535                 540

Val Val Ser Lys Tyr Thr Pro Thr Ser Asp Gly Glu Leu Asp Ile Ala
545                 550                 555                 560

Gln Gly Thr Ser Met Arg Thr Thr Asp Lys Tyr Gly Tyr Tyr Asn Tyr
                565                 570                 575

Ala Gly Tyr Ser Asn Phe Ile Val Thr Ser Asn Asp Thr Gly Gly Gly
            580                 585                 590

Asp Gly Thr Val Lys Pro Glu Glu Lys Leu Tyr Lys Ile Gly Asp Tyr
        595                 600                 605

Val Trp Glu Asp Val Asp Lys Asp Gly Val Gln Gly Thr Asp Ser Lys
    610                 615                 620

Glu Lys Pro Met Ala Asn Val Leu Val Thr Leu Thr Tyr Pro Asp Gly
625                 630                 635                 640

Thr Thr Lys Ser Val Arg Thr Asp Ala Asn Gly His Tyr Glu Phe Gly
                645                 650                 655

Gly Leu Lys Asp Gly Glu Thr Tyr Thr Val Lys Phe Glu Thr Pro Ala
            660                 665                 670

Gly Tyr Leu Pro Thr Lys Val Asn Gly Thr Thr Asp Gly Glu Lys Asp
        675                 680                 685

Ser Asn Gly Ser Ser Ile Thr Val Lys Ile Asn Gly Lys Asp Asp Met
    690                 695                 700

Ser Leu Asp Thr Gly Phe Tyr Lys Glu Pro Lys Tyr Asn Leu Gly Asp
705                 710                 715                 720

Tyr Val Trp Glu Asp Thr Asn Lys Asp Gly Ile Gln Asp Ala Asn Glu
                725                 730                 735

Pro Gly Ile Lys Asp Val Lys Val Thr Leu Lys Asp Ser Thr Gly Lys
            740                 745                 750

Val Ile Gly Thr Thr Thr Thr Asp Ala Ser Gly Lys Tyr Lys Phe Thr
        755                 760                 765

Asp Leu Asp Asn Gly Asn Tyr Thr Val Glu Phe Glu Thr Pro Ala Gly
    770                 775                 780

Tyr Thr Pro Thr Val Lys Asn Thr Thr Ala Glu Asp Lys Asp Ser Asn
785                 790                 795                 800

Gly Leu Thr Thr Thr Gly Val Ile Lys Asp Ala Asp Asn Met Thr Leu 805                 810                 815
Asp Ser Gly Phe Tyr Lys Thr Pro Lys Tyr Ser Leu Gly Asp Tyr Val
                820                 825                 830

Trp Tyr Asp Ser Asn Lys Asp Gly Lys Gln Asp Ser Thr Glu Lys Gly
            835                 840                 845

Ile Lys Asp Val Lys Val Thr Leu Leu Asn Glu Lys Gly Glu Val Ile
        850                 855                 860

Gly Thr Thr Lys Thr Asp Glu Asn Gly Lys Tyr Arg Phe Asp Asn Leu
865                 870                 875                 880

Asp Ser Gly Lys Tyr Lys Val Ile Phe Glu Lys Pro Ala Gly Leu Thr
                885                 890                 895

Gln Thr Val Thr Asn Thr Thr Glu Asp Asp Lys Asp Ala Asp Gly Gly
            900                 905                 910

Glu Val Asp Val Thr Ile Thr Asp His Asp Asp Phe Thr Leu Asp Asn
        915                 920                 925

Gly Tyr Phe Glu Glu Asp Thr Ser Asp Ser Asp Ser Asp Ser Asp Ser
930                 935                 940

Asp Ser Asp Ser Asp Ser Asp Ser Asp Ser Asp Ser Asp Ser Asp Ser
945                 950                 955                 960

Asp Ser Asp Ser Asp Ser Asp Ser Asp Ser Asp Ser Asp Ser Asp Ser
                965                 970                 975

Asp Ser Asp Ser Asp Ser Asp Ser Asp Ser Asp Ser Asp Ser Asp Ser
            980                 985                 990

Asp Ser Asp Ser Asp Ser Asp Ser Asp Ser Asp Ser Asp Ser Asp Ser
        995                 1000                1005

Asp Ser Asp Ser Asp Ser Asp Ser Asp Ser Asp Ser Asp Ser Asp
    1010                1015                1020

Ser Asp Ser Asp Ser Asp Ser Asp Ser Asp Ser Asp Ser Asp Ser
    1025                1030                1035

Asp Ser Asp Ser Asp Ser Asp Ser Asp Ser Asp Ser Asp Ser Asp
    1040                1045                1050

Ser Asp Ser Asp Ser Asp Ser Asp Ser Asp Ser Asp Ser Asp Ser
    1055                1060                1065

Asp Ser Asp Ser Asp Ser Asp Ser Asp Ser Asp Ser Asp Ala Gly
    1070                1075                1080

Lys His Thr Pro Val Lys Pro Met Ser Thr Thr Lys Asp His His
    1085                1090                1095

Asn Lys Ala Lys Ala Leu Pro Glu Thr Gly Ser Glu Asn Asn Gly
    1100                1105                1110

Ser Asn Asn Ala Thr Leu Phe Gly Gly Leu Phe Ala Ala Leu Gly
    1115                1120                1125

Ser Leu Leu Leu Phe Gly Arg Arg Lys Lys Gln Asn Lys
    1130                1135                1140

<210> SEQ ID NO 15
<211> LENGTH: 350
<212> TYPE: PRT
<213> ORGANISM: Staphylococcus sp.

<400> SEQUENCE: 15

Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
            20                  25                  30

```
Ser Leu Val Tyr Ile Gly Ala Asp Ser Gln Gln Val Asn Ala Ala Thr
         35                  40                  45

Glu Ala Thr Asn Ala Thr Asn Asn Gln Ser Thr Gln Val Ser Gln Ala
 50                  55                  60

Thr Ser Gln Pro Ile Asn Phe Gln Val Gln Lys Asp Gly Ser Ser Glu
 65                  70                  75                  80

Lys Ser His Met Asp Asp Tyr Met Gln His Pro Gly Lys Val Ile Lys
                 85                  90                  95

Gln Asn Asn Lys Tyr Tyr Phe Gln Thr Val Leu Asn Asn Ala Ser Phe
             100                 105                 110

Trp Lys Glu Tyr Lys Phe Tyr Asn Ala Asn Asn Gln Glu Leu Ala Thr
         115                 120                 125

Thr Val Val Asn Asp Asn Lys Lys Ala Asp Thr Arg Thr Ile Asn Val
130                 135                 140

Ala Val Glu Pro Gly Tyr Lys Ser Leu Thr Thr Lys Val His Ile Val
145                 150                 155                 160

Val Pro Gln Ile Asn Tyr Asn His Arg Tyr Thr Thr His Leu Glu Phe
                165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
        195                 200                 205

Thr Lys Pro Val Gln Pro Lys Val Glu Lys Val Lys Pro Thr Val Thr
210                 215                 220

Thr Thr Ser Lys Val Glu Asp Asn His Ser Thr Lys Val Val Ser Thr
225                 230                 235                 240

Asp Thr Thr Lys Asp Gln Thr Lys Thr Gln Thr Ala His Thr Val Lys
                245                 250                 255

Thr Ala Gln Thr Ala Gln Glu Gln Asn Lys Val Gln Thr Pro Val Lys
            260                 265                 270

Asp Val Ala Thr Ala Lys Ser Glu Ser Asn Asn Gln Ala Val Ser Asp
        275                 280                 285

Asn Lys Ser Gln Gln Thr Asn Lys Val Thr Lys His Asn Glu Thr Pro
290                 295                 300

Lys Gln Ala Ser Lys Ala Lys Glu Leu Pro Lys Thr Gly Leu Thr Ser
305                 310                 315                 320

Val Asp Asn Phe Ile Ser Thr Val Ala Phe Ala Thr Leu Ala Leu Leu
                325                 330                 335

Gly Ser Leu Ser Leu Leu Leu Phe Lys Arg Lys Glu Ser Lys
            340                 345                 350

<210> SEQ ID NO 16
<211> LENGTH: 645
<212> TYPE: PRT
<213> ORGANISM: Staphylococcus sp.

<400> SEQUENCE: 16

Met Asn Lys Gln Gln Lys Glu Phe Lys Ser Phe Tyr Ser Ile Arg Lys
 1               5                  10                  15

Ser Ser Leu Gly Val Ala Ser Val Ala Ile Ser Thr Leu Leu Leu Leu
             20                  25                  30

Met Ser Asn Gly Glu Ala Gln Ala Ala Ala Glu Glu Thr Gly Gly Thr
         35                  40                  45

Asn Thr Glu Ala Gln Pro Lys Thr Glu Ala Val Ala Ser Pro Thr Thr
 50                  55                  60
```

```
Thr Ser Glu Lys Ala Pro Glu Thr Lys Pro Val Ala Asn Ala Val Ser
 65                  70                  75                  80

Val Ser Asn Lys Glu Val Glu Ala Pro Thr Ser Glu Thr Lys Glu Ala
                 85                  90                  95

Lys Glu Val Lys Glu Val Lys Ala Pro Lys Glu Thr Lys Ala Val Lys
            100                 105                 110

Pro Ala Ala Lys Ala Thr Asn Asn Thr Tyr Pro Ile Leu Asn Gln Glu
            115                 120                 125

Leu Arg Glu Ala Ile Lys Asn Pro Ala Ile Lys Asp Lys Asp His Ser
        130                 135                 140

Ala Pro Asn Ser Arg Pro Ile Asp Phe Glu Met Lys Lys Glu Asn Gly
145                 150                 155                 160

Glu Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
210                 215                 220

Phe Ser Val Ser Asn Gly Thr Lys Ala Val Lys Ile Val Ser Ser Thr
225                 230                 235                 240

His Phe Asn Asn Lys Glu Gly Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
        275                 280                 285

Glu Arg Gln Val Tyr Glu Leu Asn Lys Ile Gln Asp Lys Leu Pro Glu
290                 295                 300

Lys Leu Lys Ala Glu Tyr Lys Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
        450                 455                 460

Lys Glu Gln Gln Asp Asn Ser Ala Lys Lys Glu Ala Thr Pro Ala Thr
465                 470                 475                 480
```

```
Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
            515                 520                 525

Pro Thr Lys Gly Glu Val Glu Ser Ser Thr Thr Pro Thr Lys Val
        530                 535                 540

Val Ser Thr Thr Gln Asn Val Ala Lys Pro Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
            595                 600                 605

Ser Leu Pro Gln Thr Gly Glu Glu Ser Asn Lys Asp Met Thr Leu Pro
            610                 615                 620

Leu Met Ala Leu Leu Ala Leu Ser Ser Ile Val Ala Phe Val Leu Pro
625                 630                 635                 640

Arg Lys Arg Lys Asn
                645

<210> SEQ ID NO 17
<211> LENGTH: 80
<212> TYPE: PRT
<213> ORGANISM: Staphylococcus sp.

<400> SEQUENCE: 17

Met Asn Gln His Val Lys Val Thr Phe Asp Phe Thr Asn Tyr Asn Tyr
1               5                   10                  15

Gly Thr Tyr Asp Leu Ala Val Pro Ala Tyr Leu Pro Ile Lys Asn Leu
            20                  25                  30

Ile Ala Leu Val Leu Asp Ser Leu Asp Ile Ser Ile Phe Asp Val Asn
        35                  40                  45

Thr Gln Ile Lys Val Met Thr Lys Gly Gln Leu Leu Val Glu Asn Asp
    50                  55                  60

Arg Leu Ile Asp Tyr Gln Ile Ala Asp Gly Asp Ile Leu Lys Leu Leu
65                  70                  75                  80

<210> SEQ ID NO 18
<211> LENGTH: 877
<212> TYPE: PRT
<213> ORGANISM: Staphylococcus sp.

<400> SEQUENCE: 18

Met Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80
```

```
Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asn Phe
    210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
        355                 360                 365

Pro Asn Gly Ala Asn Ile Ser Ser Gln Ile Ile Gly Val Asp Thr Ala
    370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
        435                 440                 445

Asp Pro Asn Asp Ser Asn Leu Lys Glu Val Thr Asp Gln Phe Lys Asn
    450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495
```

-continued

```
Gly Lys Asn Leu Lys Thr Gln Val Ile Gln Glu Asn Val Asp Pro Val
            500                 505                 510

Thr Asn Arg Asp Tyr Ser Ile Phe Gly Trp Asn Asn Glu Asn Val Val
            515                 520                 525

Arg Tyr Gly Gly Gly Ser Ala Asp Gly Asp Ser Ala Val Asn Pro Lys
            530                 535                 540

Asp Pro Thr Pro Gly Pro Pro Val Asp Pro Glu Pro Ser Pro Asp Pro
545                 550                 555                 560

Glu Pro Glu Pro Thr Pro Asp Pro Gly Pro Ser Pro Asp Pro Glu Pro
            565                 570                 575

Glu Pro Ser Pro Asp Pro Asp Pro Asp Ser Asp Ser Asp Ser Asp Ser
            580                 585                 590

Gly Ser Asp Ser Asp Ser Gly Ser Asp Ser Asp Ser Glu Ser Asp Ser
            595                 600                 605

Asp Ser Asp Ser Asp Ser Asp Ser Asp Ser Asp Ser Asp Ser Glu Ser
            610                 615                 620

Asp Ser Asp Ser Glu Ser Asp Ser Asp Ser Asp Ser Asp Ser Asp Ser
625                 630                 635                 640

Asp Ser Asp Ser Asp Ser Glu Ser Asp Ser Asp Ser Asp Ser Asp Ser
            645                 650                 655

Asp Ser Asp Ser Asp Ser Asp Ser Glu Ser Asp Ser Asp Ser Glu Ser
            660                 665                 670

Asp Ser Glu Ser Asp Ser Asp Ser Asp Ser Asp Ser Asp Ser Asp Ser
            675                 680                 685

Asp Ser Asp Ser Asp Ser Asp Ser Asp Ser Asp Ser Asp Ser Asp Ser
            690                 695                 700

Asp Ser Asp Ser Asp Ser Asp Ser Glu Ser Asp Ser Asp Ser Asp Ser
705                 710                 715                 720

Asp Ser Asp Ser Asp Ser Asp Ser Asp Ser Asp Ser Asp Ser Asp Ser
            725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
            755                 760                 765

Asp Ser Asp Ser Asp Ser Asp Ser Asp Ser Asp Ser Asp Ser Asp Ser
            770                 775                 780

Asp Ser Asp Ser Asp Ser Asp Ser Asp Ser Asp Ser Asp Ser Asp Ser
785                 790                 795                 800

Asp Ser Asp Ser Arg Val Thr Pro Pro Asn Asn Glu Gln Lys Ala Pro
            805                 810                 815

Ser Asn Pro Lys Gly Glu Val Asn His Ser Asn Lys Val Ser Lys Gln
            820                 825                 830

His Lys Thr Asp Ala Leu Pro Glu Thr Gly Asp Lys Ser Glu Asn Thr
            835                 840                 845

Asn Ala Thr Leu Phe Gly Ala Met Met Ala Leu Leu Gly Ser Leu Leu
            850                 855                 860

Leu Phe Arg Lys Arg Lys Gln Asp His Lys Glu Lys Ala
865                 870                 875
```

<210> SEQ ID NO 19
<211> LENGTH: 227
<212> TYPE: PRT
<213> ORGANISM: Staphylococcus sp.

```
<400> SEQUENCE: 19

Met Lys Asn Ile Leu Lys Val Phe Asn Thr Thr Ile Leu Ala Leu Ile
1               5                   10                  15

Ile Ile Ile Ala Thr Phe Ser Asn Ser Ala Asn Ala Ala Asp Ser Gly
            20                  25                  30

Thr Leu Asn Tyr Glu Val Tyr Lys Tyr Asn Thr Asn Asp Thr Ser Ile
        35                  40                  45

Ala Asn Asp Tyr Phe Asn Lys Pro Ala Lys Tyr Ile Lys Lys Asn Gly
    50                  55                  60

Lys Leu Tyr Val Gln Ile Thr Val Asn His Ser His Trp Ile Thr Gly
65                  70                  75                  80

Met Ser Ile Glu Gly His Lys Glu Asn Ile Ile Ser Lys Asn Thr Ala
                85                  90                  95

Lys Asp Glu Arg Thr Ser Glu Phe Glu Val Ser Lys Leu Asn Gly Lys
            100                 105                 110

Ile Asp Gly Lys Ile Asp Val Tyr Ile Asp Glu Lys Val Asn Gly Lys
        115                 120                 125

Pro Phe Lys Tyr Asp His His Tyr Asn Ile Thr Tyr Lys Phe Asn Gly
    130                 135                 140

Pro Thr Asp Val Ala Gly Ala Asn Ala Pro Gly Lys Asp Lys Asn
145                 150                 155                 160

Ser Ala Ser Gly Ser Asp Lys Gly Ser Asp Gly Thr Thr Thr Gly Gln
                165                 170                 175

Ser Glu Ser Asn Ser Ser Asn Lys Asp Lys Val Glu Asn Pro Gln Thr
            180                 185                 190

Asn Ala Gly Thr Pro Ala Tyr Ile Tyr Ala Ile Pro Val Ala Ser Leu
        195                 200                 205

Ala Leu Leu Ile Ala Ile Thr Leu Phe Val Arg Lys Lys Ser Lys Gly
    210                 215                 220

Asn Val Glu
225

<210> SEQ ID NO 20
<211> LENGTH: 635
<212> TYPE: PRT
<213> ORGANISM: Staphylococcus sp.

<400> SEQUENCE: 20

Met Ala Lys Tyr Arg Gly Lys Pro Phe Gln Leu Tyr Val Lys Leu Ser
1               5                   10                  15

Cys Ser Thr Met Met Ala Ser Ser Ile Ile Leu Thr Asn Ile Leu Pro
            20                  25                  30

Tyr Asp Ala Gln Ala Ala Ser Glu Lys Asp Thr Glu Ile Ser Lys Glu
        35                  40                  45

Ile Leu Ser Lys Gln Asp Leu Leu Asp Lys Val Asp Lys Ala Ile Arg
    50                  55                  60

Gln Ile Glu Gln Leu Lys Gln Leu Ser Ala Ser Lys Ala His Tyr
65                  70                  75                  80

Lys Ala Gln Leu Asn Glu Ala Lys Thr Ala Ser Gln Ile Asp Glu Ile
                85                  90                  95

Ile Lys Arg Ala Asn Glu Leu Asp Ser Lys Glu Asn Lys Ser Ser His
            100                 105                 110

Thr Glu Met Asn Gly Gln Ser Asp Ile Asp Ser Lys Leu Asp Gln Leu
        115                 120                 125
```

```
Leu Lys Asp Leu Asn Glu Val Ser Ser Asn Val Asp Arg Gly Gln Gln
    130                 135                 140

Ser Gly Glu Asp Asp Leu Asn Ala Met Lys Asn Asp Met Ser Gln Thr
145                 150                 155                 160

Ala Thr Thr Lys Tyr Gly Glu Lys Asp Lys Asn Asp Glu Ala Met
                165                 170                 175

Val Asn Lys Ala Leu Glu Asp Leu Asp His Leu Asn Gln Gln Ile His
                180                 185                 190

Lys Ser Lys Asp Ala Leu Lys Asp Ala Ser Lys Asp Pro Ala Val Ser
        195                 200                 205

Thr Thr Asp Ser Asn His Glu Val Ala Lys Thr Pro Asn Asn Asp Gly
210                 215                 220

Ser Gly His Val Val Leu Asn Lys Phe Leu Ser Asn Glu Glu Asn Gln
225                 230                 235                 240

Ser His Ser Asn Gln Leu Thr Asp Lys Leu Gln Gly Ser Asp Lys Ile
                245                 250                 255

Asn His Ala Met Ile Glu Lys Leu Ala Lys Ser Asn Ala Ser Thr Gln
                260                 265                 270

His Tyr Thr Tyr His Lys Leu Asn Thr Leu Gln Ser Leu Asp Gln Arg
            275                 280                 285

Ile Ala Asn Thr Gln Leu Pro Lys Asn Gln Lys Ser Asp Leu Met Ser
290                 295                 300

Glu Val Asn Lys Thr Lys Glu Arg Ile Lys Ser Gln Arg Asn Ile Ile
305                 310                 315                 320

Leu Glu Glu Leu Ala Arg Thr Asp Asp Lys Lys Tyr Ala Thr Gln Ser
                325                 330                 335

Ile Leu Glu Ser Ile Phe Asn Lys Asp Glu Ala Asp Lys Ile Leu Lys
            340                 345                 350

Asp Ile Arg Val Asp Gly Lys Thr Asp Gln Gln Ile Ala Asp Gln Ile
        355                 360                 365

Thr Arg His Ile Asp Gln Leu Ser Leu Thr Thr Ser Asp Asp Leu Leu
    370                 375                 380

Thr Ser Leu Ile Asp Gln Ser Gln Asp Lys Ser Leu Leu Ile Ser Gln
385                 390                 395                 400

Ile Leu Gln Thr Lys Leu Gly Lys Ala Glu Ala Asp Lys Leu Ala Lys
                405                 410                 415

Asp Trp Thr Asn Lys Gly Leu Ser Asn Arg Gln Ile Val Asp Gln Leu
                420                 425                 430

Lys Lys His Phe Ala Ser Thr Gly Asp Thr Ser Ser Asp Asp Ile Leu
        435                 440                 445

Lys Ala Ile Leu Asn Asn Ala Lys Asp Lys Gln Ala Ile Glu Thr
450                 455                 460

Ile Leu Ala Thr Arg Ile Glu Arg Gln Lys Ala Lys Leu Leu Ala Asp
465                 470                 475                 480

Leu Ile Thr Lys Ile Glu Thr Asp Gln Asn Lys Ile Phe Asn Leu Val
                485                 490                 495

Lys Ser Ala Leu Asn Gly Lys Ala Asp Asp Leu Leu Asn Leu Gln Lys
            500                 505                 510

Arg Leu Asn Gln Thr Lys Lys Asp Ile Asp Tyr Ile Leu Ser Pro Ile
        515                 520                 525

Val Asn Arg Pro Ser Leu Leu Asp Arg Leu Asn Lys Asn Gly Lys Thr
530                 535                 540

Thr Asp Leu Asn Lys Leu Ala Asn Leu Met Asn Gln Gly Ser Asn Leu
```

```
                    545                 550                 555                 560
Leu Asp Ser Ile Pro Asp Ile Pro Thr Pro Lys Pro Glu Lys Thr Leu
                565                 570                 575

Thr Leu Gly Lys Gly Asn Gly Leu Leu Ser Gly Leu Leu Asn Ala Asp
            580                 585                 590

Gly Asn Val Ser Leu Pro Lys Ala Gly Glu Thr Ile Lys Glu His Trp
        595                 600                 605

Leu Pro Ile Ser Val Ile Val Gly Ala Met Gly Val Leu Met Ile Trp
    610                 615                 620

Leu Ser Arg Arg Asn Lys Leu Lys Asn Lys Ala
625                 630                 635

<210> SEQ ID NO 21
<211> LENGTH: 953
<212> TYPE: PRT
<213> ORGANISM: Staphylococcus sp.

<400> SEQUENCE: 21

Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
            20                  25                  30

Ile Leu Val Gly Thr Thr Leu Ile Phe Gly Leu Ser Gly His Glu Ala
        35                  40                  45

Lys Ala Ala Glu His Thr Asn Gly Glu Leu Asn Gln Ser Lys Asn Glu
    50                  55                  60

Thr Thr Ala Pro Ser Glu Asn Lys Thr Thr Glu Lys Val Asp Ser Arg
65                  70                  75                  80

Gln Leu Lys Asp Asn Thr Gln Thr Ala Thr Ala Asp Gln Pro Lys Val
                85                  90                  95

Thr Met Ser Asp Ser Ala Thr Val Lys Glu Thr Ser Ser Asn Met Gln
            100                 105                 110

Ser Pro Gln Asn Ala Thr Ala Ser Gln Ser Thr Thr Gln Thr Ser Asn
        115                 120                 125

Val Thr Thr Asn Asp Lys Ser Ser Thr Thr Tyr Ser Asn Glu Thr Asp
    130                 135                 140

Lys Ser Asn Leu Thr Gln Ala Lys Asn Val Ser Thr Thr Pro Lys Thr
145                 150                 155                 160

Thr Thr Ile Lys Gln Arg Ala Leu Asn Arg Met Ala Val Asn Thr Val
                165                 170                 175

Ala Ala Pro Gln Gln Gly Thr Asn Val Asn Asp Lys Val His Phe Thr
            180                 185                 190

Asn Ile Asp Ile Ala Ile Asp Lys Gly His Val Asn Lys Thr Thr Gly
        195                 200                 205

Asn Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Lys Thr Asn Thr Thr Thr Tyr Thr Phe Thr Asn Tyr Val
        275                 280                 285
```

```
Asp Gln Tyr Thr Asn Val Ser Gly Ser Phe Glu Gln Val Ala Phe Ala
    290                 295                 300
Lys Arg Glu Asn Ala Thr Thr Asp Lys Thr Ala Tyr Lys Met Glu Val
305                 310                 315                 320
Thr Leu Gly Asn Asp Thr Tyr Ser Lys Asp Val Ile Val Asp Tyr Gly
                325                 330                 335
Asn Gln Lys Gly Gln Gln Leu Ile Ser Ser Thr Asn Tyr Ile Asn Asn
            340                 345                 350
Glu Asp Leu Ser Arg Asn Met Thr Val Tyr Val Asn Gln Pro Lys Lys
        355                 360                 365
Thr Tyr Thr Lys Glu Thr Phe Val Thr Asn Leu Thr Gly Tyr Lys Phe
    370                 375                 380
Asn Pro Asp Ala Lys Asn Phe Lys Ile Tyr Glu Val Thr Asp Gln Asn
385                 390                 395                 400
Gln Phe Val Asp Ser Phe Thr Pro Asp Thr Ser Lys Leu Lys Asp Val
                405                 410                 415
Thr Gly Gln Phe Asp Val Ile Tyr Ser Asn Asp Asn Lys Thr Ala Thr
            420                 425                 430
Val Asp Leu Leu Asn Gly Gln Ser Ser Asp Lys Gln Tyr Ile Ile
        435                 440                 445
Gln Gln Val Ala Tyr Pro Asp Asn Ser Ser Thr Asp Asn Gly Lys Ile
    450                 455                 460
Asp Tyr Thr Leu Glu Thr Gln Asn Gly Lys Ser Ser Trp Ser Asn Ser
465                 470                 475                 480
Tyr Ser Asn Val Asn Gly Ser Ser Thr Ala Asn Gly Asp Gln Lys Lys
                485                 490                 495
Tyr Asn Leu Gly Asp Tyr Val Trp Glu Asp Thr Asn Lys Asp Gly Lys
            500                 505                 510
Gln Asp Ala Asn Glu Lys Gly Ile Lys Gly Val Tyr Val Ile Leu Lys
        515                 520                 525
Asp Ser Asn Gly Lys Glu Leu Asp Arg Thr Thr Thr Asp Glu Asn Gly
    530                 535                 540
Lys Tyr Gln Phe Thr Gly Leu Ser Asn Gly Thr Tyr Ser Val Glu Phe
545                 550                 555                 560
Ser Thr Pro Ala Gly Tyr Thr Pro Thr Thr Ala Asn Ala Gly Thr Asp
                565                 570                 575
Asp Ala Val Asp Ser Asp Gly Leu Thr Thr Thr Gly Val Ile Lys Asp
            580                 585                 590
Ala Asp Asn Met Thr Leu Asp Ser Gly Phe Tyr Lys Thr Pro Lys Tyr
        595                 600                 605
Ser Leu Gly Asp Tyr Val Trp Tyr Asp Ser Asn Lys Asp Gly Lys Gln
    610                 615                 620
Asp Ser Thr Glu Lys Gly Ile Lys Gly Val Lys Val Thr Leu Gln Asn
625                 630                 635                 640
Glu Lys Gly Glu Val Ile Gly Thr Thr Glu Thr Asp Glu Asn Gly Lys
                645                 650                 655
Tyr Arg Phe Asp Asn Leu Asp Ser Gly Lys Tyr Lys Val Ile Phe Glu
            660                 665                 670
Lys Pro Ala Gly Leu Thr Gln Thr Gly Thr Asn Thr Thr Glu Asp Asp
        675                 680                 685
Lys Asp Ala Asp Gly Gly Glu Val Asp Val Thr Ile Thr Asp His Asp
    690                 695                 700
Asp Phe Thr Leu Asp Asn Gly Tyr Tyr Glu Glu Glu Thr Ser Asp Ser
```

```
                705                 710                 715                 720
Asp Ser Asp Ser Asp Ser Asp Ser Asp Ser Asp Ser Asp Ser
            725                 730                 735
Asp Ser Asp Ser Asp Ser Asp Ser Asp Ser Asp Ser Asp Ser
            740                 745                 750
Asp Ser Asp Ser Asp Ser Asp Ser Asp Ser Asp Ser Asp Ser
            755                 760                 765
Asp Ser Asp Ser Glu Ser Asp Ser Asp Ser Asp Ser Asp Ser
            770                 775                 780
Asp Ser Asp Ser Asp Ser Asp Ser Asp Ser Asp Ser Asp Ser
785                 790                 795                 800
Asp Ser Asp Ser Asp Ser Asp Ser Asp Ser Asp Ser Asp Ser
            805                 810                 815
Asp Ser Asp Ser Asp Ser Asp Asn Asp Ser Asp Ser Asp Ser
            820                 825                 830
Asp Ser Asp Ser Asp Ser Asp Ser Asp Ser Asp Ser Asp Ser
            835                 840                 845
Asp Ser Asp Ser Asp Ser Asp Ser Asp Ser Asp Ser Asp Ser
            850                 855                 860
Asp Ser Asp Ser Asp Ser Asp Ser Asp Ser Asp Ser Asp Ser
865                 870                 875                 880
Asp Ser Asp Ser Asp Ser Asp Ser Asp Ser Asp Ala Gly Lys
            885                 890                 895
His Thr Pro Thr Lys Pro Met Ser Thr Val Lys Asp Gln His Lys Thr
                900                 905                 910
Ala Lys Ala Leu Pro Glu Thr Gly Ser Glu Asn Asn Asn Ser Asn Asn
            915                 920                 925
Gly Thr Leu Phe Gly Gly Leu Phe Ala Ala Leu Gly Ser Leu Leu Leu
            930                 935                 940
Phe Gly Arg Arg Lys Lys Gln Asn Lys
945                 950

<210> SEQ ID NO 22
<211> LENGTH: 989
<212> TYPE: PRT
<213> ORGANISM: Staphylococcus sp.

<400> SEQUENCE: 22

Met Asn Met Lys Lys Lys Glu Lys His Ala Ile Arg Lys Lys Ser Ile
1               5                   10                  15
Gly Val Ala Ser Val Leu Val Gly Thr Leu Ile Gly Phe Gly Leu Leu
            20                  25                  30
Ser Ser Lys Glu Ala Asp Ala Ser Glu Asn Ser Val Thr Gln Ser Asp
        35                  40                  45
Ser Ala Ser Asn Glu Ser Lys Ser Asn Asp Ser Ser Ser Val Ser Ala
    50                  55                  60
Ala Pro Lys Thr Asp Asp Thr Asn Val Ser Asp Thr Lys Thr Ser Ser
65                  70                  75                  80
Asn Thr Asn Asn Gly Glu Thr Ser Val Ala Gln Asn Pro Ala Gln Gln
            85                  90                  95
Glu Thr Thr Gln Ser Ser Ser Thr Asn Ala Thr Thr Glu Glu Thr Pro
            100                 105                 110
Val Thr Gly Glu Ala Thr Thr Thr Thr Asn Gln Ala Asn Thr Pro
            115                 120                 125
```

```
Ala Thr Thr Gln Ser Ser Asn Thr Asn Ala Glu Glu Leu Val Asn Gln
130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
            165                 170                 175

Asp Thr Ser Thr Glu Ala Thr Pro Ser Asn Asn Glu Ser Ala Pro Gln
            180                 185                 190

Asn Thr Asp Ala Ser Asn Lys Asp Val Val Ser Gln Ala Val Asn Pro
            195                 200                 205

Ser Thr Pro Arg Met Arg Ala Phe Ser Leu Ala Ala Val Ala Ala Asp
210                 215                 220

Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asp Asn Lys Glu Asn Val Thr Ala Asn Ile Thr Met Pro
                325                 330                 335

Ala Tyr Ile Asp Pro Glu Asn Val Thr Lys Thr Gly Asn Val Thr Leu
            340                 345                 350

Thr Thr Gly Ile Gly Thr Asn Thr Ala Ser Lys Thr Val Leu Ile Asp
            355                 360                 365

Tyr Glu Lys Tyr Gly Gln Phe His Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Val Leu Pro Ala Leu Thr Gly Asn Leu
            405                 410                 415

Ile Pro Asn Thr Lys Ser Asn Ala Leu Ile Asp Ala Lys Asn Thr Asp
            420                 425                 430

Ile Lys Val Tyr Arg Val Asp Asn Ala Asn Asp Leu Ser Glu Ser Tyr
            435                 440                 445

Tyr Val Asn Pro Ser Asp Phe Glu Asp Val Thr Asn Gln Val Arg Ile
450                 455                 460

Ser Phe Pro Asn Ala Asn Gln Tyr Lys Val Glu Phe Pro Thr Asp Asp
465                 470                 475                 480

Asp Gln Ile Thr Thr Pro Tyr Ile Val Val Asn Gly His Ile Asp
            485                 490                 495

Pro Ala Ser Thr Gly Asp Leu Ala Leu Arg Ser Thr Phe Tyr Gly Tyr
            500                 505                 510

Asp Ser Asn Phe Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
530                 535                 540

Pro Glu Gln Pro Asp Glu Pro Gly Glu Ile Glu Pro Ile Pro Glu Asp
```

```
              545                 550                 555                 560
Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
                580                 585                 590

Ser Ala Ser Asp Ser Asp Ser Ala Ser Asp Ser Asp Ser Ala Ser Asp
                595                 600                 605

Ser Asp Ser Ala Ser Asp Ser Asp Ser Ala Ser Asp Ser Asp Ser Ala
            610                 615                 620

Ser Asp Ser Asp Ser Ala Ser Asp Ser Asp Ser Ala Ser Asp Ser Asp
625                 630                 635                 640

Ser Ala Ser Asp Ser Asp Ser Ala Ser Asp Ser Asp Ser Ala Ser Asp
                645                 650                 655

Ser Asp Ser Ala Ser Asp Ser Asp Ser Ala Ser Asp Ser Asp Ser Asp
                660                 665                 670

Ser Asp Ser Asp Ser Asp Ser Asp Ser Asp Ser Asp Ser Asp Ser Asp
            675                 680                 685

Ser Asp Ser Asp Ser Asp Ser Asp Ser Asp Ser Asp Ser Asp Ser Asp
    690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                725                 730                 735

Ser Asp Ser Asp Ser Asp Ser Asp Ser Asp Ser Asp Ser Asp Ser Asp
                740                 745                 750

Ser Asp Ser Asp Ser Asp Ser Asp Ser Asp Ser Asp Ser Asp Ser Asp
            755                 760                 765

Ser Asp Ser Asp Ser Asp Ser Asp Ser Asp Ser Asp Ser Asp Ser Asp
        770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Asp Ser Asp Ser Asp Ser Asp Ser Asp
                805                 810                 815

Ser Asp Ser Asp Ser Ala Ser Asp Ser Asp Ser Asp Ser Asp Ser Glu
                820                 825                 830

Ser Asp Ser Asp Ser Asp Ser Asp Ser Asp Ser Asp Ser Asp Ser Asp
            835                 840                 845

Ser Asp Ser Asp Ser Asp Ser Glu Ser Asp Ser Asp Ser Asp Ser Asp
        850                 855                 860

Ser Asp Ser Glu Ser Asp Ser Asp Ser Asp Ser Asp Ser Asp Ser Asp
865                 870                 875                 880

Ser Ala Ser Asp Ser Asp Ser Gly Ser Asp Ser Asp Ser Ser Ser Asp
                885                 890                 895

Ser Asp Ser Asp Ser Thr Ser Asp Ser Thr Gly Ser Asp Asn Asp Ser Asp
                900                 905                 910

Ser Asp Ser Asn Ser Asp Ser Glu Ser Gly Ser Asn Asn Asn Val Val
            915                 920                 925

Pro Pro Asn Ser Pro Lys Asn Gly Thr Asn Ala Ser Asn Lys Asn Glu
    930                 935                 940

Ala Lys Asp Ser Lys Glu Pro Leu Pro Asp Thr Gly Ser Glu Asp Glu
945                 950                 955                 960

Ala Asn Thr Ser Leu Ile Trp Gly Leu Leu Ala Ser Leu Gly Ser Leu
                965                 970                 975
```

```
Leu Leu Phe Arg Arg Lys Lys Glu Asn Lys Asp Lys Lys
            980                 985

<210> SEQ ID NO 23
<211> LENGTH: 584
<212> TYPE: PRT
<213> ORGANISM: Staphylococcus sp.

<400> SEQUENCE: 23

Met Lys Phe Lys Ser Leu Ile Thr Thr Thr Leu Ala Leu Gly Val Leu
1               5                   10                  15

Ala Ser Thr Gly Ala Asn Phe Asn Asn Asn Glu Ala Ser Ala Ala Ala
            20                  25                  30

Lys Pro Leu Asp Lys Ser Ser Ser Leu His His Gly Tyr Ser Lys
            35                  40                  45

Val His Val Pro Tyr Ala Ile Thr Val Asn Gly Thr Ser Gln Asn Ile
    50                  55                  60

Leu Ser Ser Leu Thr Phe Asn Lys Asn Gln Asn Ile Ser Tyr Lys Asp
65                  70                  75                  80

Leu Glu Asp Arg Val Lys Ser Val Leu Lys Ser Asp Arg Gly Ile Ser
                85                  90                  95

Asp Ile Asp Leu Arg Leu Ser Lys Gln Ala Lys Tyr Thr Val Tyr Phe
            100                 105                 110

Lys Asn Gly Thr Lys Lys Val Ile Asp Leu Lys Ala Gly Ile Tyr Thr
            115                 120                 125

Ala Asp Leu Ile Asn Thr Ser Glu Ile Lys Ala Ile Asn Ile Asn Val
130                 135                 140

Asp Thr Lys Lys Gln Val Glu Asp Lys Lys Asp Lys Ala Asn Tyr
145                 150                 155                 160

Gln Val Pro Tyr Thr Ile Thr Val Asn Gly Thr Ser Gln Asn Ile Leu
                165                 170                 175

Ser Asn Leu Thr Phe Asn Lys Asn Gln Asn Ile Ser Tyr Lys Asp Leu
            180                 185                 190

Glu Asp Lys Val Lys Ser Val Leu Glu Ser Asn Arg Gly Ile Thr Asp
            195                 200                 205

Val Asp Leu Arg Leu Ser Lys Gln Ala Lys Tyr Thr Val Asn Phe Lys
210                 215                 220

Asn Gly Thr Lys Lys Val Ile Asp Leu Lys Ser Gly Ile Tyr Thr Ala
225                 230                 235                 240

Asn Leu Ile Asn Ser Ser Asp Ile Lys Ser Ile Asn Ile Asn Val Asp
                245                 250                 255

Thr Lys Lys His Ile Glu Asn Lys Ala Lys Arg Asn Tyr Gln Val Pro
            260                 265                 270

Tyr Ser Ile Asn Leu Asn Gly Thr Ser Thr Asn Ile Leu Ser Asn Leu
            275                 280                 285

Ser Phe Ser Asn Lys Pro Trp Thr Asn Tyr Lys Asn Leu Thr Ser Gln
290                 295                 300

Ile Lys Ser Val Leu Lys His Asp Arg Gly Ile Ser Glu Gln Asp Leu
305                 310                 315                 320

Lys Tyr Ala Lys Lys Ala Tyr Tyr Thr Val Tyr Phe Lys Asn Gly Gly
                325                 330                 335

Lys Arg Ile Leu Gln Leu Asn Ser Lys Asn Tyr Thr Ala Asn Leu Val
            340                 345                 350

His Ala Lys Asp Val Lys Arg Ile Glu Ile Thr Val Lys Thr Gly Thr
```

```
            355                 360                 365
Lys Ala Lys Ala Asp Arg Tyr Val Pro Tyr Thr Ile Ala Val Asn Gly
    370                 375                 380

Thr Ser Thr Pro Ile Leu Ser Asp Leu Lys Phe Thr Gly Asp Pro Arg
385                 390                 395                 400

Val Gly Tyr Lys Asp Ile Ser Lys Lys Val Ser Val Leu Lys His
            405                 410                 415

Asp Arg Gly Ile Gly Glu Arg Glu Leu Lys Tyr Ala Lys Lys Ala Thr
            420                 425                 430

Tyr Thr Val His Phe Lys Asn Gly Thr Lys Val Ile Asn Ile Asn
            435                 440                 445

Ser Asn Ile Ser Gln Leu Asn Leu Leu Tyr Val Gln Asp Ile Lys Lys
    450                 455                 460

Ile Asp Ile Asp Val Lys Thr Gly Thr Lys Ala Lys Ala Asp Ser Tyr
465                 470                 475                 480

Val Pro Tyr Thr Ile Ala Val Asn Gly Thr Ser Thr Pro Ile Leu Ser
            485                 490                 495

Lys Leu Lys Ile Ser Asn Lys Gln Leu Ile Ser Tyr Lys Tyr Leu Asn
            500                 505                 510

Asp Lys Val Lys Ser Val Leu Lys Ser Glu Arg Gly Ile Ser Asp Leu
            515                 520                 525

Asp Leu Lys Phe Ala Lys Gln Ala Lys Tyr Thr Val Tyr Phe Lys Asn
    530                 535                 540

Gly Lys Lys Gln Val Val Asn Leu Lys Ser Asp Ile Phe Thr Pro Asn
545                 550                 555                 560

Leu Phe Ser Ala Lys Asp Ile Lys Lys Ile Asp Ile Asp Val Lys Gln
            565                 570                 575

Tyr Thr Lys Ser Lys Lys Asn Lys
            580

<210> SEQ ID NO 24
<211> LENGTH: 10419
<212> TYPE: PRT
<213> ORGANISM: Staphylococcus sp.

<400> SEQUENCE: 24

Met Asn Tyr Arg Asp Lys Ile Gln Lys Phe Ser Ile Arg Lys Tyr Thr
1               5                   10                  15

Val Gly Thr Phe Ser Thr Val Ile Ala Thr Leu Val Phe Leu Gly Phe
            20                  25                  30

Asn Thr Ser Gln Ala His Ala Ala Glu Thr Asn Gln Pro Ala Ser Val
        35                  40                  45

Val Lys Gln Lys Gln Gln Ser Asn Asn Glu Gln Thr Glu Asn Arg Glu
    50                  55                  60

Ser Gln Val Gln Asn Ser Gln Asn Ser Gln Asn Gly Gln Ser Leu Ser
65                  70                  75                  80

Ala Thr His Glu Asn Glu Gln Pro Asn Ile Ser Gln Ala Asn Leu Val
            85                  90                  95

Asp Gln Lys Val Ala Gln Ser Ser Thr Thr Asn Asp Glu Gln Pro Ala
            100                 105                 110

Ser Gln Asn Val Asn Thr Lys Lys Asp Ser Ala Thr Ala Ala Thr Thr
        115                 120                 125

Gln Pro Asp Lys Glu Gln Ser Lys His Lys Gln Asn Glu Ser Gln Ser
    130                 135                 140
```

-continued

Ala Asn Lys Asn Gly Asn Asp Asn Arg Ala Ala His Val Glu Asn His
145                 150                 155                 160

Glu Ala Asn Val Val Thr Ala Ser Asp Ser Asp Asn Gly Asn Val
                165                 170                 175

Gln His Asp Arg Asn Glu Leu Gln Ala Phe Phe Asp Ala Asn Tyr His
            180                 185                 190

Asp Tyr Arg Phe Ile Asp Arg Glu Asn Ala Asp Ser Gly Thr Phe Asn
        195                 200                 205

Tyr Val Lys Gly Ile Phe Asp Lys Ile Asn Thr Leu Leu Gly Ser Asn
    210                 215                 220

Asp Pro Ile Asn Asn Lys Asp Leu Gln Leu Ala Tyr Lys Glu Leu Glu
225                 230                 235                 240

Gln Ala Val Ala Leu Ile Arg Thr Met Pro Gln Arg Gln Gln Thr Ser
                245                 250                 255

Arg Arg Ser Asn Arg Ile Gln Thr Arg Ser Val Glu Ser Arg Ala Ala
            260                 265                 270

Glu Pro Arg Ser Val Ser Asp Tyr Gln Asn Ala Asn Ser Ser Tyr Tyr
        275                 280                 285

Val Glu Asn Ala Asn Asp Gly Ser Gly Tyr Pro Val Gly Thr Tyr Ile
    290                 295                 300

Asn Ala Ser Ser Lys Gly Ala Pro Tyr Asn Leu Pro Thr Thr Pro Trp
305                 310                 315                 320

Asn Thr Leu Lys Ala Ser Asp Ser Lys Glu Ile Ala Leu Met Thr Ala
                325                 330                 335

Lys Gln Thr Gly Asp Gly Tyr Gln Trp Val Ile Lys Phe Asn Lys Gly
            340                 345                 350

His Ala Pro His Gln Asn Met Ile Phe Trp Phe Ala Leu Pro Ala Asp
        355                 360                 365

Gln Val Pro Val Gly Arg Thr Asp Phe Val Thr Val Asn Ser Asp Gly
    370                 375                 380

Thr Asn Val Gln Trp Ser His Gly Ala Gly Ala Gly Ala Asn Lys Pro
385                 390                 395                 400

Leu Gln Gln Met Trp Glu Tyr Gly Val Asn Asp Pro His Arg Ser His
                405                 410                 415

Asp Phe Lys Ile Arg Asn Arg Ser Gly Gln Val Ile Tyr Asp Trp Pro
            420                 425                 430

Thr Val His Ile Tyr Ser Leu Glu Asp Leu Ser Arg Ala Ser Asp Tyr
        435                 440                 445

Phe Ser Glu Ala Gly Ala Thr Pro Ala Thr Lys Ala Phe Gly Arg Gln
    450                 455                 460

Asn Phe Glu Tyr Ile Asn Gly Gln Lys Pro Ala Glu Ser Pro Gly Val
465                 470                 475                 480

Pro Lys Val Tyr Thr Phe Ile Gly Gln Gly Asp Ala Ser Tyr Thr Ile
                485                 490                 495

Ser Phe Lys Thr Gln Gly Pro Thr Val Asn Lys Leu Tyr Ala Ala
            500                 505                 510

Gly Gly Arg Ala Leu Glu Tyr Asn Gln Leu Phe Met Tyr Ser Gln Leu
        515                 520                 525

Tyr Val Glu Ser Thr Gln Asp His Gln Gln Arg Leu Asn Gly Leu Arg
    530                 535                 540

Gln Val Val Asn Arg Thr Tyr Arg Ile Gly Thr Thr Lys Arg Val Glu
545                 550                 555                 560

Val Ser Gln Gly Asn Val Gln Thr Lys Lys Val Leu Glu Ser Thr Asn

-continued

```
                565                 570                 575
Leu Asn Ile Asp Asp Phe Val Asp Asp Pro Leu Ser Tyr Val Lys Thr
            580                 585                 590

Pro Ser Asn Lys Val Leu Gly Phe Tyr Ser Asn Asn Ala Asn Thr Asn
        595                 600                 605

Ala Phe Arg Pro Gly Gly Ala Gln Gln Leu Asn Glu Tyr Gln Leu Ser
    610                 615                 620

Gln Leu Phe Thr Asp Gln Lys Leu Gln Glu Ala Ala Arg Thr Arg Asn
625                 630                 635                 640

Pro Ile Arg Leu Met Ile Gly Phe Asp Tyr Pro Asp Ala Tyr Gly Asn
                645                 650                 655

Ser Glu Thr Leu Val Pro Val Asn Leu Thr Val Leu Pro Glu Ile Gln
            660                 665                 670

His Asn Ile Lys Phe Phe Lys Asn Asp Asp Thr Gln Asn Ile Ala Glu
        675                 680                 685

Lys Pro Phe Ser Lys Gln Ala Gly His Pro Val Phe Tyr Val Tyr Ala
    690                 695                 700

Gly Asn Gln Gly Asn Ala Ser Val Asn Leu Gly Gly Ser Val Thr Ser
705                 710                 715                 720

Ile Gln Pro Leu Arg Ile Asn Leu Thr Ser Asn Glu Asn Phe Thr Asp
                725                 730                 735

Lys Asp Trp Gln Ile Thr Gly Ile Pro Arg Thr Leu His Ile Glu Asn
            740                 745                 750

Ser Thr Asn Arg Pro Asn Asn Ala Arg Glu Arg Asn Ile Glu Leu Val
        755                 760                 765

Gly Asn Leu Leu Pro Gly Asp Tyr Phe Gly Thr Ile Arg Phe Gly Arg
    770                 775                 780

Lys Glu Gln Leu Phe Glu Ile Arg Val Lys Pro His Thr Pro Thr Ile
785                 790                 795                 800

Thr Thr Thr Ala Glu Gln Leu Arg Gly Thr Ala Leu Gln Lys Val Pro
                805                 810                 815

Val Asn Ile Ser Gly Ile Pro Leu Asp Pro Ser Ala Leu Val Tyr Leu
            820                 825                 830

Val Ala Pro Thr Asn Gln Thr Thr Asn Gly Gly Ser Glu Ala Asp Gln
        835                 840                 845

Ile Pro Ser Gly Tyr Thr Ile Leu Ala Thr Gly Thr Pro Asp Gly Val
    850                 855                 860

His Asn Thr Ile Thr Ile Arg Pro Gln Asp Tyr Val Val Phe Ile Pro
865                 870                 875                 880

Pro Val Gly Lys Gln Ile Arg Ala Val Val Tyr Tyr Asn Lys Val Val
                885                 890                 895

Ala Ser Asn Met Ser Asn Ala Val Thr Ile Leu Pro Asp Ile Pro
            900                 905                 910

Pro Thr Ile Asn Asn Pro Val Gly Ile Asn Ala Lys Tyr Tyr Arg Gly
        915                 920                 925

Asp Glu Val Asn Phe Thr Met Gly Val Ser Asp Arg His Ser Gly Ile
    930                 935                 940

Lys Asn Thr Thr Ile Thr Thr Leu Pro Asn Gly Trp Thr Ser Asn Leu
945                 950                 955                 960

Thr Lys Ala Asp Lys Asn Asn Gly Ser Leu Ser Ile Thr Gly Arg Val
                965                 970                 975

Ser Met Asn Gln Ala Phe Asn Ser Asp Ile Thr Phe Lys Val Ser Ala
            980                 985                 990
```

```
        Thr Asp Asn Val Asn Asn Thr Thr  Asn Asp Ser Gln Ser  Lys His Val
                995              1000                1005

Ser Ile His Val Gly Lys Ile  Ser Glu Asp Ala His  Pro Ile Val
            1010            1015                1020

Leu Gly Asn Thr Glu Lys Val  Val Val Asn Pro  Thr Ala Val
            1025            1030            1035

Ser Asn Asp Glu Lys Gln Ser  Ile Ile Thr Ala Phe  Met Asn Lys
            1040            1045                1050

Asn Gln Asn Ile Arg Gly Tyr  Leu Ala Ser Thr Asp  Pro Val Thr
            1055            1060                1065

Val Asp Asn Asn Gly Asn Val  Thr Leu His Tyr Arg  Asp Gly Ser
            1070            1075                1080

Ser Thr Thr Leu Asp Ala Thr  Asn Val Met Thr Tyr  Glu Pro Val
            1085            1090                1095

Val Lys Pro Glu Tyr Gln Thr  Val Asn Ala Ala Lys  Thr Ala Thr
            1100            1105                1110

Val Thr Ile Ala Lys Gly Gln  Ser Phe Ser Ile Gly  Asp Ile Lys
            1115            1120                1125

Gln Tyr Phe Thr Leu Ser Asn  Gly Gln Pro Ile Pro  Ser Gly Thr
            1130            1135                1140

Phe Thr Asn Ile Thr Ser Asp  Arg Thr Ile Pro  Thr Ala Gln Glu
            1145            1150            1155

Val Ser Gln Met Asn Ala Gly  Thr Gln Leu Tyr His  Ile Thr Ala
            1160            1165                1170

Thr Asn Ala Tyr His Lys Asp  Ser Glu Asp Phe Tyr  Ile Ser Leu
            1175            1180                1185

Lys Ile Ile Asp Val Lys Gln  Pro Glu Gly Asp Gln  Arg Val Tyr
            1190            1195                1200

Arg Thr Ser Thr Tyr Asp Leu  Thr Thr Asp Glu Ile  Ser Lys Val
            1205            1210                1215

Lys Gln Ala Phe Ile Asn Ala  Asn Arg Asp Val Ile  Thr Leu Ala
            1220            1225                1230

Glu Gly Asp Ile Ser Val Thr  Asn Thr Pro Asn Gly  Ala Asn Val
            1235            1240                1245

Ser Thr Ile Thr Val Asn Ile  Asn Lys Gly Arg Leu  Thr Lys Ser
            1250            1255                1260

Phe Ala Ser Asn Leu Ala Asn  Met Asn Phe Leu Arg  Trp Val Asn
            1265            1270                1275

Phe Pro Gln Asp Tyr Thr Val  Thr Trp Thr Asn Ala  Lys Ile Ala
            1280            1285                1290

Asn Arg Pro Thr Asp Gly Gly  Leu Ser Trp Ser Asp  Asp His Lys
            1295            1300                1305

Ser Leu Ile Tyr Arg Tyr Asp  Ala Thr Leu Gly Thr  Gln Ile Thr
            1310            1315                1320

Thr Asn Asp Ile Leu Thr Met  Leu Lys Ala Thr Thr  Thr Val Pro
            1325            1330                1335

Gly Leu Arg Asn Asn Ile Thr  Gly Asn Glu Lys Ser  Gln Ala Glu
            1340            1345                1350

Ala Gly Gly Arg Pro Asn Phe  Arg Thr Thr Gly Tyr  Ser Gln Ser
            1355            1360                1365

Asn Ala Thr Thr Asp Gly Gln  Arg Gln Phe Thr Leu  Asn Gly Gln
            1370            1375                1380
```

-continued

Val Ile Gln Val Leu Asp Ile Ile Asn Pro Ser Asn Gly Tyr Gly
1385                1390                1395

Gly Gln Pro Val Thr Asn Ser Asn Thr Arg Ala Asn His Ser Asn
1400                1405                1410

Ser Thr Val Val Asn Val Asn Glu Pro Ala Ala Asn Gly Ala Gly
1415                1420                1425

Ala Phe Thr Ile Asp His Val Val Lys Ser Asn Ser Thr His Asn
1430                1435                1440

Ala Ser Asp Ala Val Tyr Lys Ala Gln Leu Tyr Leu Thr Pro Tyr
1445                1450                1455

Gly Pro Lys Gln Tyr Val Glu His Leu Asn Gln Asn Thr Gly Asn
1460                1465                1470

Thr Thr Asp Ala Ile Asn Ile Tyr Phe Val Pro Ser Asp Leu Val
1475                1480                1485

Asn Pro Thr Ile Ser Val Gly Asn Tyr Thr Asn His Gln Val Phe
1490                1495                1500

Ser Gly Glu Thr Phe Thr Asn Thr Ile Thr Ala Asn Asp Asn Phe
1505                1510                1515

Gly Val Gln Ser Val Thr Val Pro Asn Thr Ser Gln Ile Thr Gly
1520                1525                1530

Thr Val Asp Asn Asn His Gln His Val Ser Ala Thr Ala Pro Asn
1535                1540                1545

Val Thr Ser Ala Thr Asn Lys Thr Ile Asn Leu Leu Ala Thr Asp
1550                1555                1560

Thr Ser Gly Asn Thr Ala Thr Thr Ser Phe Asn Val Thr Val Lys
1565                1570                1575

Pro Leu Arg Asp Lys Tyr Arg Val Gly Thr Ser Ser Thr Ala Ala
1580                1585                1590

Asn Pro Val Arg Ile Ala Asn Ile Ser Asn Asn Ala Thr Val Ser
1595                1600                1605

Gln Ala Asp Gln Thr Thr Ile Ile Asn Ser Leu Thr Phe Thr Glu
1610                1615                1620

Thr Val Pro Asn Arg Ser Tyr Ala Arg Ala Ser Ala Asn Glu Ile
1625                1630                1635

Thr Ser Lys Thr Val Ser Asn Val Ser Arg Thr Gly Asn Asn Ala
1640                1645                1650

Asn Val Thr Val Thr Val Thr Tyr Gln Asp Gly Thr Thr Ser Thr
1655                1660                1665

Val Thr Val Pro Val Lys His Val Ile Pro Glu Ile Val Ala His
1670                1675                1680

Ser His Tyr Thr Val Gln Gly Gln Asp Phe Pro Ala Gly Asn Gly
1685                1690                1695

Ser Ser Ala Ser Asp Tyr Phe Lys Leu Ser Asn Gly Ser Asp Ile
1700                1705                1710

Ala Asp Ala Thr Ile Thr Trp Val Ser Gly Gln Ala Pro Asn Lys
1715                1720                1725

Asp Asn Thr Arg Ile Gly Glu Asp Ile Thr Val Thr Ala His Ile
1730                1735                1740

Leu Ile Asp Gly Glu Thr Thr Pro Ile Thr Lys Thr Ala Thr Tyr
1745                1750                1755

Lys Val Val Arg Thr Val Pro Lys His Val Phe Glu Thr Ala Arg
1760                1765                1770

Gly Val Leu Tyr Pro Gly Val Ser Asp Met Tyr Asp Ala Lys Gln

-continued

```
                1775                1780                1785

Tyr Val Lys Pro Val Asn Asn Ser Trp Ser Thr Asn Ala Gln His
        1790                1795                1800

Met Asn Phe Gln Phe Val Gly Thr Tyr Gly Pro Asn Lys Asp Val
        1805                1810                1815

Val Gly Ile Ser Thr Arg Leu Ile Arg Val Thr Tyr Asp Asn Arg
        1820                1825                1830

Gln Thr Glu Asp Leu Thr Ile Leu Ser Lys Val Lys Pro Asp Pro
        1835                1840                1845

Pro Arg Ile Asp Ala Asn Ser Val Thr Tyr Lys Ala Gly Leu Thr
        1850                1855                1860

Asn Gln Glu Ile Lys Val Asn Asn Val Leu Asn Asn Ser Ser Val
        1865                1870                1875

Lys Leu Phe Lys Ala Asp Asn Thr Pro Leu Asn Val Thr Asn Ile
        1880                1885                1890

Thr His Gly Ser Gly Phe Ser Ser Val Val Thr Val Ser Asp Ala
        1895                1900                1905

Leu Pro Asn Gly Gly Ile Lys Ala Lys Ser Ser Ile Ser Met Asn
        1910                1915                1920

Asn Val Thr Tyr Thr Thr Gln Asp Glu His Gly Gln Val Val Thr
        1925                1930                1935

Val Thr Arg Asn Glu Ser Val Asp Ser Asn Asp Ser Ala Thr Val
        1940                1945                1950

Thr Val Thr Pro Gln Leu Gln Ala Thr Thr Glu Gly Ala Val Phe
        1955                1960                1965

Ile Lys Gly Gly Asp Gly Phe Asp Phe Gly His Val Glu Arg Phe
        1970                1975                1980

Ile Gln Asn Pro Pro His Gly Ala Thr Val Ala Trp His Asp Ser
        1985                1990                1995

Pro Asp Thr Trp Lys Asn Thr Val Gly Asn Thr His Lys Thr Ala
        2000                2005                2010

Val Val Thr Leu Pro Asn Gly Gln Gly Thr Arg Asn Val Glu Val
        2015                2020                2025

Pro Val Lys Val Tyr Pro Val Ala Asn Ala Lys Ala Pro Ser Arg
        2030                2035                2040

Asp Val Lys Gly Gln Asn Leu Thr Asn Gly Thr Asp Ala Met Asn
        2045                2050                2055

Tyr Ile Thr Phe Asp Pro Asn Thr Asn Thr Asn Gly Ile Thr Ala
        2060                2065                2070

Ala Trp Ala Asn Arg Gln Gln Pro Asn Asn Gln Gln Ala Gly Val
        2075                2080                2085

Gln His Leu Asn Val Asp Val Thr Tyr Pro Gly Ile Ser Ala Ala
        2090                2095                2100

Lys Arg Val Pro Val Thr Val Asn Val Tyr Gln Phe Glu Phe Pro
        2105                2110                2115

Gln Thr Thr Tyr Thr Thr Thr Val Gly Gly Thr Leu Ala Ser Gly
        2120                2125                2130

Thr Gln Ala Ser Gly Tyr Ala His Met Gln Asn Ala Thr Gly Leu
        2135                2140                2145

Pro Thr Asp Gly Phe Thr Tyr Lys Trp Asn Arg Asp Thr Thr Gly
        2150                2155                2160

Thr Asn Asp Ala Asn Trp Ser Ala Met Asn Lys Pro Asn Val Ala
        2165                2170                2175
```

-continued

```
Lys Val Val Asn Ala Lys Tyr Asp Val Ile Tyr Asn Gly His Thr
2180                2185                2190

Phe Ala Thr Ser Leu Pro Ala Lys Phe Val Val Lys Asp Val Gln
2195                2200                2205

Pro Ala Lys Pro Thr Val Thr Glu Thr Ala Ala Gly Ala Ile Thr
2210                2215                2220

Ile Ala Pro Gly Ala Asn Gln Thr Val Asn Thr His Ala Gly Asn
2225                2230                2235

Val Thr Thr Tyr Ala Asp Lys Leu Val Ile Lys Arg Asn Gly Asn
2240                2245                2250

Val Val Thr Thr Phe Thr Arg Arg Asn Asn Thr Ser Pro Trp Val
2255                2260                2265

Lys Glu Ala Ser Ala Ala Thr Val Ala Gly Ile Ala Gly Thr Asn
2270                2275                2280

Asn Gly Ile Thr Val Ala Ala Gly Thr Phe Asn Pro Ala Asp Thr
2285                2290                2295

Ile Gln Val Val Ala Thr Gln Gly Ser Gly Glu Thr Val Ser Asp
2300                2305                2310

Glu Gln Arg Ser Asp Asp Phe Thr Val Val Ala Pro Gln Pro Asn
2315                2320                2325

Gln Ala Thr Thr Lys Ile Trp Gln Asn Gly His Ile Asp Ile Thr
2330                2335                2340

Pro Asn Asn Pro Ser Gly His Leu Ile Asn Pro Thr Gln Ala Met
2345                2350                2355

Asp Ile Ala Tyr Thr Glu Lys Val Gly Asn Gly Ala Glu His Ser
2360                2365                2370

Lys Thr Ile Asn Val Val Arg Gly Gln Asn Asn Gln Trp Thr Ile
2375                2380                2385

Ala Asn Lys Pro Asp Tyr Val Thr Leu Asp Ala Gln Thr Gly Lys
2390                2395                2400

Val Thr Phe Asn Ala Asn Thr Ile Lys Pro Asn Ser Ser Ile Thr
2405                2410                2415

Ile Thr Pro Lys Ala Gly Thr Gly His Ser Val Ser Ser Asn Pro
2420                2425                2430

Ser Thr Leu Thr Ala Pro Ala Ala His Thr Val Asn Thr Thr Glu
2435                2440                2445

Ile Val Lys Asp Tyr Gly Ser Asn Val Thr Ala Ala Glu Ile Asn
2450                2455                2460

Asn Ala Val Gln Val Ala Asn Lys Arg Thr Ala Thr Ile Lys Asn
2465                2470                2475

Gly Thr Ala Met Pro Thr Asn Leu Ala Gly Gly Ser Thr Thr Thr
2480                2485                2490

Ile Pro Val Thr Val Thr Tyr Asn Asp Gly Ser Thr Glu Glu Val
2495                2500                2505

Gln Glu Ser Ile Phe Thr Lys Ala Asp Lys Arg Glu Leu Ile Thr
2510                2515                2520

Ala Lys Asn His Leu Asp Asp Pro Val Ser Thr Glu Gly Lys Lys
2525                2530                2535

Pro Gly Thr Ile Thr Gln Tyr Asn Asn Ala Met His Asn Ala Gln
2540                2545                2550

Gln Gln Ile Asn Thr Ala Lys Thr Glu Ala Gln Gln Val Ile Asn
2555                2560                2565
```

-continued

| | | | | | | | | | | | |
|---|---|---|---|---|---|---|---|---|---|---|---|
| Asn | Glu | Arg | Ala | Thr | Pro | Gln | Gln | Val | Ser | Asp | Ala | Leu | Thr | Lys |
| | 2570 | | | | | 2575 | | | | | 2580 | | | |
| Val | Arg | Ala | Ala | Gln | Thr | Lys | Ile | Asp | Gln | Ala | Lys | Ala | Leu | Leu |
| | 2585 | | | | | 2590 | | | | | 2595 | | | |
| Gln | Asn | Lys | Glu | Asp | Asn | Ser | Gln | Leu | Val | Thr | Ser | Lys | Asn | Asn |
| | 2600 | | | | | 2605 | | | | | 2610 | | | |
| Leu | Gln | Ser | Ser | Val | Asn | Gln | Val | Pro | Ser | Thr | Ala | Gly | Met | Thr |
| | 2615 | | | | | 2620 | | | | | 2625 | | | |
| Gln | Gln | Ser | Ile | Asp | Asn | Tyr | Asn | Ala | Lys | Lys | Arg | Glu | Ala | Glu |
| | 2630 | | | | | 2635 | | | | | 2640 | | | |
| Thr | Glu | Ile | Thr | Ala | Ala | Gln | Arg | Val | Ile | Asp | Asn | Gly | Asp | Ala |
| | 2645 | | | | | 2650 | | | | | 2655 | | | |
| Thr | Ala | Gln | Gln | Ile | Ser | Asp | Glu | Lys | His | Arg | Val | Asp | Asn | Ala |
| | 2660 | | | | | 2665 | | | | | 2670 | | | |
| Leu | Thr | Ala | Leu | Asn | Gln | Ala | Lys | His | Asp | Leu | Thr | Ala | Asp | Thr |
| | 2675 | | | | | 2680 | | | | | 2685 | | | |
| His | Ala | Leu | Glu | Gln | Ala | Val | Gln | Gln | Leu | Asn | Arg | Thr | Gly | Thr |
| | 2690 | | | | | 2695 | | | | | 2700 | | | |
| Thr | Thr | Gly | Lys | Lys | Pro | Ala | Ser | Ile | Thr | Ala | Tyr | Asn | Asn | Ser |
| | 2705 | | | | | 2710 | | | | | 2715 | | | |
| Ile | Arg | Ala | Leu | Gln | Ser | Asp | Leu | Thr | Ser | Ala | Lys | Asn | Ser | Ala |
| | 2720 | | | | | 2725 | | | | | 2730 | | | |
| Asn | Ala | Ile | Ile | Gln | Lys | Pro | Ile | Arg | Thr | Val | Gln | Glu | Val | Gln |
| | 2735 | | | | | 2740 | | | | | 2745 | | | |
| Ser | Ala | Leu | Thr | Asn | Val | Asn | Arg | Val | Asn | Glu | Arg | Leu | Thr | Gln |
| | 2750 | | | | | 2755 | | | | | 2760 | | | |
| Ala | Ile | Asn | Gln | Leu | Val | Pro | Leu | Ala | Asp | Asn | Ser | Ala | Leu | Lys |
| | 2765 | | | | | 2770 | | | | | 2775 | | | |
| Thr | Ala | Lys | Thr | Lys | Leu | Asp | Glu | Glu | Ile | Asn | Lys | Ser | Val | Thr |
| | 2780 | | | | | 2785 | | | | | 2790 | | | |
| Thr | Asp | Gly | Met | Thr | Gln | Ser | Ser | Ile | Gln | Ala | Tyr | Glu | Asn | Ala |
| | 2795 | | | | | 2800 | | | | | 2805 | | | |
| Lys | Arg | Ala | Gly | Gln | Thr | Glu | Ser | Thr | Asn | Ala | Gln | Asn | Val | Ile |
| | 2810 | | | | | 2815 | | | | | 2820 | | | |
| Asn | Asn | Gly | Asp | Ala | Thr | Asp | Gln | Gln | Ile | Ala | Ala | Glu | Lys | Thr |
| | 2825 | | | | | 2830 | | | | | 2835 | | | |
| Lys | Val | Glu | Glu | Lys | Tyr | Asn | Ser | Leu | Lys | Gln | Ala | Ile | Ala | Gly |
| | 2840 | | | | | 2845 | | | | | 2850 | | | |
| Leu | Thr | Pro | Asp | Leu | Ala | Pro | Leu | Gln | Thr | Ala | Lys | Thr | Gln | Leu |
| | 2855 | | | | | 2860 | | | | | 2865 | | | |
| Gln | Asn | Asp | Ile | Asp | Gln | Pro | Thr | Ser | Thr | Thr | Gly | Met | Thr | Ser |
| | 2870 | | | | | 2875 | | | | | 2880 | | | |
| Ala | Ser | Ile | Ala | Ala | Phe | Asn | Glu | Lys | Leu | Ser | Ala | Ala | Arg | Thr |
| | 2885 | | | | | 2890 | | | | | 2895 | | | |
| Lys | Ile | Gln | Glu | Ile | Asp | Arg | Val | Leu | Ala | Ser | His | Pro | Asp | Val |
| | 2900 | | | | | 2905 | | | | | 2910 | | | |
| Ala | Thr | Ile | Arg | Gln | Asn | Val | Thr | Ala | Ala | Asn | Ala | Ala | Lys | Ser |
| | 2915 | | | | | 2920 | | | | | 2925 | | | |
| Ala | Leu | Asp | Gln | Ala | Arg | Asn | Gly | Leu | Thr | Val | Asp | Lys | Ala | Pro |
| | 2930 | | | | | 2935 | | | | | 2940 | | | |
| Leu | Glu | Asn | Ala | Lys | Asn | Gln | Leu | Gln | His | Ser | Ile | Asp | Thr | Gln |
| | 2945 | | | | | 2950 | | | | | 2955 | | | |
| Thr | Ser | Thr | Thr | Gly | Met | Thr | Gln | Asp | Ser | Ile | Asn | Ala | Tyr | Asn |

```
              2960                2965                2970
Ala Lys Leu Thr Ala Ala Arg Asn Lys Ile Gln Gln Ile Asn Gln
         2975                2980                2985

Val Leu Ala Gly Ser Pro Thr Val Glu Gln Ile Asn Thr Asn Thr
         2990                2995                3000

Ser Thr Ala Asn Gln Ala Lys Ser Asp Leu Asp His Ala Arg Gln
         3005                3010                3015

Ala Leu Thr Pro Asp Lys Ala Pro Leu Gln Thr Ala Lys Thr Gln
         3020                3025                3030

Leu Glu Gln Ser Ile Asn Gln Pro Thr Asp Thr Gly Met Thr
         3035                3040                3045

Thr Ala Ser Leu Asn Ala Tyr Asn Gln Lys Leu Gln Ala Ala Arg
         3050                3055                3060

Gln Lys Leu Thr Glu Ile Asn Gln Val Leu Asn Gly Asn Pro Thr
         3065                3070                3075

Val Gln Asn Ile Asn Asp Lys Val Thr Glu Ala Asn Gln Ala Lys
         3080                3085                3090

Asp Gln Leu Asn Thr Ala Arg Gln Gly Leu Thr Leu Asp Arg Gln
         3095                3100                3105

Pro Ala Leu Thr Thr Leu His Gly Ala Ser Asn Leu Asn Gln Ala
         3110                3115                3120

Gln Gln Asn Asn Phe Thr Gln Gln Ile Asn Ala Ala Gln Asn His
         3125                3130                3135

Ala Ala Leu Glu Thr Ile Lys Ser Asn Ile Thr Ala Leu Asn Thr
         3140                3145                3150

Ala Met Thr Lys Leu Lys Asp Ser Val Ala Asp Asn Asn Thr Ile
         3155                3160                3165

Lys Ser Asp Gln Asn Tyr Thr Asp Ala Thr Pro Ala Asn Lys Gln
         3170                3175                3180

Ala Tyr Asp Asn Ala Val Asn Ala Ala Lys Gly Val Ile Gly Glu
         3185                3190                3195

Thr Thr Asn Pro Thr Met Asp Val Asn Thr Val Asn Gln Lys Ala
         3200                3205                3210

Ala Ser Val Lys Ser Thr Lys Asp Ala Leu Asp Gly Gln Gln Asn
         3215                3220                3225

Leu Gln Arg Ala Lys Thr Glu Ala Thr Asn Ala Ile Thr His Ala
         3230                3235                3240

Ser Asp Leu Asn Gln Ala Gln Lys Asn Ala Leu Thr Gln Gln Val
         3245                3250                3255

Asn Ser Ala Gln Asn Val Gln Ala Val Asn Asp Ile Lys Gln Thr
         3260                3265                3270

Thr Gln Ser Leu Asn Thr Ala Met Thr Gly Leu Lys Arg Gly Val
         3275                3280                3285

Ala Asn His Asn Gln Val Val Gln Ser Asp Asn Tyr Val Asn Ala
         3290                3295                3300

Asp Thr Asn Lys Lys Asn Asp Tyr Asn Ala Tyr Asn His Ala
         3305                3310                3315

Asn Asp Ile Ile Asn Gly Asn Ala Gln His Pro Val Ile Thr Pro
         3320                3325                3330

Ser Asp Val Asn Asn Ala Leu Ser Asn Val Thr Ser Lys Glu His
         3335                3340                3345

Ala Leu Asn Gly Glu Ala Lys Leu Asn Ala Ala Lys Gln Glu Ala
         3350                3355                3360
```

```
Asn Thr Ala Leu Gly His Leu Asn Asn Leu Asn Asn Ala Gln Arg
3365                 3370                3375

Gln Asn Leu Gln Ser Gln Ile Asn Gly Ala His Gln Ile Asp Ala
3380                 3385                3390

Val Asn Thr Ile Lys Gln Asn Ala Thr Asn Leu Asn Ser Ala Met
3395                 3400                3405

Gly Asn Leu Arg Gln Ala Val Ala Asp Lys Asp Gln Val Lys Arg
3410                 3415                3420

Thr Glu Asp Tyr Ala Asp Ala Asp Thr Ala Lys Gln Asn Ala Tyr
3425                 3430                3435

Asn Ser Ala Val Ser Ser Ala Glu Thr Ile Ile Asn Gln Thr Thr
3440                 3445                3450

Asn Pro Thr Met Ser Val Asp Asp Val Asn Arg Ala Thr Ser Ala
3455                 3460                3465

Val Thr Ser Asn Lys Asn Ala Leu Asn Gly Tyr Glu Lys Leu Ala
3470                 3475                3480

Gln Ser Lys Thr Asp Ala Ala Arg Ala Ile Asp Ala Leu Pro His
3485                 3490                3495

Leu Asn Asn Ala Gln Lys Ala Asp Val Lys Ser Lys Ile Asn Ala
3500                 3505                3510

Ala Ser Asn Ile Ala Gly Val Asn Thr Val Lys Gln Gln Gly Thr
3515                 3520                3525

Asp Leu Asn Thr Ala Met Gly Asn Leu Gln Gly Ala Ile Asn Asp
3530                 3535                3540

Glu Gln Thr Thr Leu Asn Ser Gln Asn Tyr Gln Asp Ala Thr Pro
3545                 3550                3555

Ser Lys Lys Thr Ala Tyr Thr Asn Ala Val Gln Ala Ala Lys Asp
3560                 3565                3570

Ile Leu Asn Lys Ser Asn Gly Gln Asn Lys Thr Lys Asp Gln Val
3575                 3580                3585

Thr Glu Ala Met Asn Gln Val Asn Ser Ala Lys Asn Asn Leu Asp
3590                 3595                3600

Gly Thr Arg Leu Leu Asp Gln Ala Lys Gly Thr Ala Lys Gln Gln
3605                 3610                3615

Leu Asn Asn Met Thr His Leu Thr Thr Ala Gln Lys Thr Asn Leu
3620                 3625                3630

Thr Asn Gln Ile Asn Ser Gly Thr Thr Val Ala Gly Val Gln Thr
3635                 3640                3645

Val Gln Ser Asn Ala Asn Thr Leu Asp Gln Ala Met Asn Thr Leu
3650                 3655                3660

Arg Gln Ser Ile Ala Asn Lys Asp Ala Thr Lys Ala Ser Glu Asp
3665                 3670                3675

Tyr Val Asp Ala Asn Asn Asp Lys Gln Thr Ala Tyr Asn Asn Ala
3680                 3685                3690

Val Ala Ala Ala Glu Thr Ile Ile Asn Ala Asn Ser Asn Pro Glu
3695                 3700                3705

Met Asn Pro Ser Thr Ile Thr Gln Lys Ala Glu Gln Val Asn Ser
3710                 3715                3720

Ser Lys Thr Ala Leu Asn Gly Asp Glu Asn Leu Ala Ala Ala Lys
3725                 3730                3735

Gln Asn Ala Lys Thr Tyr Leu Asn Thr Leu Thr Ser Ile Thr Asp
3740                 3745                3750
```

Ala Gln Lys Asn Asn Leu Ile Ser Gln Ile Thr Ser Ala Thr Arg
    3755                3760                3765

Val Ser Gly Val Asp Thr Val Lys Gln Asn Ala Gln His Leu Asp
    3770                3775                3780

Gln Ala Met Ala Ser Leu Gln Asn Gly Ile Asn Asn Glu Ser Gln
    3785                3790                3795

Val Lys Ser Ser Glu Lys Tyr Arg Asp Ala Asp Thr Asn Lys Gln
    3800                3805                3810

Gln Glu Tyr Asp Asn Ala Ile Thr Ala Ala Lys Ala Ile Leu Asn
    3815                3820                3825

Lys Ser Thr Gly Pro Asn Thr Ala Gln Asn Ala Val Glu Ala Ala
    3830                3835                3840

Leu Gln Arg Val Asn Asn Ala Lys Asp Ala Leu Asn Gly Asp Ala
    3845                3850                3855

Lys Leu Ile Ala Ala Gln Asn Ala Ala Lys Gln His Leu Gly Thr
    3860                3865                3870

Leu Thr His Ile Thr Thr Ala Gln Arg Asn Asp Leu Thr Asn Gln
    3875                3880                3885

Ile Ser Gln Ala Thr Asn Leu Ala Gly Val Glu Ser Val Lys Gln
    3890                3895                3900

Asn Ala Asn Ser Leu Asp Gly Ala Met Gly Asn Leu Gln Thr Ala
    3905                3910                3915

Ile Asn Asp Lys Ser Gly Thr Leu Ala Ser Gln Asn Phe Leu Asp
    3920                3925                3930

Ala Asp Glu Gln Lys Arg Asn Ala Tyr Asn Gln Ala Val Ser Ala
    3935                3940                3945

Ala Glu Thr Ile Leu Asn Lys Gln Thr Gly Pro Asn Thr Ala Lys
    3950                3955                3960

Thr Ala Val Glu Gln Ala Leu Asn Asn Val Asn Asn Ala Lys His
    3965                3970                3975

Ala Leu Asn Gly Thr Gln Asn Leu Asn Asn Ala Lys Gln Ala Ala
    3980                3985                3990

Ile Thr Ala Ile Asn Gly Ala Ser Asp Leu Asn Gln Lys Gln Lys
    3995                4000                4005

Asp Ala Leu Lys Ala Gln Ala Asn Gly Ala Gln Arg Val Ser Asn
    4010                4015                4020

Ala Gln Asp Val Gln His Asn Ala Thr Glu Leu Asn Thr Ala Met
    4025                4030                4035

Gly Thr Leu Lys His Ala Ile Ala Asp Lys Thr Asn Thr Leu Ala
    4040                4045                4050

Ser Ser Lys Tyr Val Asn Ala Asp Ser Thr Lys Gln Asn Ala Tyr
    4055                4060                4065

Thr Thr Lys Val Thr Asn Ala Glu His Ile Ile Ser Gly Thr Pro
    4070                4075                4080

Thr Val Val Thr Thr Pro Ser Glu Val Thr Ala Ala Ala Asn Gln
    4085                4090                4095

Val Asn Ser Ala Lys Gln Glu Leu Asn Gly Asp Glu Arg Leu Arg
    4100                4105                4110

Glu Ala Lys Gln Asn Ala Asn Thr Ala Ile Asp Ala Leu Thr Gln
    4115                4120                4125

Leu Asn Thr Pro Gln Lys Ala Lys Leu Lys Glu Gln Val Gly Gln
    4130                4135                4140

Ala Asn Arg Leu Glu Asp Val Gln Thr Val Gln Thr Asn Gly Gln

```
                    4145              4150              4155
Ala Leu Asn Asn Ala Met Lys Gly Leu Arg Asp Ser Ile Ala Asn
                4160              4165              4170
Glu Thr Thr Val Lys Thr Ser Gln Asn Tyr Thr Asp Ala Ser Pro
                4175              4180              4185
Asn Asn Gln Ser Thr Tyr Asn Ser Ala Val Ser Asn Ala Lys Gly
                4190              4195              4200
Ile Ile Asn Gln Thr Asn Asn Pro Thr Met Asp Thr Ser Ala Ile
                4205              4210              4215
Thr Gln Ala Thr Thr Gln Val Asn Asn Ala Lys Asn Gly Leu Asn
                4220              4225              4230
Gly Ala Glu Asn Leu Arg Asn Ala Gln Asn Thr Ala Lys Gln Asn
                4235              4240              4245
Leu Asn Thr Leu Ser His Leu Thr Asn Asn Gln Lys Ser Ala Ile
                4250              4255              4260
Ser Ser Gln Ile Asp Arg Ala Gly His Val Ser Glu Val Thr Ala
                4265              4270              4275
Thr Lys Asn Ala Ala Thr Glu Leu Asn Thr Gln Met Gly Asn Leu
                4280              4285              4290
Glu Gln Ala Ile His Asp Gln Asn Thr Val Lys Gln Ser Val Lys
                4295              4300              4305
Phe Thr Asp Ala Asp Lys Ala Lys Arg Asp Ala Tyr Thr Asn Ala
                4310              4315              4320
Val Ser Arg Ala Glu Ala Ile Leu Asn Lys Thr Gln Gly Ala Asn
                4325              4330              4335
Thr Ser Lys Gln Asp Val Glu Ala Ala Ile Gln Asn Val Ser Ser
                4340              4345              4350
Ala Lys Asn Ala Leu Asn Gly Asp Gln Asn Val Thr Asn Ala Lys
                4355              4360              4365
Asn Ala Ala Lys Asn Ala Leu Asn Asn Leu Thr Ser Ile Asn Asn
                4370              4375              4380
Ala Gln Lys Arg Asp Leu Thr Thr Lys Ile Asp Gln Ala Thr Thr
                4385              4390              4395
Val Ala Gly Val Glu Ala Val Ser Asn Thr Ser Thr Gln Leu Asn
                4400              4405              4410
Thr Ala Met Ala Asn Leu Gln Asn Gly Ile Asn Asp Lys Thr Asn
                4415              4420              4425
Thr Leu Ala Ser Glu Asn Tyr His Asp Ala Asp Ser Asp Lys Lys
                4430              4435              4440
Thr Ala Tyr Thr Gln Ala Val Thr Asn Ala Glu Asn Ile Leu Asn
                4445              4450              4455
Lys Asn Ser Gly Ser Asn Leu Asp Lys Thr Ala Val Glu Asn Ala
                4460              4465              4470
Leu Ser Gln Val Ala Asn Ala Lys Gly Ala Leu Asn Gly Asn His
                4475              4480              4485
Asn Leu Glu Gln Ala Lys Ser Asn Ala Asn Thr Thr Ile Asn Gly
                4490              4495              4500
Leu Gln His Leu Thr Thr Ala Gln Lys Asp Lys Leu Lys Gln Gln
                4505              4510              4515
Val Gln Gln Ala Gln Asn Val Ala Gly Val Asp Thr Val Lys Ser
                4520              4525              4530
Ser Ala Asn Thr Leu Asn Gly Ala Met Gly Thr Leu Arg Asn Ser
                4535              4540              4545
```

-continued

```
Ile Gln Asp Asn Thr Ala Thr Lys Asn Gly Gln Asn Tyr Leu Asp
    4550                4555            4560
Ala Thr Glu Arg Asn Lys Thr Asn Tyr Asn Asn Ala Val Asp Ser
    4565                4570            4575
Ala Asn Gly Val Ile Asn Ala Thr Ser Asn Pro Asn Met Asp Ala
    4580                4585            4590
Asn Ala Ile Asn Gln Ile Ala Thr Gln Val Thr Ser Thr Lys Asn
    4595                4600            4605
Ala Leu Asp Gly Thr His Asn Leu Thr Gln Ala Lys Gln Thr Ala
    4610                4615            4620
Thr Asn Ala Ile Asp Gly Ala Thr Asn Leu Asn Lys Ala Gln Lys
    4625                4630            4635
Asp Ala Leu Lys Ala Gln Val Thr Ser Ala Gln Arg Val Ala Asn
    4640                4645            4650
Val Thr Ser Ile Gln Gln Thr Ala Asn Glu Leu Asn Thr Ala Met
    4655                4660            4665
Gly Gln Leu Gln His Gly Ile Asp Asp Glu Asn Ala Thr Lys Gln
    4670                4675            4680
Thr Gln Lys Tyr Arg Asp Ala Glu Gln Ser Lys Lys Thr Ala Tyr
    4685                4690            4695
Asp Gln Ala Val Ala Ala Ala Lys Ala Ile Leu Asn Lys Gln Thr
    4700                4705            4710
Gly Ser Asn Ser Asp Lys Ala Ala Val Asp Arg Ala Leu Gln Gln
    4715                4720            4725
Val Thr Ser Thr Lys Asp Ala Leu Asn Gly Asp Ala Lys Leu Ala
    4730                4735            4740
Glu Ala Lys Ala Ala Ala Lys Gln Asn Leu Gly Thr Leu Asn His
    4745                4750            4755
Ile Thr Asn Ala Gln Arg Thr Asp Leu Glu Gly Gln Ile Asn Gln
    4760                4765            4770
Ala Thr Thr Val Asp Gly Val Asn Thr Val Lys Thr Asn Ala Asn
    4775                4780            4785
Thr Leu Asp Gly Ala Met Asn Ser Leu Gln Gly Ser Ile Asn Asp
    4790                4795            4800
Lys Asp Ala Thr Leu Arg Asn Gln Asn Tyr Leu Asp Ala Asp Glu
    4805                4810            4815
Ser Lys Arg Asn Ala Tyr Thr Gln Ala Val Thr Ala Ala Glu Gly
    4820                4825            4830
Ile Leu Asn Lys Gln Thr Gly Gly Asn Thr Ser Lys Ala Asp Val
    4835                4840            4845
Asp Asn Ala Leu Asn Ala Val Thr Arg Ala Lys Ala Ala Leu Asn
    4850                4855            4860
Gly Ala Asp Asn Leu Arg Asn Ala Lys Thr Ser Ala Thr Asn Thr
    4865                4870            4875
Ile Asp Gly Leu Pro Asn Leu Thr Gln Leu Gln Lys Asp Asn Leu
    4880                4885            4890
Lys His Gln Val Glu Gln Ala Gln Asn Val Ala Gly Val Asn Gly
    4895                4900            4905
Val Lys Asp Lys Gly Asn Thr Leu Asn Thr Ala Met Gly Ala Leu
    4910                4915            4920
Arg Thr Ser Ile Gln Asn Asp Asn Thr Thr Lys Thr Ser Gln Asn
    4925                4930            4935
```

```
Tyr Leu Asp Ala Ser Asp Ser Asn Lys Asn Asn Tyr Asn Thr Ala
    4940            4945                4950
Val Asn Asn Ala Asn Gly Val Ile Asn Ala Thr Asn Asn Pro Asn
    4955            4960                4965
Met Asp Ala Asn Ala Ile Asn Gly Met Ala Asn Gln Val Asn Thr
    4970            4975                4980
Thr Lys Ala Ala Leu Asn Gly Ala Gln Asn Leu Ala Gln Ala Lys
    4985            4990                4995
Thr Asn Ala Thr Asn Thr Ile Asn Asn Ala His Asp Leu Asn Gln
    5000            5005                5010
Lys Gln Lys Asp Ala Leu Lys Thr Gln Val Asn Asn Ala Gln Arg
    5015            5020                5025
Val Ser Asp Ala Asn Asn Val Gln His Thr Ala Thr Glu Leu Asn
    5030            5035                5040
Ser Ala Met Thr Ala Leu Lys Ala Ala Ile Ala Asp Lys Glu Arg
    5045            5050                5055
Thr Lys Ala Ser Gly Asn Tyr Val Asn Ala Asp Gln Glu Lys Arg
    5060            5065                5070
Gln Ala Tyr Asp Ser Lys Val Thr Asn Ala Glu Asn Ile Ile Ser
    5075            5080                5085
Gly Thr Pro Asn Ala Thr Leu Thr Val Asn Asp Val Asn Ser Ala
    5090            5095                5100
Ala Ser Gln Val Asn Ala Ala Lys Thr Ala Leu Asn Gly Asp Asn
    5105            5110                5115
Asn Leu Arg Val Ala Lys Glu His Ala Asn Asn Thr Ile Asp Gly
    5120            5125                5130
Leu Ala Gln Leu Asn Asn Ala Gln Lys Ala Lys Leu Lys Glu Gln
    5135            5140                5145
Val Gln Ser Ala Thr Thr Leu Asp Gly Val Gln Thr Val Lys Asn
    5150            5155                5160
Ser Ser Gln Thr Leu Asn Thr Ala Met Lys Gly Leu Arg Asp Ser
    5165            5170                5175
Ile Ala Asn Glu Ala Thr Ile Lys Ala Gly Gln Asn Tyr Thr Asp
    5180            5185                5190
Ala Ser Pro Asn Asn Arg Asn Glu Tyr Asp Ser Ala Val Thr Ala
    5195            5200                5205
Ala Lys Ala Ile Ile Asn Gln Thr Ser Asn Pro Thr Met Glu Pro
    5210            5215                5220
Asn Thr Ile Thr Gln Val Thr Ser Gln Val Thr Thr Lys Glu Gln
    5225            5230                5235
Ala Leu Asn Gly Ala Arg Asn Leu Ala Gln Ala Lys Thr Thr Ala
    5240            5245                5250
Lys Asn Asn Leu Asn Asn Leu Thr Ser Ile Asn Asn Ala Gln Lys
    5255            5260                5265
Asp Ala Leu Thr Arg Ser Ile Asp Gly Ala Thr Thr Val Ala Gly
    5270            5275                5280
Val Asn Gln Glu Thr Ala Lys Ala Thr Glu Leu Asn Asn Ala Met
    5285            5290                5295
His Ser Leu Gln Asn Gly Ile Asn Asp Glu Thr Gln Thr Lys Gln
    5300            5305                5310
Thr Gln Lys Tyr Leu Asp Ala Glu Pro Ser Lys Lys Ser Ala Tyr
    5315            5320                5325
Asp Gln Ala Val Asn Ala Ala Lys Ala Ile Leu Thr Lys Ala Ser
```

-continued

| | 5330 | | | 5335 | | | 5340 | | |

Gly Gln Asn Val Asp Lys Ala Val Glu Gln Ala Leu Gln Asn
5345                5350            5355

Val Asn Ser Thr Lys Thr Ala Leu Asn Gly Asp Ala Lys Leu Asn
5360                5365            5370

Glu Ala Lys Ala Ala Lys Gln Thr Leu Gly Thr Leu Thr His
5375                5380            5385

Ile Asn Asn Ala Gln Arg Thr Ala Leu Asp Asn Glu Ile Thr Gln
5390                5395            5400

Ala Thr Asn Val Glu Gly Val Asn Thr Val Lys Ala Lys Ala Gln
5405                5410            5415

Gln Leu Asp Gly Ala Met Gly Gln Leu Glu Thr Ser Ile Arg Asp
5420                5425            5430

Lys Asp Thr Thr Leu Gln Ser Gln Asn Tyr Gln Asp Ala Asp Asp
5435                5440            5445

Ala Lys Arg Thr Ala Tyr Ser Gln Ala Val Asn Ala Ala Ala Thr
5450                5455            5460

Ile Leu Asn Lys Thr Ala Gly Gly Asn Thr Pro Lys Ala Asp Val
5465                5470            5475

Glu Arg Ala Met Gln Ala Val Thr Gln Ala Asn Thr Ala Leu Asn
5480                5485            5490

Gly Ile Gln Asn Leu Asp Arg Ala Lys Gln Ala Ala Asn Thr Ala
5495                5500            5505

Ile Thr Asn Ala Ser Asp Leu Asn Thr Lys Gln Lys Glu Ala Leu
5510                5515            5520

Lys Ala Gln Val Thr Ser Ala Gly Arg Val Ser Ala Ala Asn Gly
5525                5530            5535

Val Glu His Thr Ala Thr Glu Leu Asn Thr Ala Met Thr Ala Leu
5540                5545            5550

Lys Arg Ala Ile Ala Asp Lys Ala Glu Thr Lys Ala Ser Gly Asn
5555                5560            5565

Tyr Val Asn Ala Asp Ala Asn Lys Arg Gln Ala Tyr Asp Glu Lys
5570                5575            5580

Val Thr Ala Ala Glu Asn Ile Val Ser Gly Thr Pro Thr Pro Thr
5585                5590            5595

Leu Thr Pro Ala Asp Val Thr Asn Ala Ala Thr Gln Val Thr Asn
5600                5605            5610

Ala Lys Thr Gln Leu Asn Gly Asn His Asn Leu Glu Val Ala Lys
5615                5620            5625

Gln Asn Ala Asn Thr Ala Ile Asp Gly Leu Thr Ser Leu Asn Gly
5630                5635            5640

Pro Gln Lys Ala Lys Leu Lys Glu Gln Val Gly Gln Ala Thr Thr
5645                5650            5655

Leu Pro Asn Val Gln Thr Val Arg Asp Asn Ala Gln Thr Leu Asn
5660                5665            5670

Thr Ala Met Lys Gly Leu Arg Asp Ser Ile Ala Asn Glu Ala Thr
5675                5680            5685

Ile Lys Ala Gly Gln Asn Tyr Thr Asp Ala Ser Gln Asn Lys Gln
5690                5695            5700

Thr Asp Tyr Asn Ser Ala Val Thr Ala Ala Lys Ala Ile Ile Gly
5705                5710            5715

Gln Thr Thr Ser Pro Ser Met Asn Ala Gln Glu Ile Asn Gln Ala
5720                5725            5730

-continued

```
Lys Asp Gln Val Thr Ala Lys Gln Gln Ala Leu Asn Gly Gln Glu
    5735              5740                5745
Asn Leu Arg Thr Ala Gln Thr Asn Ala Lys Gln His Leu Asn Gly
    5750              5755                5760
Leu Ser Asp Leu Thr Asp Ala Gln Lys Asp Ala Val Lys Arg Gln
    5765              5770                5775
Ile Glu Gly Ala Thr His Val Asn Glu Val Thr Gln Ala Gln Asn
    5780              5785                5790
Asn Ala Asp Ala Leu Asn Thr Ala Met Thr Asn Leu Lys Asn Gly
    5795              5800                5805
Ile Gln Asp Gln Asn Thr Ile Lys Gln Gly Val Asn Phe Thr Asp
    5810              5815                5820
Ala Asp Glu Ala Lys Arg Asn Ala Tyr Thr Asn Ala Val Thr Gln
    5825              5830                5835
Ala Glu Gln Ile Leu Asn Lys Ala Gln Gly Pro Asn Thr Ser Lys
    5840              5845                5850
Asp Gly Val Glu Thr Ala Leu Glu Asn Val Gln Arg Ala Lys Asn
    5855              5860                5865
Glu Leu Asn Gly Asn Gln Asn Val Ala Asn Ala Lys Thr Thr Ala
    5870              5875                5880
Lys Asn Ala Leu Asn Asn Leu Thr Ser Ile Asn Asn Ala Gln Lys
    5885              5890                5895
Glu Ala Leu Lys Ser Gln Ile Glu Gly Ala Thr Thr Val Ala Gly
    5900              5905                5910
Val Asn Gln Val Ser Thr Thr Ala Ser Glu Leu Asn Thr Ala Met
    5915              5920                5925
Ser Asn Leu Gln Asn Gly Ile Asn Asp Glu Ala Ala Thr Lys Ala
    5930              5935                5940
Ala Gln Lys Tyr Thr Asp Ala Asp Arg Glu Lys Gln Thr Ala Tyr
    5945              5950                5955
Asn Asp Ala Val Thr Ala Ala Lys Thr Leu Leu Asp Lys Thr Ala
    5960              5965                5970
Gly Ser Asn Asp Asn Lys Ala Ala Val Glu Gln Ala Leu Gln Arg
    5975              5980                5985
Val Asn Thr Ala Lys Thr Ala Leu Asn Gly Asp Glu Arg Leu Asn
    5990              5995                6000
Glu Ala Lys Asn Thr Ala Lys Gln Gln Val Ala Thr Met Ser His
    6005              6010                6015
Leu Thr Asp Ala Gln Lys Ala Asn Leu Thr Ser Gln Ile Glu Ser
    6020              6025                6030
Gly Thr Thr Val Ala Gly Val Gln Gly Ile Gln Ala Asn Ala Gly
    6035              6040                6045
Thr Leu Asp Gln Ala Met Asn Gln Leu Arg Gln Ser Ile Ala Ser
    6050              6055                6060
Lys Asp Ala Thr Lys Ser Ser Glu Asp Tyr Gln Asp Ala Asn Ala
    6065              6070                6075
Asp Leu Gln Asn Ala Tyr Asn Asp Ala Val Thr Asn Ala Glu Gly
    6080              6085                6090
Ile Ile Ser Ala Thr Asn Asn Pro Glu Met Asn Pro Asp Thr Ile
    6095              6100                6105
Asn Gln Lys Ala Ser Gln Val Asn Ser Ala Lys Ser Ala Leu Asn
    6110              6115                6120
```

```
Gly Asp Glu Lys Leu Ala Ala Lys Gln Thr Ala Lys Ser Asp
    6125                6130                6135

Ile Gly Arg Leu Thr Asp Leu Asn Asn Ala Gln Arg Thr Ala Ala
    6140                6145                6150

Asn Ala Glu Val Asp Gln Ala Pro Asn Leu Ala Ala Val Thr Ala
    6155                6160                6165

Ala Lys Asn Lys Ala Thr Ser Leu Asn Thr Ala Met Gly Asn Leu
    6170                6175                6180

Lys His Ala Leu Ala Glu Lys Asp Asn Thr Lys Arg Ser Val Asn
    6185                6190                6195

Tyr Thr Asp Ala Asp Gln Pro Lys Gln Gln Ala Tyr Asp Thr Ala
    6200                6205                6210

Val Thr Gln Ala Glu Ala Ile Thr Asn Ala Asn Gly Ser Asn Ala
    6215                6220                6225

Asn Glu Thr Gln Val Gln Ala Ala Leu Asn Gln Leu Asn Gln Ala
    6230                6235                6240

Lys Asn Asp Leu Asn Gly Asp Asn Lys Val Ala Gln Ala Lys Glu
    6245                6250                6255

Ser Ala Lys Arg Ala Leu Ala Ser Tyr Ser Asn Leu Asn Asn Ala
    6260                6265                6270

Gln Ser Thr Ala Ala Ile Ser Gln Ile Asp Asn Ala Thr Thr Val
    6275                6280                6285

Ala Gly Val Thr Ala Ala Gln Asn Thr Ala Asn Glu Leu Asn Thr
    6290                6295                6300

Ala Met Gly Gln Leu Gln Asn Gly Ile Asn Asp Gln Asn Thr Val
    6305                6310                6315

Lys Gln Gln Val Asn Phe Thr Asp Ala Asp Gln Gly Lys Lys Asp
    6320                6325                6330

Ala Tyr Thr Asn Ala Val Thr Asn Ala Gln Gly Ile Leu Asp Lys
    6335                6340                6345

Ala His Gly Gln Asn Met Thr Lys Ala Gln Val Glu Ala Ala Leu
    6350                6355                6360

Asn Gln Val Thr Thr Ala Lys Asn Ala Leu Asn Gly Asp Ala Asn
    6365                6370                6375

Val Arg Gln Ala Lys Ser Asp Ala Lys Ala Asn Leu Gly Thr Leu
    6380                6385                6390

Thr His Leu Asn Asn Ala Gln Lys Gln Asp Leu Thr Ser Gln Ile
    6395                6400                6405

Glu Gly Ala Thr Thr Val Asn Gly Val Asn Gly Val Lys Thr Lys
    6410                6415                6420

Ala Gln Asp Leu Asp Gly Ala Met Gln Arg Leu Gln Ser Ala Ile
    6425                6430                6435

Ala Asn Lys Asp Gln Thr Lys Ala Ser Glu Asn Tyr Ile Asp Ala
    6440                6445                6450

Asp Pro Thr Lys Lys Thr Ala Phe Asp Asn Ala Ile Thr Gln Ala
    6455                6460                6465

Glu Ser Tyr Leu Asn Lys Asp His Gly Ala Asn Lys Asp Lys Gln
    6470                6475                6480

Ala Val Glu Gln Ala Ile Gln Ser Val Thr Ser Thr Glu Asn Ala
    6485                6490                6495

Leu Asn Gly Asp Ala Asn Leu Gln Arg Ala Lys Thr Glu Ala Ile
    6500                6505                6510

Gln Ala Ile Asp Asn Leu Thr His Leu Asn Thr Pro Gln Lys Thr
```

```
                    6515                    6520                    6525

Ala  Leu  Lys  Gln  Gln  Val  Asn  Ala  Ala  Gln  Arg  Val  Ser  Gly  Val
          6530                    6535                    6540

Thr  Asp  Leu  Lys  Asn  Ser  Ala  Thr  Ser  Leu  Asn  Asn  Ala  Met  Asp
          6545                    6550                    6555

Gln  Leu  Lys  Gln  Ala  Ile  Ala  Asp  His  Asp  Thr  Ile  Val  Ala  Ser
          6560                    6565                    6570

Gly  Asn  Tyr  Thr  Asn  Ala  Ser  Pro  Asp  Lys  Gln  Gly  Ala  Tyr  Thr
          6575                    6580                    6585

Asp  Ala  Tyr  Asn  Ala  Ala  Lys  Asn  Ile  Val  Asn  Gly  Ser  Pro  Asn
          6590                    6595                    6600

Val  Ile  Thr  Asn  Ala  Ala  Asp  Val  Thr  Ala  Ala  Thr  Gln  Arg  Val
          6605                    6610                    6615

Asn  Asn  Ala  Glu  Thr  Gly  Leu  Asn  Gly  Asp  Thr  Asn  Leu  Ala  Thr
          6620                    6625                    6630

Ala  Lys  Gln  Gln  Ala  Lys  Asp  Ala  Leu  Arg  Gln  Met  Thr  His  Leu
          6635                    6640                    6645

Ser  Asp  Ala  Gln  Lys  Gln  Ser  Ile  Thr  Gly  Gln  Ile  Asp  Ser  Ala
          6650                    6655                    6660

Thr  Gln  Val  Thr  Gly  Val  Gln  Ser  Val  Lys  Asp  Asn  Ala  Thr  Asn
          6665                    6670                    6675

Leu  Asp  Asn  Ala  Met  Asn  Gln  Leu  Arg  Asn  Ser  Ile  Ala  Asn  Lys
          6680                    6685                    6690

Asp  Asp  Val  Lys  Ala  Ser  Gln  Pro  Tyr  Val  Asp  Ala  Asp  Arg  Asp
          6695                    6700                    6705

Lys  Gln  Asn  Ala  Tyr  Asn  Thr  Ala  Val  Thr  Asn  Ala  Glu  Asn  Ile
          6710                    6715                    6720

Ile  Asn  Ala  Thr  Ser  Gln  Pro  Thr  Leu  Asp  Pro  Ser  Ala  Val  Thr
          6725                    6730                    6735

Gln  Ala  Ala  Asn  Gln  Val  Ser  Thr  Asn  Lys  Thr  Ala  Leu  Asn  Gly
          6740                    6745                    6750

Ala  Gln  Asn  Leu  Ala  Asn  Lys  Lys  Gln  Glu  Thr  Thr  Ala  Asn  Ile
          6755                    6760                    6765

Asn  Gln  Leu  Ser  His  Leu  Asn  Asn  Ala  Gln  Lys  Gln  Asp  Leu  Asn
          6770                    6775                    6780

Thr  Gln  Val  Thr  Asn  Ala  Pro  Asn  Ile  Ser  Thr  Val  Asn  Gln  Val
          6785                    6790                    6795

Lys  Thr  Lys  Ala  Glu  Gln  Leu  Asp  Gln  Ala  Met  Glu  Arg  Leu  Ile
          6800                    6805                    6810

Asn  Gly  Ile  Gln  Asp  Lys  Asp  Gln  Val  Lys  Gln  Ser  Val  Asn  Phe
          6815                    6820                    6825

Thr  Asp  Ala  Asp  Pro  Glu  Lys  Gln  Thr  Ala  Tyr  Asn  Asn  Ala  Val
          6830                    6835                    6840

Thr  Ala  Ala  Glu  Asn  Ile  Ile  Asn  Gln  Ala  Asn  Gly  Thr  Asn  Ala
          6845                    6850                    6855

Asn  Gln  Ser  Gln  Val  Glu  Ala  Ala  Leu  Ser  Thr  Val  Thr  Thr  Thr
          6860                    6865                    6870

Lys  Gln  Ala  Leu  Asn  Gly  Asp  Arg  Lys  Val  Thr  Asp  Ala  Lys  Asn
          6875                    6880                    6885

Asn  Ala  Asn  Gln  Thr  Leu  Ser  Thr  Leu  Asp  Asn  Leu  Asn  Asn  Ala
          6890                    6895                    6900

Gln  Lys  Gly  Ala  Val  Thr  Gly  Asn  Ile  Asn  Gln  Ala  His  Thr  Val
          6905                    6910                    6915
```

```
Ala Glu Val Thr Gln Ala Ile Gln Thr Ala Gln Glu Leu Asn Thr
6920                 6925                 6930

Ala Met Gly Asn Leu Lys Asn Ser Leu Asn Asp Lys Asp Thr Thr
6935                 6940                 6945

Leu Gly Ser Gln Asn Phe Ala Asp Ala Asp Pro Glu Lys Lys Asn
6950                 6955                 6960

Ala Tyr Asn Glu Ala Val His Asn Ala Glu Asn Ile Leu Asn Lys
6965                 6970                 6975

Ser Thr Gly Thr Asn Val Pro Lys Asp Gln Val Glu Ala Ala Met
6980                 6985                 6990

Asn Gln Val Asn Ala Thr Lys Ala Ala Leu Asn Gly Thr Gln Asn
6995                 7000                 7005

Leu Glu Lys Ala Lys Gln His Ala Asn Thr Ala Ile Asp Gly Leu
7010                 7015                 7020

Ser His Leu Thr Asn Ala Gln Lys Glu Ala Leu Lys Gln Leu Val
7025                 7030                 7035

Gln Gln Ser Thr Thr Val Ala Glu Ala Gln Gly Asn Glu Gln Lys
7040                 7045                 7050

Ala Asn Asn Val Asp Ala Ala Met Asp Lys Leu Arg Gln Ser Ile
7055                 7060                 7065

Ala Asp Asn Ala Thr Thr Lys Gln Asn Gln Asn Tyr Thr Asp Ala
7070                 7075                 7080

Ser Gln Asn Lys Lys Asp Ala Tyr Asn Asn Ala Val Thr Thr Ala
7085                 7090                 7095

Gln Gly Ile Ile Asp Gln Thr Thr Ser Pro Thr Leu Asp Pro Thr
7100                 7105                 7110

Val Ile Asn Gln Ala Ala Gly Gln Val Ser Thr Thr Lys Asn Ala
7115                 7120                 7125

Leu Asn Gly Asn Glu Asn Leu Glu Ala Ala Lys Gln Gln Ala Ser
7130                 7135                 7140

Gln Ser Leu Gly Ser Leu Asp Asn Leu Asn Asn Ala Gln Lys Gln
7145                 7150                 7155

Thr Val Thr Asp Gln Ile Asn Gly Ala His Thr Val Asp Glu Ala
7160                 7165                 7170

Asn Gln Ile Lys Gln Asn Ala Gln Asn Leu Asn Thr Ala Met Gly
7175                 7180                 7185

Asn Leu Lys Gln Ala Ile Ala Asp Lys Asp Ala Thr Lys Ala Thr
7190                 7195                 7200

Val Asn Phe Thr Asp Ala Asp Gln Ala Lys Gln Gln Ala Tyr Asn
7205                 7210                 7215

Thr Ala Val Thr Asn Ala Glu Asn Ile Ser Lys Ala Asn Gly Asn
7220                 7225                 7230

Ala Thr Gln Ala Glu Val Glu Gln Ala Ile Lys Gln Val Asn Ala
7235                 7240                 7245

Ala Lys Gln Ala Leu Asn Gly Asn Ala Asn Val Gln His Ala Lys
7250                 7255                 7260

Asp Glu Ala Thr Ala Leu Ile Asn Ser Ser Asn Asp Leu Asn Gln
7265                 7270                 7275

Ala Gln Lys Asp Ala Leu Lys Gln Gln Val Gln Asn Ala Thr Thr
7280                 7285                 7290

Val Ala Gly Val Asn Asn Val Lys Gln Thr Ala Gln Glu Leu Asn
7295                 7300                 7305
```

-continued

Asn Ala Met Thr Gln Leu Lys Gln Gly Ile Ala Asp Lys Glu Gln
7310               7315               7320

Thr Lys Ala Asp Gly Asn Phe Val Asn Ala Asp Pro Asp Lys Gln
7325               7330               7335

Asn Ala Tyr Asn Gln Ala Val Ala Lys Ala Glu Ala Leu Ile Ser
7340               7345               7350

Ala Thr Pro Asp Val Val Val Thr Pro Ser Glu Ile Thr Ala Ala
7355               7360               7365

Leu Asn Lys Val Thr Gln Ala Lys Asn Asp Leu Asn Gly Asn Thr
7370               7375               7380

Asn Leu Ala Thr Ala Lys Gln Asn Val Gln His Ala Ile Asp Gln
7385               7390               7395

Leu Pro Asn Leu Asn Gln Ala Gln Arg Asp Glu Tyr Ser Lys Gln
7400               7405               7410

Ile Thr Gln Ala Thr Leu Val Pro Asn Val Asn Ala Ile Gln Gln
7415               7420               7425

Ala Ala Thr Thr Leu Asn Asp Ala Met Thr Gln Leu Lys Gln Gly
7430               7435               7440

Ile Ala Asn Lys Ala Gln Ile Lys Gly Ser Glu Asn Tyr His Asp
7445               7450               7455

Ala Asp Thr Asp Lys Gln Thr Ala Tyr Asp Asn Ala Val Thr Lys
7460               7465               7470

Ala Glu Glu Leu Leu Lys Gln Thr Thr Asn Pro Thr Met Asp Pro
7475               7480               7485

Asn Thr Ile Gln Gln Ala Leu Thr Lys Val Asn Asp Thr Asn Gln
7490               7495               7500

Ala Leu Asn Gly Asn Gln Lys Leu Ala Asp Ala Lys Gln Asp Ala
7505               7510               7515

Lys Thr Thr Leu Gly Thr Leu Asp His Leu Asn Asp Ala Gln Lys
7520               7525               7530

Gln Ala Leu Thr Thr Gln Val Glu Gln Ala Pro Asp Ile Ala Thr
7535               7540               7545

Val Asn Asn Val Lys Gln Asn Ala Gln Asn Leu Asn Asn Ala Met
7550               7555               7560

Thr Asn Leu Asn Asn Ala Leu Gln Asp Lys Thr Glu Thr Leu Asn
7565               7570               7575

Ser Ile Asn Phe Thr Asp Ala Asp Gln Ala Lys Lys Asp Ala Tyr
7580               7585               7590

Thr Asn Ala Val Ser His Ala Glu Gly Ile Leu Ser Lys Ala Asn
7595               7600               7605

Gly Ser Asn Ala Ser Gln Thr Glu Val Glu Gln Ala Met Gln Arg
7610               7615               7620

Val Asn Glu Ala Lys Gln Ala Leu Asn Gly Asn Asp Asn Val Gln
7625               7630               7635

Arg Ala Lys Asp Ala Ala Lys Gln Val Ile Thr Asn Ala Asn Asp
7640               7645               7650

Leu Asn Gln Ala Gln Lys Asp Ala Leu Lys Gln Gln Val Asp Ala
7655               7660               7665

Ala Gln Thr Val Ala Asn Val Asn Thr Ile Lys Gln Thr Ala Gln
7670               7675               7680

Asp Leu Asn Gln Ala Met Thr Gln Leu Lys Gln Gly Ile Ala Asp
7685               7690               7695

Lys Asp Gln Thr Lys Ala Asn Gly Asn Phe Val Asn Ala Asp Thr

```
                    7700              7705              7710
Asp Lys Gln Asn Ala Tyr Asn Asn Ala Val Ala His Ala Glu Gln
    7715              7720              7725

Ile Ile Ser Gly Thr Pro Asn Ala Asn Val Asp Pro Gln Gln Val
    7730              7735              7740

Ala Gln Ala Leu Gln Gln Val Asn Gln Ala Lys Gly Asp Leu Asn
    7745              7750              7755

Gly Asn His Asn Leu Gln Val Ala Lys Asp Asn Ala Asn Thr Ala
    7760              7765              7770

Ile Asp Gln Leu Pro Asn Leu Asn Gln Pro Gln Lys Thr Ala Leu
    7775              7780              7785

Lys Asp Gln Val Ser His Ala Glu Leu Val Thr Gly Val Asn Ala
    7790              7795              7800

Ile Lys Gln Asn Ala Asp Ala Leu Asn Asn Ala Met Gly Thr Leu
    7805              7810              7815

Lys Gln Gln Ile Gln Ala Asn Ser Gln Val Pro Gln Ser Val Asp
    7820              7825              7830

Phe Thr Gln Ala Asp Gln Asp Lys Gln Gln Ala Tyr Asn Asn Ala
    7835              7840              7845

Ala Asn Gln Ala Gln Gln Ile Ala Asn Gly Ile Pro Thr Pro Val
    7850              7855              7860

Leu Thr Pro Asp Thr Val Thr Gln Ala Val Thr Thr Met Asn Gln
    7865              7870              7875

Ala Lys Asp Ala Leu Asn Gly Asp Glu Lys Leu Ala Gln Ala Lys
    7880              7885              7890

Gln Glu Ala Leu Ala Asn Leu Asp Thr Leu Arg Asp Leu Asn Gln
    7895              7900              7905

Pro Gln Arg Asp Ala Leu Arg Asn Gln Ile Asn Gln Ala Gln Ala
    7910              7915              7920

Leu Ala Thr Val Glu Gln Thr Lys Gln Asn Ala Gln Asn Val Asn
    7925              7930              7935

Thr Ala Met Ser Asn Leu Lys Gln Gly Ile Ala Asn Lys Asp Thr
    7940              7945              7950

Val Lys Ala Ser Glu Asn Tyr His Asp Ala Asp Ala Asp Lys Gln
    7955              7960              7965

Thr Ala Tyr Thr Asn Ala Val Ser Gln Ala Glu Gly Ile Ile Asn
    7970              7975              7980

Gln Thr Thr Asn Pro Thr Leu Asn Pro Asp Glu Ile Thr Arg Ala
    7985              7990              7995

Leu Thr Gln Val Thr Asp Ala Lys Asn Gly Leu Asn Gly Glu Ala
    8000              8005              8010

Lys Leu Ala Thr Glu Lys Gln Asn Ala Lys Asp Ala Val Ser Gly
    8015              8020              8025

Met Thr His Leu Asn Asp Ala Gln Lys Gln Ala Leu Lys Gly Gln
    8030              8035              8040

Ile Asp Gln Ser Pro Glu Ile Ala Thr Val Asn Gln Val Lys Gln
    8045              8050              8055

Thr Ala Thr Ser Leu Asp Gln Ala Met Asp Gln Leu Ser Gln Ala
    8060              8065              8070

Ile Asn Asp Lys Ala Gln Thr Leu Ala Asp Gly Asn Tyr Leu Asn
    8075              8080              8085

Ala Asp Pro Asp Lys Gln Asn Ala Tyr Lys Gln Ala Val Ala Lys
    8090              8095              8100
```

```
Ala Glu Ala Leu Leu Asn Lys Gln Ser Gly Thr Asn Glu Val Gln
    8105            8110                8115

Ala Gln Val Glu Ser Ile Thr Asn Glu Val Asn Ala Ala Lys Gln
    8120            8125                8130

Ala Leu Asn Gly Asn Asp Asn Leu Ala Asn Ala Lys Gln Gln Ala
    8135            8140                8145

Lys Gln Gln Leu Ala Asn Leu Thr His Leu Asn Asp Ala Gln Lys
    8150            8155                8160

Gln Ser Phe Glu Ser Gln Ile Thr Gln Ala Pro Leu Val Thr Asp
    8165            8170                8175

Val Thr Thr Ile Asn Gln Lys Ala Gln Thr Leu Asp His Ala Met
    8180            8185                8190

Glu Leu Leu Arg Asn Ser Val Ala Asp Asn Gln Thr Thr Leu Ala
    8195            8200                8205

Ser Glu Asp Tyr His Asp Ala Thr Ala Gln Arg Gln Asn Asp Tyr
    8210            8215                8220

Asn Gln Ala Val Thr Ala Ala Asn Asn Ile Ile Asn Gln Thr Thr
    8225            8230                8235

Ser Pro Thr Met Asn Pro Asp Asp Val Asn Gly Ala Thr Thr Gln
    8240            8245                8250

Val Asn Asn Thr Lys Val Ala Leu Asp Gly Asp Glu Asn Leu Ala
    8255            8260                8265

Ala Ala Lys Gln Gln Ala Asn Asn Arg Leu Asp Gln Leu Asp His
    8270            8275                8280

Leu Asn Asn Ala Gln Lys Gln Gln Leu Gln Ser Gln Ile Thr Gln
    8285            8290                8295

Ser Ser Asp Ile Ala Ala Val Asn Gly His Lys Gln Thr Ala Glu
    8300            8305                8310

Ser Leu Asn Thr Ala Met Gly Asn Leu Ile Asn Ala Ile Ala Asp
    8315            8320                8325

His Gln Ala Val Glu Gln Arg Gly Asn Phe Ile Asn Ala Asp Thr
    8330            8335                8340

Asp Lys Gln Thr Ala Tyr Asn Thr Ala Val Asn Glu Ala Ala Ala
    8345            8350                8355

Met Ile Asn Lys Gln Thr Gly Gln Asn Ala Asn Gln Thr Glu Val
    8360            8365                8370

Glu Gln Ala Ile Thr Lys Val Gln Thr Thr Leu Gln Ala Leu Asn
    8375            8380                8385

Gly Asp His Asn Leu Gln Val Ala Lys Thr Asn Ala Thr Gln Ala
    8390            8395                8400

Ile Asp Ala Leu Thr Ser Leu Asn Asp Pro Gln Lys Thr Ala Leu
    8405            8410                8415

Lys Asp Gln Val Thr Ala Ala Thr Leu Val Thr Ala Val His Gln
    8420            8425                8430

Ile Glu Gln Asn Ala Asn Thr Leu Asn Gln Ala Met His Gly Leu
    8435            8440                8445

Arg Gln Ser Ile Gln Asp Asn Ala Ala Thr Lys Ala Asn Ser Lys
    8450            8455                8460

Tyr Ile Asn Glu Asp Gln Pro Glu Gln Asn Tyr Asp Gln Ala
    8465            8470                8475

Val Gln Ala Ala Asn Asn Ile Ile Asn Glu Gln Thr Ala Thr Leu
    8480            8485                8490
```

```
Asp Asn Asn Ala Ile Asn Gln Ala Ala Thr Thr Val Asn Thr Thr
    8495            8500            8505

Lys Ala Ala Leu His Gly Asp Val Lys Leu Gln Asn Asp Lys Asp
    8510            8515            8520

His Ala Lys Gln Thr Val Ser Gln Leu Ala His Leu Asn Asn Ala
    8525            8530            8535

Gln Lys His Met Glu Asp Thr Leu Ile Asp Ser Glu Thr Thr Arg
    8540            8545            8550

Thr Ala Val Lys Gln Asp Leu Thr Glu Ala Gln Ala Leu Asp Gln
    8555            8560            8565

Leu Met Asp Ala Leu Gln Gln Ser Ile Ala Asp Lys Asp Ala Thr
    8570            8575            8580

Arg Ala Ser Ser Ala Tyr Val Asn Ala Glu Pro Asn Lys Lys Gln
    8585            8590            8595

Ser Tyr Asp Glu Ala Val Gln Asn Ala Glu Ser Ile Ile Ala Gly
    8600            8605            8610

Leu Asn Asn Pro Thr Ile Asn Lys Gly Asn Val Ser Ser Ala Thr
    8615            8620            8625

Gln Ala Val Ile Ser Ser Lys Asn Ala Leu Asp Gly Val Glu Arg
    8630            8635            8640

Leu Ala Gln Asp Lys Gln Thr Ala Gly Asn Ser Leu Asn His Leu
    8645            8650            8655

Asp Gln Leu Thr Pro Ala Gln Gln Ala Leu Glu Asn Gln Ile
    8660            8665            8670

Asn Asn Ala Thr Thr Arg Gly Glu Val Ala Gln Lys Leu Thr Glu
    8675            8680            8685

Ala Gln Ala Leu Asn Gln Ala Met Glu Ala Leu Arg Asn Ser Ile
    8690            8695            8700

Gln Asp Gln Gln Gln Thr Glu Ala Gly Ser Lys Phe Ile Asn Glu
    8705            8710            8715

Asp Lys Pro Gln Lys Asp Ala Tyr Gln Ala Ala Val Gln Asn Ala
    8720            8725            8730

Lys Asp Leu Ile Asn Gln Thr Asn Asn Pro Thr Leu Asp Lys Ala
    8735            8740            8745

Gln Val Glu Gln Leu Thr Gln Ala Val Asn Gln Ala Lys Asp Asn
    8750            8755            8760

Leu His Gly Asp Gln Lys Leu Ala Asp Lys Gln His Ala Val
    8765            8770            8775

Thr Asp Leu Asn Gln Leu Asn Gly Leu Asn Asn Pro Gln Arg Gln
    8780            8785            8790

Ala Leu Glu Ser Gln Ile Asn Asn Ala Ala Thr Arg Gly Glu Val
    8795            8800            8805

Ala Gln Lys Leu Ala Glu Ala Lys Ala Leu Asp Gln Ala Met Gln
    8810            8815            8820

Ala Leu Arg Asn Ser Ile Gln Asp Gln Gln Gln Thr Glu Ser Gly
    8825            8830            8835

Ser Lys Phe Ile Asn Glu Asp Lys Pro Gln Lys Asp Ala Tyr Gln
    8840            8845            8850

Ala Ala Val Gln Asn Ala Lys Asp Leu Ile Asn Gln Thr Gly Asn
    8855            8860            8865

Pro Thr Leu Asp Lys Ser Gln Val Glu Gln Leu Thr Gln Ala Val
    8870            8875            8880

Thr Thr Ala Lys Asp Asn Leu His Gly Asp Gln Lys Leu Ala Arg
```

-continued

```
         8885                 8890                 8895

Asp Gln Gln Gln Ala Val  Thr Thr Val Asn Ala Leu  Pro Asn Leu
    8900                 8905                 8910

Asn His Ala Gln Gln Gln  Ala Leu Thr Asp Ala Ile  Asn Ala Ala
    8915                 8920                 8925

Pro Thr Arg Thr Glu Val  Ala Gln His Val Gln Thr  Ala Thr Glu
    8930                 8935                 8940

Leu Asp His Ala Met Glu  Thr Leu Lys Asn Lys Val  Asp Gln Val
    8945                 8950                 8955

Asn Thr Asp Lys Ala Gln  Pro Asn Tyr Thr Glu Ala  Ser Thr Asp
    8960                 8965                 8970

Lys Lys Glu Ala Val Asp  Gln Ala Leu Gln Ala Ala  Glu Ser Ile
    8975                 8980                 8985

Thr Asp Pro Thr Asn Gly  Ser Asn Ala Asn Lys Asp  Ala Val Asp
    8990                 8995                 9000

Gln Val Leu Thr Lys Leu  Gln Glu Lys Glu Asn Glu  Leu Asn Gly
    9005                 9010                 9015

Asn Glu Arg Val Ala Glu  Ala Lys Thr Gln Ala Lys  Gln Thr Ile
    9020                 9025                 9030

Asp Gln Leu Thr His Leu  Asn Ala Asp Gln Ile Ala  Thr Ala Lys
    9035                 9040                 9045

Gln Asn Ile Asp Gln Ala  Thr Lys Leu Gln Pro Ile  Ala Glu Leu
    9050                 9055                 9060

Val Asp Gln Ala Thr Gln  Leu Asn Gln Ser Met Asp  Gln Leu Gln
    9065                 9070                 9075

Gln Ala Val Asn Glu His  Ala Asn Val Glu Gln Thr  Val Asp Tyr
    9080                 9085                 9090

Thr Gln Ala Asp Ser Asp  Lys Gln Asn Ala Tyr Lys  Gln Ala Ile
    9095                 9100                 9105

Ala Asp Ala Glu Asn Val  Leu Lys Gln Asn Ala Asn  Lys Gln Gln
    9110                 9115                 9120

Val Asp Gln Ala Leu Gln  Asn Ile Leu Asn Ala Lys  Gln Ala Leu
    9125                 9130                 9135

Asn Gly Asp Glu Arg Val  Ala Leu Ala Lys Thr Asn  Gly Lys His
    9140                 9145                 9150

Asp Ile Asp Gln Leu Asn  Ala Leu Asn Asn Ala Gln  Gln Asp Gly
    9155                 9160                 9165

Phe Lys Gly Arg Ile Asp  Gln Ser Asn Asp Leu Asn  Gln Ile Gln
    9170                 9175                 9180

Gln Ile Val Asp Glu Ala  Lys Ala Leu Asn Arg Ala  Met Asp Gln
    9185                 9190                 9195

Leu Ser Gln Glu Ile Thr  Asp Asn Glu Gly Arg Thr  Lys Gly Ser
    9200                 9205                 9210

Thr Asn Tyr Val Asn Ala  Asp Thr Gln Val Lys Gln  Val Tyr Asp
    9215                 9220                 9225

Glu Thr Val Asp Lys Ala  Lys Gln Ala Leu Asp Lys  Ser Thr Gly
    9230                 9235                 9240

Gln Asn Leu Thr Ala Lys  Gln Val Ile Lys Leu Asn  Asp Ala Val
    9245                 9250                 9255

Thr Ala Ala Lys Lys Ala  Leu Asn Gly Glu Glu Arg  Leu Asn Asn
    9260                 9265                 9270

Arg Lys Ala Glu Ala Leu  Gln Arg Leu Asp Gln Leu  Thr His Leu
    9275                 9280                 9285
```

-continued

```
Asn Asn Ala Gln Arg Gln Leu Ala Ile Gln Gln Ile Asn Asn Ala
    9290                9295                9300

Glu Thr Leu Asn Lys Ala Ser Arg Ala Ile Asn Arg Ala Thr Lys
    9305                9310                9315

Leu Asp Asn Ala Met Gly Ala Val Gln Gln Tyr Ile Asp Glu Gln
    9320                9325                9330

His Leu Gly Val Ile Ser Ser Thr Asn Tyr Ile Asn Ala Asp Asp
    9335                9340                9345

Asn Leu Lys Ala Asn Tyr Asp Asn Ala Ile Ala Asn Ala Ala His
    9350                9355                9360

Glu Leu Asp Lys Val Gln Gly Asn Ala Ile Ala Lys Ala Glu Ala
    9365                9370                9375

Glu Gln Leu Lys Gln Asn Ile Ile Asp Ala Gln Asn Ala Leu Asn
    9380                9385                9390

Gly Asp Gln Asn Leu Ala Asn Ala Lys Asp Lys Ala Asn Ala Phe
    9395                9400                9405

Val Asn Ser Leu Asn Gly Leu Asn Gln Gln Gln Asp Leu Ala
    9410                9415                9420

His Lys Ala Ile Asn Asn Ala Asp Thr Val Ser Asp Val Thr Asp
    9425                9430                9435

Ile Val Asn Asn Gln Ile Asp Leu Asn Asp Ala Met Glu Thr Leu
    9440                9445                9450

Lys His Leu Val Asp Asn Glu Ile Pro Asn Ala Glu Gln Thr Val
    9455                9460                9465

Asn Tyr Gln Asn Ala Asp Asp Asn Ala Lys Thr Asn Phe Asp Asp
    9470                9475                9480

Ala Lys Arg Leu Ala Asn Thr Leu Leu Asn Ser Asp Asn Thr Asn
    9485                9490                9495

Val Asn Asp Ile Asn Gly Ala Ile Gln Ala Val Asn Asp Ala Ile
    9500                9505                9510

His Asn Leu Asn Gly Asp Gln Arg Leu Gln Asp Ala Lys Asp Lys
    9515                9520                9525

Ala Ile Gln Ser Ile Asn Gln Ala Leu Ala Asn Lys Leu Lys Glu
    9530                9535                9540

Ile Glu Ala Ser Asn Ala Thr Asp Gln Asp Lys Leu Ile Ala Lys
    9545                9550                9555

Asn Lys Ala Glu Glu Leu Ala Asn Ser Ile Ile Asn Asn Ile Asn
    9560                9565                9570

Lys Ala Thr Ser Asn Gln Ala Val Ser Gln Val Gln Thr Ala Gly
    9575                9580                9585

Asn His Ala Ile Glu Gln Val His Ala Asn Glu Ile Pro Lys Ala
    9590                9595                9600

Lys Ile Asp Ala Asn Lys Asp Val Asp Lys Gln Val Gln Ala Leu
    9605                9610                9615

Ile Asp Glu Ile Asp Arg Asn Pro Asn Leu Thr Asp Lys Glu Lys
    9620                9625                9630

Gln Ala Leu Lys Asp Arg Ile Asn Gln Ile Leu Gln Gln Gly His
    9635                9640                9645

Asn Gly Ile Asn Asn Ala Met Thr Lys Glu Glu Ile Glu Gln Ala
    9650                9655                9660

Lys Ala Gln Leu Ala Gln Ala Leu Gln Asp Ile Lys Asp Leu Val
    9665                9670                9675
```

```
Lys Ala Lys Glu Asp Ala Lys Gln Asp Val Asp Lys Gln Val Gln
9680              9685              9690

Ala Leu Ile Asp Glu Ile Asp Gln Asn Pro Asn Leu Thr Asp Lys
9695              9700              9705

Glu Lys Gln Ala Leu Lys Tyr Arg Ile Asn Gln Ile Leu Gln Gln
9710              9715              9720

Gly His Asn Asp Ile Asn Asn Ala Leu Thr Lys Glu Glu Ile Glu
9725              9730              9735

Gln Ala Lys Ala Gln Leu Ala Gln Ala Leu Gln Asp Ile Lys Asp
9740              9745              9750

Leu Val Lys Ala Lys Glu Asp Ala Lys Asn Ala Ile Lys Ala Leu
9755              9760              9765

Ala Asn Ala Lys Arg Asp Gln Ile Asn Ser Asn Pro Asp Leu Thr
9770              9775              9780

Pro Glu Gln Lys Ala Lys Ala Leu Lys Glu Ile Asp Glu Ala Glu
9785              9790              9795

Lys Arg Ala Leu Gln Asn Val Glu Asn Ala Gln Thr Ile Asp Gln
9800              9805              9810

Leu Asn Arg Gly Leu Asn Leu Gly Leu Asp Asp Ile Arg Asn Thr
9815              9820              9825

His Val Trp Glu Val Asp Glu Gln Pro Ala Val Asn Glu Ile Phe
9830              9835              9840

Glu Ala Thr Pro Glu Gln Ile Leu Val Asn Gly Glu Leu Ile Val
9845              9850              9855

His Arg Asp Asp Ile Ile Thr Glu Gln Asp Ile Leu Ala His Ile
9860              9865              9870

Asn Leu Ile Asp Gln Leu Ser Ala Glu Val Ile Asp Thr Pro Ser
9875              9880              9885

Thr Ala Thr Ile Ser Asp Ser Leu Thr Ala Lys Val Glu Val Thr
9890              9895              9900

Leu Leu Asp Gly Ser Lys Val Ile Val Asn Val Pro Val Lys Val
9905              9910              9915

Val Glu Lys Glu Leu Ser Val Val Lys Gln Gln Ala Ile Glu Ser
9920              9925              9930

Ile Glu Asn Ala Ala Gln Gln Lys Ile Asn Glu Ile Asn Asn Ser
9935              9940              9945

Val Thr Leu Thr Leu Glu Gln Lys Glu Ala Ala Ile Ala Glu Val
9950              9955              9960

Asn Lys Leu Lys Gln Gln Ala Ile Asp His Val Asn Asn Ala Pro
9965              9970              9975

Asp Val His Ser Val Glu Glu Ile Gln Gln Gln Glu Gln Ala His
9980              9985              9990

Ile Glu Gln Phe Asn Pro Glu Gln Phe Thr Ile Glu Gln Ala Lys
9995              10000              10005

Ser Asn Ala Ile Lys Ser Ile Glu Asp Ala Ile Gln His Met Ile
10010             10015              10020

Asp Glu Ile Lys Ala Arg Thr Asp Leu Thr Asp Lys Glu Lys Gln
10025             10030              10035

Glu Ala Ile Ala Lys Leu Asn Gln Leu Lys Glu Gln Ala Ile Gln
10040             10045              10050

Ala Ile Gln Arg Ala Gln Ser Ile Asp Glu Ile Ser Glu Gln Leu
10055             10060              10065

Glu Gln Phe Lys Ala Gln Met Lys Ala Ala Asn Pro Thr Ala Lys
```

```
                10070               10075               10080
Glu Leu Ala Lys Arg Lys Gln Glu Ala Ile Ser Arg Ile Lys Asp
                10085               10090               10095
Phe Ser Asn Glu Lys Ile Asn Ser Ile Arg Asn Ser Glu Ile Gly
                10100               10105               10110
Thr Ala Asp Glu Lys Gln Ala Ala Met Asn Gln Ile Asn Glu Ile
                10115               10120               10125
Val Leu Glu Thr Ile Arg Asp Ile Asn Asn Ala His Thr Leu Gln
                10130               10135               10140
Gln Val Glu Ala Ala Leu Asn Asn Gly Ile Ala Arg Ile Ser Ala
                10145               10150               10155
Val Gln Ile Val Thr Ser Asp Arg Ala Lys Gln Ser Ser Ser Thr
                10160               10165               10170
Gly Asn Glu Ser Asn Ser His Leu Thr Ile Gly Tyr Gly Thr Ala
                10175               10180               10185
Asn His Pro Phe Asn Ser Ser Thr Ile Gly His Lys Lys Lys Leu
                10190               10195               10200
Asp Glu Asp Asp Asp Ile Asp Pro Leu His Met Arg His Phe Ser
                10205               10210               10215
Asn Asn Phe Gly Asn Val Ile Lys Asn Ala Ile Gly Val Val Gly
                10220               10225               10230
Ile Ser Gly Leu Leu Ala Ser Phe Trp Phe Phe Ile Ala Lys Arg
                10235               10240               10245
Arg Arg Lys Glu Asp Glu Glu Glu Glu Leu Glu Ile Arg Asp Asn
                10250               10255               10260
Asn Lys Asp Ser Ile Lys Glu Thr Leu Asp Asp Thr Lys His Leu
                10265               10270               10275
Pro Leu Leu Phe Ala Lys Arg Arg Arg Lys Glu Asp Glu Glu Asp
                10280               10285               10290
Val Thr Val Glu Glu Lys Asp Ser Leu Asn Asn Gly Glu Ser Leu
                10295               10300               10305
Asp Lys Val Lys His Thr Pro Phe Phe Leu Pro Lys Arg Arg Arg
                10310               10315               10320
Lys Glu Asp Glu Glu Asp Val Glu Val Thr Asn Glu Asn Thr Asp
                10325               10330               10335
Glu Lys Val Leu Lys Asp Asn Glu His Ser Pro Leu Leu Phe Ala
                10340               10345               10350
Lys Arg Arg Lys Asp Lys Glu Glu Asp Val Glu Thr Thr Thr Ser
                10355               10360               10365
Ile Glu Ser Lys Asp Glu Asp Val Pro Leu Leu Leu Ala Lys Lys
                10370               10375               10380
Lys Asn Gln Lys Asp Asn Gln Ser Lys Asp Lys Lys Ser Ala Ser
                10385               10390               10395
Lys Asn Thr Ser Lys Lys Val Ala Ala Lys Lys Lys Lys Lys Lys
                10400               10405               10410
Ala Lys Lys Asn Lys Lys
        10415
```

<210> SEQ ID NO 25
<211> LENGTH: 340
<212> TYPE: PRT
<213> ORGANISM: Staphylococcus sp.

<400> SEQUENCE: 25

Met Lys Lys Lys Leu Leu Val Leu Thr Met Ser Thr Leu Phe Ala Thr
1               5                   10                  15

Gln Ile Met Asn Ser Asn His Ala Lys Ala Ser Val Thr Glu Ser Val
            20                  25                  30

Asp Lys Lys Phe Val Val Pro Glu Ser Gly Ile Asn Lys Ile Ile Pro
        35                  40                  45

Ala Tyr Asp Glu Phe Lys Asn Ser Pro Lys Val Asn Val Ser Asn Leu
    50                  55                  60

Thr Asp Asn Lys Asn Phe Val Ala Ser Glu Lys Leu Asn Lys Ile
65                  70                  75                  80

Ala Asp Ser Ser Ala Ala Ser Lys Ile Val Asp Lys Asn Phe Val Val
            85                  90                  95

Pro Glu Ser Lys Leu Gly Asn Ile Val Pro Glu Tyr Lys Glu Ile Asn
            100                 105                 110

Asn Arg Val Asn Val Ala Thr Asn Asn Pro Ala Ser Gln Gln Val Asp
            115                 120                 125

Lys His Phe Val Ala Lys Gly Pro Glu Val Asn Arg Phe Ile Thr Gln
    130                 135                 140

Asn Lys Val Asn His His Phe Ile Thr Thr Gln Thr His Tyr Lys Lys
145                 150                 155                 160

Val Ile Thr Ser Tyr Lys Ser Thr His Val His Lys His Val Asn His
                165                 170                 175

Ala Lys Asp Ser Ile Asn Lys His Phe Ile Val Lys Pro Ser Glu Ser
            180                 185                 190

Pro Arg Tyr Thr His Pro Ser Gln Ser Leu Ile Ile Lys His His Phe
    195                 200                 205

Ala Val Pro Gly Tyr His Ala His Lys Phe Val Thr Pro Gly His Ala
    210                 215                 220

Ser Ile Lys Ile Asn His Phe Cys Val Val Pro Gln Ile Asn Ser Phe
225                 230                 235                 240

Lys Val Ile Pro Pro Tyr Gly His Asn Ser His Arg Met His Val Pro
            245                 250                 255

Ser Phe Gln Asn Asn Thr Thr Ala Thr His Gln Asn Ala Lys Val Asn
            260                 265                 270

Lys Ala Tyr Asp Tyr Lys Tyr Phe Tyr Ser Tyr Lys Val Val Lys Gly
    275                 280                 285

Val Lys Lys Tyr Phe Ser Phe Ser Gln Ser Asn Gly Tyr Lys Ile Gly
    290                 295                 300

Lys Pro Ser Leu Asn Ile Lys Asn Val Asn Tyr Gln Tyr Ala Val Pro
305                 310                 315                 320

Ser Tyr Ser Pro Thr His Tyr Val Pro Glu Phe Lys Gly Ser Leu Pro
                325                 330                 335

Ala Pro Arg Val
            340

<210> SEQ ID NO 26
<211> LENGTH: 130
<212> TYPE: PRT
<213> ORGANISM: Staphylococcus sp.

<400> SEQUENCE: 26

Met Asn Phe Asn Asp Ile Glu Thr Met Val Lys Ser Lys Phe Lys Asp
1               5                   10                  15

Ile Lys Lys His Ala Glu Glu Ile Ala His Glu Ile Glu Val Arg Ser
            20                  25                  30

```
Gly Tyr Leu Arg Lys Ala Glu Gln Tyr Lys Arg Leu Glu Phe Asn Leu
            35                  40                  45

Ser Phe Ala Leu Asp Asp Ile Glu Ser Thr Ala Lys Asp Val Gln Thr
 50                      55                  60

Ala Lys Ser Ser Ala Asn Lys Asp Ser Val Thr Val Lys Gly Lys Ala
 65                  70                  75                  80

Pro Asn Thr Leu Tyr Ile Glu Lys Arg Asn Leu Met Lys Gln Lys Leu
                 85                  90                  95

Glu Met Leu Gly Glu Asp Ile Asp Lys Asn Lys Glu Ser Leu Gln Lys
            100                 105                 110

Ala Lys Glu Ile Ala Gly Glu Lys Ala Ser Glu Tyr Phe Asn Lys Ala
            115                 120                 125

Met Asn
    130

<210> SEQ ID NO 27
<211> LENGTH: 636
<212> TYPE: PRT
<213> ORGANISM: Staphylococcus sp.

<400> SEQUENCE: 27

Met Lys Lys Gln Ile Ile Ser Leu Gly Ala Leu Ala Val Ala Ser Ser
 1               5                  10                  15

Leu Phe Thr Trp Asp Asn Lys Ala Asp Ala Ile Val Thr Lys Asp Tyr
             20                  25                  30

Ser Gly Lys Ser Gln Val Asn Ala Gly Ser Lys Asn Gly Thr Leu Ile
            35                  40                  45

Asp Ser Arg Tyr Leu Asn Ser Ala Leu Tyr Tyr Leu Glu Asp Tyr Ile
 50                      55                  60

Ile Tyr Ala Ile Gly Leu Thr Asn Lys Tyr Glu Tyr Gly Asp Asn Ile
 65                  70                  75                  80

Tyr Lys Glu Ala Lys Asp Arg Leu Leu Glu Lys Val Leu Arg Glu Asp
                 85                  90                  95

Gln Tyr Leu Leu Glu Arg Lys Lys Ser Gln Tyr Glu Asp Tyr Lys Gln
            100                 105                 110

Trp Tyr Ala Asn Tyr Lys Lys Glu Asn Pro Arg Thr Asp Leu Lys Met
            115                 120                 125

Ala Asn Phe His Lys Tyr Asn Leu Glu Glu Leu Ser Met Lys Glu Tyr
130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
            195                 200                 205

Glu His Ala Lys Glu Leu Arg Ala Lys Leu Asp Leu Ile Leu Gly Asp
210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Asp Phe Phe Met Glu Thr Lys
                245                 250                 255

Gln Asn Arg Pro Lys Ser Ile Thr Lys Tyr Asn Pro Thr Thr His Asn
```

```
                260                 265                 270
Tyr Lys Thr Asn Ser Asp Asn Lys Pro Asn Phe Asp Lys Leu Val Glu
            275                 280                 285

Glu Thr Lys Lys Ala Val Lys Glu Ala Asp Asp Ser Trp Lys Lys Lys
        290                 295                 300

Thr Val Lys Lys Tyr Gly Glu Thr Glu Thr Lys Ser Pro Val Val Lys
305                 310                 315                 320

Glu Glu Lys Lys Val Glu Glu Pro Gln Ala Pro Lys Val Asp Asn Gln
                325                 330                 335

Gln Glu Val Lys Thr Thr Ala Gly Lys Ala Glu Glu Thr Thr Gln Pro
            340                 345                 350

Val Ala Gln Pro Leu Val Lys Ile Pro Gln Gly Thr Ile Thr Gly Glu
        355                 360                 365

Ile Val Lys Gly Pro Glu Tyr Pro Thr Met Glu Asn Lys Thr Val Gln
370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
                405                 410                 415

Leu Glu Gly Leu Glu Gly Ser Ser Ser Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Glu Ala Ser Gln Tyr Gly
            450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr His Ala Asn Gly Gln Val Ser Tyr Gly Ala Arg Pro Thr Tyr
        515                 520                 525

Lys Lys Pro Ser Glu Thr Asn Ala Tyr Asn Val Thr Thr His Ala Asn
530                 535                 540

Gly Gln Val Ser Tyr Gly Ala Arg Pro Thr Gln Asn Lys Pro Ser Lys
545                 550                 555                 560

Thr Asn Ala Tyr Asn Val Thr Thr His Gly Asn Gly Gln Val Ser Tyr
                565                 570                 575

Gly Ala Arg Pro Thr Gln Asn Lys Pro Ser Lys Thr Asn Ala Tyr Asn
            580                 585                 590

Val Thr Thr His Ala Asn Gly Gln Val Ser Tyr Gly Ala Arg Pro Thr
        595                 600                 605

Tyr Lys Lys Pro Ser Lys Thr Asn Ala Tyr Asn Val Thr Thr His Ala
610                 615                 620

Asp Gly Thr Ala Thr Tyr Gly Pro Arg Val Thr Lys
625                 630                 635

<210> SEQ ID NO 28
<211> LENGTH: 745
<212> TYPE: PRT
<213> ORGANISM: Staphylococcus sp.

<400> SEQUENCE: 28
```

```
Ala Glu Gln His Thr Pro Met Lys Ala His Ala Val Thr Thr Ile Asp
1               5                   10                  15

Lys Ala Thr Thr Asp Lys Gln Gln Val Pro Pro Thr Lys Glu Ala Ala
            20                  25                  30

His His Ser Gly Lys Glu Ala Ala Thr Asn Val Ser Ala Ser Ala Gln
        35                  40                  45

Gly Thr Ala Asp Asp Thr Asn Ser Lys Val Thr Ser Asn Ala Pro Ser
    50                  55                  60

Asn Lys Pro Ser Thr Val Val Ser Thr Lys Val Asn Glu Thr Arg Asp
65                  70                  75                  80

Val Asp Thr Gln Gln Ala Ser Thr Gln Lys Pro Thr His Thr Ala Thr
                85                  90                  95

Phe Lys Leu Ser Asn Ala Lys Thr Ala Ser Leu Ser Pro Arg Met Phe
            100                 105                 110

Ala Ala Asn Ala Pro Gln Thr Thr Thr His Lys Ile Leu His Thr Asn
            115                 120                 125

Asp Ile His Gly Arg Leu Ala Glu Glu Lys Gly Arg Val Ile Gly Met
        130                 135                 140

Ala Lys Leu Lys Thr Val Lys Glu Gln Glu Lys Pro Asp Leu Met Leu
145                 150                 155                 160

Asp Ala Gly Asp Ala Phe Gln Gly Leu Pro Leu Ser Asn Gln Ser Lys
                165                 170                 175

Gly Glu Glu Met Ala Lys Ala Met Asn Ala Val Gly Tyr Asp Ala Met
            180                 185                 190

Ala Val Gly Asn His Glu Phe Asp Phe Gly Tyr Asp Gln Leu Lys Lys
        195                 200                 205

Leu Glu Gly Met Leu Asp Phe Pro Met Leu Ser Thr Asn Val Tyr Lys
210                 215                 220

Asp Gly Lys Arg Ala Phe Lys Pro Ser Thr Ile Val Thr Lys Asn Gly
225                 230                 235                 240

Ile Arg Tyr Gly Ile Ile Gly Val Thr Thr Pro Glu Thr Lys Thr Lys
                245                 250                 255

Thr Arg Pro Glu Gly Ile Lys Gly Val Glu Phe Arg Asp Pro Leu Gln
            260                 265                 270

Ser Val Thr Ala Glu Met Met Arg Ile Tyr Lys Asp Val Asp Thr Phe
            275                 280                 285

Val Val Ile Ser His Leu Gly Ile Asp Pro Ser Thr Gln Glu Thr Trp
        290                 295                 300

Arg Gly Asp Tyr Leu Val Lys Gln Leu Ser Gln Asn Pro Gln Leu Lys
305                 310                 315                 320

Lys Arg Ile Thr Val Ile Asp Gly His Ser His Thr Val Leu Gln Asn
                325                 330                 335

Gly Gln Ile Tyr Asn Asn Asp Ala Leu Ala Gln Thr Gly Thr Ala Leu
            340                 345                 350

Ala Asn Ile Gly Lys Ile Thr Phe Asn Tyr Arg Asn Gly Glu Val Ser
        355                 360                 365

Asn Ile Lys Pro Ser Leu Ile Asn Val Lys Asp Val Glu Asn Val Thr
    370                 375                 380

Pro Asn Lys Ala Leu Ala Glu Gln Ile Asn Gln Ala Asp Gln Thr Phe
385                 390                 395                 400

Arg Ala Gln Thr Ala Glu Val Ile Ile Pro Asn Asn Thr Ile Asp Phe
                405                 410                 415

Lys Gly Glu Arg Asp Asp Val Arg Thr Arg Glu Thr Asn Leu Gly Asn
```

Ala Ile Ala Asp Ala Met Glu Ala Tyr Gly Val Lys Asn Phe Ser Lys
            420                 425                 430

Lys Thr Asp Phe Ala Val Thr Asn Gly Gly Ile Arg Ala Ser Ile
    435                 440                 445

Ala Lys Gly Lys Val Thr Arg Tyr Asp Leu Ile Ser Val Leu Pro Phe
465                 470                 475                 480

Gly Asn Thr Ile Ala Gln Ile Asp Val Lys Gly Ser Asp Val Trp Thr
                485                 490                 495

Ala Phe Glu His Ser Leu Gly Ala Pro Thr Thr Gln Lys Asp Gly Lys
                500                 505                 510

Thr Val Leu Thr Ala Asn Gly Leu Leu His Ile Ser Asp Ser Ile
    515                 520                 525

Arg Val Tyr Tyr Asp Ile Asn Lys Pro Ser Gly Lys Arg Ile Asn Ala
    530                 535                 540

Ile Gln Ile Leu Asn Lys Glu Thr Gly Lys Phe Glu Asn Ile Asp Leu
545                 550                 555                 560

Lys Arg Val Tyr His Val Thr Met Asn Asp Phe Thr Ala Ser Gly Gly
                565                 570                 575

Asp Gly Tyr Ser Met Phe Gly Gly Pro Arg Glu Gly Ile Ser Leu
                580                 585                 590

Asp Gln Val Leu Ala Ser Tyr Leu Lys Thr Ala Asn Leu Ala Lys Tyr
                595                 600                 605

Asp Thr Thr Glu Pro Gln Arg Met Leu Leu Gly Lys Pro Ala Val Ser
    610                 615                 620

Glu Gln Pro Ala Lys Gly Gln Gly Ser Lys Gly Ser Lys Ser Gly
625                 630                 635                 640

Lys Asp Thr Gln Pro Ile Gly Asp Asp Lys Val Met Asp Pro Ala Lys
                645                 650                 655

Lys Pro Ala Pro Gly Lys Val Val Leu Leu Ala His Arg Gly Thr
                660                 665                 670

Val Ser Ser Gly Thr Glu Gly Ser Gly Arg Thr Ile Glu Gly Ala Thr
    675                 680                 685

Val Ser Ser Lys Ser Gly Lys Gln Leu Ala Arg Met Ser Val Pro Lys
    690                 695                 700

Gly Ser Ala His Glu Lys Gln Leu Pro Lys Thr Gly Thr Asn Gln Ser
705                 710                 715                 720

Ser Ser Pro Glu Ala Met Phe Val Leu Leu Ala Gly Ile Gly Leu Ile
                725                 730                 735

Ala Thr Val Arg Arg Arg Lys Ala Ser
                740                 745

<210> SEQ ID NO 29
<211> LENGTH: 628
<212> TYPE: PRT
<213> ORGANISM: Staphylococcus sp.

<400> SEQUENCE: 29

Met Ser Asp Arg Phe Ile Lys Phe Asn Asp Glu Gln Leu Asp Ala Lys
1               5                   10                  15

Gln Val Met Met Leu Gln Asp Leu Ala Arg Leu Leu Leu Lys Asn Glu
                20                  25                  30

Gln Thr Gln Val Lys Ile Gln Lys Phe Pro Tyr Tyr Asn Pro Val Gln
            35                  40                  45

```
Asn Val Leu Ile Thr Ser Trp Phe Trp Ser His Arg Pro Ser His Ile
 50                  55                  60
Glu Met Ala Gly Leu Lys Thr Asp Val Met Leu Ala Ala Tyr Gly Tyr
 65                  70                  75                  80
His Met Met Asp Val Gln Ile Val Asn Glu Val Val Gln Asp Lys Thr
                     85                  90                  95
Phe Lys His Pro Lys Phe Tyr Gln Gln Leu Phe Lys Leu Leu Glu Asp
                    100                 105                 110
Met Arg Val Leu Asn Ser Ile Lys Val Glu Arg Pro Ser Thr Ala Lys
                115                 120                 125
Leu Ile Asp Leu Arg Leu Asp Thr Arg Ile Ser Tyr Thr Glu Ser Gln
130                 135                 140
Ile Lys Val Tyr Arg Thr Lys Thr Gln Tyr Thr Asp Leu Leu Phe Leu
145                 150                 155                 160
Tyr Leu Glu His Ala Phe Leu Ser Gln Asp Phe Phe Asp Ile Pro Ser
                165                 170                 175
Ile His Ser Asp Leu Asp Asp Ile Leu Val Asn Met Phe Leu Tyr Leu
                180                 185                 190
Pro Asn Phe Phe Gln Asn Gln Asn Ser Glu Asp Asn Met Tyr Leu Ala
                195                 200                 205
Gln Arg Ile Met Tyr Gln Val Asp Asp Ile Leu Lys Glu Asp Met Leu
                210                 215                 220
Asn Glu Tyr Tyr Tyr Leu Pro Lys Thr Leu Tyr Asn Thr Leu Ala Ser
225                 230                 235                 240
Pro Glu Phe Asp Asp Leu Lys Arg Thr Asp Ala Ser Gln Val Asp Gly
                245                 250                 255
Gln Asp Asp Thr Ser Glu Asp Asp Asn Glu Ser Glu Lys Ala Asp
                260                 265                 270
Ser Lys Ser Ala Asp Ser Glu Ser Lys Gly Gly Ala Tyr Leu Glu Met
            275                 280                 285
Glu Leu His Glu Gly Gln Asn Ser Glu Thr Leu Gly Asn Asp Glu Ala
                290                 295                 300
Arg Glu Gly Asp Ala Thr Asp Asp Met Thr Asp Met Met Thr Lys Lys
305                 310                 315                 320
Gly Lys Gly Ser Asn Asp Thr Leu Asn Arg Glu Glu Gly Asp Ala Val
                325                 330                 335
Gly Gln Ser Gln Ala Phe Gln Leu Asp Gly Val Asn Lys Asn Val Glu
            340                 345                 350
Ile Lys Trp Gln Ile Pro Glu Ile Glu Pro Gln Tyr Val Leu Glu Tyr
            355                 360                 365
Gln Glu Ser Lys Gln Asp Val Gln Tyr Glu Ile Lys Asp Leu Ile Gln
        370                 375                 380
Ile Ile Lys Lys Thr Ile Glu Arg Glu Gln Arg Asp Ala Arg Phe Asn
385                 390                 395                 400
Leu Thr Lys Gly Arg Leu Gln Lys Asp Leu Ile Asn Trp Phe Ile Asp
                405                 410                 415
Asp Gln Tyr Lys Leu Phe Tyr Lys Lys Gln Asp Leu Ser Lys Ser Phe
                420                 425                 430
Asp Ala Thr Phe Thr Leu Leu Ile Asp Ala Ser Ala Ser Met His Asp
                435                 440                 445
Lys Met Ala Glu Thr Lys Lys Gly Val Val Leu Phe His Glu Thr Leu
                450                 455                 460
Lys Ala Leu Asn Ile Lys His Glu Ile Leu Ser Phe Ser Glu Asp Ala
```

```
            465                 470                 475                 480

Phe Asp Ser Asp Glu His Ala Gln Pro Asn Ile Ile Asn Glu Ile Ile
                    485                 490                 495

Asn Tyr Asp Tyr Ser Thr Phe Glu Lys Asp Gly Pro Arg Ile Met Ala
                500                 505                 510

Leu Glu Pro Gln Asp Asp Asn Arg Asp Gly Val Ala Ile Arg Val Ala
                515                 520                 525

Ser Glu Arg Leu Met Arg Arg Asn Gln His Gln Arg Phe Leu Ile Val
                530                 535                 540

Phe Ser Asp Gly Glu Pro Ser Ala Phe Asn Tyr Ser Gln Asp Gly Ile
    545                 550                 555                 560

Ile Asp Thr Tyr Glu Ala Val Glu Met Ser Arg Lys Phe Gly Ile Glu
                    565                 570                 575

Val Phe Asn Val Phe Leu Ser Gln Asp Pro Ile Thr Glu Asp Val Glu
                    580                 585                 590

Gln Thr Ile His Asn Ile Tyr Gly Gln Tyr Ala Ile Phe Val Glu Gly
                    595                 600                 605

Val Ala His Leu Pro Gly His Leu Ser Pro Leu Leu Lys Leu Leu
                610                 615                 620

Leu Lys Ser Leu
    625

<210> SEQ ID NO 30
<211> LENGTH: 154
<212> TYPE: PRT
<213> ORGANISM: Staphylococcus sp.

<400> SEQUENCE: 30

Ala Glu Ile Asn Lys Gln Thr Thr Ser Gln Gly Val Thr Thr Glu Lys
    1               5                   10                  15

Asn Asn Gly Ile Ala Val Leu Glu Gln Asp Val Ile Thr Pro Thr Val
                    20                  25                  30

Lys Pro Gln Ala Lys Gln Asp Ile Ile Gln Ala Val Thr Thr Arg Lys
                35                  40                  45

Gln Gln Ile Lys Lys Ser Asn Ala Ser Leu Gln Asp Glu Lys Asp Val
                50                  55                  60

Ala Asn Asp Lys Ile Gly Lys Ile Glu Thr Lys Ala Ile Lys Asp Ile
    65                  70                  75                  80

Asp Ala Ala Thr Thr Asn Ala Gln Val Glu Ala Ile Lys Thr Lys Ala
                    85                  90                  95

Ile Asn Asp Ile Asn Gln Thr Thr Pro Ala Thr Thr Ala Lys Ala Ala
                    100                 105                 110

Ala Leu Glu Glu Phe Asp Glu Val Val Gln Ala Gln Ile Asp Gln Ala
                115                 120                 125

Pro Leu Asn Pro Asp Thr Thr Asn Glu Glu Val Ala Glu Ala Ile Glu
                130                 135                 140

Arg Ile Asn Ala Ala Lys Val Ser Gly Val
    145                 150

<210> SEQ ID NO 31
<211> LENGTH: 584
<212> TYPE: PRT
<213> ORGANISM: Staphylococcus sp.

<400> SEQUENCE: 31

Met Lys Phe Lys Ser Leu Ile Thr Thr Thr Leu Ala Leu Gly Val Leu
```

-continued

```
1               5                   10                  15
Ala Ser Thr Gly Ala Asn Phe Asn Asn Asn Glu Ala Ser Ala Ala Ala
                20                  25                  30

Lys Pro Leu Asp Lys Ser Ser Ser Leu His His Gly Tyr Ser Lys
            35                  40                  45

Val His Val Pro Tyr Ala Ile Thr Val Asn Gly Thr Ser Gln Asn Ile
        50                  55                  60

Leu Ser Ser Leu Thr Phe Asn Lys Asn Gln Asn Ile Ser Tyr Lys Asp
65                  70                  75                  80

Leu Glu Asp Arg Val Lys Ser Val Leu Lys Ser Asp Arg Gly Ile Ser
                85                  90                  95

Asp Ile Asp Leu Arg Leu Ser Lys Gln Ala Lys Tyr Thr Val Tyr Phe
                100                 105                 110

Lys Asn Gly Thr Lys Lys Val Ile Asp Leu Lys Ala Gly Ile Tyr Thr
                115                 120                 125

Ala Asp Leu Ile Asn Thr Ser Glu Ile Lys Ala Ile Asn Ile Asn Val
        130                 135                 140

Asp Thr Lys Lys Gln Val Glu Asp Lys Lys Asp Lys Ala Asn Tyr
145                 150                 155                 160

Gln Val Pro Tyr Thr Ile Thr Val Asn Gly Thr Ser Gln Asn Ile Leu
                165                 170                 175

Ser Asn Leu Thr Phe Asn Lys Asn Gln Asn Ile Ser Tyr Lys Asp Leu
            180                 185                 190

Glu Asp Lys Val Lys Ser Val Leu Glu Ser Asn Arg Gly Ile Thr Asp
            195                 200                 205

Val Asp Leu Arg Leu Ser Lys Gln Ala Lys Tyr Thr Val Asn Phe Lys
        210                 215                 220

Asn Gly Thr Lys Lys Val Ile Asp Leu Lys Ser Gly Ile Tyr Thr Ala
225                 230                 235                 240

Asn Leu Ile Asn Ser Ser Asp Ile Lys Ser Ile Asn Ile Asn Val Asp
                245                 250                 255

Thr Lys Lys His Ile Glu Asn Lys Ala Lys Arg Asn Tyr Gln Val Pro
                260                 265                 270

Tyr Ser Ile Asn Leu Asn Gly Thr Ser Thr Asn Ile Leu Ser Asn Leu
        275                 280                 285

Ser Phe Ser Asn Lys Pro Trp Thr Asn Tyr Lys Asn Leu Thr Ser Gln
        290                 295                 300

Ile Lys Ser Val Leu Lys His Asp Arg Gly Ile Ser Glu Gln Asp Leu
305                 310                 315                 320

Lys Tyr Ala Lys Lys Ala Tyr Tyr Thr Val Tyr Phe Lys Asn Gly Gly
                325                 330                 335

Lys Arg Ile Leu Gln Leu Asn Ser Asn Tyr Thr Ala Asn Leu Val
            340                 345                 350

His Ala Lys Asp Val Lys Arg Ile Glu Ile Thr Val Lys Thr Gly Thr
        355                 360                 365

Lys Ala Lys Ala Asp Arg Tyr Val Pro Tyr Thr Ile Ala Val Asn Gly
        370                 375                 380

Thr Ser Thr Pro Ile Leu Ser Asp Leu Lys Phe Thr Gly Asp Pro Arg
385                 390                 395                 400

Val Gly Tyr Lys Asp Ile Ser Lys Val Lys Ser Val Leu Lys His
            405                 410                 415

Asp Arg Gly Ile Gly Glu Arg Glu Leu Lys Tyr Ala Lys Lys Ala Thr
        420                 425                 430
```

```
Tyr Thr Val His Phe Lys Asn Gly Thr Lys Val Ile Asn Ile Asn
            435                 440                 445

Ser Asn Ile Ser Gln Leu Asn Leu Leu Tyr Val Gln Asp Ile Lys Lys
    450                 455                 460

Ile Asp Ile Asp Val Lys Thr Gly Thr Lys Ala Lys Ala Asp Ser Tyr
465                 470                 475                 480

Val Pro Tyr Thr Ile Ala Val Asn Gly Thr Ser Thr Pro Ile Leu Ser
                485                 490                 495

Lys Leu Lys Ile Ser Asn Lys Gln Leu Ile Ser Tyr Lys Tyr Leu Asn
                500                 505                 510

Asp Lys Val Lys Ser Val Leu Lys Ser Glu Arg Gly Ile Ser Asp Leu
            515                 520                 525

Asp Leu Lys Phe Ala Lys Gln Ala Lys Tyr Thr Val Tyr Phe Lys Asn
            530                 535                 540

Gly Lys Lys Gln Val Val Asn Leu Lys Ser Asp Ile Phe Thr Pro Asn
545                 550                 555                 560

Leu Phe Ser Ala Lys Asp Ile Lys Lys Ile Asp Ile Asp Val Lys Gln
                565                 570                 575

Tyr Thr Lys Ser Lys Lys Asn Lys
            580

<210> SEQ ID NO 32
<211> LENGTH: 508
<212> TYPE: PRT
<213> ORGANISM: Staphylococcus sp.

<400> SEQUENCE: 32

Met Lys Asn Lys Leu Leu Val Leu Ser Leu Gly Ala Leu Cys Val Ser
1               5                   10                  15

Gln Ile Trp Glu Ser Asn Arg Ala Ser Ala Val Val Ser Gly Glu Lys
            20                  25                  30

Asn Pro Tyr Val Ser Glu Ser Leu Lys Leu Thr Asn Asn Lys Asn Lys
        35                  40                  45

Ser Arg Thr Val Glu Glu Tyr Lys Lys Ser Leu Asp Asp Leu Ile Trp
    50                  55                  60

Ser Phe Pro Asn Leu Asp Asn Glu Arg Phe Asp Asn Pro Glu Tyr Lys
65                  70                  75                  80

Glu Ala Met Lys Lys Tyr Gln Gln Arg Phe Met Ala Glu Asp Glu Ala
                85                  90                  95

Leu Lys Lys Phe Phe Ser Glu Lys Lys Ile Lys Asn Gly Asn Thr
            100                 105                 110

Asp Asn Leu Asp Tyr Leu Gly Leu Ser His Glu Arg Tyr Glu Ser Val
            115                 120                 125

Phe Asn Thr Leu Lys Lys Gln Ser Glu Glu Phe Leu Lys Glu Ile Glu
    130                 135                 140

Asp Ile Lys Lys Asp Asn Pro Glu Leu Lys Asp Phe Asn Glu Glu
145                 150                 155                 160

Gln Leu Lys Cys Asp Leu Glu Leu Asn Lys Leu Glu Asn Gln Ile Leu
                165                 170                 175

Met Leu Gly Lys Thr Phe Tyr Gln Asn Tyr Arg Asp Asp Val Glu Ser
            180                 185                 190

Leu Tyr Ser Lys Leu Asp Leu Ile Met Gly Tyr Lys Asp Glu Glu Arg
            195                 200                 205

Ala Asn Lys Lys Ala Val Asn Lys Arg Met Leu Glu Asn Lys Lys Glu
```

```
            210                 215                 220
Asp Leu Glu Thr Ile Ile Asp Glu Phe Phe Ser Asp Ile Asp Lys Thr
225                 230                 235                 240

Arg Pro Asn Asn Ile Pro Val Leu Glu Asp Glu Lys Gln Glu Glu Lys
                245                 250                 255

Asn His Lys Asn Met Ala Gln Leu Lys Ser Asp Thr Glu Ala Ala Lys
                260                 265                 270

Ser Asp Glu Ser Lys Arg Ser Lys Arg Ser Lys Arg Ser Leu Asn Thr
            275                 280                 285

Gln Asn His Lys Pro Ala Ser Gln Glu Val Ser Glu Gln Gln Lys Ala
        290                 295                 300

Glu Tyr Asp Lys Arg Ala Glu Glu Arg Lys Ala Arg Phe Leu Asp Asn
305                 310                 315                 320

Gln Lys Ile Lys Lys Thr Pro Val Val Ser Leu Glu Tyr Asp Phe Glu
                325                 330                 335

His Lys Gln Arg Ile Asp Asn Glu Asn Asp Lys Lys Leu Val Val Ser
                340                 345                 350

Ala Pro Thr Lys Lys Pro Thr Ser Pro Thr Thr Tyr Thr Glu Thr Thr
            355                 360                 365

Thr Gln Val Pro Met Pro Thr Val Glu Arg Gln Thr Gln Gln Gln Ile
370                 375                 380

Ile Tyr Asn Ala Pro Lys Gln Leu Ala Gly Leu Asn Gly Glu Ser His
385                 390                 395                 400

Asp Phe Thr Thr Thr His Gln Ser Pro Thr Thr Ser Asn His Thr His
                405                 410                 415

Asn Asn Val Val Glu Phe Glu Glu Thr Ser Ala Leu Pro Gly Arg Lys
                420                 425                 430

Ser Gly Ser Leu Val Gly Ile Ser Gln Ile Asp Ser Ser His Leu Thr
            435                 440                 445

Glu Arg Glu Lys Arg Val Ile Lys Arg Glu His Val Arg Glu Ala Gln
        450                 455                 460

Lys Leu Val Asp Asn Tyr Lys Asp Thr His Ser Tyr Lys Asp Arg Ile
465                 470                 475                 480

Asn Ala Gln Gln Lys Val Asn Thr Leu Ser Glu Gly His Gln Lys Arg
                485                 490                 495

Phe Asn Lys Gln Ile Asn Lys Val Tyr Asn Gly Lys
                500                 505

<210> SEQ ID NO 33
<211> LENGTH: 520
<212> TYPE: PRT
<213> ORGANISM: Staphylococcus sp.

<400> SEQUENCE: 33

Met Leu Thr Leu Gln Ile His Thr Gly Gly Ile Asn Leu Lys Lys Lys
1               5                   10                  15

Asn Ile Tyr Ser Ile Arg Lys Leu Gly Val Gly Ile Ala Ser Val Thr
                20                  25                  30

Leu Gly Thr Leu Leu Ile Ser Gly Gly Val Thr Pro Ala Ala Asn Ala
            35                  40                  45

Ala Gln His Asp Glu Ala Gln Gln Asn Ala Phe Tyr Gln Val Leu Asn
        50                  55                  60

Met Pro Asn Leu Asn Ala Asp Gln Arg Asn Gly Phe Ile Gln Ser Leu
65                  70                  75                  80
```

-continued

```
Lys Asp Asp Pro Ser Gln Ser Ala Asn Val Leu Gly Glu Ala Gln Lys
                85                  90                  95

Leu Asn Asp Ser Gln Ala Pro Lys Ala Asp Ala Gln Gln Asn Asn Phe
            100                 105                 110

Asn Lys Asp Gln Gln Ser Ala Phe Tyr Glu Ile Leu Asn Met Pro Asn
        115                 120                 125

Leu Asn Glu Ala Gln Arg Asn Gly Phe Ile Gln Ser Leu Lys Asp Asp
    130                 135                 140

Pro Ser Gln Ser Thr Asn Val Leu Gly Glu Ala Lys Lys Leu Asn Glu
145                 150                 155                 160

Ser Gln Ala Pro Lys Ala Asp Asn Asn Phe Asn Lys Glu Gln Gln Asn
                165                 170                 175

Ala Phe Tyr Glu Ile Leu Asn Met Pro Asn Leu Asn Glu Glu Gln Arg
            180                 185                 190

Asn Gly Phe Ile Gln Ser Leu Lys Asp Asp Pro Ser Gln Ser Ala Asn
        195                 200                 205

Leu Leu Ser Glu Ala Lys Lys Leu Asn Glu Ser Gln Ala Pro Lys Ala
    210                 215                 220

Asp Asn Lys Phe Asn Lys Glu Gln Gln Asn Ala Phe Tyr Glu Ile Leu
225                 230                 235                 240

His Leu Pro Asn Leu Asn Glu Glu Gln Arg Asn Gly Phe Ile Gln Ser
                245                 250                 255

Leu Lys Asp Asp Pro Ser Gln Ser Ala Asn Leu Leu Ala Glu Ala Lys
            260                 265                 270

Lys Leu Asn Asp Ala Gln Ala Pro Lys Ala Asp Asn Lys Phe Asn Lys
        275                 280                 285

Glu Gln Gln Asn Ala Phe Tyr Glu Ile Leu His Leu Pro Asn Leu Thr
    290                 295                 300

Glu Glu Gln Arg Asn Gly Phe Ile Gln Ser Leu Lys Asp Asp Pro Ser
305                 310                 315                 320

Val Ser Lys Glu Ile Leu Ala Glu Ala Lys Lys Leu Asn Asp Ala Gln
                325                 330                 335

Ala Pro Lys Glu Glu Asp Asn Asn Lys Pro Gly Lys Glu Asp Gly Asn
            340                 345                 350

Lys Pro Gly Lys Glu Asp Asn Asn Lys Pro Gly Lys Glu Asp Asn Lys
        355                 360                 365

Lys Pro Gly Lys Glu Asp Asn Asn Lys Pro Gly Lys Glu Asp Asn Asn
        370                 375                 380

Lys Pro Gly Lys Glu Asp Gly Asn Lys Pro Gly Lys Glu Asp Asn Lys
385                 390                 395                 400

Lys Pro Gly Lys Glu Asp Asn Asn Lys Pro Gly Lys Glu Asp Gly Asn
                405                 410                 415

Lys Pro Gly Lys Glu Asp Gly Asn Gly Val His Val Val Lys Pro Gly
            420                 425                 430

Asp Thr Val Asn Asp Ile Ala Lys Ala Asn Gly Thr Thr Ala Asp Lys
        435                 440                 445

Ile Ala Ala Asp Asn Lys Leu Ala Asp Lys Asn Met Ile Lys Pro Gly
        450                 455                 460

Gln Glu Leu Val Val Asp Lys Lys Gln Pro Ala Asn His Ala Asp Ala
465                 470                 475                 480

Asn Lys Ala Gln Ala Leu Pro Glu Thr Gly Glu Glu Asn Pro Phe Ile
                485                 490                 495

Gly Thr Thr Val Phe Gly Gly Leu Ser Leu Ala Leu Gly Ala Ala Leu
```

```
                500             505             510
Leu Ala Gly Arg Arg Glu Leu
        515             520

<210> SEQ ID NO 34
<211> LENGTH: 291
<212> TYPE: PRT
<213> ORGANISM: Staphylococcus sp.

<400> SEQUENCE: 34

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 35
<211> LENGTH: 34
<212> TYPE: DNA
<213> ORGANISM: Staphylococcus sp.

<400> SEQUENCE: 35
gctgcacata tggcgcaaca cgatgaagct caac                             34
```

<210> SEQ ID NO 36
<211> LENGTH: 30
<212> TYPE: DNA
<213> ORGANISM: Staphylococcus sp.

<400> SEQUENCE: 36
agtggatcct tatgctttgt tagcatctgc                              30

<210> SEQ ID NO 37
<211> LENGTH: 19
<212> TYPE: PRT
<213> ORGANISM: Staphylococcus sp.

<400> SEQUENCE: 37

Met Gly Ser Ser His His His His His His Ser Ser Gly Leu Val Pro
1               5                   10                  15

Arg Gly Ser

<210> SEQ ID NO 38
<211> LENGTH: 29
<212> TYPE: DNA
<213> ORGANISM: Staphylococcus sp.

<400> SEQUENCE: 38
aacatatgtt caacaaagat caacaaagc                               29

<210> SEQ ID NO 39
<211> LENGTH: 29
<212> TYPE: DNA
<213> ORGANISM: Staphylococcus sp.

<400> SEQUENCE: 39
aaggatccag attcgtttaa tttttttagc                              29

<210> SEQ ID NO 40
<211> LENGTH: 43
<212> TYPE: DNA
<213> ORGANISM: Staphylococcus sp.

<400> SEQUENCE: 40
cttcattcaa agtcttaaag ccgccccaag ccaaagcact aac                43

<210> SEQ ID NO 41
<211> LENGTH: 43
<212> TYPE: DNA
<213> ORGANISM: Staphylococcus sp.

<400> SEQUENCE: 41
gttagtgctt tggcttgggg cggctttaag actttgaatg aag                43

<210> SEQ ID NO 42
<211> LENGTH: 42
<212> TYPE: DNA
<213> ORGANISM: Staphylococcus sp.

<400> SEQUENCE: 42
catatgttca acaaagataa aaaaagcgcc ttctatgaaa tc                 42

<210> SEQ ID NO 43
<211> LENGTH: 42
<212> TYPE: DNA
<213> ORGANISM: Staphylococcus sp.

```
<400> SEQUENCE: 43
gatttcatag aaggcgcttt ttttatcttt gttgaacata tg                           42

<210> SEQ ID NO 44
<211> LENGTH: 42
<212> TYPE: DNA
<213> ORGANISM: Staphylococcus sp.

<400> SEQUENCE: 44
catatgttca acaaagatgg aggaagcgcc ttctatgaaa tc                           42

<210> SEQ ID NO 45
<211> LENGTH: 42
<212> TYPE: DNA
<213> ORGANISM: Staphylococcus sp.

<400> SEQUENCE: 45
gatttcatag aaggcgcttc ctccatcttt gttgaacata tg                           42

<210> SEQ ID NO 46
<211> LENGTH: 52
<212> TYPE: DNA
<213> ORGANISM: Staphylococcus sp.

<400> SEQUENCE: 46
ggggacaagt ttgtacaaaa aagcaggctg atgactaagt tgaaaaaga ag                 52

<210> SEQ ID NO 47
<211> LENGTH: 28
<212> TYPE: DNA
<213> ORGANISM: Staphylococcus sp.

<400> SEQUENCE: 47
aaggatcccc tccaaaatgt aattgccc                                           28

<210> SEQ ID NO 48
<211> LENGTH: 30
<212> TYPE: DNA
<213> ORGANISM: Staphylococcus sp.

<400> SEQUENCE: 48
aaggatccgt ttgtaactct atccaaagac                                         30

<210> SEQ ID NO 49
<211> LENGTH: 49
<212> TYPE: DNA
<213> ORGANISM: Staphylococcus sp.

<400> SEQUENCE: 49
ggggaccact ttgtacaaga aagctgggtg acacctattg cacgattcg                    49

<210> SEQ ID NO 50
<211> LENGTH: 50
<212> TYPE: DNA
<213> ORGANISM: Staphylococcus sp.

<400> SEQUENCE: 50
ggggacaagt ttgtacaaaa aagcaggctc agatagcgat tcagattcag                   50

<210> SEQ ID NO 51
<211> LENGTH: 31
<212> TYPE: DNA
```

<213> ORGANISM: Staphylococcus sp.

<400> SEQUENCE: 51
aaggatccct gtattttctc cttaattttc c                              31

<210> SEQ ID NO 52
<211> LENGTH: 30
<212> TYPE: DNA
<213> ORGANISM: Staphylococcus sp.

<400> SEQUENCE: 52
aaggatccca tggctgcaaa gcaaataatg                                30

<210> SEQ ID NO 53
<211> LENGTH: 51
<212> TYPE: DNA
<213> ORGANISM: Staphylococcus sp.

<400> SEQUENCE: 53
ggggaccact ttgtacaaga aagctgggtg ccctggtgta acaaatttat g        51

<210> SEQ ID NO 54
<211> LENGTH: 37
<212> TYPE: DNA
<213> ORGANISM: Staphylococcus sp.

<400> SEQUENCE: 54
gaaggatccg tttattctag ttaatatata gttaatg                        37

<210> SEQ ID NO 55
<211> LENGTH: 33
<212> TYPE: DNA
<213> ORGANISM: Staphylococcus sp.

<400> SEQUENCE: 55
gaactgcagc tgtatgtctt tggatagagt tac                            33

<210> SEQ ID NO 56
<211> LENGTH: 33
<212> TYPE: DNA
<213> ORGANISM: Staphylococcus sp.

<400> SEQUENCE: 56
gaaggatccg gtggcttttt tacttggatt ttc                            33

<210> SEQ ID NO 57
<211> LENGTH: 33
<212> TYPE: DNA
<213> ORGANISM: Staphylococcus sp.

<400> SEQUENCE: 57
gaactgcagc gacaaactca ttatttgctt tgc                            33

<210> SEQ ID NO 58
<211> LENGTH: 27
<212> TYPE: DNA
<213> ORGANISM: Staphylococcus sp.

<400> SEQUENCE: 58
gaactcgagt ctagcttatt tacatgg                                   27

<210> SEQ ID NO 59
<211> LENGTH: 45

```
<212> TYPE: DNA
<213> ORGANISM: Staphylococcus sp.

<400> SEQUENCE: 59
gaactcgaga tagaaggcag aatagtaaca aaggattata gtggg         45

<210> SEQ ID NO 60
<211> LENGTH: 27
<212> TYPE: DNA
<213> ORGANISM: Staphylococcus sp.

<400> SEQUENCE: 60
gtaggatcct gggatagagt tacaaac                              27

<210> SEQ ID NO 61
<211> LENGTH: 34
<212> TYPE: DNA
<213> ORGANISM: Staphylococcus sp.

<400> SEQUENCE: 61
gaactcgagg cattatgtgt atcacaaatt tggg                      34

<210> SEQ ID NO 62
<211> LENGTH: 43
<212> TYPE: DNA
<213> ORGANISM: Staphylococcus sp.

<400> SEQUENCE: 62
gaactcgaga tagaaggcag agtggtttct ggggagaaga atc            43

<210> SEQ ID NO 63
<211> LENGTH: 33
<212> TYPE: DNA
<213> ORGANISM: Staphylococcus sp.

<400> SEQUENCE: 63
gaactcgagg cagccatgca ttaattattt gcc                       33

<210> SEQ ID NO 64
<211> LENGTH: 940
<212> TYPE: PRT
<213> ORGANISM: Staphylococcus aureus subst. Newman

<400> SEQUENCE: 64
```

Met Lys Ser Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Glu
                20                  25                  30

Lys Glu Ala Ala Ala Ser Glu Gln Asn Asn Thr Thr Val Glu Glu Ser
            35                  40                  45

Gly Ser Ser Ala Thr Glu Ser Lys Ala Ser Glu Thr Gln Thr Thr Thr
        50                  55                  60

Asn Asn Val Asn Thr Ile Asp Glu Thr Gln Ser Tyr Ser Ala Thr Ser
65                  70                  75                  80

Thr Glu Gln Pro Ser Gln Ser Thr Gln Val Thr Thr Glu Glu Ala Pro
                85                  90                  95

Lys Thr Val Gln Ala Pro Lys Val Glu Thr Ser Arg Val Asp Leu Pro
            100                 105                 110

Ser Glu Lys Val Ala Asp Lys Glu Thr Thr Gly Thr Gln Val Asp Ile
        115                 120                 125

```
Ala Gln Pro Ser Asn Val Ser Glu Ile Lys Pro Arg Met Lys Arg Ser
    130                 135                 140

Thr Asp Val Thr Ala Val Ala Glu Lys Glu Val Val Glu Glu Thr Lys
145                 150                 155                 160

Ala Thr Gly Thr Asp Val Thr Asn Lys Val Glu Val Glu Glu Gly Ser
                165                 170                 175

Glu Ile Val Gly His Lys Gln Asp Thr Asn Val Val Asn Pro His Asn
                180                 185                 190

Ala Glu Arg Val Thr Leu Lys Tyr Lys Trp Lys Phe Gly Glu Gly Ile
            195                 200                 205

Lys Ala Gly Asp Tyr Phe Asp Phe Thr Leu Ser Asp Asn Val Glu Thr
        210                 215                 220

His Gly Ile Ser Thr Leu Arg Lys Val Pro Glu Ile Lys Ser Thr Asp
225                 230                 235                 240

Gly Gln Val Met Ala Thr Gly Glu Ile Ile Gly Glu Arg Lys Val Arg
                245                 250                 255

Tyr Thr Phe Lys Glu Tyr Val Gln Glu Lys Lys Asp Leu Thr Ala Glu
            260                 265                 270

Leu Ser Leu Asn Leu Phe Ile Asp Pro Thr Thr Val Thr Gln Lys Gly
        275                 280                 285

Asn Gln Asn Val Glu Val Lys Leu Gly Glu Thr Thr Val Ser Lys Ile
    290                 295                 300

Phe Asn Ile Gln Tyr Leu Gly Gly Val Arg Asp Asn Trp Gly Val Thr
305                 310                 315                 320

Ala Asn Gly Arg Ile Asp Thr Leu Asn Lys Val Asp Gly Lys Phe Ser
                325                 330                 335

His Phe Ala Tyr Met Lys Pro Asn Asn Gln Ser Leu Ser Ser Val Thr
            340                 345                 350

Val Thr Gly Gln Val Thr Lys Gly Asn Lys Pro Gly Val Asn Asn Pro
        355                 360                 365

Thr Val Lys Val Tyr Lys His Ile Gly Ser Asp Leu Ala Glu Ser
    370                 375                 380

Val Tyr Ala Lys Leu Asp Asp Val Ser Lys Phe Glu Asp Val Thr Asp
385                 390                 395                 400

Asn Met Ser Leu Asp Phe Asp Thr Asn Gly Gly Tyr Ser Leu Asn Phe
                405                 410                 415

Asn Asn Leu Asp Gln Ser Lys Asn Tyr Val Ile Lys Tyr Glu Gly Tyr
            420                 425                 430

Tyr Asp Ser Asn Ala Ser Asn Leu Glu Phe Gln Thr His Leu Phe Gly
        435                 440                 445

Tyr Tyr Asn Tyr Tyr Thr Ser Asn Leu Thr Trp Lys Asn Gly Val
    450                 455                 460

Ala Phe Tyr Ser Asn Asn Ala Gln Gly Asp Gly Lys Asp Lys Leu Lys
465                 470                 475                 480

Glu Pro Ile Ile Glu His Ser Thr Pro Ile Leu Glu Phe Lys Ser
                485                 490                 495

Glu Pro Pro Val Glu Lys His Glu Leu Thr Gly Thr Ile Glu Glu Ser
            500                 505                 510

Asn Asp Ser Lys Pro Ile Asp Phe Glu Tyr His Thr Ala Val Glu Gly
        515                 520                 525

Ala Glu Gly His Ala Glu Gly Thr Ile Glu Thr Glu Glu Asp Ser Ile
    530                 535                 540

His Val Asp Phe Glu Glu Ser Thr His Glu Asn Ser Lys His His Ala
```

```
            545                 550                 555                 560
        Asp Val Val Glu Tyr Glu Glu Asp Thr Asn Pro Gly Gly Gln Val
                        565                 570                 575

Thr Thr Glu Ser Asn Leu Val Glu Phe Asp Glu Asp Ser Thr Lys Gly
                        580                 585                 590

Ile Val Thr Gly Ala Val Ser Asp His Thr Thr Ile Glu Asp Thr Lys
                        595                 600                 605

Glu Tyr Thr Thr Glu Ser Asn Leu Ile Glu Leu Val Asp Glu Leu Pro
                        610                 615                 620

Glu Glu His Gly Gln Ala Gln Gly Pro Ile Glu Glu Ile Thr Glu Asn
        625                 630                 635                 640

Asn His His Ile Ser His Ser Gly Leu Gly Thr Glu Asn Gly His Gly
                        645                 650                 655

Asn Tyr Gly Val Ile Glu Glu Ile Glu Glu Asn Ser His Val Asp Ile
                        660                 665                 670

Lys Ser Glu Leu Gly Tyr Glu Gly Gln Asn Ser Gly Asn Gln Ser
                        675                 680                 685

Phe Glu Glu Asp Thr Glu Glu Asp Lys Pro Lys Tyr Glu Gln Gly Gly
                        690                 695                 700

Asn Ile Val Asp Ile Asp Phe Asp Ser Val Pro Gln Ile His Gly Gln
        705                 710                 715                 720

Asn Asn Gly Asn Gln Ser Phe Glu Glu Asp Thr Glu Lys Asp Lys Pro
                        725                 730                 735

Lys Tyr Glu Gln Gly Gly Asn Ile Ile Asp Ile Asp Phe Asp Ser Val
                        740                 745                 750

Pro His Ile His Gly Phe Asn Lys His Thr Glu Ile Ile Glu Glu Asp
                        755                 760                 765

Thr Asn Lys Asp Lys Pro Asn Tyr Gln Phe Gly His Asn Ser Val
                        770                 775                 780

Asp Phe Glu Glu Asp Thr Leu Pro Gln Val Ser Gly His Asn Glu Gly
        785                 790                 795                 800

Gln Gln Thr Ile Glu Glu Asp Thr Thr Pro Pro Ile Val Pro Pro Thr
                        805                 810                 815

Pro Pro Thr Pro Glu Val Pro Ser Glu Pro Glu Thr Pro Thr Pro Pro
                        820                 825                 830

Thr Pro Glu Val Pro Ser Glu Pro Glu Thr Pro Thr Pro Thr Pro
                        835                 840                 845

Glu Val Pro Thr Glu Pro Gly Lys Pro Ile Pro Pro Ala Lys Glu Glu
        850                 855                 860

Pro Lys Lys Pro Ser Lys Pro Val Glu Gln Gly Lys Val Val Thr Pro
        865                 870                 875                 880

Val Ile Glu Ile Asn Glu Lys Val Lys Ala Val Val Pro Thr Lys Lys
                        885                 890                 895

Ala Gln Ser Lys Lys Ser Glu Leu Pro Glu Thr Gly Gly Glu Glu Ser
                        900                 905                 910

Thr Asn Asn Gly Met Leu Phe Gly Gly Leu Phe Ser Ile Leu Gly Leu
                        915                 920                 925

Ala Leu Leu Arg Arg Asn Lys Lys Asn His Lys Ala
                        930                 935                 940

<210> SEQ ID NO 65
<211> LENGTH: 1315
<212> TYPE: PRT
<213> ORGANISM: Staphylococcus aureus subst. Newman
```

```
<400> SEQUENCE: 65

Met Leu Asn Arg Glu Asn Lys Thr Ala Ile Thr Arg Lys Gly Met Val
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Ser Thr Asn Lys Glu Leu Asn Glu Ala Thr
    50                  55                  60

Thr Ser Ala Ser Asp Asn Gln Ser Ser Asp Lys Val Asp Met Gln Gln
65                  70                  75                  80

Leu Asn Gln Glu Asp Asn Thr Lys Asn Asp Asn Gln Lys Glu Met Val
                85                  90                  95

Ser Ser Gln Gly Asn Glu Thr Thr Ser Asn Gly Asn Lys Leu Ile Glu
            100                 105                 110

Lys Glu Ser Val Gln Ser Thr Thr Gly Asn Lys Val Glu Val Ser Thr
            115                 120                 125

Ala Lys Ser Asp Glu Gln Ala Ser Pro Lys Ser Thr Asn Glu Asp Leu
    130                 135                 140

Asn Thr Lys Gln Thr Ile Ser Asn Gln Glu Ala Leu Gln Pro Asp Leu
145                 150                 155                 160

Gln Glu Asn Lys Ser Val Val Asn Val Gln Pro Thr Asn Glu Glu Asn
                165                 170                 175

Lys Lys Val Asp Ala Lys Thr Glu Ser Thr Thr Leu Asn Val Lys Ser
            180                 185                 190

Asp Ala Ile Lys Ser Asn Asp Glu Thr Leu Val Asp Asn Asn Ser Asn
            195                 200                 205

Ser Asn Asn Glu Asn Asn Ala Asp Ile Ile Leu Pro Lys Ser Thr Ala
    210                 215                 220

Pro Lys Arg Leu Asn Thr Arg Met Arg Ile Ala Ala Val Gln Pro Ser
225                 230                 235                 240

Ser Thr Glu Ala Lys Asn Val Asn Asp Leu Ile Thr Ser Asn Thr Thr
                245                 250                 255

Leu Thr Val Val Asp Ala Asp Lys Asn Asn Lys Ile Val Pro Ala Gln
            260                 265                 270

Asp Tyr Leu Ser Leu Lys Ser Gln Ile Thr Val Asp Lys Val Lys
            275                 280                 285

Ser Gly Asp Tyr Phe Thr Ile Lys Tyr Ser Asp Thr Val Gln Val Tyr
    290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
            340                 345                 350

Gln Met Gly Ile Asn Tyr Ser Ile Tyr Met Asp Ala Asp Thr Ile Pro
    355                 360                 365

Val Ser Lys Asn Asp Val Glu Phe Asn Val Thr Ile Gly Asn Thr Thr
    370                 375                 380

Thr Lys Thr Thr Ala Asn Ile Gln Tyr Pro Asp Tyr Val Val Asn Glu
385                 390                 395                 400

Lys Asn Ser Ile Gly Ser Ala Phe Thr Glu Thr Val Ser His Val Gly
```

-continued

```
            405                 410                 415
Asn Lys Glu Asn Pro Gly Tyr Tyr Lys Gln Thr Ile Tyr Val Asn Pro
            420                 425                 430

Ser Glu Asn Ser Leu Thr Asn Ala Lys Leu Lys Val Gln Ala Tyr His
            435                 440                 445

Ser Ser Tyr Pro Asn Asn Ile Gly Gln Ile Asn Lys Asp Val Thr Asp
450                 455                 460

Ile Lys Ile Tyr Gln Val Pro Lys Gly Tyr Thr Leu Asn Lys Gly Tyr
465                 470                 475                 480

Asp Val Asn Thr Lys Glu Leu Thr Asp Val Thr Asn Gln Tyr Leu Gln
            485                 490                 495

Lys Ile Thr Tyr Gly Asp Asn Ser Ala Val Ile Asp Phe Gly Asn
            500                 505                 510

Ala Asp Ser Ala Tyr Val Met Val Asn Thr Lys Phe Gln Tyr Thr
            515                 520                 525

Asn Ser Glu Ser Pro Thr Leu Val Gln Met Ala Thr Leu Ser Ser Thr
            530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
                580                 585                 590

Val Gly Asn Val Thr Val Thr Val Phe Asp Asn Asn Thr Asn Thr Lys
            595                 600                 605

Val Gly Glu Ala Val Thr Lys Glu Asp Gly Ser Tyr Leu Ile Pro Asn
610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
            660                 665                 670

Ala Asp Leu Gly Ile Tyr Lys Pro Lys Tyr Asn Leu Gly Asp Tyr Val
            675                 680                 685

Trp Glu Asp Thr Asn Lys Asn Gly Ile Gln Asp Gln Asp Glu Lys Gly
            690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
            740                 745                 750

Pro Thr Thr Val Thr Ser Gly Ser Asp Ile Glu Lys Asp Ser Asn Gly
            755                 760                 765

Leu Thr Thr Thr Gly Val Ile Asn Gly Ala Asp Asn Met Thr Leu Asp
770                 775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                805                 810                 815

Ser Gly Val Thr Val Thr Leu Lys Asn Glu Asn Gly Glu Val Leu Gln
            820                 825                 830
```

```
Thr Thr Lys Thr Asp Lys Asp Gly Lys Tyr Gln Phe Thr Gly Leu Glu
        835                 840                 845

Asn Gly Thr Tyr Lys Val Glu Phe Glu Thr Pro Ser Gly Tyr Thr Pro
850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
            885                 890                 895

Gly Phe Tyr Lys Pro Thr Tyr Asn Leu Gly Asp Tyr Val Trp Glu Asp
                900                 905                 910

Thr Asn Lys Asn Gly Val Gln Asp Lys Asp Glu Lys Gly Ile Ser Gly
            915                 920                 925

Val Thr Val Thr Leu Lys Asp Glu Asn Asp Lys Val Leu Lys Thr Val
        930                 935                 940

Thr Thr Asp Glu Asn Gly Lys Tyr Gln Phe Thr Asp Leu Asn Asn Gly
945                 950                 955                 960

Thr Tyr Lys Val Glu Phe Glu Thr Pro Ser Gly Tyr Thr Pro Thr Ser
                965                 970                 975

Val Thr Ser Gly Asn Asp Thr Glu Lys Asp Ser Asn Gly Leu Thr Thr
            980                 985                 990

Thr Gly Val Ile Lys Asp Ala Asp  Asn Met Thr Leu Asp  Ser Gly Phe
            995                 1000                1005

Tyr Lys  Thr Pro Lys Tyr Ser  Leu Gly Asp Tyr Val  Trp Tyr Asp
    1010                1015                1020

Ser Asn  Lys Asp Gly Lys Gln  Asp Ser Thr Glu Lys  Gly Ile Lys
    1025                1030                1035

Asp Val  Lys Val Thr Leu Leu  Asn Glu Lys Gly Glu  Val Ile Gly
    1040                1045                1050

Thr Thr  Lys Thr Asp Glu Asn  Gly Lys Tyr Cys Phe  Asp Asn Leu
    1055                1060                1065

Asp Ser  Gly Lys Tyr Lys Val  Ile Phe Glu Lys Pro  Ala Gly Leu
    1070                1075                1080

Thr Gln  Thr Gly Thr Asn Thr  Thr Glu Asp Asp Lys  Asp Ala Asp
    1085                1090                1095

Gly Gly  Glu Val Asp Val Thr  Ile Thr Asp His Asp  Asp Phe Thr
    1100                1105                1110

Leu Asp  Asn Gly Tyr Tyr Glu  Glu Glu Thr Ser Asp  Ser Asp Ser
    1115                1120                1125

Asp Ser  Asp Ser Asp Ser Asp  Ser Asp Arg Asp Ser  Asp Ser Asp
    1130                1135                1140

Ser Asp  Ser Asp Ser Asp Ser  Asp Ser Asp Ser Asp  Ser Asp Ser
    1145                1150                1155

Asp Ser  Asp Ser Asp Ser Asp  Ser Asp Arg Asp Ser  Asp Ser Asp
    1160                1165                1170

Ser Asp  Ser Asp Ser Asp Ser  Asp Ser Asp Ser Asp  Ser Asp Ser
    1175                1180                1185

Asp Ser  Asp Ser Asp Ser Asp  Ser Asp Ser Asp Ser  Asp Ser Asp
    1190                1195                1200

Ser Asp  Ser Asp Ser Asp Ser  Asp Ser Asp Ser Asp  Ser Asp Ser
    1205                1210                1215

Asp Ser  Asp Ser Asp Ser Asp  Ser Asp Ser Asp Ser  Asp Ser Asp
    1220                1225                1230
```

```
Ser Asp Ser Asp Ser Asp Ser Asp Ser Asp Ser Asp
    1235            1240            1245

Asp Ser Asp Ser Asp Ser Asp Ala Gly Lys His Thr Pro Val Lys
1250            1255            1260

Pro Met Ser Thr Thr Lys Asp His His Asn Lys Ala Lys Ala Leu
1265            1270            1275

Pro Glu Thr Gly Asn Glu Asn Ser Gly Ser Asn Asn Ala Thr Leu
1280            1285            1290

Phe Gly Gly Leu Phe Ala Ala Leu Gly Ser Leu Leu Leu Phe Gly
1295            1300            1305

Arg Arg Lys Lys Gln Asn Lys
1310            1315
```

<210> SEQ ID NO 66
<211> LENGTH: 933
<212> TYPE: PRT
<213> ORGANISM: Staphylococcus aureus subst. Newman

<400> SEQUENCE: 66

```
Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285
```

```
Thr Ser Thr Ala Lys Val Pro Pro Ile Met Ala Gly Asp Gln Val Leu
    290                 295                 300
Ala Asn Gly Val Ile Asp Ser Asp Gly Asn Val Ile Tyr Thr Phe Thr
305                 310                 315                 320
Asp Tyr Val Asn Thr Lys Asp Asp Val Lys Ala Thr Leu Thr Met Pro
                325                 330                 335
Ala Tyr Ile Asp Pro Glu Asn Val Lys Lys Thr Gly Asn Val Thr Leu
                340                 345                 350
Ala Thr Gly Ile Gly Ser Thr Thr Ala Asn Lys Thr Val Leu Val Asp
                355                 360                 365
Tyr Glu Lys Tyr Gly Lys Phe Tyr Asn Leu Ser Ile Lys Gly Thr Ile
    370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Ile Ala Pro Val Leu Thr Gly Asn Leu
                405                 410                 415
Lys Pro Asn Thr Asp Ser Asn Ala Leu Ile Asp Gln Gln Asn Thr Ser
                420                 425                 430
Ile Lys Val Tyr Lys Val Asp Asn Ala Ala Asp Leu Ser Glu Ser Tyr
                435                 440                 445
Phe Val Asn Pro Glu Asn Phe Glu Asp Val Thr Asn Ser Val Asn Ile
    450                 455                 460
Thr Phe Pro Asn Pro Asn Gln Tyr Lys Val Glu Phe Asn Thr Pro Asp
465                 470                 475                 480
Asp Gln Ile Thr Thr Pro Tyr Ile Val Val Asn Gly His Ile Asp
                485                 490                 495
Pro Asn Ser Lys Gly Asp Leu Ala Leu Arg Ser Thr Leu Tyr Gly Tyr
                500                 505                 510
Asn Ser Asn Ile Ile Trp Arg Ser Met Ser Trp Asp Asn Glu Val Ala
    515                 520                 525
Phe Asn Asn Gly Ser Gly Ser Gly Asp Gly Ile Asp Lys Pro Val Val
    530                 535                 540
Pro Glu Gln Pro Asp Glu Pro Gly Glu Ile Pro Ile Pro Glu Asp
545                 550                 555                 560
Ser Asp Ser Asp Pro Gly Ser Asp Ser Gly Ser Asp Ser Asn Ser Asp
                565                 570                 575
Ser Gly Ser Asp Ser Gly Ser Asp Ser Thr Ser Asp Ser Gly Ser Asp
                580                 585                 590
Ser Ala Ser Asp Ser Asp Ser Ala Ser Asp Ser Asp Ser Ala Ser Asp
                595                 600                 605
Ser Asp Ser Ala Ser Asp Ser Asp Ser Ala Ser Asp Ser Asp Ser Asp
                610                 615                 620
Asn Asp Ser Asp Ser Asp Ser Asp Ser Asp Ser Asp Ser Asp Ser Asp
625                 630                 635                 640
Ser Asp Ser Asp Ser Asp Ser Asp Ser Asp Ser Asp Ser Asp Ser Asp
                645                 650                 655
Ser Asp Ser Asp Ser Asp Ser Asp Ser Asp Ser Asp Ser Asp Ser Asp
                660                 665                 670
Ser Asp Ser Asp Ser Asp Ser Asp Ser Asp Ser Asp Ser Asp Ser Asp
                675                 680                 685
Ser Asp Ser Asp Ser Asp Ser Asp Ser Asp Ser Asp Ser Asp Ser Asp
                690                 695                 700
```

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Ala
            755                 760                 765

Ser Asp Ser Asp Ser Asp Ser Asp Ser Asp Ser Asp Ser Asp Ser Asp
    770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Glu Ser Asp
            805                 810                 815

Ser Asp Ser Asp Ser Asp Ser Asp Ser Asp Ser Asp Ser Asp Ser Asp
            820                 825                 830

Ser Asp Ser Asp Ser Ala Ser Asp Ser Asp Ser Gly Ser Asp Ser Asp
            835                 840                 845

Ser Ser Ser Asp Ser Asp Ser Glu Ser Asp Ser Asn Ser Asp Ser Glu
    850                 855                 860

Ser Gly Ser Asn Asn Asn Val Val Pro Pro Asn Ser Pro Lys Asn Gly
865                 870                 875                 880

Thr Asn Ala Ser Asn Lys Asn Glu Ala Lys Asp Ser Lys Glu Pro Leu
            885                 890                 895

Pro Asp Thr Gly Ser Glu Asp Glu Ala Asn Thr Ser Leu Ile Trp Gly
            900                 905                 910

Leu Leu Ala Ser Ile Gly Ser Leu Leu Leu Phe Arg Arg Lys Lys Glu
            915                 920                 925

Asn Lys Asp Lys Lys
            930

<210> SEQ ID NO 67
<211> LENGTH: 677
<212> TYPE: PRT
<213> ORGANISM: Staphylococcus aureus subst. Newman

<400> SEQUENCE: 67

Met Lys Ser Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Glu
            20                  25                  30

Lys Glu Ala Ala Ala Ser Glu Gln Asn Asn Thr Thr Val Glu Glu Ser
        35                  40                  45

Gly Ser Ser Ala Thr Glu Ser Lys Ala Ser Glu Thr Gln Thr Thr Thr
    50                  55                  60

Asn Asn Val Asn Thr Ile Asp Glu Thr Gln Ser Tyr Ser Ala Thr Ser
65                  70                  75                  80

Thr Glu Gln Pro Ser Gln Ser Thr Gln Val Thr Thr Glu Glu Ala Pro
            85                  90                  95

Lys Thr Val Gln Ala Pro Lys Val Glu Thr Ser Arg Val Asp Leu Pro
            100                 105                 110

Ser Glu Lys Val Ala Asp Lys Glu Thr Thr Gly Thr Gln Val Asp Ile
        115                 120                 125

Ala Gln Pro Ser Asn Val Ser Glu Ile Lys Pro Arg Met Lys Arg Ser
    130                 135                 140

-continued

Thr Asp Val Thr Ala Val Ala Glu Lys Glu Val Glu Glu Thr Lys
145                 150                 155                 160

Ala Thr Gly Thr Asp Val Thr Asn Lys Val Glu Val Glu Gly Ser
            165                 170                 175

Glu Ile Val Gly His Lys Gln Asp Thr Asn Val Val Asn Pro His Asn
        180                 185                 190

Ala Glu Arg Val Thr Leu Lys Tyr Lys Trp Lys Phe Gly Glu Gly Ile
    195                 200                 205

Lys Ala Gly Asp Tyr Phe Asp Phe Thr Leu Ser Asp Asn Val Glu Thr
210                 215                 220

His Gly Ile Ser Thr Leu Arg Lys Val Pro Glu Ile Lys Ser Thr Asp
225                 230                 235                 240

Gly Gln Val Met Ala Thr Gly Glu Ile Ile Gly Glu Arg Lys Val Arg
            245                 250                 255

Tyr Thr Phe Lys Glu Tyr Val Gln Glu Lys Lys Asp Leu Thr Ala Glu
            260                 265                 270

Leu Ser Leu Asn Leu Phe Ile Asp Pro Thr Thr Val Thr Gln Lys Gly
        275                 280                 285

Asn Gln Asn Val Glu Val Lys Leu Gly Glu Thr Thr Val Ser Lys Ile
290                 295                 300

Phe Asn Ile Gln Tyr Leu Gly Gly Val Arg Asp Asn Trp Gly Val Thr
305                 310                 315                 320

Ala Asn Gly Arg Ile Asp Thr Leu Asn Lys Val Asp Gly Lys Phe Ser
            325                 330                 335

His Phe Ala Tyr Met Lys Pro Asn Asn Gln Ser Leu Ser Ser Val Thr
            340                 345                 350

Val Thr Gly Gln Val Thr Lys Gly Asn Lys Pro Gly Val Asn Asn Pro
        355                 360                 365

Thr Val Lys Val Tyr Lys His Ile Gly Ser Asp Asp Leu Ala Glu Ser
370                 375                 380

Val Tyr Ala Lys Leu Asp Asp Val Ser Lys Phe Glu Asp Val Thr Asp
385                 390                 395                 400

Asn Met Ser Leu Asp Phe Asp Thr Asn Gly Gly Tyr Ser Leu Asn Phe
            405                 410                 415

Asn Asn Leu Asp Gln Ser Lys Asn Tyr Val Ile Lys Tyr Glu Gly Tyr
        420                 425                 430

Tyr Asp Ser Asn Ala Ser Asn Leu Glu Phe Gln Thr His Leu Phe Gly
        435                 440                 445

Tyr Tyr Asn Tyr Tyr Tyr Thr Ser Asn Leu Thr Trp Lys Asn Gly Val
    450                 455                 460

Ala Phe Tyr Ser Asn Asn Ala Gln Gly Asp Gly Lys Asp Lys Leu Lys
465                 470                 475                 480

Glu Pro Ile Ile Glu His Ser Thr Pro Ile Glu Leu Glu Phe Lys Ser
            485                 490                 495

Glu Pro Pro Val Glu Lys His Glu Leu Thr Gly Thr Ile Glu Glu Ser
        500                 505                 510

Asn Asp Ser Lys Pro Ile Asp Phe Glu Tyr His Thr Ala Val Glu Gly
        515                 520                 525

Ala Glu Gly His Ala Glu Gly Thr Ile Glu Thr Glu Glu Asp Ser Ile
    530                 535                 540

His Val Asp Phe Glu Glu Ser Thr His Glu Asn Ser Lys His His Ala
545                 550                 555                 560

-continued

```
Asp Val Val Glu Tyr Glu Glu Asp Thr Asn Pro Gly Gly Gly Gln Val
            565             570             575

Thr Thr Glu Ser Asn Leu Val Glu Phe Asp Glu Asp Ser Thr Lys Gly
            580             585             590

Ile Val Thr Gly Ala Val Ser Asp His Thr Thr Ile Glu Asp Thr Lys
            595             600             605

Glu Tyr Thr Thr Glu Ser Asn Leu Ile Glu Leu Val Asp Glu Leu Pro
            610             615             620

Glu Glu His Gly Gln Ala Gln Gly Pro Ile Glu Glu Ile Thr Glu Asn
625             630             635             640

Asn His His Ile Ser His Ser Gly Leu Gly Thr Glu Asn Gly His Gly
            645             650             655

Asn Tyr Gly Val Ile Glu Glu Ile Glu Glu Asn Ser His Val Asp Ile
            660             665             670

Lys Ser Glu Leu Gly
            675
```

METHODS AND COMPOSITIONS INVOLVING PROTECTIVE STAPHYLOCOCCAL ANTIGENS

This application is a national phase application under 35 U.S.C. §371 of International Application No. PCT/US2011/051079 filed Sep. 9, 2011, which claims the benefit of U.S. Provisional Patent Application Nos. 61/381,372 and 61/435,617, filed Sep. 9, 2010 and Jan. 24, 2011, respectively, the entirety of which are incorporated herein by reference.

This invention was made with government support under AI057153, AI052474, and GM007281 awarded by the National Institutes of Health. The government has certain rights in the invention.

This work was supported by grants from the U.S. National Institute of Allergy and Infectious Diseases (NIAID), Infectious Diseases Branch (AI52747 and AI92711 to O.S. and AI75258 to D.M.). D.M. and O.S. acknowledge membership within and support from the Region V Great Lakes Regional Center of Excellence in Biodefense and Emerging Infectious Diseases Consortium (National Institutes of Health award 1-U54-AI-057153).

BACKGROUND OF THE INVENTION

I. Field of the Invention

The present invention relates generally to the fields of immunology, microbiology, and pathology. More particularly, it concerns methods and compositions involving bacterial Protein A variants, which can be used to invoke an immune response against the bacteria.

II. Background

The number of both community acquired and hospital acquired infections have increased over recent years with the increased use of intravascular devices. Hospital acquired (nosocomial) infections are a major cause of morbidity and mortality, more particularly in the United States, where it affects more than 2 million patients annually. The most frequent infections are urinary tract infections (33% of the infections), followed by pneumonia (15.5%), surgical site infections (14.8%) and primary bloodstream infections (13%) (Emorl and Gaynes, 1993).

The major nosocomial pathogens include *Staphylococcus aureus*, coagulase-negative Staphylococci (mostly *Staphylococcus epidermidis*), *enterococcus* spp., *Escherichia coli* and *Pseudomonas aeruginosa*. Although these pathogens cause approximately the same number of infections, the severity of the disorders they can produce combined with the frequency of antibiotic resistant isolates balance this ranking towards *S. aureus* and *S. epidermidis* as being the most significant nosocomial pathogens.

Staphylococci can cause a wide variety of diseases in humans and other animals through either toxin production or invasion. Staphylococcal toxins are also a common cause of food poisoning, as the bacteria can grow in improperly-stored food.

*Staphylococcus epidermidis* is a normal skin commensal which is also an important opportunistic pathogen responsible for infections of impaired medical devices and infections at sites of surgery. Medical devices infected by *S. epidermidis* include cardiac pacemakers, cerebrospinal fluid shunts, continuous ambulatory peritoneal dialysis catheters, orthopedic devices and prosthetic heart valves.

*Staphylococcus aureus* is the most common cause of nosocomial infections with a significant morbidity and mortality. It is the cause of some cases of osteomyelitis, endocarditis, septic arthritis, pneumonia, abscesses, and toxic shock syndrome. *S. aureus* can survive on dry surfaces, increasing the chance of transmission. Any *S. aureus* infection can cause the staphylococcal scalded skin syndrome, a cutaneous reaction to exotoxin absorbed into the bloodstream. It can also cause a type of septicemia called pyaemia that can be life-threatening. Problematically, Methicillin-resistant *Staphylococcus aureus* (MRSA) has become a major cause of hospital-acquired infections.

*S. aureus* and *S. epidermidis* infections are typically treated with antibiotics, with penicillin being the drug of choice, whereas vancomycin is used for methicillin resistant isolates. The percentage of staphylococcal strains exhibiting wide-spectrum resistance to antibiotics has become increasingly prevalent, posing a threat for effective antimicrobial therapy. In addition, the recent emergence of vancomycin resistant *S. aureus* strain has aroused fear that MRSA strains are emerging and spreading for which no effective therapy is available.

An alternative to antibiotic treatment for staphylococcal infections is under investigation that uses antibodies directed against staphylococcal antigens. This therapy involves administration of polyclonal antisera (WO00/15238, WO00/12132) or treatment with monoclonal antibodies against lipoteichoic acid (WO98/57994).

An alternative approach would be the use of active vaccination to generate an immune response against staphylococci. The *S. aureus* genome has been sequenced and many of the coding sequences have been identified (WO02/094868, EP0786519), which can lead to the identification of potential antigens. The same is true for *S. epidermidis* (WO01/34809). As a refinement of this approach, others have identified proteins that are recognized by hyperimmune sera from patients who have suffered staphylococcal infection (WO01/98499, WO02/059148).

*S. aureus* secretes a plethora of virulence factors into the extracellular milieu (Archer, 1998; Dinges et al., 2000; Foster, 2005; Shaw et al., 2004; Sibbald et al., 2006). Like most secreted proteins, these virulence factors are translocated by the Sec machinery across the plasma membrane. Proteins secreted by the Sec machinery bear an N-terminal leader peptide that is removed by leader peptidase once the pre-protein is engaged in the Sec translocon (Dalbey and Wickner, 1985; van Wely et al., 2001). Recent genome analysis suggests that Actinobacteria and members of the Firmicutes encode an additional secretion system that recognizes a subset of proteins in a Sec-independent manner (Pallen, 2002). ESAT-6 (early secreted antigen target 6 kDa) and CFP-10 (culture filtrate antigen 10 kDa) of *Mycobacterium tuberculosis* represent the first substrates of this novel secretion system termed ESX-1 or 5 nm in *M. tuberculosis* (Andersen et al., 1995; Hsu et al., 2003; Pym et al., 2003; Stanley et al., 2003). In *S. aureus*, two ESAT-6 like factors designated EsxA and EsxB are secreted by the Ess pathway (ESAT-6 secretion system) (Burts et al., 2005).

The first generation of vaccines targeted against *S. aureus* or against the exoproteins it produces have met with limited success (Lee, 1996). There remains a need to develop effective vaccines against staphylococcal infections. Additional compositions for treating staphylococcal infections are also needed.

SUMMARY OF THE INVENTION

Protein A (SpA) (SEQ ID NO:33), a cell wall anchored surface protein of *Staphylococcus aureus*, provides for bacterial evasion from innate and adaptive immune responses. Protein A binds immunoglobulins at their Fc portion, interacts with the VH3 domain of B cell receptors inappropriately stimulating B cell proliferation and apotosis, binds to von Willebrand factor A1 domains to activate intracellular clotting, and also binds to the TNF Receptor-1 to contribute to the pathogenesis of staphylococcal pneumonia. Due to the fact that Protein A captures immunoglobulin and displays toxic attributes, the possibility that this surface molecule may function as a vaccine in humans has not been rigorously pursued. Here the inventors demonstrate that Protein A variants no longer able to bind to immunoglobulins, which are thereby removed of their toxigenic potential, i.e., are non-toxigenic, stimulate humoral immune responses that protect against staphylococcal disease.

In certain embodiments the SpA variant is a full length SpA variant comprising a variant A, B, C, D, and/or E domain. In certain aspects, the SpA variant comprises or consists of the amino acid sequence that is 80, 90, 95, 98, 99, or 100% identical to the amino acid sequence of SEQ ID NO:34 In other embodiments the SpA variant comprises a segment of SpA. The SpA segment can comprise at least or at most 1, 2, 3, 4, 5 or more IgG binding domains. The IgG domains can be at least or at most 1, 2, 3, 4, 5 or more variant A, B, C, D, or E domains. In certain aspects the SpA variant comprises at least or at most 1, 2, 3, 4, 5, or more variant A domains. In a further aspect the SpA variant comprises at least or at most 1, 2, 3, 4, 5, or more variant B domains. In still a further aspect the SpA variant comprises at least or at most 1, 2, 3, 4, 5, or more variant C domains. In yet a further aspect the SpA variant comprises at least or at most 1, 2, 3, 4, 5, or more variant D domains. In certain aspects the SpA variant comprises at least or at most 1, 2, 3, 4, 5, or more variant E domains. In a further aspect the SpA variant comprises a combination of A, B, C, D, and E domains in various combinations and permutations. The combinations can include all or part of a SpA signal peptide segment, a SpA region X segment, and/or a SpA sorting signal segment. In other aspects the SpA variant does not include a SpA signal peptide segment, a SpA region X segment, and/or a SpA sorting signal segment. In certain aspects a variant A domain comprises a substitution at position(s) 7, 8, 34, and/or 35 of SEQ ID NO:4. In another aspect a variant B domain comprises a substitution at position(s) 7, 8, 34, and/or 35 of SEQ ID NO:6. In still anther aspect a variant C domain comprises a substitution at position(s) 7, 8, 34, and/or 35 of SEQ ID NO:5. In certain aspects a variant D domain comprises a substitution at position(s) 9, 10, 36, and/or 37 of SEQ ID NO:2. In a further aspect a variant E domain comprises a substitution at position(s) 6, 7, 33, and/or 34 of SEQ ID NO:3.

In certain aspects, an SpA domain D variant or its equivalent can comprise a mutation at position 9 and 36; 9 and 37; 9 and 10; 36 and 37; 10 and 36; 10 and 37; 9, 36, and 37; 10, 36, and 37, 9, 10 and 36; or 9, 10 and 37 of SEQ ID NO:2. In a further aspect, analogous mutations can be included in one or more of domains A, B, C, or E.

In further aspects, the amino acid glutamine (Q) at position 9 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 9 can be substituted with an arginine (R). In a further aspect, the glutamine at position 9 of SEQ ID NO:2, or its equivalent, can be substituted with a lysine or a glycine. Any 1, 2, 3, 4, 5, 6, 7, 8, 9, 10, or more of the substitutions can be explicitly excluded.

In another aspect, the amino acid glutamine (Q) at position 10 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 10 can be substituted with an arginine (R). In a further aspect, the glutamine at position 10 of SEQ ID NO:2, or its equivalent, can be substituted with a lysine or a glycine. Any 1, 2, 3, 4, 5, 6, 7, 8, 9, 10, or more of the substitutions can be explicitly excluded.

In certain aspects, the aspartic acid (D) at position 36 of SEQ ID NO:2 (or its analogous amino acid in other SpA domains) can be replaced with an alanine (A), an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 36 can be substituted with a glutamic acid (E). In certain aspects, an aspartic acid at position 36 of SEQ ID NO:2, or its equivalent, can be substituted with an alanine or a serine. Any 1, 2, 3, 4, 5, 6, 7, 8, 9, 10, or more of the substitutions can be explicitly excluded.

In another aspect, the aspartic acid (D) at position 37 of SEQ ID NO:2 (or its analogous amino acid in other SpA domains) can be replaced with an alanine (A), a an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 37 can be substituted with a glutamic acid (E). In certain aspects, an aspartic acid at position 37 of SEQ ID NO:2, or its equivalent, can be substituted with an alanine or a serine. Any 1, 2, 3, 4, 5, 6, 7, 8, 9, 10, or more of the substitutions can be explicitly excluded.

In a particular embodiment the amino at position 9 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 9 of SEQ ID NO:2 is replaced by a glycine. In a further aspect the amino acid at position 9 of SEQ ID NO:2 is replaced by a lysine.

In a particular embodiment the amino at position 10 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 10 of SEQ ID NO:2 is replaced by a glycine. In a further aspect the amino acid at position 10 of SEQ ID NO:2 is replaced by a lysine.

In a particular embodiment the amino at position 36 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 36 of SEQ ID NO:2 is replaced by a serine. In a further aspect the amino acid at position 36 of SEQ ID NO:2 is replaced by an alanine.

In a particular embodiment the amino at position 37 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 37 of SEQ ID NO:2 is replaced by a serine. In a further aspect the amino acid at position 37 of SEQ ID NO:2 is replaced by an alanine.

In certain aspects the SpA variant includes (a) one or more amino acid substitution in an IgG Fc binding sub-domain of SpA domain A, B, C, D, and/or E that disrupts or decreases binding to IgG Fc, and (b) one or more amino acid substitution in a $V_H3$ binding sub-domain of SpA domain A, B, C, D, and/or E that disrupts or decreases binding to $V_H3$. In still further aspects the amino acid sequence of a SpA variant comprises an amino acid sequence that is at least 50%, 60%, 70%, 80%, 90%, 95%, or 100% identical, including all values and ranges there between, to the amino acid sequence of SEQ ID NOs:2-6.

In a further aspect the SpA variant includes (a) one or more amino acid substitution in an IgG Fc binding sub-domain of SpA domain D, or at a corresponding amino acid position in other IgG domains, that disrupts or decreases binding to IgG Fc, and (b) one or more amino acid substitution in a $V_H3$ binding sub-domain of SpA domain D, or at a corresponding amino acid position in other IgG domains, that disrupts or decreases binding to $V_H3$. In certain aspects amino acid residue F5, Q9, Q10, S11, F13, Y14, L17, N28, I31, and/or K35 (SEQ ID NO:2, QQNNFNKDQQSAFYEILNMPNL-NEAQRNGFIQSLKDDPSQSTNVLGEAKKLNES) of the IgG Fc binding sub-domain of domain D are modified or substituted. In certain aspects amino acid residue Q26, G29, F30, S33, D36, D37, Q40, N43, and/or E47 (SEQ ID NO:2) of the $V_H3$ binding sub-domain of domain D are modified or substituted such that binding to Fc or $V_H3$ is attenuated. In further aspects corresponding modifications or substitutions can be engineered in corresponding positions of the domain A, B, C, and/or E. Corresponding positions are defined by alignment of the domain D amino acid sequence with one or more of the amino acid sequences from other IgG binding domains of SpA, for example see FIG. 2A. In certain aspects the amino acid substitution can be any of the other 20 amino acids. In a further aspect conservative amino acid substitutions can be specifically excluded from possible amino acid substitutions. In other aspects only non-conservative substitutions are included. In any event, any substitution or combination of substitutions that reduces the binding of the domain such that SpA toxicity is significantly reduced is contemplated. The significance of the reduction in binding refers to a variant that produces minimal to no toxicity when introduced into a subject and can be assessed using in vitro methods described herein.

In certain embodiments, a variant SpA comprises at least or at most 1, 2, 3, 4, 5, 6, 7, 8, 9, 10, or more variant SpA domain D peptides. In certain aspects 1, 2, 3, 4, 5, 6, 7, 8, 9, 10, 11, 12, 13, 14, 15, 16, 17, 18, or 19 or more amino acid residues of the variant SpA are substituted or modified—including but not limited to amino acids F5, Q9, Q10, S11, F13, Y14, L17, N28, I31, and/or K35 (SEQ ID NO:2) of the IgG Fc binding sub-domain of domain D and amino acid residue Q26, G29, F30, S33, D36, D37, Q40, N43, and/or E47 (SEQ ID NO:2) of the $V_H3$ binding sub-domain of domain D. In one aspect of the invention glutamine residues at position 9 and/or 10 of SEQ ID NO:2 (or corresponding positions in other domains) are mutated. In another aspect, aspartic acid residues 36 and/or 37 of SEQ ID NO:2 (or corresponding positions in other domains) are mutated. In a further aspect, glutamine 9 and 10, and aspartic acid residues 36 and 37 are mutated. Purified non-toxigenic SpA or SpA-D mutants/variants described herein are no longer able to significantly bind (i.e., demonstrate attenuated or disrupted binding affinity) Fcγ or F(ab)$_2$ $V_H3$ and also do not stimulate B cell apoptosis. These non-toxigenic Protein A variants can be used as subunit vaccines and raise humoral immune responses and confer protective immunity against S. aureus challenge. Compared to wild-type full-length Protein A or the wild-type SpA-domain D, immunization with SpA-D variants resulted in an increase in Protein A specific antibody. Using a mouse model of staphylococcal challenge and abscess formation, it was observed that immunization with the non-toxigenic Protein A variants generated significant protection from staphylococcal infection and abscess formation. As virtually all S. aureus strains express Protein A, immunization of humans with the non-toxigenic Protein A variants can neutralize this virulence factor and thereby establish protective immunity. In certain aspects the protective immunity protects or ameliorates infection by drug resistant strains of Staphylococcus, such as USA300 and other MRSA strains.

Embodiments include the use of Protein A variants in methods and compositions for the treatment of bacterial and/or staphylococcal infection. This application also provides an immunogenic composition comprising a Protein A variant or immunogenic fragment thereof. In certain aspects, the immunogenic fragment is a Protein A domain D segment. Furthermore, the present invention provides methods and compositions that can be used to treat (e.g., limiting staphylococcal abscess formation and/or persistence in a subject) or prevent bacterial infection. In some cases, methods for stimulating an immune response involve administering to the subject an effective amount of a composition including or encoding all or part of a Protein A variant polypeptide or antigen, and in certain aspects other bacterial proteins. Other bacterial proteins include, but are not limited to (i) a secreted virulence factor, and/or a cell surface protein or peptide, or (ii) a recombinant nucleic acid molecule encoding a secreted virulence factor, and/or a cell surface protein or peptide.

In other aspects, the subject can be administered all or part of a Protein A variant, such as a variant Protein A domain D segment. The polypeptide of the invention can be formulated in a pharmaceutically acceptable composition. The composition can further comprise one or more of at least or at most 1, 2, 3, 4, 5, 6, 7, 8, 9, 10, 11, 12, 13, 14, 15, 16, 17, 18, or 19 additional staphylococcal antigen or immunogenic fragment thereof (e.g., Eap, Ebh, Emp, EsaB, EsaC, EsxA, EsxB, an EsxA-B fusion protein (i.e., EsxAB or EsxBA), SdrC, SdrD, SdrE, IsdA, IsdB, ClfA, ClfB, Coa, Hla (e.g., H35 mutants), IsdC, SasF, vWbp, FhuD2, sta011, sta0048, sta0069 or vWh). Additional staphylococcal antigens that can be used in combination with a Protein A variant include, but are not limited to 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, $Mg^{2+}$ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, Vitronectin binding protein (see PCT publications WO2007/113222, WO2007/113223, WO2006/032472, WO2006/032475, WO2006/032500, each of which is incorporated herein by reference in their entirety) and/or any of those antigens described in PCT Publn. No. WO2010119343, incorporated herein by reference.

In certain aspects, the SpA variant composition can further comprise SdrD, ClfA, and/or FnbpB (FnbB) staphylococcal antigens or immunogenic fragments thereof. Thus, in certain aspects, a composition of the embodiments comprises a SpA variant, SdrD, ClfA, and FnbpB (FnbB) staphylococcal antigens. Such a composition can, in some aspects be essentially free of other staphylococcal antigens, such as staphylococcal polypeptides or carbohydrates (e.g., a composition comprising staphylococcal antigens that essentially comprise the SpA variant, SdrD, ClfA, and FnbpB (FnbB) staphylococcal antigens). In a further aspect, embodiments of the invention provide for the use of a SpA variant, SdrD, ClfA, and FnbpB polypeptide in the preparation of a medicament for the treatment or prevention of a staphylococcal infection.

The staphylococcal antigen(s) or immunogenic fragment(s) of the embodiments can be administered concurrently with the Protein A variant. The staphylococcal antigen or immunogenic fragment and the Protein A variant can be administered in the same composition. The Protein A variant can also be a recombinant nucleic acid molecule encoding a Protein A variant. A recombinant nucleic acid molecule can encode the Protein A variant and at least one staphylococcal antigen or immunogenic fragment thereof. As used herein, the term "modulate" or "modulation" encompasses the meanings of the words "enhance," or "inhibit." "Modulation" of activity may be either an increase or a decrease in activity. As used herein, the term "modulator" refers to compounds that effect the function of a moiety, including up-regulation, induction, stimulation, potentiation, inhibition, down-regulation, or suppression of a protein, nucleic acid, gene, organism or the like.

In further aspects, an immunogenic composition comprises SdrD, ClfA, and/or FnbpB (FnbB) staphylococcal antigens or immunogenic fragments thereof. In other embodiments an immunogenic composition comprising SdrD, ClfA, and/or FnbpB (FnbB) staphylococcal antigens or immunogenic fragments thereof can be used in treating, ameliorating or inhibiting staphylococcal infection, as described herein. Thus, some embodiments of the invention concern compositions comprising SdrD, ClfA, and FnbpB (FnbB) staphylococcal antigens. Such a composition can, in some aspects, be essentially free of other staphylococcal antigens, such as staphylococcal polypeptides or carbohydrates (e.g., a composition comprising staphylococcal antigens that essentially comprise SdrD, ClfA, and FnbpB (FnbB) staphylococcal antigens). In a further aspect, embodiments of the invention provide for the use of a SdrD, ClfA, and FnbpB polypeptide in the preparation of a medicament for the treatment or prevention of a staphylococcal infection. In certain aspects, a SdrD, ClfA, and/or FnbpB (FnbB) staphylococcal antigen is from S. aureus.

In certain embodiments the methods and compositions use or include or encode all or part of the Protein A variant or antigen. In other aspects, the Protein A variant may be used in combination with secreted factors or surface antigens including, but not limited to one or more of an isolated Eap, Ebh, Emp, EsaB, EsaC, EsxA, EsxB, an EsxA-B fusion protein (i.e., EsxAB or EsxBA), SdrC, SdrD, SdrE, IsdA, IsdB, ClfA, ClfB, Coa, Hla, IsdC, SasF, vWbp, FhuD2, sta011, sta0048, sta0069 or vWh polypeptide or immunogenic segment thereof. Additional staphylococcal antigens that can be used in combination with a Protein A variant include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, $Mg^{2+}$ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In certain embodiments, 1, 2, 3, 4, 5, 6, 7, 8, 9, 10 or more of Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein can be specifically excluded from a formulation of the invention. In further embodiments the methods and compositions use or include or encode all or part of the SdrD, ClfA and/or FnbpB (FnbB) antigens.

In some embodiments, the methods and compositions use, include or encode a Protein A variant in combination with the FhuD2, sta011, Hla (e.g., a H35 mutant such as $HLA_{35L}$ or $HLA_{35A}$) and EsxAB (i.e., an EsxA-B fusion protein) staphylococcal antigens or protions of these antigens. In further aspects, such a combination further includes SdrD, ClfA and/or FnbpB antigens The following table lists (Table 1) combinations of SpA variants of the embodiments and various other Staphylococcal antigens. It will be apparent to one skilled in the art that there are, for example, 378 possible pairwise combinations selected from a set of 28 antigens, 3,276 possible three-way combinations, and 20,475 possible four-way combinations, and so on for larger subsets of antigens, all of which are contemplated herein.

Thus, any of the combinations of antigens of Table 1 can also be combined with one, two or more of the antigens selected from the group consisting of Eap, Ebh, Emp, EsaB, EsaC, EsxA, EsxB, SdrC, SdrD, SdrE, IsdA, IsdB, ClfA, ClfB, Coa, Hla, $Hla_{H35A}$, IsdC, SasF, vWbp, vWh, FnbpB, FhuD2, sta011, sta0048, sta0069, and fusion proteins of EsxA and EsxB (i.e., EsxAB or EsxBA). Additional antigens that can be included in such combinations include, but are not limited to, those described in PCT Publn. No. WO2010119343, incorporated herein by reference.

TABLE 1

SpA and staphylococcal antigen combinations.

| | Eap | Ebh | Emp | EsaB | EsaC | EsxA | EsxB | SdrC | SdrD | SdrE | IsdA | IsdB | ClfA | ClfB | Coa | Hla | Hla$_{H35A}$ | IsdC | SasF | vWbp | vWh | FnbpB | FhuD2 | sta011 | sta0048 | sta0069 | EsxAB | EsxBA |
|---|---|---|---|---|---|---|---|---|---|---|---|---|---|---|---|---|---|---|---|---|---|---|---|---|---|---|---|---|
| Eap | | + | + | + | + | + | + | + | + | + | + | + | + | + | + | + | + | + | + | + | + | + | + | + | + | + | + | + |
| Ebh | | | + | + | + | + | + | + | + | + | + | + | + | + | + | + | + | + | + | + | + | + | + | + | + | + | + | + |
| Emp | | | | + | + | + | + | + | + | + | + | + | + | + | + | + | + | + | + | + | + | + | + | + | + | + | + | + |
| EsaB | | | | | + | + | + | + | + | + | + | + | + | + | + | + | + | + | + | + | + | + | + | + | + | + | + | + |
| EsaC | | | | | | + | + | + | + | + | + | + | + | + | + | + | + | + | + | + | + | + | + | + | + | + | + | + |
| EsxA | | | | | | | + | + | + | + | + | + | + | + | + | + | + | + | + | + | + | + | + | + | + | + | + | + |
| EsxB | | | | | | | | + | + | + | + | + | + | + | + | + | + | + | + | + | + | + | + | + | + | + | + | + |
| SdrC | | | | | | | | | + | + | + | + | + | + | + | + | + | + | + | + | + | + | + | + | + | + | + | + |
| SdrD | | | | | | | | | | + | + | + | + | + | + | + | + | + | + | + | + | + | + | + | + | + | + | + |
| SdrE | | | | | | | | | | | + | + | + | + | + | + | + | + | + | + | + | + | + | + | + | + | + | + |
| IsdA | | | | | | | | | | | | + | + | + | + | + | + | + | + | + | + | + | + | + | + | + | + | + |
| IsdB | | | | | | | | | | | | | + | + | + | + | + | + | + | + | + | + | + | + | + | + | + | + |
| ClfA | | | | | | | | | | | | | | + | + | + | + | + | + | + | + | + | + | + | + | + | + | + |
| ClfB | | | | | | | | | | | | | | | + | + | + | + | + | + | + | + | + | + | + | + | + | + |
| Coa | | | | | | | | | | | | | | | | + | + | + | + | + | + | + | + | + | + | + | + | + |
| Hla | | | | | | | | | | | | | | | | | + | + | + | + | + | + | + | + | + | + | + | + |
| Hla$_{H35A}$ | | | | | | | | | | | | | | | | | | + | + | + | + | + | + | + | + | + | + | + |
| IsdC | | | | | | | | | | | | | | | | | | | + | + | + | + | + | + | + | + | + | + |
| SasF | | | | | | | | | | | | | | | | | | | | + | + | + | + | + | + | + | + | + |
| vWbp | | | | | | | | | | | | | | | | | | | | | + | + | + | + | + | + | + | + |
| vWh | | | | | | | | | | | | | | | | | | | | | | + | + | + | + | + | + | + |
| FnbpB | | | | | | | | | | | | | | | | | | | | | | | + | + | + | + | + | + |
| FhuD2 | | | | | | | | | | | | | | | | | | | | | | | | + | + | + | + | + |
| sta011 | | | | | | | | | | | | | | | | | | | | | | | | | + | + | + | + |
| sta0048 | | | | | | | | | | | | | | | | | | | | | | | | | | + | + | + |
| sta0069 | | | | | | | | | | | | | | | | | | | | | | | | | | | + | + |
| EsxAB | | | | | | | | | | | | | | | | | | | | | | | | | | | | + |
| EsxBA | | | | | | | | | | | | | | | | | | | | | | | | | | | | |

In still further aspects, the isolated Protein A variant is multimerized, e.g., dimerized or a linear fusion of two or more polypeptides or peptide segments. In certain aspects of the invention, a composition comprises multimers or concatamers of 1, 2, 3, 4, 5, 6, 7, 8, 9, 10, 11, 12, 13, 14, 15, 16, 17, 18, 19, 20 or more isolated cell surface proteins or segments thereof. Concatamers are linear polypeptides having one or more repeating peptide units. SpA polypeptides or fragments can be consecutive or separated by a spacer or other peptide sequences, e.g., one or more additional bacterial peptide. In a further aspect, the other polypeptides or peptides contained in the multimer or concatamer can include, but are not limited to 1, 2, 3, 4, 5, 6, 7, 8, 9, 10, 11, 12, 13, 14, 15, 16, 17, 18, 19 of Eap, Ebh, Emp, EsaB, EsaC, EsxA, EsxB, SdrC, SdrD, SdrE, IsdA, IsdB, ClfA, CHB, Coa, Hla, IsdC, SasF, vWbp, vWh or immunogenic fragments thereof. Additional staphylococcal antigens that can be used in combination with a Protein A variant include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In certain aspects the SpA variant is used in combination with SdrD, ClfA, and/or FnbpB (FnB) antigens.

The term "Protein A variant" or "SpA variant" refers to polypeptides that include a SpA IgG domain having two or more amino acid substitutions that disrupt binding to Fc and $V_H3$. In certain aspect, a SpA variant includes a variant domain D peptide, as well as variants of SpA polypeptides and segments thereof that are non-toxigenic and stimulate an immune response against staphylococcus bacteria Protein A and/or bacteria expressing such.

Embodiments of the present invention include methods for eliciting an immune response against a staphylococcus bacterium or staphylococci in a subject comprising providing to the subject an effective amount of a Protein A variant or a segment thereof. In certain aspects, the methods for eliciting an immune response against a staphylococcus bacterium or staphylococci in a subject comprising providing to the subject an effective amount of 1, 2, 3, 4, 5, 6, 7, 8, 9, 10, 11, 12, 13, 14, 15, 16, 17, 18, 19 or more secreted proteins and/or cell surface proteins or segments/fragments thereof A secreted protein or cell surface protein includes, but is not limited to Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, and/or vWh proteins and immunogenic fragments thereof. Additional staphylococcal antigens that can be used in combination with a Protein A variant include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In certain aspects an SpA variant is used in combination with SdrD, ClfA, and/or FnbpB (FnB) antigens.

Embodiments of the invention include compositions that include a polypeptide, peptide, or protein that is or is at least 70%, 75%, 80%, 85%, 90%, 95%, 96%, 97%, 98%, or 99% identical or similar to Protein A, or a second protein or peptide that is a secreted bacterial protein or a bacterial cell surface protein. In a further embodiment of the invention a composition may include a polypeptide, peptide, or protein that is or is at least 70%, 75%, 80%, 85%, 90%, 95%, 96%, 97%, 98%, or 99% identical or similar to a Protein A domain D polypeptide (SEQ ID NO:2), domain E (SEQ ID NO:3), domain A (SEQ ID NO:4), domain C (SEQ ID NO:5), domain B (SEQ ID NO:6), or a nucleic acid sequence encoding a Protein A domain D, domain E, domain A, domain C, or domain B polypeptide. In certain aspects a Protein A polypeptide segment will have an amino acid sequence of SEQ ID NO:8. Similarity or identity, with identity being preferred, is known in the art and a number of different programs can be used to identify whether a protein (or nucleic acid) has sequence identity or similarity to a known sequence. Sequence identity and/or similarity is determined using standard techniques known in the art, including, but not limited to, the local sequence identity algorithm of Smith & Waterman (1981), by the sequence identity alignment algorithm of Needleman & Wunsch (1970), by the search for similarity method of Pearson & Lipman (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984), preferably using the default settings, or by inspection. Preferably, percent identity is calculated by using alignment tools known to and readily ascertainable to those of skill in the art. Percent identity is essentially the number of identical amino acids divided by the total number of amino acids compared times one hundred.

Still further embodiments include methods for stimulating in a subject a protective or therapeutic immune response against a staphylococcus bacterium comprising administering to the subject an effective amount of a composition including (i) a SpA variant, e.g., a variant SpA domain D polypeptide or peptide thereof; or, (ii) a nucleic acid molecule encoding such a SpA variant polypeptide or peptide thereof, or (iii) administering a SpA variant domain D polypeptide with any combination or permutation of bacterial proteins described herein. In a preferred embodiment the composition is not a staphylococcus bacterium. In certain aspects the subject is a human or a cow. In a further aspect the composition is formulated in a pharmaceutically acceptable formulation. The staphylococci may be Staphylococcus aureus.

Yet still further embodiments include vaccines comprising a pharmaceutically acceptable composition having an isolated SpA variant polypeptide, or any other combination or permutation of protein(s) or peptide(s) described herein, wherein the composition is capable of stimulating an immune response against a staphylococcus bacterium. The vaccine may comprise an isolated SpA variant polypeptide, or any other combination or permutation of protein(s) or peptide(s) described. In certain aspects of the invention the isolated SpA variant polypeptide, or any other combination or permutation of protein(s) or peptide(s) described are multimerized, e.g., dimerized or concatamerized. In a further aspect, the vaccine composition is contaminated by less than about 10, 9, 8, 7, 6, 5, 4, 3, 2, 1, 0.5, 0.25, 0.05% (or any range derivable therein) of other Staphylococcal proteins. A composition may further comprise an isolated non-SpA polypeptide. Typically the vaccine comprises an adjuvant. In certain aspects a protein or peptide of the invention is linked (covalently or non-covalently) to the adjuvant, preferably the adjuvant is chemically conjugated to the protein.

In still yet further embodiments, a vaccine composition is a pharmaceutically acceptable composition having a recombinant nucleic acid encoding all or part of a SpA variant polypeptide, or any other combination or permutation of protein(s) or peptide(s) described herein, wherein the composition is capable of stimulating an immune response against a staphylococcus bacteria. The vaccine composition may comprise a recombinant nucleic acid encoding all or part of a SpA variant polypeptide, or any other combination or permutation of protein(s) or peptide(s) described herein. In certain embodiments the recombinant nucleic acid contains a heterologous promoter. Preferably the recombinant nucleic acid is a vector. More preferably the vector is a plasmid or a viral vector. In some aspects the vaccine includes a recombinant, non-staphylococcus bacterium containing the nucleic acid. The recombinant non-staphylococci may be *Salmonella* or another gram-positive bacteria. The vaccine may comprise a pharmaceutically acceptable excipient, more preferably an adjuvant.

Still further embodiments include methods for stimulating in a subject a protective or therapeutic immune response against a *staphylococcus* bacterium comprising administering to the subject an effective amount of a composition of a SpA variant polypeptide or segment/fragment thereof and further comprising one or more of a Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, or vWh protein or peptide thereof. In a preferred embodiment the composition comprises a non-staphylococcus bacterium. In a further aspect the composition is formulated in a pharmaceutically acceptable formulation. The staphylococci for which a subject is being treated may be *Staphylococcus aureus*. Methods of the invention also include SpA variant compositions that contain 1, 2, 3, 4, 5, 6, 7, 8, 9, 10, 11, 12, 13, 14, 15, 16, 17, 18, 19 or more secreted virulence factors and/or cell surface proteins, such as Eap, Ebh, Emp, EsaC, EsxA, EsxB, SdrC, SdrD, SdrE, IsdA, IsdB, ClfA, ClfB, Coa, Hla, IsdC, SasF, vWbp, or vWh in various combinations. In certain aspects a vaccine formulation includes Eap, Ebh, Emp, EsaC, EsxA, EsxB, SdrC, SdrD, SdrE, IsdA, IsdB, ClfA, ClfB, Coa, Hla, IsdC, SasF, vWbp, and vWh. In certain aspects an antigen combination can include (1) a SpA variant and IsdA; (2) SpA variant and ClfB; (3) SpA variant and SdrD; (4) SpA variant and Hla or Hla variant; (5) SpA variant and ClfB, SdrD, and Hla or Hla variant; (6) SpA variant, IsdA, SdrD, and Hla or Hla variant; (7) SpA variant, IsdA, ClfB, and Hla or Hla variant; (8) SpA variant, IsdA, ClfB, and SdrD; (9) SpA variant, IsdA, ClfB, SdrD and Hla or Hla variant; (10) SpA variant, IsdA, ClfB, and SdrD; (11) SpA variant, IsdA, SdrD, and Hla or Hla variant; (12) SpA variant, IsdA, and Hla or Hla variant; (13) SpA variant, IsdA, ClfB, and Hla or Hla variant; (14) SpA variant, ClfB, and SdrD; (15) SpA variant, ClfB, and Hla or Hla variant; or (16) SpA variant, SdrD, and Hla or Hla variant.

In certain aspects, a bacterium delivering a composition of the invention will be limited or attenuated with respect to prolonged or persistent growth or abscess formation. In yet a further aspect, SpA variant(s) can be overexpressed in an attenuated bacterium to further enhance or supplement an immune response or vaccine formulation.

The term "EsxA protein" refers to a protein that includes isolated wild-type EsxA polypeptides from *staphylococcus* bacteria and segments thereof, as well as variants that stimulate an immune response against *staphylococcus* bacteria EsxA proteins.

The term "EsxB protein" refers to a protein that includes isolated wild-type EsxB polypeptides from *staphylococcus* bacteria and segments thereof, as well as variants that stimulate an immune response against *staphylococcus* bacteria EsxB proteins.

The term "SdrD protein" refers to a protein that includes isolated wild-type SdrD polypeptides from *staphylococcus* bacteria and segments thereof, as well as variants that stimulate an immune response against *staphylococcus* bacteria SdrD proteins. For example, a wild type SdrD amino acid sequence is provided in NCBI accession no. CAA06651 (SEQ ID NO:65). A SrdD polypeptide for use an antigen according to the embodiments can comprise an amino acid sequence comprising SEQ ID NO:65 or a sequence at least about 70%, 75%, 80%, 85%, 90%, 95%, 97%, 98% or 99% identical to SEQ ID NO:65. In a further aspect, the SrdD polypeptide comprises 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 30, 310, 320, 330, 340, 350, 360, 370, 380, 390, 400, 410, 420, 430, 440, 450, 460, 470, 480, 490, 500, 550, 600, 650, 700, 750, 800, 850, 900, 950, 1000, 1050, 1100, 1150, 1200, 1250, 1300 or 1315 amino acids in length, including all values and ranges there between, that are at least 80, 85, 90, 95, 96, 97, 98, 99, or 100% identical to amino acid segments of SEQ ID NO:65.

The term "SdrE protein" refers to a protein that includes isolated wild-type SdrE polypeptides from *staphylococcus* bacteria and segments thereof, as well as variants that stimulate an immune response against *staphylococcus* bacteria SdrE proteins.

The term "IsdA protein" refers to a protein that includes isolated wild-type IsdA polypeptides from *staphylococcus* bacteria and segments thereof, as well as variants that stimulate an immune response against *staphylococcus* bacteria IsdA proteins.

The term "IsdB protein" refers to a protein that includes isolated wild-type IsdB polypeptides from *staphylococcus* bacteria and segments thereof, as well as variants that stimulate an immune response against *staphylococcus* bacteria IsdB proteins.

The term "Eap protein" refers to a protein that includes isolated wild-type Eap polypeptides from *staphylococcus* bacteria and segments thereof, as well as variants that stimulate an immune response against *staphylococcus* bacteria Eap proteins.

The term "Ebh protein" refers to a protein that includes isolated wild-type Ebh polypeptides from *staphylococcus* bacteria and segments thereof, as well as variants that stimulate an immune response against *staphylococcus* bacteria Ebh proteins.

The term "Emp protein" refers to a protein that includes isolated wild-type Emp polypeptides from *staphylococcus* bacteria and segments thereof, as well as variants that stimulate an immune response against *staphylococcus* bacteria Emp proteins.

The term "EsaB protein" refers to a protein that includes isolated wild-type EsaB polypeptides from *staphylococcus* bacteria and segments thereof, as well as variants that stimulate an immune response against *staphylococcus* bacteria EsaB proteins.

The term "EsaC protein" refers to a protein that includes isolated wild-type EsaC polypeptides, from *staphylococcus* bacteria and segments thereof, as well as variants that stimulate an immune response against *staphylococcus* bacteria EsaC proteins.

The team "SdrC protein" refers to a protein that includes isolated wild-type SdrC polypeptides from *staphylococcus* bacteria and segments thereof, as well as variants that stimulate an immune response against *staphylococcus* bacteria SdrC proteins.

The term "ClfA protein" refers to a protein that includes isolated wild-type ClfA polypeptides from *staphylococcus* bacteria and segments thereof, as well as variants that stimulate an immune response against *staphylococcus* bacteria ClfA proteins. For example, a wild type ClfA amino acid sequence is provided in NCBI accession no. YP_001331790 (SEQ ID NO:66). A ClfA polypeptide for use an antigen according to the embodiments can comprise an amino acid sequence comprising SEQ ID NO:66 or a sequence at least about 70%, 75%, 80%, 85%, 90%, 95%, 97%, 98% or 99% identical to SEQ ID NO:66. In a further aspect, the ClfA polypeptide comprises 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 30, 310, 320, 330, 340, 350, 360, 370, 380, 390, 400, 410, 420, 430, 440, 450, 460, 470, 480, 490, 500, 550, 600, 650, 700, 750, 800, 850, 900, or 933 amino acids in length, including all values and ranges there between, that are at least 80, 85, 90, 95, 96, 97, 98, 99, or 100% identical to amino acid segments of SEQ ID NO:66.

The term "ClfB protein" refers to a protein that includes isolated wild-type ClfB polypeptides from *staphylococcus* bacteria and segments thereof, as well as variants that stimulate an immune response against *staphylococcus* bacteria ClfB proteins.

The term "Coa protein" refers to a protein that includes isolated wild-type Coa polypeptides from *staphylococcus* bacteria and segments thereof, as well as variants that stimulate an immune response against *staphylococcus* bacteria Coa proteins.

The term "FnbpB protein" or "FnbB protein" refers to a protein that includes isolated wild-type FnbpB polypeptides from *staphylococcus* bacteria and segments thereof, as well as variants that stimulate an immune response against *staphylococcus* bacteria FnbpB proteins. For example, a wild type FnbpB amino acid sequence is provided in NCBI accession no. YP_001333431 (SEQ ID NO:67). A FnbpB polypeptide for use an antigen according to the embodiments can comprise an amino acid sequence comprising SEQ ID NO:67 or a sequence at least about 70%, 75%, 80%, 85%, 90%, 95%, 97%, 98% or 99% identical to SEQ ID NO:67. In a further aspect, the FnbpB polypeptide comprises 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 30, 310, 320, 330, 340, 350, 360, 370, 380, 390, 400, 410, 420, 430, 440, 450, 460, 470, 480, 490, 500, 550, 600, 650 or 677 amino acids in length, including all values and ranges there between, that are at least 80, 85, 90, 95, 96, 97, 98, 99, or 100% identical to amino acid segments of SEQ ID NO:67.

The term "Hla protein" refers to a protein that includes isolated wild-type Hla polypeptides from *staphylococcus* bacteria and segments thereof, as well as variants that stimulate an immune response against *staphylococcus* bacteria Hla proteins.

The term "IsdC protein" refers to a protein that includes isolated wild-type IsdC polypeptides from *staphylococcus* bacteria and segments thereof, as well as variants that stimulate an immune response against *staphylococcus* bacteria IsdC proteins.

The term "SasF protein" refers to a protein that includes isolated wild-type SasF polypeptides from *staphylococcus* bacteria and segments thereof, as well as variants that stimulate an immune response against *staphylococcus* bacteria SasF proteins.

The term "vWbp protein" refers to a protein that includes isolated wild-type vWbp (von Willebrand factor binding protein) polypeptides from *staphylococcus* bacteria and segments thereof, as well as variants that stimulate an immune response against *staphylococcus* bacteria vWbp proteins.

The term "vWh protein" refers to a protein that includes isolated wild-type vWh (von Willebrand factor binding protein homolog) polypeptides from *staphylococcus* bacteria and segments thereof, as well as variants that stimulate an immune response against *staphylococcus* bacteria vWh proteins.

An immune response refers to a humoral response, a cellular response, or both a humoral and cellular response in an organism. An immune response can be measured by assays that include, but are not limited to, assays measuring the presence or amount of antibodies that specifically recognize a protein or cell surface protein, assays measuring T-cell activation or proliferation, and/or assays that measure modulation in terms of activity or expression of one or more cytokines.

In still further embodiments of the invention a composition may include a polypeptide, peptide, or protein that is or is at least 70%, 75%, 80%, 85%, 90%, 95%, 96%, 97%, 98%, or 99% identical or similar to an EsxA protein. In certain aspects the EsxA protein will have all or part of the amino acid sequence of SEQ ID NO:11.

In still further embodiments of the invention a composition may include a polypeptide, peptide, or protein that is or is at least 70%, 75%, 80%, 85%, 90%, 95%, 96%, 97%, 98%, or 99% identical or similar to an EsxB protein. In certain aspects the EsxB protein will have all or part of the amino acid sequence of SEQ ID NO:12.

In yet still further embodiments of the invention a composition may include a polypeptide, peptide, or protein that is or is at least 70%, 75%, 80%, 85%, 90%, 95%, 96%, 97%, 98%, or 99% identical or similar to an SdrD protein. In certain aspects the SdrD protein will have all or part of the amino acid sequence of SEQ ID NO:13.

In further embodiments of the invention a composition may include a polypeptide, peptide, or protein that is or is at least 70%, 75%, 80%, 85%, 90%, 95%, 96%, 97%, 98%, or 99% identical or similar to an SdrE protein. In certain aspects the SdrE protein will have all or part of the amino acid sequence of SEQ ID NO:14.

In still further embodiments of the invention a composition may include a polypeptide, peptide, or protein that is or is at least 70%, 75%, 80%, 85%, 90%, 95%, 96%, 97%, 98%, or 99% identical or similar to an IsdA protein. In certain aspects the IsdA protein will have all or part of the amino acid sequence of SEQ ID NO:15.

In yet still further embodiments of the invention a composition may include a polypeptide, peptide, or protein that is or is at least 70%, 75%, 80%, 85%, 90%, 95%, 96%, 97%, 98%, or 99% identical or similar to an IsdB protein. In certain aspects the IsdB protein will have all or part of the amino acid sequence of SEQ ID NO:16.

Embodiments of the invention include compositions that include a polypeptide, peptide, or protein that is or is at least 70%, 75%, 80%, 85%, 90%, 95%, 96%, 97%, 98%, or 99% identical or similar to a EsaB protein. In certain aspects the EsaB protein will have all or part of the amino acid sequence of SEQ ID NO:17.

In a further embodiments of the invention a composition may include a polypeptide, peptide, or protein that is or is at least 70%, 75%, 80%, 85%, 90%, 95%, 96%, 97%, 98%, or 99% identical or similar to a ClfB protein. In certain aspects the ClfB protein will have all or part of the amino acid sequence of SEQ ID NO:18.

In still further embodiments of the invention a composition may include a polypeptide, peptide, or protein that is or is at least 70%, 75%, 80%, 85%, 90%, 95%, 96%, 97%, 98%, or 99% identical or similar to an IsdC protein. In certain aspects the IsdC protein will have all or part of the amino acid sequence of SEQ ID NO:19.

In yet further embodiments of the invention a composition may include a polypeptide, peptide, or protein that is or is at least 70%, 75%, 80%, 85%, 90%, 95%, 96%, 97%, 98%, or 99% identical or similar to a SasF protein. In certain aspects the SasF protein will have all or part of the amino acid sequence of SEQ ID NO:20.

In yet still further embodiments of the invention a composition may include a polypeptide, peptide, or protein that is or is at least 70%, 75%, 80%, 85%, 90%, 95%, 96%, 97%, 98%, or 99% identical or similar to a SdrC protein. In certain aspects the SdrC protein will have all or part of the amino acid sequence of SEQ ID NO:21.

In yet still further embodiments of the invention a composition may include a polypeptide, peptide, or protein that is or is at least 70%, 75%, 80%, 85%, 90%, 95%, 96%, 97%, 98%, or 99% identical or similar to a ClfA protein. In certain aspects the ClfA protein will have all or part of the amino acid sequence of SEQ ID NO:22.

In yet still further embodiments of the invention a composition may include a polypeptide, peptide, or protein that is or is at least 70%, 75%, 80%, 85%, 90%, 95%, 96%, 97%, 98%, or 99% identical or similar to an Eap protein. In certain aspects the Eap protein will have all or part of the amino acid sequence of SEQ ID NO:23.

In yet still further embodiments of the invention a composition may include a polypeptide, peptide, or protein that is or is at least 70%, 75%, 80%, 85%, 90%, 95%, 96%, 97%, 98%, or 99% identical or similar to an Ebh protein. In certain aspects the Ebh protein will have all or part of the amino acid sequence of SEQ ID NO:24.

In yet still further embodiments of the invention a composition may include a polypeptide, peptide, or protein that is or is at least 70%, 75%, 80%, 85%, 90%, 95%, 96%, 97%, 98%, or 99% identical or similar to an Emp protein. In certain aspects the Emp protein will have all or part of the amino acid sequence of SEQ ID NO:25.

In yet still further embodiments of the invention a composition may include a polypeptide, peptide, or protein that is or is at least 70%, 75%, 80%, 85%, 90%, 95%, 96%, 97%, 98%, or 99% identical or similar to an EsaC protein. In certain aspects the EsaC protein will have all or part of the amino acid sequence of SEQ ID NO:26. Sequence of EsaC polypeptides can be found in the protein databases and include, but are not limited to accession numbers ZP_02760162 (GI: 168727885), NP_645081.1 (GI:21281993), and NP_370813.1 (GI:15923279), each of which is incorporated herein by reference as of the priority date of this application.

In yet still further embodiments of the invention a composition may include a polypeptide, peptide, or protein that is or is at least 70%, 75%, 80%, 85%, 90%, 95%, 96%, 97%, 98%, or 99% identical or similar to a Coa protein. In certain aspects the Coa protein will have all or part of the amino acid sequence of SEQ ID NO:27.

In yet still further embodiments of the invention a composition may include a polypeptide, peptide, or protein that is or is at least 70%, 75%, 80%, 85%, 90%, 95%, 96%, 97%, 98%, or 99% identical or similar to a Hla protein. In certain aspects the Hla protein will have all or part of the amino acid sequence of SEQ ID NO:28.

In yet still further embodiments of the invention a composition may include a polypeptide, peptide, or protein that is or is at least 70%, 75%, 80%, 85%, 90%, 95%, 96%, 97%, 98%, or 99% identical or similar to a vWa protein. In certain aspects the vWa protein will have all or part of the amino acid sequence of SEQ ID NO:29.

In yet still further embodiments of the invention a composition may include a polypeptide, peptide, or protein that is or is at least 70%, 75%, 80%, 85%, 90%, 95%, 96%, 97%, 98%, or 99% identical or similar to a vWbp protein. In certain aspects the vWbp protein will have all or part of the amino acid sequence of SEQ ID NO:32.

In yet still further embodiments of the invention a composition may include a polypeptide, peptide, or protein that is or is at least 70%, 75%, 80%, 85%, 90%, 95%, 96%, 97%, 98%, or 99% identical or similar to a FnbpB protein. In certain aspects the FnbpB protein will have all or part of the amino acid sequence of SEQ ID NO:64.

In certain aspects, a polypeptide or segment/fragment can have a sequence that is at least 85%, at least 90%, at least 95%, at least 98%, or at least 99% or more identical to the amino acid sequence of the reference polypeptide. The term "similarity" refers to a polypeptide that has a sequence that has a certain percentage of amino acids that are either identical with the reference polypeptide or constitute conservative substitutions with the reference polypeptides.

The polypeptides described herein may include 1, 2, 3, 4, 5, 6, 7, 8, 9, 10, 11, 12, 13, 14, 15, or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:2-30, or SEQ ID NO:32-34.

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:2-30, or SEQ ID NO:33-34, or SEQ ID NO:64.

The compositions may be formulated in a pharmaceutically acceptable composition. In certain aspects of the invention the *staphylococcus* bacterium is an *S. aureus* bacterium.

In further aspects, a composition may be administered more than one time to the subject, and may be administered 1, 2, 3, 4, 5, 6, 7, 8, 9, 10, 15, 20 or more times. The administration of the compositions include, but is not limited to oral, parenteral, subcutaneous, intramuscular, intravenous, or various combinations thereof, including inhalation or aspiration.

In still further embodiments, a composition comprises a recombinant nucleic acid molecule encoding a polypeptide described herein or segments/fragments thereof. Typically a recombinant nucleic acid molecule encoding a polypeptide described herein contains a heterologous promoter. In certain aspects, a recombinant nucleic acid molecule of the invention is a vector, in still other aspects the vector is a plasmid. In certain embodiments the vector is a viral vector. In certain aspects a composition includes a recombinant, non-*staphylococcus* bacterium containing or expressing a polypeptide described herein. In particular aspects the recombinant non-staphylococcus bacteria is *Salmonella* or another gram-positive bacteria. A composition is typically administered to mammals, such as human subjects, but administration to other animals that are capable of eliciting an immune response is contemplated. In further aspects the *staphylococcus* bacterium containing or expressing the polypeptide is *Staphylococcus aureus*. In further embodiments the immune response is a protective immune response.

In further embodiments a composition comprises a recombinant nucleic acid molecule encoding all or part of one or more of a Eap, Ebh, Emp, EsaB, EsaC, EsxA, EsxB, SdrC, SdrD, SdrE, IsdA, IsdB, ClfA, ClfB, Coa, Hla, IsdC, SasF, SpA, vWbp, or vWh protein or peptide or variant thereof. Additional staphylococcal antigens that can be used in combination with the polypeptides described herein include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In particular aspects, a bacteria is a recombinant non-staphylococcus bacteria, such as a *Salmonella* or other gram-positive bacteria.

Compositions of the invention are typically administered to human subjects, but administration to other animals that are capable of eliciting an immune response to a *staphylococcus* bacterium is contemplated, particularly cattle, horses, goats, sheep and other domestic animals, i.e., mammals.

In certain aspects the *staphylococcus* bacterium is a *Staphylococcus aureus*. In further embodiments the immune response is a protective immune response. In still further aspects, the methods and compositions of the invention can be used to prevent, ameliorate, reduce, or treat infection of tissues or glands, e.g., mammary glands, particularly mastitis and other infections. Other methods include, but are not limited to prophylactically reducing bacterial burden in a subject not exhibiting signs of infection, particularly those subjects suspected of or at risk of being colonized by a target bacteria, e.g., patients that are or will be at risk or susceptible to infection during a hospital stay, treatment, and/or recovery.

Any embodiment discussed with respect to one aspect of the invention applies to other aspects of the invention as well. In particular, any embodiment discussed in the context of a SpA variant polypeptide or peptide or nucleic acid may be implemented with respect to other antigens, such as Eap, Ebh, Emp, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (or nucleic acids), and vice versa. It is also understood that any one or more of Eap, Ebh, Emp, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein can be specifically excluded from a claimed composition.

Embodiments of the invention include compositions that contain or do not contain a bacterium. A composition may or may not include an attenuated or viable or intact staphylococcal bacterium. In certain aspects, the composition comprises a bacterium that is not a staphylococcal bacterium or does not contain staphylococcal bacteria. In certain embodiments a bacterial composition comprises an isolated or recombinantly expressed staphylococcal Protein A variant or a nucleotide encoding the same. The composition may be or include a recombinantly engineered *staphylococcus* bacterium that has been altered in a way that comprises specifically altering the bacterium with respect to a secreted virulence factor or cell surface protein. For example, the bacteria may be recombinantly modified to express more of the virulence factor or cell surface protein than it would express if unmodified.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The subject will have (e.g., are diagnosed with a staphylococcal infection), will be suspected of having, or will be at risk of developing a staphylococcal infection. Compositions of the present invention include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

(FIG. 1A) Primary structure of the Protein A precursor with an N-terminal YSIRK motif signal peptide, five immunoglobulin binding domains as tandem repeats designated E, D, A, B, C, region X, and the LPXTG sorting signal. (FIG. 1B) Following synthesis of the Protein A precursor, staphylococci secrete this product via the Sec pathway, and sortase A cleaves the LPXTG sorting signal between the T and G residues. Nucleophilic attack of the amino group within lipid II at the sortase-Protein A thioester-linked intermediate forms the amide bond that links Protein A to the cell wall envelope and enables its display on the bacterial surface.

DETAILED DESCRIPTION

Figures 1A, 1B:
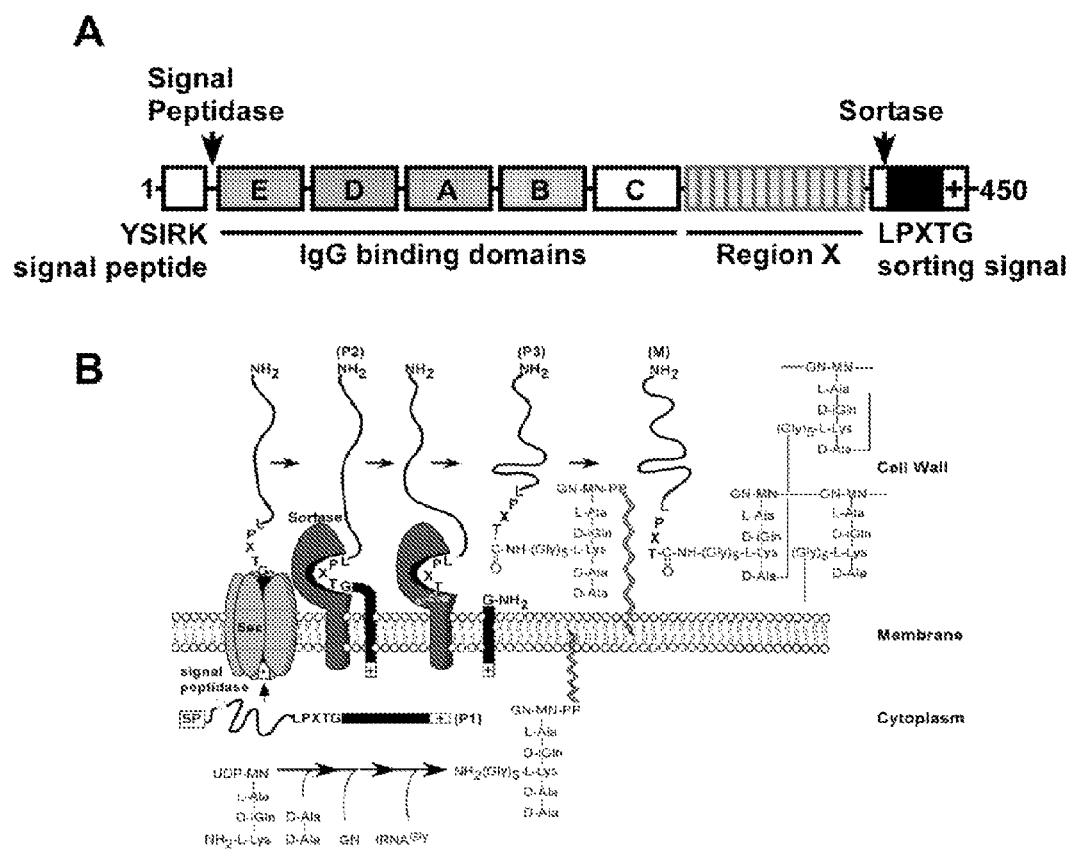
FIGS. 1A-1B.
Figure 2:
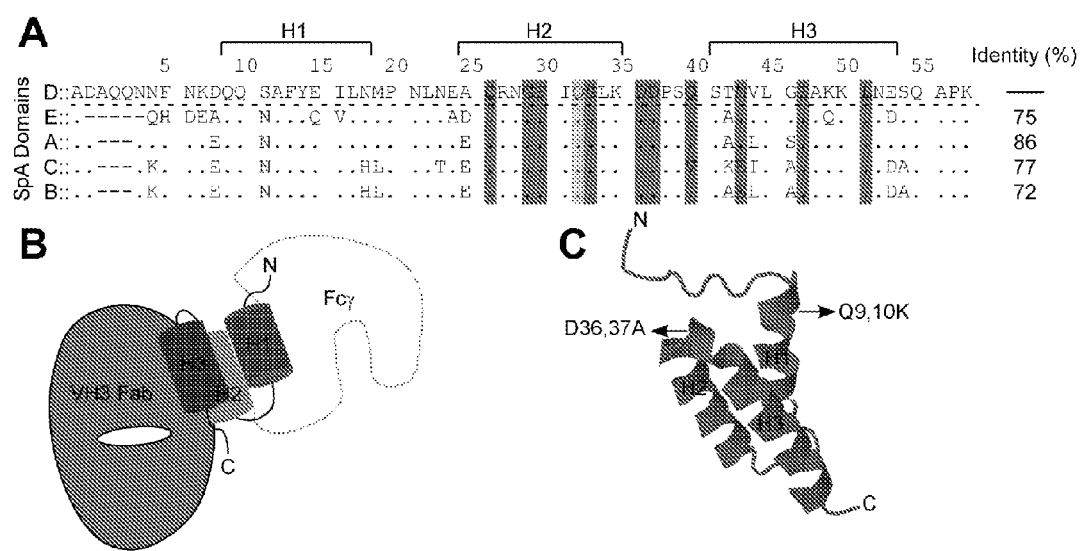
FIG. 2. Three dimensional model of the molecular interactions between the SpA-domain D of Protein A, the VH3 Fab domain of the B cell receptor, and of the Fcγ domain of immunoglobulin. The model is derived from two crystal structures (Graille et al., 2000 and Gouda et al., 1992) that revealed side chain residues involved in the formation of ionic bonds that enable these complexes. Gln-9 and Gln-10 of SpA-D promote binding to Fcγ, whereas Asp-36 and Asp-37 enable complex formation with VH3 Fab.

Staphylococcus aureus is a commensal of the human skin and nares, and the leading cause of bloodstream, skin and soft tissue infections (Klevens et al., 2007). Recent dramatic increases in the mortality of staphylococcal diseases are attributed to the spread of methicillin-resistant S. aureus (MRSA) strains often not susceptible to antibiotics (Kennedy et al., 2008). In a large retrospective study, the incidence of MRSA infections was 4.6% of all hospital admissions in the United States (Klevens et al., 2007). The annual health care costs for 94,300 MRSA infected individuals in the United States exceed $2.4 billion (Klevens et al., 2007). The current MRSA epidemic has precipitated a public health crisis that needs to be addressed by development of a preventive vaccine (Boucher and Corey, 2008). To date, an FDA licensed vaccine that prevents S. aureus diseases is not available.

The inventors describe here the use of Protein A, a cell wall anchored surface protein of staphylococci, for the generation of variants that can serve as subunit vaccines. The pathogenesis of staphylococcal infections is initiated as bacteria invade the skin or blood stream via trauma, surgical wounds, or medical devices (Lowy, 1998). Although the invading pathogen may be phagocytosed and killed, staphylococci can also escape innate immune defenses and seed infections in organ tissues, inducing inflammatory responses that attract macrophages, neutrophils, and other phagocytes (Lowy, 1998). The responsive invasion of immune cells to the site of infection is accompanied by liquefaction necrosis as the host seeks to prevent staphylococcal spread and allow for removal of necrotic tissue debris (Lam et al., 1963). Such lesions can be observed by microscopy as hypercellular areas containing necrotic tissue, leukocytes, and a central nidus of bacteria (Lam et al., 1963). Unless staphylococcal abscesses are surgically drained and treated with antibiotics, disseminated infection and septicemia produce a lethal outcome (Sheagren, 1984).

I. Staphylococcal Antigens

A. Staphylcoccal Protein A (SpA)

All *Staphylococcus aureus* strains express the structural gene for Protein A (spa) (Jensen, 1958; Said-Salim et al., 2003), a well characterized virulence factor whose cell wall anchored surface protein product (SpA) encompasses five highly homologous immunoglobulin binding domains designated E, D, A, B, and C (Sjodahl, 1977). These domains display ~80% identity at the amino acid level, are 56 to 61 residues in length, and are organized as tandem repeats (Uhlen et al., 1984). SpA is synthesized as a precursor protein with an N-terminal YSIRK/GS signal peptide and a C-terminal LPXTG motif sorting signal (DeDent et al., 2008; Schneewind et al., 1992). Cell wall anchored Protein A is displayed in great abundance on the staphylococcal surface (DeDent et al., 2007; Sjoquist et al., 1972). Each of its immunoglobulin binding domains is composed of anti-parallel α-helices that assemble into a three helix bundle and bind the Fc domain of immunoglobulin G (IgG) (Deisenhofer, 1981; Deisenhofer et al., 1978), the VH3 heavy chain (Fab) of IgM (i.e., the B cell receptor) (Graille et al., 2000), the von Willebrand factor at its A1 domain [vWF AI is a ligand for platelets] (O'Seaghdha et al., 2006) and the tumor necrosis factor α (TNF-α) receptor I (TNFRI) (Gomez et al., 2006), which is displayed on surfaces of airway epithelia (Gomez et al., 2004; Gomez et al., 2007).

SpA impedes neutrophil phagocytosis of staphylococci through its attribute of binding the Fc component of IgG (Jensen, 1958; Uhlen et al., 1984). Moreover, SpA is able to activate intravascular clotting via its binding to von Willebrand factor AI domains (Hartleib et al., 2000). Plasma proteins such as fibrinogen and fibronectin act as bridges between staphylococci (ClfA and ClfB) and the platelet integrin GPIIb/IIIa (O'Brien et al., 2002), an activity that is supplemented through Protein A association with vWF AI, which allows staphylococci to capture platelets via the GPIb-α platelet receptor (Foster, 2005; O'Seaghdha et al., 2006). SpA also binds TNFRI and this interaction contributes to the pathogenesis of staphylococcal pneumonia (Gomez et al., 2004). SpA activates proinflammatory signaling through TNFR1 mediated activation of TRAF2, the p38/c-Jun kinase, mitogen activate protein kinase (MAPK) and the Rel-transcription factor NF-KB. SpA binding further induces TNFR1 shedding, an activity that appears to require the TNF-converting enzyme (TACE) (Gomez et al., 2007). All of the aforementioned SpA activities are mediated through its five IgG binding domains and can be perturbed by the same amino acid substitutions, initially defined by their requirement for the interaction between Protein A and human IgG1 (Cedergren et al., 1993).

SpA also functions as a B cell superantigen by capturing the Fab region of VH3 bearing IgM, the B cell receptor (Gomez et al., 2007; Goodyear et al., 2003; Goodyear and Silverman, 2004; Roben et al., 1995). Following intravenous challenge, staphylococcal Protein A (SpA) mutations show a reduction in staphylococcal load in organ tissues and dramatically diminished ability to form abscesses (described herein). During infection with wildtype *S. aureus*, abscesses are formed within forty-eight hours and are detectable by light microscopy of hematoxylin-eosin stained, thin-sectioned kidney tissue, initially marked by an influx of polymorphonuclear leukocytes (PMNs). On day 5 of infection, abscesses increase in size and enclosed a central population of staphylococci, surrounded by a layer of eosinophilic, amorphous material and a large cuff of PMNs. Histopathology revealed massive necrosis of PMNs in proximity to the staphylococcal nidus at the center of abscess lesions as well as a mantle of healthy phagocytes. The inventors also observed a rim of necrotic PMNs at the periphery of abscess lesions, bordering the eosinophilic pseudocapsule that separated healthy renal tissue from the infectious lesion. Staphylococcal variants lacking Protein A are unable to establish the histopathology features of abscesses and are cleared during infection.

In previous studies, Cedergren et al. (1993) engineered five individual substitutions in the Fc frgament binding sub-domain of the B domain of SpA, L17D, N28A, I31A and K35A. These authors created these proteins to test data gathered from a three dimensional structure of a complex between one domain of SpA and $Fc_1$. Cedergren et al. determined the effects of these mutations on stability and binding, but did not contemplate use of such substitutions for the production of a vaccine antigen.

Brown et al. (1998) describe studies designed to engineer new proteins based on SpA that allow the use of more favorable elution conditions when used as affinity ligands. The mutations studied included single mutations of Q13A, Q 14H, N15A, N15H, F 17H, Y18F, L21H, N32H, or K39H. Brown et al. report that Q13A, N15A, N15H, and N32H substitutions made little difference to the dissociation constant values and that the Y18F substitution resulted in a 2 fold decrease in binding affinity as compared to wild type SpA. Brown et al. also report that L21H and F 17H substitutions decrease the binding affinity by five-fold and a hundred-fold respectively. The authors also studied analogous substitutions in two tandem domains. Thus, the Brown et al. studies were directed to generating a SpA with a more favorable elution profile, hence the use of H is substitutions to provide a pH sensitive alteration in the binding affinity. Brown et al. is silent on the use of SpA as a vaccine antigen.

Graille et al. (2000) describe a crystal structure of domain D of SpA and the Fab fragment of a human IgM antibody. Graille et al. define by analysis of a crystal structure the D domain amino acid residues that interact with the Fab fragment as residues Q26, G29, F30, Q32, S33, D36, D37, Q40, N43, E47, or L51, as well as the amino acid residues that form the interface between the domain D sub-domains. Graille et al. define the molecular interactions of these two proteins, but is silent in regard to any use of substitutions in the interacting residues in producing a vaccine antigen.

O'Seaghdha et al. (2006) describe studies directed at elucidating which sub-domain of domain D binds vWF. The authors generated single mutations in either the Fc or VH3 binding sub-domains, i.e., amino acid residues F5A, Q9A, Q10A, F13A, Y14A, L17A, N28A, I31A, K35A, G29A, F30A, S33A, D36A, D37A, Q40A, E47A, or Q32A. The authors discovered that vWF binds the same sub-domain that binds Fc. O'Seaghda et al. define the sub-domain of domain D responsible for binding vWF, but is silent in regard to any use of substitutions in the interacting residues in producing a vaccine antigen.

Gomez et al. (2006) describe the identification of residues responsible for activation of the TNFR1 by using single mutations of F5A, F13A, Y14A, L17A, N21A, I31A, Q32A, and K35A. Gomez et al. is silent in regard to any use of substitutions in the interacting residues in producing a vaccine antigen.

Recombinant affinity tagged Protein A, a polypeptide encompassing the five IgG domains (EDCAB) (Sjodahl, 1977) but lacking the C-terminal Region X (Guss et al., 1984), was purified from recombinant *E. coli* and used as a vaccine antigen (Stranger-Jones et al., 2006). Because of the attributes of SpA in binding the Fc portion of IgG, a specific humoral immune response to Protein A could not be measured (Stranger-Jones et al., 2006). The inventors have overcome this obstacle through the generation of SpA-DQ9,10K; D36,37A. BALB/c mice immunized with recombinant Protein A (SpA) displayed significant protection against intravenous challenge with *S. aureus* strains: a 2.951 log reduction in staphylococcal load as compared to the wild-type (P>0.005; Student's t-test) (Stranger-Jones et al., 2006). SpA specific antibodies may cause phagocytic clearance prior to abscess formation and/or impact the formation of the aforementioned eosinophilic barrier in abscesses that separate staphylococcal communities from immune cells since these do not form during infection with Protein A mutant strains. Each of the five SpA domains (i.e., domains formed from three helix bundles designated E, D, A, B, and C) exerts similar binding properties (Jansson et al., 1998). The solution and crystal structure of the domain D has been solved both with and without the Fc and VH3 (Fab) ligands, which bind Protein A in a non-competitive manner at distinct sites (Graille et al., 2000). Mutations in residues known to be involved in IgG binding (FS, Q9, Q10, S11, F13, Y14, L17, N28, I31 and K35) are also required for vWF AI and TNFR1 binding (Cedergren et al., 1993; Gomez et al., 2006; O'Seaghdha et al., 2006), whereas residues important for the VH3 interaction (Q26, G29, F30, S33, D36, D37, Q40, N43, E47) appear to have no impact on the other binding activities (Graille et al., 2000; Jansson et al., 1998). SpA specifically targets a subset of B cells that express VH3 family related IgM on their surface, i.e., VH3 type B cell receptors (Roben et al., 1995). Upon interaction with SpA, these B cells proliferate and commit to apoptosis, leading to preferential and prolonged deletion of innate-like B lymphocytes (i.e., marginal zone B cells and follicular B2 cells)(Goodyear et al., 2003; Goodyear et al., 2004).

Molecular basis of Protein A surface display and function. Protein A is synthesized as a precursor in the bacterial cytoplasm and secreted via its YSIRK signal peptide at the cross wall, i.e. the cell division septum of staphylococci (FIG. 1) (DeDent et al., 2007; DeDent et al., 2008). Following cleavage of the C-terminal LPXTG sorting signal, Protein A is anchored to bacterial peptidoglycan crossbridges by sortase A (Mazmanian et al., 1999; Schneewind et al., 1995; Mazmanian et al., 2000). Protein A is the most abundant surface protein of staphylococci; the molecule is expressed by virtually all *S. aureus* strains (Cespedes et al., 2005; Kennedy et al., 2008; Said-Salim et al., 2003). Staphylococci turn over 15-20% of their cell wall per division cycle (Navarre and Schneewind, 1999). Murine hydrolases cleave the glycan strands and wall peptides of peptidoglycan, thereby releasing Protein A with its attached C-terminal cell wall disaccharide tetrapeptide into the extracellular medium (Ton-That et al., 1999). Thus, by physiological design, Protein A is both anchored to the cell wall and displayed on the bacterial surface but also released into surrounding tissues during host infection (Marraffini et al., 2006).

Protein A captures immunoglobulins on the bacterial surface and this biochemical activity enables staphylococcal escape from host innate and acquired immune responses (Jensen, 1958; Goodyear et al., 2004). Interestingly, region X of Protein A (Guss et al., 1984), a repeat domain that tethers the IgG binding domains to the LPXTG sorting signal/cell wall anchor, is perhaps the most variable portion of the staphylococcal genome (Said-Salim, 2003; Schneewind et al., 1992). Each of the five immunoglobulin binding domains of Protein A (SpA), formed from three helix bundles and designated E, D, A, B, and C, exerts similar structural and functional properties (Sjodahl, 1977; Jansson et al., 1998). The solution and crystal structure of the domain D has been solved both with and without the Fc and $V_H3$ (Fab) ligands, which bind Protein A in a non-competitive manner at distinct sites (Graille 2000).

In the crystal structure complex, the Fab interacts with helix II and helix III of domain D via a surface composed of four VH region β-strands (Graille 2000). The major axis of helix II of domain D is approximately 50° to the orientation of the strands, and the interhelical portion of domain D is most proximal to the C0 strand. The site of interaction on Fab is remote from the Ig light chain and the heavy chain constant region. The interaction involves the following domain D residues: Asp-36 of helix II, Asp-37 and Gln-40 in the loop between helix II and helix III and several other residues (Graille 2000). Both interacting surfaces are composed predominantly of polar side chains, with three negatively charged residues on domain D and two positively charged residues on the 2A2 Fab buried by the interaction, providing an overall electrostatic attraction between the two molecules. Of the five polar interactions identified between Fab and domain D, three are between side chains. A salt bridge is formed between Arg-H19 and Asp-36 and two hydrogen bonds are made between Tyr-H59 and Asp-37 and between Asn-H82a and Ser-33. Because of the conservation of Asp-36 and Asp-37 in all five IgG binding domains of Protein A, the inventors mutated these residues.

The SpA-D sites responsible for Fab binding are structurally separate from the domain surface that mediates Fcγ binding. The interaction of Fcγ with domain D primarily involves residues in helix I with lesser involvement of helix II (Gouda et al., 1992; Deisenhofer, 1981). With the exception of the Gln-32, a minor contact in both complexes, none of the residues that mediate the Fcγ interaction are involved in Fab binding. To examine the spatial relationship between these different Ig-binding sites, the SpA domains in these complexes have been superimposed to construct a model of a complex between Fab, the SpA-domain D, and the Fcγ molecule. In this ternary model, Fab and Fcγ form a sandwich about opposite faces of the helix II without evidence of steric hindrance of either interaction. These findings illustrate how, despite its small size (i.e., 56-61 aa), an SpA domain can simultaneously display both activities, explaining experimental evidence that the interactions of Fab with an individual domain are noncompetitive. Residues for the interaction between SpA-D and Fcγ are Gln-9 and Gln-10.

In contrast, occupancy of the Fc portion of IgG on the domain D blocks its interaction with vWF A1 and probably also TNFR1 (O'Seaghdha et al., 2006). Mutations in residues essential for IgG Fc binding (F5, Q9, Q10, S11, F13, Y14, L17, N28, I31 and K35) are also required for vWF A1 and TNFR1 binding (O'Seaghdha et al., 2006; Cedergren et al., 1993; Gomez et al., 2006), whereas residues critical for the VH3 interaction (Q26, G29, F30, S33, D36, D37, Q40, N43, E47) have no impact on the binding activities of IgG Fc, vWF A1 or TNFR1 (Jansson et al., 1998; Graille et al., 2000). The Protein A immunoglobulin Fab binding activity targets a subset of B cells that express $V_H3$ family related IgM on their surface, i.e., these molecules function as VH3type B cell receptors (Roben et al., 1995). Upon interaction with SpA, these B cells rapidly proliferate and then commit to apoptosis, leading to preferential and prolonged deletion of innate-like B lymphocytes (i.e., marginal zone B cells and follicular B2 cells) (Goodyear and Silverman, 2004; Goodyear and Silverman, 2003). More than 40% of circulating B cells are targeted by the Protein A interaction and the $V_H3$ family represents the largest family of human B cell receptors to impart protective humoral responses against pathogens (Goodyear and Silverman, 2004; Goodyear and Silverman, 2003). Thus, Protein A functions analogously to staphylococcal superantigens (Roben et al., 1995), albeit that the latter class of molecules, for example SEB, TSST-1, TSST-2, form complexes with the T cell receptor to inappropriately stimulate host immune responses and thereby precipitating characteristic disease features of staphylococcal infections (Roben et al., 1995; Tiedemann et al., 1995). Together these findings document the contributions of Protein A in establishing staphylococcal infections and in modulating host immune responses.

In sum, Protein A domains can viewed as displaying two different interfaces for binding with host molecules and any development of Protein A based vaccines must consider the generation of variants that do not perturb host cell signaling, platelet aggregation, sequestration of immunoglobulins or the induction of B cell proliferation and apoptosis. Such Protein A variants should also be useful in analyzing vaccines for the ability of raising antibodies that block the aforementioned SpA activities and occupy the five repeat domains at their dual binding interfaces. This goal is articulated and pursued here for the first time and methods are described in detail for the generation of Protein A variants that can be used as a safe vaccine for humans. To perturb IgG Fcγ, vWF A1 and TNFR1 binding, glutamine (Q) 9 and 10 [numbering derived from the SpA domain D as described in Uhlen et al., 1984] were mutated, and generated lysine substitutions for both glutamines with the expectation that these abolish the ligand attributes at the first binding interface. To perturb IgM Fab VH3 binding, aspartate (D) 36 and 37 were mutated, each of which is required for the association with the B cell receptor. D36 and D37 were both substituted with alanine. Q9,10K and D36,37A mutations are here combined in the recombinant molecule SpA-DQ9,10K;D36,37A and tested for the binding attributes of Protein A. Further, SpA-D and SpA-DQ9,10K; D36,37A are subjected to immunization studies in mice and rabbits and analyzed for [1] the production of specific antibodies (SpA-D Ab); [2] the ability of SpA-D Ab to block the association between Protein A and its four different ligands; and, [3] the attributes of SpA-D Ab to generate protective immunity against staphylococcal infections. (See Examples section below).

B. Staphylococcal Coagulases

Coagulases are enzymes produced by *Staphylococcus* bacteria that convert fibrinogen to fibrin. Coa and $vW_h$ activate prothrombin without proteolysis (Friedrich et al., 2003). The coagulase•prothrombin complex recognizes fibrinogen as a specific substrate, converting it directly into fibrin. The crystal structure of the active complex revealed binding of the D1 and D2 domains to prothrombin and insertion of its Ile1-Val$^2$ N-terminus into the Ile$^{16}$ pocket, inducing a functional active site in the zymogen through conformational change (Friedrich et al., 2003). Exosite I of α-thrombin, the fibrinogen recognition site, and proexosite I on prothrombin are blocked by the D2 of Coa (Friedrich et al., 2003). Nevertheless, association of the tetrameric $(\text{Coa•prothrombin})_2$ complex binds fibrinogen at a new site with high affinity (Panizzi et al., 2006). This model explains the coagulant properties and efficient fibrinogen conversion by coagulase (Panizzi et al., 2006).

Fibrinogen is a large glycoprotein (Mr ~340,000), formed by three pairs of Aα-, Bβ-, and γ-chains covalently linked to form a "dimer of trimers," where A and B designate the fibrinopeptides released by thrombin cleavage (Panizzi et al., 2006). The elongated molecule folds into three separate domains, a central fragment E that contains the N-termini of all six chains and two flanking fragments D formed mainly by the C-termini of the Bβ- and γ-chains. These globular domains are connected by long triple-helical structures. Coagulase-prothrombin complexes, which convert human fibrinogen to the self-polymerizing fibrin, are not targeted by circulating thrombin inhibitors (Panizzi et al., 2006). Thus, staphylococcal coagulases bypass the physiological blood coagulation pathway.

All *S. aureus* strains secrete coagulase and vWbp (Bjerketorp et al., 2004; Field and Smith, 1945). Although early work reported important contributions of coagulase to the pathogenesis of staphylococcal infections (Ekstedt and Yotis, 1960; Smith et al., 1947), more recent investigations with molecular genetics tools challenged this view by observing no virulence phenotypes with endocarditis, skin abscess and mastitis models in mice (Moreillon et al., 1995; Phonimdaeng et al., 1990). Generating isogenic variants of *S. aureus* Newman, a fully virulent clinical isolate (Duthie et al., 1952), it is described herein that coa mutants indeed display virulence defects in a lethal bacteremia and renal abscess model in mice. In the inventors experience, *S. aureus* 8325-4 is not fully virulent and it is presumed that mutational lesions in this strain may not be able to reveal virulence defects in vivo. Moreover, antibodies raised against Coa or vWbp perturb the pathogenesis of *S. aureus* Newman infections to a degree mirroring the impact of gene deletions. Coa and vWbp contribute to staphylococcal abscess formation and lethal bacteremia and may also function as protective antigens in subunit vaccines.

Biochemical studies document the biological value of antibodies against Coa and vWbp. By binding to antigen and blocking its association with clotting factors, the antibodies prevent the formation of Coa•prothrombin and vWbp•prothrombin complexes. Passive transfer studies revealed protection of experimental animals against staphylococcal abscess formation and lethal challenge by Coa and vWbp antibodies. Thus, Coa and vWbp neutralizing antibodies generate immune protection against staphylococcal disease.

Earlier studies revealed a requirement of coagulase for resisting phagocytosis in blood (Smith et al., 1947) and the inventors observed a similar phenotype for Δcoa mutants in lepirudin-treated mouse blood (see Example 3 below). As vWbp displays higher affinity for human prothrombin than the mouse counterpart, it is suspected the same may be true for ΔvWbp variants in human blood. Further, expression of Coa and vWbp in abscess lesions as well as their striking distribution in the eosinophilic pseudocapsule surrounding (staphylococcal abscess communities (SACs) or the peripheral fibrin wall, suggest that secreted coagulases contribute to the establishment of these lesions. This hypothesis was tested and, indeed, Δcoa mutants were defective in the establishment of abscesses. A corresponding test, blocking Coa function with specific antibodies, produced the same effect. Consequently, it is proposed that the clotting of fibrin is a critical event in the establishment of staphylococcal abscesses that can be targeted for the development of protective vaccines. Due to their overlapping function on human prothrombin, both Coa and vWbp are considered excellent candidates for vaccine development.

C. Other Staphylococcal Antigens

Research over the past several decades identified *S. aureus* exotoxins, surface proteins and regulatory molecules as important virulence factors (Foster, 2005; Mazmanian et al., 2001; Novick, 2003). Much progress has been achieved regarding the regulation of these genes. For example, staphylococci perform a bacterial census via the secretion of autoinducing peptides that bind to a cognate receptor at threshold concentration, thereby activating phospho-relay reactions and transcriptional activation of many of the exotoxin genes (Novick, 2003). The pathogenesis of staphylococcal infections relies on these virulence factors (secreted exotoxins, exopolysaccharides, and surface adhesins). The development of staphylococcal vaccines is hindered by the multifaceted nature of staphylococcal invasion mechanisms. It is well established that live attenuated micro-organisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. Embodiments of the invention are directed to compositions and methods including variant SpA polypeptides and peptides, as well as other immunogenic extracellular proteins, polypeptides, and peptides (including both secreted and cell surface proteins or peptides) of gram positive bacteria for the use in mitigating or immunizing against infection. In particular embodiments the bacteria is a *staphylococcus* bacteria. Extracellular proteins, polypeptides, or peptides include, but are not limited to secreted and cell surface proteins of the targeted bacteria.

The human pathogen *S. aureus* secretes EsxA and EsxB, two ESAT-6 like proteins, across the bacterial envelope (Burts et al., 2005, which is incorporated herein by reference). Staphylococcal esxA and esxB are clustered with six other genes in the order of transcription: esxA esaA esaB essB essC esaC esxB. The acronyms esa, ess, and esx stand for ESAT-6 secretion accessory, system, and extracellular, respectively, depending whether the encoded proteins play an accessory (esa) or direct (ess) role for secretion, or are secreted (esx) in the extracellular milieu. The entire cluster of eight genes is herein referred to as the Ess cluster. EsxA, esxB, essA, essB, and essC are all required for synthesis or secretion of EsxA and EsxB. Mutants that fail to produce EsxA, EsxB, and EssC display defects in the pathogenesis of *S. aureus* murine abscesses, suggesting that this specialized secretion system may be a general strategy of human bacterial pathogenesis. Secretion of non-WXG100 substrates by the ESX-1 pathway has been reported for several antigens including EspA, EspB, Rv3483c, and Rv3615c (Fortune et al., 2005; MacGurn et al., 2005; McLaughlin et al., 2007; Xu et al., 2007). The alternate ESX-5 pathway has also been shown to secrete both WXG100 and non-WXG100 proteins in pathogenic mycobacteria (Abdallah et al., 2007; Abdallah et al., 2006).

The *Staphylococcus aureus* Ess pathway can be viewed as a secretion module equipped with specialized transport components (Ess), accessory factors (Esa) and cognate secretion substrates (Esx). EssA, EssB and EssC are required for EsxA and EsxB secretion. Because EssA, EssB and EssC are predicted to be transmembrane proteins, it is contemplated that these proteins form a secretion apparatus. Some of the proteins in the ess gene cluster may actively transport secreted substrates (acting as motor) while others may regulate transport (regulator). Regulation may be achieved, but need not be limited to, transcriptional or post-translational mechanisms for secreted polypeptides, sorting of specific substrates to defined locations (e.g., extracellular medium or host cells), or timing of secretion events during infection. At this point, it is unclear whether all secreted Esx proteins function as toxins or contribute indirectly to pathogenesis.

Staphylococci rely on surface protein mediated-adhesion to host cells or invasion of tissues as a strategy for escape from immune defenses. Furthermore, *S. aureus* utilize surface proteins to sequester iron from the host during infection. The majority of surface proteins involved in staphylococcal pathogenesis carry C-terminal sorting signals, i.e., they are covalently linked to the cell wall envelope by sortase. Further, staphylococcal strains lacking the genes required for surface protein anchoring, i.e., sortase A and B, display a dramatic defect in the virulence in several different mouse models of disease. Thus, surface protein antigens represent a validated vaccine target as the corresponding genes are essential for the development of staphylococcal disease and can be exploited in various embodiments of the invention. The sortase enzyme superfamily are Gram-positive transpeptidases responsible for anchoring surface protein virulence factors to the peptidoglycan cell wall layer. Two sortase isoforms have been identified in *Staphylococcus aureus*, SrtA and SrtB. These enzymes have been shown to recognize a LPXTG motif in substrate proteins. The SrtB isoform appears to be important in heme iron acquisition and iron homeostasis, whereas the SrtA isoform plays a critical role in the pathogenesis of Gram-positive bacteria by modulating the ability of the bacterium to adhere to host tissue via the covalent anchoring of adhesins and other proteins to the cell wall peptidoglycan. In certain embodiments the SpA variants described herein can be used in combination with other staphylococcal proteins such as Coa, Eap, Ebh, Emp, EsaC, EsaB, EsxA, EsxB, Hla, SdrC, SdrD, SdrE, IsdA, IsdB, ClfA, ClfB, IsdC, SasF, vWbp, and/or vWh proteins.

Certain aspects of the invention include methods and compositions concerning proteinaceous compositions including polypeptides, peptides, or nucleic acid encoding SpA variant(s) and other staphylococcal antigens such as other proteins transported by the Ess pathway, or sortase substrates. These proteins may be modified by deletion, insertion, and/or substitution.

The Esx polypeptides include the amino acid sequence of Esx proteins from bacteria in the *Staphylococcus* genus. The Esx sequence may be from a particular *staphylococcus* species, such as *Staphylococcus aureus*, and may be from a particular strain, such as Newman. In certain embodiments, the EsxA sequence is SAV0282 from strain Mu50 (which is the same amino acid sequence for Newman) and can be accessed using Genbank Accession Number Q99WU4 (gi|68565539), which is hereby incorporated by reference. In other embodiments, the EsxB sequence is SAV0290 from strain Mu50 (which is the same amino acid sequence for Newman) and can be accessed using Genbank Accession Number Q99WT7 (gi|68565532), which is hereby incorporated by reference. In further embodiments, other polypeptides transported by the Ess pathway may be used, the sequences of which may be identified by one of skill in the art using databases and interne accessible resources.

The sortase substrate polypeptides include, but are not limited to the amino acid sequence of SdrC, SdrD, SdrE, IsdA, IsdB, ClfA, ClfB, IsdC or SasF proteins from bacteria in the *Staphylococcus* genus. The sortase substrate polypeptide sequence may be from a particular *staphylococcus* species, such as *Staphylococcus aureus*, and may be from a particular strain, such as Newman. In certain embodiments, the SdrD sequence is from strain N315 and can be accessed using Genbank Accession Number NP_373773.1 (gi|15926240), which is incorporated by reference. In other embodiments, the SdrE sequence is from strain N315 and can be accessed using Genbank Accession Number NP_373774.1 (gi|15926241), which is incorporated by reference. In other embodiments, the IsdA sequence is SAV 1130 from strain Mu50 (which is the same amino acid sequence for Newman) and can be accessed using Genbank Accession Number NP_371654.1 (gi|15924120), which is incorporated by reference. In other embodiments, the IsdB sequence is SAV1129 from strain Mu50 (which is the same amino acid sequence for Newman) and can be accessed using Genbank Accession Number NP_371653.1 (gi|15924119), which is incorporated by reference. In further embodiments, other polypeptides transported by the Ess pathway or processed by sortase may be used, the sequences of which may be identified by one of skill in the art using databases and interne accessible resources.

In certain embodiments, fibronectin binding protein B sequence can include all or part of the precursor or mature foam of FnbpB. FnbpB sequence can be found in SEQ ID NO:64 or in GenBank entries having accession numbers NC_009641.1, AAW37288. (GI:57285194), ZP_07362431 (GI:304379700), EEV81932 (GI:257859074), NP_373026 (GI:15925492) or other FnbpB amino acid sequences identified in GenBank.

Examples of various proteins that can be used in the context of the present invention can be identified by analysis of database submissions of bacterial genomes, including but not limited to accession numbers NC_002951 (GI:57650036 and GenBank CP000046), NC_002758 (GI:57634611 and GenBank BA000017), NC_002745 (GI:29165615 and GenBank BA000018), NC_003923 (GI:21281729 and GenBank BA000033), NC_002952 (GI:49482253 and GenBank BX571856), NC_002953 (GI:49484912 and GenBank BX571857), NC_007793 (GI:87125858 and GenBank CP000255), NC_007795 (GI:87201381 and GenBank CP000253) each of which are incorporated by reference.

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of SpA, coagulases and other polypeptides of the invention can be substitutional, insertional, or deletion variants. A variation in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, or 90%, including all values and ranges there between, identical to any sequence provided or referenced herein, e.g., SEQ ID NO:2-8 or SEQ ID NO:11-30, A variant can include 2, 3, 4, 5, 6, 7, 8, 9, 10, 11, 12, 13, 14, 15, 16, 17, 18, 19, 20, or more substitute amino acids. A polypeptide processed or secreted by the Ess pathway or other surface proteins (see Table 2) or sortase substrates from any *staphylococcus* species and strain are contemplated for use in compositions and methods described herein.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

TABLE 2

Exemplary surface proteins of S. aureus strains.

| SAV # | SA# | Surface | MW2 | Mu50 | N315 | Newman | MRSA252* | MSSA476* |
|---|---|---|---|---|---|---|---|---|
| SAV0111 | SA0107 | Spa | 492 | 450 | 450 | 520 | 516 | 492 |
| SAV2503 | SA2291 | FnBPA | 1015 | 1038 | 1038 | 741 | — | 1015 |
| SAV2502 | SA2290 | FnBPB | 943 | 961 | 961 | 677 | 965 | 957 |
| SAV0811 | SA0742 | ClfA | 946 | 935 | 989 | 933 | 1029 | 928 |
| SAV2630 | SA2423 | ClfB | 907 | 877 | 877 | 913 | 873 | 905 |
| Np | Np | Cna | 1183 | — | — | — | 1183 | 1183 |
| SAV0561 | SA0519 | SdrC | 955 | 953 | 953 | 947 | 906 | 957 |
| SAV0562 | SA0520 | SdrD | 1347 | 1385 | 1385 | 1315 | — | 1365 |
| SAV0563 | SA0521 | SdrE | 1141 | 1141 | 1141 | 1166 | 1137 | 1141 |
| Np | Np | Pls | — | — | — | — | — | — |
| SAV2654 | SA2447 | SasA | 2275 | 2271 | 2271 | 2271 | 1351 | 2275 |
| SAV2160 | SA1964 | SasB | 686 | 2481 | 2481 | 2481 | 2222 | 685 |
|  | SA1577 | SasC | 2186 | 213 | 2186 | 2186 | 2189 | 2186 |
| SAV0134 | SA0129 | SasD | 241 | 241 | 241 | 241 | 221 | 241 |
| SAV1130 | SA0977 | SasE/IsdA | 350 | 350 | 350 | 350 | 354 | 350 |
| SAV2646 | SA2439 | SasF | 635 | 635 | 635 | 635 | 627 | 635 |
| SAV2496 |  | SasG | 1371 | 525 | 927 | — | — | 1371 |
| SAV0023 | SA0022 | SasH | 772 | — | 772 | 772 | 786 | 786 |
| SAV1731 | SA1552 | SasI | 895 | 891 | 891 | 891 | 534 | 895 |
| SAV1129 | SA0976 | SasJ/IsdB | 645 | 645 | 645 | 645 | 652 | 645 |
|  | SA2381 | SasK | 198 | 211 | 211 | — | — | 197 |
| Np | Np | SasL | — | 232 | — | — | — | — |
| SAV1131 | SA0978 | IsdC | 227 | 227 | 227 | 227 | 227 | 227 |

Proteins of the invention may be recombinant, or synthesized in vitro. Alternatively, a non-recombinant or recombinant protein may be isolated from bacteria. It is also contemplated that a bacteria containing such a variant may be implemented in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids (see Table 3, below).

TABLE 3

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |

TABLE 3-continued

Codon Table

| Amino Acids | | | Codons |
|---|---|---|---|
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

TABLE 3-continued

Codon Table

| Amino Acids | | | Codons |
|---|---|---|---|
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create a variant polypeptide or peptide. For example, certain amino acids may be substituted for other amino acids in a protein structure with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence, and in its underlying DNA coding sequence, and nevertheless produce a protein with a desirable property. It is thus contemplated by the inventors that various changes may be made in the DNA sequences of genes.

It is contemplated that in compositions of the invention, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an SpA variant or a coagulase, and may be used in combination with other peptides or polypeptides, such as other bacterial peptides and/or antigens.

The present invention contemplates the administration of variant SpA polypeptides or peptides to effect a preventative therapy or therapeutic effect against the development of a disease or condition associated with infection by a *staphylococcus* pathogen.

In certain aspects, combinations of staphylococcal antigens are used in the production of an immunogenic composition that is effective at treating or preventing staphylococcal infection. Staphylococcal infections progress through several different stages. For example, the staphylococcal life cycle involves commensal colonization, initiation of infection by accessing adjoining tissues or the bloodstream, and/or anaerobic multiplication in the blood. The interplay between *S. aureus* virulence determinants and the host defense mechanisms can induce complications such as endocarditis, metastatic abscess formation, and sepsis syndrome. Different molecules on the surface of the bacterium are involved in different steps of the infection cycle. Combinations of certain antigens can elicit an immune response which protects against multiple stages of staphylococcal infection. The effectiveness of the immune response can be measured either in animal model assays and/or using an opsonophagocytic assay.

D. Polypeptides and Polypeptide Production

The present invention describes polypeptides, peptides, and proteins and immunogenic fragments thereof for use in various embodiments of the present invention. For example, specific polypeptides are assayed for or used to elicit an immune response. In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production and/or presentation of polypeptides or peptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified.

Another embodiment of the present invention uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk−, hgprt− or aprt− cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Where a protein is specifically mentioned herein, it is preferably a reference to a native or recombinant protein or optionally a protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, 20 amino acids, 30 amino acids, 40 amino acids, 50 amino acids, or 100 amino acids, including all values and ranges there between, taken contiguously from the amino acid sequence of the protein. In addition, such immunogenic fragments are immunologically reactive with antibodies generated against the Staphylococcal proteins or with antibodies generated by infection of a mammalian host with Staphylococci. Immunogenic fragments also include fragments that when administered at an effective dose, (either alone or as a hapten bound to a carrier), elicit a protective or therapeutic immune response against Staphylococcal infection, in certain aspects it is protective against *S. aureus* and/or *S. epidermidis* infection. Such an immunogenic fragment may include, for example, the protein lacking an N-terminal leader sequence, and/or a transmembrane domain and/or a C-terminal anchor domain. In a preferred aspect the immunogenic fragment according to the invention comprises substantially all of the extracellular domain of a protein which has at least 80% identity, at least 85% identity, at least 90% identity, at least 95% identity, or at least 97-99% identity, including all values and ranges there between, to a sequence selected segment of a polypeptide described or referenced herein.

Also included in immunogenic compositions of the invention are fusion proteins composed of one or more Staphylococcal proteins, or immunogenic fragments of staphylococcal proteins. Such fusion proteins may be made recombinantly and may comprise one portion of at least 1, 2, 3, 4, 5, or 6 staphylococcal proteins or segments. Alternatively, a fusion protein may comprise multiple portions of at least 1, 2, 3, 4 or 5 staphylococcal proteins. These may combine different Staphylococcal proteins and/or multiples of the same protein or protein fragment, or immunogenic fragments in the same protein (forming a multimer or a concatamer). Alternatively, the invention also includes individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, or CRM197.

II. Nucleic Acids

In certain embodiments, the present invention concerns recombinant polynucleotides encoding the proteins, polypeptides, peptides of the invention. The nucleic acid sequences for SpA, coagulases and other bacterial proteins are included, all of which are incorporated by reference, and can be used to prepare peptides or polypeptides.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the teen "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges therebetween, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein (see Table 3 above).

In particular embodiments, the invention concerns isolated nucleic acid segments and recombinant vectors incorporating nucleic acid sequences that encode a variant SpA or coagulase. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a variant SpA or coagulase polypeptide or peptide to generate an immune response in a subject. In various embodiments the nucleic acids of the invention may be used in genetic vaccines.

The nucleic acid segments used in the present invention can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain other embodiments, the invention concerns isolated nucleic acid segments and recombinant vectors that include within their sequence a contiguous nucleic acid sequence from SEQ ID NO:1 (SpA domain D) or SEQ ID NO:3 (SpA) or any other nucleic acid sequences encoding coagulases or other secreted virulence factors and/or surface proteins including proteins transported by the Ess pathway, processed by sortase, or proteins incorporated herein by reference.

In certain embodiments, the present invention provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this invention using the methods described herein (e.g., BLAST analysis using standard parameters).

The invention also contemplates the use of polynucleotides which are complementary to all the above described polynucleotides.

A. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a variant SpA polypeptide the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ a and/or DQ (3 (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRa (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), $H_2B$ (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II—Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); β-Interferon—poly(rI) x/poly(rc) (Tavernier et al., 1983); Adenovirus 5 E2—E1A (Imperiale et al., 1984); Collagenase—Phorbol Ester (TPA) (Angel et al., 1987a); Stromelysin—Phorbol Ester (TPA) (Angel et al., 1987b); SV40—Phorbol Ester (TPA) (Angel et al., 1987b); Murine MX Gene—Interferon, Newcastle Disease Virus (Hug et al., 1988); GRP78 Gene—A23187 (Resendez et al., 1988); α-2-Macroglobulin—IL-6 (Kunz et al., 1989); Vimentin—Serum (Rittling et al., 1989); MHC Class I Gene H-2κb—Interferon (Blanar et al., 1989); HSP70—E1A/SV40 Large T Antigen (Taylor et al., 1989, 1990a, 1990b); Proliferin—Phorbol Ester/TPA (Mordacq et al., 1989); Tumor Necrosis Factor—PMA (Hensel et al., 1989); and Thyroid Stimulating Hormone α Gene—Thyroid Hormone (Chatterjee et al., 1989).

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In embodiments in which a vector is administered to a subject for expression of the protein, it is contemplated that a desirable promoter for use with the vector is one that is not down-regulated by cytokines or one that is strong enough that even if down-regulated, it produces an effective amount of a variant SpA for eliciting an immune response. Non-limiting examples of these are CMV IE and RSV LTR. Tissue specific promoters can be used, particularly if expression is in cells in which expression of an antigen is desirable, such as dendritic cells or macrophages. The mammalian MHC I and MHC II promoters are examples of such tissue-specific promoters.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

3. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expresion systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. Polysaccharides

The immunogenic compositions of the invention may further comprise capsular polysaccharides including one or more of PIA (also known as PNAG) and/or *S. aureus* Type V and/or type VIII capsular polysaccharide and/or *S. epidermidis* Type I, and/or Type II and/or Type III capsular polysaccharide.

A. PIA (PNAG)

It is now clear that the various forms of staphylococcal surface polysaccharides identified as PS/A, PIA and SAA are the same chemical entity—PNAG (Maira-Litran et al., 2004). Therefore the term PIA or PNAG encompasses all these polysaccharides or oligosaccharides derived from them.

PIA is a polysaccharide intercellular adhesin and is composed of a polymer of (β-(1→6)-linked glucosamine substituted with N-acetyl and O-succinyl constituents. This polysaccharide is present in both *S. aureus* and *S. epidermidis* and can be isolated from either source (Joyce et al., 2003; Maira-Litran et al., 2002). For example, PNAG may be isolated from *S. aureus* strain MN8m (WO04/43407). PIA isolated from *S. epidermidis* is a integral constituent of biofilm. It is responsible for mediating cell-cell adhesion and probably also functions to shield the growing colony from the host's immune response. The polysaccharide previously known as poly-N-succinyl-β-(1→6)-glucosamine (PNSG) was recently shown not to have the expected structure since the identification of N-succinylation was incorrect (Maira-Litran et al., 2002). Therefore the polysaccharide formally known as PNSG and now found to be PNAG is also encompassed by the term PIA.

PIA (or PNAG) may be of different sizes varying from over 400 kDa to between 75 and 400 kDa to between 10 and 75 kDa to oligosaccharides composed of up to 30 repeat units (of β-(1→6)-linked glucosamine substituted with N-acetyl and O-succinyl constituents). Any size of PIA polysaccharide or oligosaccharide may be use in an immunogenic composition of the invention, in one aspect the polysaccharide is over 40 kDa. Sizing may be achieved by any method known in the art, for instance by microfluidization, ultrasonic irradiation or by chemical cleavage (WO 03/53462, EP497524, EP497525). In certain aspects PIA (PNAG) is at least or at most 40-400 kDa, 40-300 kDa, 50-350 kDa, 60-300 kDa, 50-250 kDa and 60-200 kDa.

PIA (PNAG) can have different degree of acetylation due to substitution on the amino groups by acetate. PIA produced in vitro is almost fully substituted on amino groups (95-100%). Alternatively, a deacetylated PIA (PNAG) can be used having less than 60%, 50%, 40%, 30%, 20%, 10% acetylation. Use of a deacetylated PIA (PNAG) is preferred since non-acetylated epitopes of PNAG are efficient at mediating opsonic killing of Gram positive bacteria, preferably *S. aureus* and/or *S. epidermidis*. In certain aspects, the PIA (PNAG) has a size between 40 kDa and 300 kDa and is deacetylated so that less than 60%, 50%, 40%, 30% or 20% of amino groups are acetylated.

The term deacetylated PNAG (dPNAG) refers to a PNAG polysaccharide or oligosaccharide in which less than 60%, 50%, 40%, 30%, 20% or 10% of the amino agroups are acetylated. In certain aspects, PNAG is deaceylated to form dPNAG by chemically treating the native polysaccharide. For example, the native PNAG is treated with a basic solution such that the pH rises to above 10. For instance the PNAG is treated with 0.1-5 M, 0.2-4 M, 0.3-3 M, 0.5-2 M, 0.75-1.5 M or 1 M NaOH, KOH or NH$_4$OH. Treatment is for at least 10 to 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

The polysaccharide(s) can be conjugated or unconjugated to a carrier protein.

B. Type 5 and Type 8 Polysaccharides from *S. aureus*

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al., (1990) and Fournier et al., (1984). Both have FucNAcp in their repeat unit as well as ManNAcA which can be used to introduce a sulfhydryl group. The structures are:

Type 5
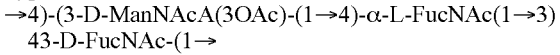
43-D-FucNAc-(1→

Type 8
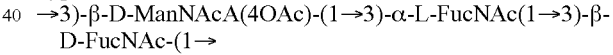
D-FucNAc-(1→

Recently (Jones, 2005) NMR spectroscopy revised the structures to:

Type 5
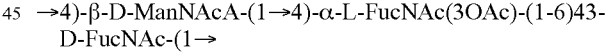
D-FucNAc-(1→

Type 8
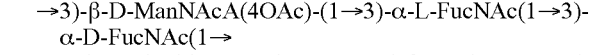
α-D-FucNAc(1→

Polysaccharides may be extracted from the appropriate strain of *S. aureus* using method well known to of skill in the art, See U.S. Pat. No. 6,294,177. For example, ATCC 12902 is a Type 5 *S. aureus* strain and ATCC 12605 is a Type 8 *S. aureus* strain.

Polysaccharides are of native size or alternatively may be sized, for instance by microfluidisation, ultrasonic irradiation, or by chemical treatment. The invention also covers oligosaccharides derived from the type 5 and 8 polysaccharides from *S. aureus*. The type 5 and 8 polysaccharides included in the immunogenic composition of the invention are preferably conjugated to a carrier protein as described below or are alternatively unconjugated. The immunogenic compositions of the invention alternatively contains either type 5 or type 8 polysaccharide.

C. *S. aureus* 336 Antigen

In an embodiment, the immunogenic composition of the invention comprises the *S. aureus* 336 antigen described in U.S. Pat. No. 6,294,177. The 336 antigen comprises n-linked hexosamine, contains no O-acetyl groups, and specifically binds to antibodies to *S. aureus* Type 336 deposited under ATCC 55804. In an embodiment, the 336 antigen is a polysaccharide which is of native size or alternatively may be sized, for instance by microfluidisation, ultrasonic irradiation, or by chemical treatment. The invention also covers oligosaccharides derived from the 336 antigen. The 336 antigen can be unconjugated or conjugated to a carrier protein.

D. Type I, II and III Polysaccharides from *S. epidermidis*

Amongst the problems associated with the use of polysaccharides in vaccination, is the fact that polysaccharides per se are poor immunogens. It is preferred that the polysaccharides utilized in the invention are linked to a protein carrier which provide bystander T-cell help to improve immunogenicity. Examples of such carriers which may be conjugated to polysaccharide immunogens include the Diphtheria and Tetanus toxoids (DT, DT CRM197 and TT respectively), Keyhole Limpet Haemocyanin (KLH), and the purified protein derivative of Tuberculin (PPD), *Pseudomonas aeruginosa* exoprotein A (rEPA), protein D from *Haemophilus influenzae*, pneumolysin or fragments of any of the above. Fragments suitable for use include fragments encompassing T-helper epitopes. In particular the protein D fragment from *H. influenza* will preferably contain the N-terminal ⅓ of the protein. Protein D is an IgD-binding protein from *Haemophilus influenzae* (EP 0 594 610 B1) and is a potential immunogen. In addition, staphylococcal proteins may be used as a carrier protein in the polysaccharide conjugates of the invention.

A carrier protein that would be particularly advantageous to use in the context of a staphylococcal vaccine is staphylococcal alpha toxoid. The native form may be conjugated to a polysaccharide since the process of conjugation reduces toxicity. Preferably genetically detoxified alpha toxins such as the His35Leu or His35Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity.

The polysaccharides may be linked to the carrier protein(s) by any known method (for example those methods described in U.S. Pat. Nos. 4,372,945, 4,474,757, and 4,356,170). Preferably, CDAP conjugation chemistry is carried out (see WO95/08348). In CDAP, the cyanylating reagent 1-cyano-dimethylaminopyridinium tetrafluoroborate (CDAP) is preferably used for the synthesis of polysaccharide-protein conjugates. The cyaniation reaction can be performed under relatively mild conditions, which avoids hydrolysis of the alkaline sensitive polysaccharides. This synthesis allows direct coupling to a carrier protein.

Conjugation preferably involves producing a direct linkage between the carrier protein and polysaccharide. Optionally a spacer (such as adipic dihydride (ADH)) may be introduced between the carrier protein and the polysaccharide.

IV. Immune Response and Assays

As discussed above, the invention concerns evoking or inducing an immune response in a subject against a variant SpA or coagulase peptide. In one embodiment, the immune response can protect against or treat a subject having, suspected of having, or at risk of developing an infection or related disease, particularly those related to staphylococci. One use of the immunogenic compositions of the invention is to prevent nosocomial infections by inoculating a subject prior to undergoing procedures in a hospital or other environment having an increased risk of infection.

A. Immunoassays

The present invention includes the implementation of serological assays to evaluate whether and to what extent an immune response is induced or evoked by compositions of the invention. There are many types of immunoassays that can be implemented. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

B. Diagnosis of Bacterial Infection

In addition to the use of proteins, polypeptides, and/or peptides, as well as antibodies binding these polypeptides, proteins, and/or peptides, to treat or prevent infection as described above, the present invention contemplates the use of these polypeptides, proteins, peptides, and/or antibodies in a variety of ways, including the detection of the presence of Staphylococci to diagnose an infection, whether in a patient or on medical equipment which may also become infected. In accordance with the invention, a preferred method of detecting the presence of infections involves the steps of obtaining a sample suspected of being infected by one or more staphylococcal bacteria species or strains, such as a sample taken from an individual, for example, from one's blood, saliva, tissues, bone, muscle, cartilage, or skin. Following isolation of the sample, diagnostic assays utilizing the polypeptides, proteins, peptides, and/or antibodies of the present invention may be carried out to detect the presence of staphylococci, and such assay techniques for determining such presence in a sample are well known to those skilled in the art and include methods such as radioimmunoassay, western blot analysis and ELISA assays. In general, in accordance with the invention, a method of diagnosing an infection is contemplated wherein a sample suspected of being infected with staphylococci has added to it the polypeptide, protein, peptide, antibody, or monoclonal antibody in accordance with the present invention, and staphylococci are indicated by antibody binding to the polypeptides, proteins, and/or peptides, or polypeptides, proteins, and/or peptides binding to the antibodies in the sample.

Accordingly, antibodies in accordance with the invention may be used for the prevention of infection from staphylococcal bacteria (i.e., passive immunization), for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies, including the products of an Fab immunoglobulin expression library. Accordingly, the invention contemplates the use of single chains such as the variable heavy and light chains of the antibodies. Generation of any of these types of antibodies or antibody fragments is well known to those skilled in the art. Specific examples of the generation of an antibody to a bacterial protein can be found in U.S. Patent Application Pub. No. 20030153022, which is incorporated herein by reference in its entirety.

Any of the above described polypeptides, proteins, peptides, and/or antibodies may be labeled directly with a detectable label for identification and quantification of staphylococcal bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

C. Protective Immunity

In some embodiments of the invention, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide or peptide refer to a stretch of amino acids covalently linked there amongst via peptide bonds. Different polypeptides have different functionalities according to the present invention. While according to one aspect, a polypeptide is derived from an immunogen designed to induce an active immune response in a recipient, according to another aspect of the invention, a polypeptide is derived from an antibody which results following the elicitation of an active immune response in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge with the antigenic composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins according to the invention are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Mernaugh et al., 1995).

As used herein and in the claims, the phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

D. Treatment Methods

A method of the present invention includes treatment for a disease or condition caused by a *staphylococcus* pathogen. An immunogenic polypeptide of the invention can be given to induce an immune response in a person infected with *staphylococcus* or suspected of having been exposed to *staphylococcus*. Methods may be employed with respect to individuals who have tested positive for exposure to *staphylococcus* or who are deemed to be at risk for infection based on possible exposure.

In particular, the invention encompasses a method of treatment for staphylococcal infection, particularly hospital acquired nosocomial infections. The immunogenic compositions and vaccines of the invention are particularly advantageous to use in cases of elective surgery. Such patients will know the date of surgery in advance and could be inoculated in advance. The immunogenic compositions and vaccines of the invention are also advantageous to use to inoculate health care workers.

In some embodiments, the treatment is administered in the presence of adjuvants or carriers or other staphylococcal antigens. Furthermore, in some examples, treatment comprises administration of other agents commonly used against bacterial infection, such as one or more antibiotics.

The use of peptides for vaccination can require, but not necessarily, conjugation of the peptide to an immunogenic carrier protein, such as hepatitis B surface antigen, keyhole limpet hemocyanin, or bovine serum albumin. Methods for performing this conjugation are well known in the art.

V. Vaccine and other pharmaceutical compositions and Administration

A. Vaccines

The present invention includes methods for preventing or ameliorating staphylococcal infections, particularly hospital acquired nosocomial infections. As such, the invention contemplates vaccines for use in both active and passive immunization embodiments. Immunogenic compositions, proposed to be suitable for use as a vaccine, may be prepared from immunogenic SpA polypeptide(s), such as a SpA domain D variant, or immunogenic coagulases. In other embodiments SpA or coagulases can be used in combination with other secreted virulence proteins, surface proteins or immunogenic fragments thereof. In certain aspects, antigenic material is extensively dialyzed to remove undesired small molecular weight molecules and/or lyophilized for more ready formulation into a desired vehicle.

Other options for a protein/peptide-based vaccine involve introducing nucleic acids encoding the antigen(s) as DNA vaccines. In this regard, recent reports described construction of recombinant vaccinia viruses expressing either 10 contiguous minimal CTL epitopes (Thomson, 1996) or a combination of B cell, cytotoxic T-lymphocyte (CTL), and T-helper (Th) epitopes from several microbes (An, 1997), and successful use of such constructs to immunize mice for priming protective immune responses. Thus, there is ample evidence in the literature for successful utilization of peptides, peptide-pulsed antigen presenting cells (APCs), and peptide-encoding constructs for efficient in vivo priming of protective immune responses. The use of nucleic acid sequences as vaccines is exemplified in U.S. Pat. Nos. 5,958,895 and 5,620,896.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the foam of solutions, suspensions, tablets, pills, capsules, sustained release formulations or powders and contain about 10% to about 95% of active ingredient, preferably about 25% to about 70%.

The polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

1. Carriers

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against a variant SpA polypeptide or coagulase, or any other bacterial protein or combination contemplated herein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (Fluosol-DA®) used as a block substitute may also be employed to produce an adjuvant effect.

Examples of and often preferred adjuvants include complete Freund's adjuvant (a non-specific stimulator of the immune response containing killed *Mycobacterium tuberculosis*), incomplete Freund's adjuvants, and aluminum hydroxide.

In some aspects, it is preferred that the adjuvant be selected to be a preferential inducer of either a Th1 or a Th2 type of response. High levels of Th1-type cytokines tend to favor the induction of cell mediated immune responses to a given antigen, while high levels of Th2-type cytokines tend to favor the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4+ T cell clones by Mosmann and Coffman (Mosmann, and Coffman, 1989). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

B. Lipid Components and Moieties

In certain embodiments, the present invention concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-poxvirus-associated composition of the present invention is not limited to any particular structure. For example, they may also simply be interspersed in a solution, possibly fowling aggregates which are not uniform in either size or shape. In another example, they may be present in a bilayer structure, as micelles, or with a "collapsed" structure. In another non-limiting example, a lipofectamine(Gibco BRL)-poxvirus or Superfect (Qiagen)-poxvirus complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range therebetween, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

C. Combination Therapy

The compositions and related methods of the present invention, particularly administration of a secreted virulence factor or surface protein, including a variant SpA polypeptide or peptide, and/or other bacterial peptides or proteins to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a polypeptide vaccine and/or therapy is used in conjunction with antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the immunogenic molecule given as part of an immune therapy regime, such as an antigen, is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | | A/A/B/B | A/B/A/B | A/B/B/A | | B/B/A/A |
| B/A/B/A | B/A/A/B | | A/A/A/B | B/A/A/A | A/B/A/A | | A/A/B/A |

Administration of the immunogenic compositions of the present invention to a patient/subject will follow general protocols for the administration of such compounds, taking into account the toxicity, if any, of the SpA composition, or other compositions described herein. It is expected that the treatment cycles would be repeated as necessary. It also is contemplated that various standard therapies, such as hydration, may be applied in combination with the described therapy.

D. General Pharmaceutical Compositions

In some embodiments, pharmaceutical compositions are administered to a subject. Different aspects of the present invention involve administering an effective amount of a composition to a subject. In some embodiments of the present invention, staphylococcal antigens, members of the Ess pathway, including polypeptides or peptides of the Esa or Esx class, and/or members of sortase substrates may be administered to the patient to protect against infection by one or more *staphylococcus* pathogens. Alternatively, an expression vector encoding one or more such polypeptides or peptides may be given to a patient as a preventative treatment. Additionally, such compounds can be administered in combination with an antibiotic or an antibacterial. Such compositions will generally be dissolved or dispersed in a pharmaceutically acceptable carrier or aqueous medium.

In addition to the compounds formulated for parenteral administration, such as those for intravenous or intramuscular injection, other pharmaceutically acceptable foims include, e.g., tablets or other solids for oral administration; time release capsules; and any other form currently used, including creams, lotions, mouthwashes, inhalants and the like.

The active compounds of the present invention can be formulated for parenteral administration, e.g., formulated for injection via the intravenous, intramuscular, sub-cutaneous, or even intraperitoneal routes. The preparation of an aqueous composition that contains a compound or compounds that increase the expression of an MHC class 1 molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

E. In vitro, Ex vivo, or In vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject.

In certain aspects of the present invention, the compositions may be administered either in vitro, ex vivo, or in vivo. In certain in vitro embodiments, autologous B-lymphocyte cell lines are incubated with a virus vector of the instant invention for 24 to 48 hours or with a variant SpA and/or cogaulase and/or any other composition described herein for two hours. The transduced cells can then be used for in vitro analysis, or alternatively for ex vivo administration. U.S. Pat. Nos. 4,690,915 and 5,199,942, both incorporated herein by reference, disclose methods for ex vivo manipulation of blood mononuclear cells and bone marrow cells for use in therapeutic applications.

F. Antibodies And Passive Immunization

Another aspect of the invention is a method of preparing an immunoglobulin for use in prevention or treatment of staphylococcal infection comprising the steps of immunizing a recipient or donor with the vaccine of the invention and isolating immunoglobulin from the recipient or donor. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of staphylococcal disease. A method for treatment or prevention of staphylococcal infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well known techniques such as affinity chromatography (Harlow and Lane, 1988). Antibodies can include antiserum preparations from a variety of commonly used animals, e.g. goats, primates, donkeys, swine, horses, guinea pigs, rats or man.

An immunoglobulin produced in accordance with the present invention can include whole antibodies, antibody fragments or subfragments. Antibodies can be whole immunoglobulins of any class (e.g., IgG, IgM, IgA, IgD or IgE), chimeric antibodies or hybrid antibodies with dual specificity to two or more antigens of the invention. They may also be fragments (e.g., F(ab')2, Fab', Fab, Fv and the like) including hybrid fragments. An immunoglobulin also includes natural, synthetic, or genetically engineered proteins that act like an antibody by binding to specific antigens to form a complex.

A vaccine of the present invention can be administered to a recipient who then acts as a source of immunoglobulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat staphylococcal infection. Hyperimmune globulins of the invention are particularly useful for treatment or prevention of staphylococcal disease in infants, immune compromised individuals, or where treatment is required and there is no time for the individual to produce antibodies in response to vaccination.

An additional aspect of the invention is a pharmaceutical composition comprising two of more monoclonal antibodies (or fragments thereof; preferably human or humanised) reactive against at least two constituents of the immunogenic composition of the invention, which could be used to treat or prevent infection by Gram positive bacteria, preferably staphylococci, more preferably *S. aureus* or *S. epidermidis*. Such pharmaceutical compositions comprise monoclonal antibodies that can be whole immunoglobulins of any class, chimeric antibodies, or hybrid antibodies with specificity to two or more antigens of the invention. They may also be fragments (e.g., F(ab')2, Fab', Fab, Fv and the like) including hybrid fragments.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be humanized or part humanized by known methods.

VI. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Non-Toxigenic Protein A Variants as Subunit Vaccines to Prevent *Staphylococcus aureus* Infections A. Results An Animal Model for *S. aureus* Infection BALB/c mice were infected by intravenous injection with $1 \times 10^7$ CFU of the human clinical isolate *S. aureus* Newman (Baba et al., 2007). Within 6 hours following infection, 99.999% of staphylococci disappeared from the blood stream and were distributed via the vasculature. Staphylococcal dissemination to peripheral tissues occurred rapidly, as the bacterial load in kidney and other peripheral organ tissues reached $1 \times 10^5$ CFU $g^{-1}$ within the first three hours. The staphylococcal load in kidney tissues increased by 1.5 log CFU within twenty-four hours. Forty-eight hours following infection, mice developed disseminated abscesses in multiple organs, detectable by light microscopy of hematoxylin-eosin stained, thin-sectioned kidney tissue. The initial abscess diameter was 524 µM (±65 µM); lesions were initially marked by an influx of polymorphonuclear leukocytes (PMNs) and harbored no discernable organization of staphylococci, most of which appeared to reside within PMNs. On day 5 of infection, abscesses increased in size and enclosed a central population of staphylococci, surrounded by a layer of eosinophilic, amorphous material and a large cuff of PMNs. Histopathology revealed massive necrosis of PMNs in proximity to the staphylococcal nidus at the center of abscess lesions as well as a mantle of healthy phagocytes. A rim of necrotic PMNs were observed at the periphery of abscess lesions, bordering eosinophilic, amorphous material that separates healthy renal tissue from lesions. Abscesses eventually reached a diameter of 1,524 µM on day 15 or 36. At later time intervals, the staphylococcal load was increased to $10^4$-$10^6$ CFU $g^{-1}$ and growing abscess lesions migrated towards the organ capsule. Peripheral lesions were prone to rupture, thereby releasing necrotic material and staphylococci into the peritoneal cavity or the retroperitoneal space. These events resulted in bacteremia as well as a secondary wave of abscesses, eventually precipitating a lethal outcome.

To enumerate staphylococcal load in renal tissue, animals were killed, their kidneys excised and tissue homogenate spread on agar media for colony formation. On day 5 of infection, a mean of $1 \times 10^6$ CFU $g^{-1}$ renal tissue for *S. aureus* Newman was observed. To quantify abscess formation, kidneys were visually inspected, and each individual organ was given a score of one or zero. The final sum was divided by the total number of kidneys to calculate percent surface abscesses (Table 4). In addition, randomly chosen kidneys were fixed in formalin, embedded, thin sectioned, and stained with hematoxylin-eosin. For each kidney, four sagittal sections at 200 µM intervals were viewed by microscopy. The numbers of lesions were counted for each section and averaged to quantify the number of abscesses within the kidneys. *S. aureus* Newman caused 4.364±0.889 abscesses per kidney, and surface abscesses were observed on 14 out of 20 kidneys (70%) (Table 4).

When examined by scanning electron microscopy, *S. aureus* Newman was located in tightly associated lawns at the center of abscesses. Staphylococci were contained by an amorphous pseudocapsule that separated bacteria from the cuff of abscesses leukocytes. No immune cells were observed in these central nests of staphylococci, however occasional red blood cells were located among the bacteria. Bacterial populations at the abscess center, designated staphylococcal abscess communities (SAC), appeared homogenous and coated by an electron-dense, granular material. The kinetics of the appearance of infectious lesions and the morphological attributes of abscesses Ruined by *S. aureus* Newman were similar to those observed following mouse infection with *S. aureus* USA300 (LAC), the current epidemic community-acquired methicillin-resistant *S. aureus* (CA-MRSA) clone in the United States (Diep et al., 2006).

TABLE 4

Genetic requirements for *S. aureus* Newman abscess formation in mice

| Genotype | Staphylococcal load in kidney tissue | | | Abscess formation in kidney tissue | | |
|---|---|---|---|---|---|---|
| | [a]$\log_{10}$ CFU $g^{-1}$ tissue | [b]Significance (P-value) | [c]Reduction ($\log_{10}$ CFU $g^{-1}$) | [d]Surface abscesses (%) | [e]Number of abscesses per kidney | [f]Significance (P-value) |
| wild-type | 6.141 ± 0.192 | — | — | 70 | 4.364 ± 0.889 | — |
| ΔsrtA | 4.095 ± 0.347 | $6.7 \times 10^{-6}$ | 2.046 | 0 | 0.000 ± 0.000 | 0.0216 |
| spa | 5.137 ± 0.374 | 0.0144 | 1.004 | 13 | 0.375 ± 0.374 | 0.0356 |

[a]Means of staphylococcal load calculated as $\log_{10}$ CFU $g^{-1}$ in homogenized renal tissues 5 days following infection in cohorts of fifteen BALB/c mice per challenge strain. Standard error of the means (±SEM) is indicated.

TABLE 4-continued

Genetic requirements for *S. aureus* Newman abscess formation in mice

| | Staphylococcal load in kidney tissue | | | Abscess formation in kidney tissue | | |
|---|---|---|---|---|---|---|
| | | | | [d]Surface | [e]Number of | |
| Genotype | [a]$\log_{10}$ CFU g$^{-1}$ tissue | [b]Significance (P-value) | [c]Reduction ($\log_{10}$ CFU g$^{-1}$) | abscesses (%) | abscesses per kidney | [f]Significance (P-value) |

[b]Statistical significance was calculated with the Students t-test and P-values recorded; P-values <0.05 were deemed significant.
[c]Reduction in bacterial load calculated as $\log_{10}$ CFU g$^{-1}$.
[d]Abscess formation in kidney tissues five days following infection was measured by macroscopic inspection (% positive)
[e]Histopathology of hematoxylin-eosin stained, thin sectioned kidneys from eight to ten animals; the average number of abscesses per kidney was recorded and averaged again for the final mean (±SEM).
[f]Statistical significance was calculated with the Students t-test and P-values recorded; P-values <0.05 were deemed significant.

*S. aureus* Protein A (spa) mutants are avirulent and cannot form abscesses Sortase A is a transpeptidase that immobilizes nineteen surface proteins in the envelope of *S. aureus* strain Newman (Mazmanian et al., 1999; Mazmanian et al., 2000). Earlier work identified sortase A as a virulence factor in multiple animal model systems, however the contributions of this enzyme and its anchored surface proteins to abscess formation or persistence have not yet been revealed (Jonsson et al., 2002; Weiss et al., 2004). Compared to the wild-type parent (Baba et al., 2007), an isogenic srtA variant (ΔsrtA) failed to form abscess lesions on either macroscopic or histopathology examination on days 2, 5, or 15. In mice infected with the strA mutant, only 1×10$^4$ CFU g$^{-1}$ was recovered from kidney tissue on day 5 of infection, which is a 2.046 $\log_{10}$ CFU g$^{-1}$ reduction compared to the wild-type parent strain (P=6.73×10$^{-6}$). A similar defect was observed for the srtA mutant of MRSA strain USA300 (data not shown). Scanning electron microscopy showed that srtA mutants were highly dispersed and often associated with leukocytes in otherwise healthy renal tissue. On day fifteen following infection, srtA mutants were cleared from renal tissues, a ≥3.5 $\log_{10}$ CFU g$^{-1}$ reduction compared to the wild-type (Table 4). Thus, sortase A anchored surface proteins enable the formation of abscess lesions and the persistence of bacteria in host tissues, wherein staphylococci replicate as communities embedded in an extracellular matrix and shielded from surrounding leukocytes by an amorphous pseudocapsule.

Sortase A anchors a large spectrum of proteins with LPXTG motif sorting signals to the cell wall envelope, thereby providing for the surface display of many virulence factors (Mazmanian et al., 2002). To identify surface proteins required for staphylococcal abscess formation, *bursa aurealis* insertions were introduced in 5' coding sequences of genes that encode polypeptides with LPXTG motif proteins (Bae et al., 2004) and these mutations were transduced into *S. aureus* Newman. Mutations in the structural gene for Protein A (spa) reduced the staphylococcal load in infected mouse kidney tissues by 1.004 $\log_{10}$ (P=0.0144). When analyzed for their ability to form abscesses in kidney tissues by histopathology, we observed that the spa mutants were unable to form abscesses as compared with the wild-type parent strain *S. aureus* Newman (wild-type *S. aureus* Newman 4.364±0.889 abscesses per kidney vs. the isogenic spa mutant with 0.375±0.374 lesions; P=0.0356).

Protein A blocks innate and adaptive immune responses. Studies identified Protein A as a critical virulence factor during the pathogenesis of *S. aureus* infections. Earlier work demonstrated that Protein A impedes phagocytosis of staphylococci by binding the Fc component of immunoglobulin (Jensen 1958; Uhlén et al., 1984), activates platelet aggregation via the von Willebrand factor (Hartleib et al., 2000), functions as a B cell superantigen by capturing the F(ab)$_2$ region of VH3 bearing IgM (Roben et al., 1995), and, through its activation of TNFR1, can initiate staphylococcal pneumonia (Gomez et al., 2004). Due to the fact that Protein A captures immunoglobulin and displays toxic attributes, the possibility that this surface molecule may function as a vaccine in humans has not been rigorously pursued. The inventors demonstrate for the first time that Protein A variants no longer able to bind to immunoglobulins, vWF and TNFR-1 are removed of their toxigenic potential and are able to stimulate humoral immune responses that protect against staphylococcal disease.

Molecular basis of protein A surface display and function. Protein A is synthesized as a precursor in the bacterial cytoplasm and secreted via its YSIRK signal peptide at the cross wall, i.e., the cell division septum of staphylococci (FIG. 1). (DeDent et al., 2007; DeDent et al., 2008). Following cleavage of the C-terminal LPXTG sorting signal, Protein A is anchored to bacterial peptidoglycan crossbridges by sortase A (Schneewind et al., 1995; Mazmanian et al., 1999; Mazmanian et al., 2000). Protein A is the most abundant surface protein of staphylococci; the molecule is expressed by virtually all *S. aureus* strains (Saïd-Salim et al., 2003; Cespedes et al., 2005; Kennedy et al., 2008). Staphylococci turn over 15-20% of their cell wall per division cycle (Navarre and Schneewind 1999). Murine hydrolases cleave the glycan strands and wall peptides of peptidoglycan, thereby releasing Protein A with its attached C-terminal cell wall disaccharide tetrapeptide into the extracellular medium (Ton-That et al., 1999). Thus, by physiological design, Protein A is both anchored to the cell wall and displayed on the bacterial surface but also released into surrounding tissues during host infection (Marraffini et al., 2006).

Protein A captures immunoglobulins on the bacterial surface and this biochemical activity enables staphylococcal escape from host innate and acquired immune responses (Jensen 1958; Goodyear and Silveanan 2004). Interestingly, region X of Protein A (Guss et al., 1984), a repeat domain that tethers the IgG binding domains to the LPXTG sorting signal/cell wall anchor, is perhaps the most variable portion of the staphylococcal genome (Schneewind et al., 1992; Sad-Salim et al., 2003). Each of the five immunoglobulin binding domains of Protein A (SpA), formed from three helix bundles and designated E, D, A, B, and C, exerts similar structural and functional properties (Sjodahl 1977; Jansson et al., 1998). The solution and crystal structure of domain D has been solved both with and without the Fc and $V_H3$ (Fab) ligands, which bind Protein A in a non-competitive manner at distinct sites (Graille et al., 2000).

In the crystal structure complex, the Fab interacts with helix II and helix III of domain D via a surface composed of four VH region β-strands (Graille et al., 2000). The major axis of helix II of domain D is approximately 50° to the orientation of the strands, and the interhelical portion of domain D is most proximal to the C0 strand. The site of interaction on Fab is remote from the Ig light chain and the heavy chain constant region. The interaction involves the following domain D residues: Asp-36 of helix II as well as Asp-37 and Gln-40 in the loop between helix II and helix III, in addition to several other residues with SpA-D (Graille et al., 2000). Both interacting surfaces are composed predominantly of polar side chains, with three negatively charged residues on domain D and two positively charged residues on the 2A2 Fab buried by the interaction, providing an overall electrostatic attraction between the two molecules. Of the five polar interactions identified between Fab and domain D, three are between side chains. A salt bridge is formed between Arg-H19 and Asp-36 and two hydrogen bonds are made between Tyr-H59 and Asp-37 and between Asn-H82a and Ser-33. Because of the conservation of Asp-36 and Asp-37 in all five IgG binding domains of Protein A, these residues were selected for mutagenesis.

The SpA-D sites responsible for Fab binding are structurally separate from the domain surface that mediates Fcγ binding. The interaction of Fcγ with domain B primarily involves residues in helix I with lesser involvement of helix II (Deisenhofer 1981; Gouda et al., 1992). With the exception of the Gln-32, a minor contact in both complexes, none of the residues that mediate the Fcγ interaction are involved in Fab binding. To examine the spatial relationship between these different Ig-binding sites, the SpA domains in these complexes have been superimposed to construct a model of a complex between Fab, the SpA-domain D, and the Fcγ molecule. In this ternary model, Fab and Fcγ form a sandwich about opposite faces of the helix II without evidence of steric hindrance of either interaction. These findings illustrate how, despite its small size (i.e., 56-61 aa), a SpA domain can simultaneously display both activities, explaining experimental evidence that the interactions of Fab with an individual domain are noncompetitive. Residues for the interaction between SpA-D and Fcγ are Gln-9 and Gln-10.

In contrast, occupancy of the Fc portion of IgG on the domain D blocks its interaction with vWF A1 and probably also TNFR1 (O'Seaghdha et al., 2006). Mutations in residues essential for IgG Fc binding (F5, Q9, Q10, S11, F13, Y14, L17, N28, I31 and K35) are also required for vWF A1 and TNFR1 binding (Cedergren et al., 1993; Gomez et al., 2006; O'Seaghdha et al. 2006), whereas residues critical for the $V_H3$ interaction (Q26, G29, F30, S33, D36, D37, Q40, N43, E47) have no impact on the binding activities of IgG Fc, vWF A1 or TNFR1 (Jansson et al., 1998; Graille et al., 2000). The Protein A immunoglobulin Fab binding activity targets a subset of B cells that express VH3 family related IgM on their surface, i.e. these molecules function as VH3 type B cell receptors (Roben et al., 1995). Upon interaction with SpA, these B cells rapidly proliferate and then commit to apoptosis, leading to preferential and prolonged deletion of innate-like B lymphocytes (i.e. marginal zone B cells and follicular B2 cells) (Goodyear and Silverman 2003; Goodyear and Silverman 2004). It is important to note that more than 40% of circulating B cells are targeted by the Protein A interaction and the VH3 family represents the largest family of human B cell receptors to impart protective humoral responses against pathogens (Goodyear and Silverman 2003; Goodyear and Silverman 2004). Thus, Protein A functions analogously to staphylococcal superantigens (Roben et al., 1995), albeit that the latter class of molecules, for example SEB, TSST-1, TSST-2, form complexes with the T cell receptor to inappropriately stimulate host immune responses and thereby precipitating characteristic disease features of staphylococcal infections (Roben et al., 1995; Tiedemann et al., 1995). Together these findings document the contributions of Protein A in establishing staphylococcal infections and in modulating host immune responses.

Non-toxigenic variant of Protein A. The inventors have developed a non-toxigenic variant of staphylococcal Protein A and, with this reagent in hand, aimed for the first time to measure the immune response of animals to Protein A immunization. Further, the inventors address whether immunization of animals with a non-toxigenic variant of Protein A could generate immune responses that raise protective immunity against staphylococcal infection.

To perturb the IgG Fc, vWF A1 and TNFR1 binding activities of Protein A, glutamine (Q) residues 9 and 10 [the numbering here is derived from that established for the SpA domain D] were modified generating lysine or glycine substitutions for both glutamines with the expectation that these substitutions abolish the ion bonds formed between wild-type Protein A and its ligands. The added effect of the dual lysine substitutions may be that these positively charged residues institute a repellent charge for immunoglobulins. To perturb IgM Fab VH3 binding, the inventors selected the aspartate (D) residues 36 and 37 of SpA-D, each of which is required for the association of Protein A with the B cell receptor. D36 and D37 were both substituted with alanine. The Q9,10K and D36,37A mutations were combined in the recombinant molecule SpA-D$_{Q9,10K;D36,37A}$ and examined for the binding attributes of Protein A.

In brief, the Protein A (spa) genomic sequence of *Staphylococcus aureus* N315 was PCR amplified with the primers (GCTGCACATATGGCGCAACACGATGAAGCTCAAC [5' primer](SEQ ID NO:35) and AGTGGATCCTTATGCTTTGTTAGCATCTGC [3' primer] (SEQ ID NO:36)), cloned into the pET15b vector (pYSJ1, codons 48-486) (Stranger-Jones, et al., 2006) and recombinant plasmid transformed into *E. coli* BL21(DE3) (Studier et al., 1990). The Protein A product derived from pYSJ1 harbors SpA residues 36-265 fused to the N-terminal His tag (MGSSHHHHHHSSGLVPRGS (SEQ ID NO:37)). Following IPTG inducible expression, recombinant N-terminal His$_6$-tagged SpA was purified by affinity chromatography on Ni-NTA resin (Stranger-Jones et al., 2006). The domain D of SpA (SpA-D) was PCR amplified with a pair of specific primers (AA-CATATGTTCAACAAAGATCAACAAAGC [5' primer] (SEQ ID NO:38) and AAGGATCCAGATTCGTTTAATTTTTTAGC [3' primer] (SEQ ID NO:39)), sub-cloned into the pET15b vector (pHAN 1, spa codons 212-261) and recombinant plasmid transformed into *E. coli* BL21(DE3) to express and purify recombinant N-terminal His$_6$-tagged protein. To generate mutations in the SpA-D coding sequence, sets of two pairs of primers were synthesized (for D to A substitutions: CTTCATTCAAAGTCTTAAAGCCGCCCCAAGCCAAAGCACTAAC [5' primer] (SEQ ID NO:40) and GTTAGTGCTTTGGCTTGGGGCGGCTTTAAGACTTTGAATGAAG [3' primer] (SEQ ID NO:41); for Q to K substitutions CATATGTTCAACAAAGATAAAAAAAGCGCCTTCTATGAAATC [5' primer] (SEQ ID NO:42) and GATTTCATAGAAGGCGCTTTTTTATCTTTGTTGAACATATG [3' primer] (SEQ ID NO:43); for Q to G substitutions CATATGTTCAACAAAGATGGAGGAAGCGCCTTCTATGAAATC [5' primer] (SEQ ID NO:44) and GATTTCATAGAAGGCGCTTCCTCCATCTTTGTTGAACATATG' [3' primer] (SEQ ID NO:45). Primers were used for quick-change mutagenesis protocols. Following mutagenesis, DNA sequences were confirmed for each of the recombinant proteins: SpA, SpA-D and SpA-D$_{Q9,10G,D36,37A}$ and SpA-D$_{Q9,10K,D36,37A}$. All proteins were purified from lysates of recombinant *E. coli* using Ni-NTA chromatography and subsequently dialyzed against PBS and stored at 4° C.

Figure 3:
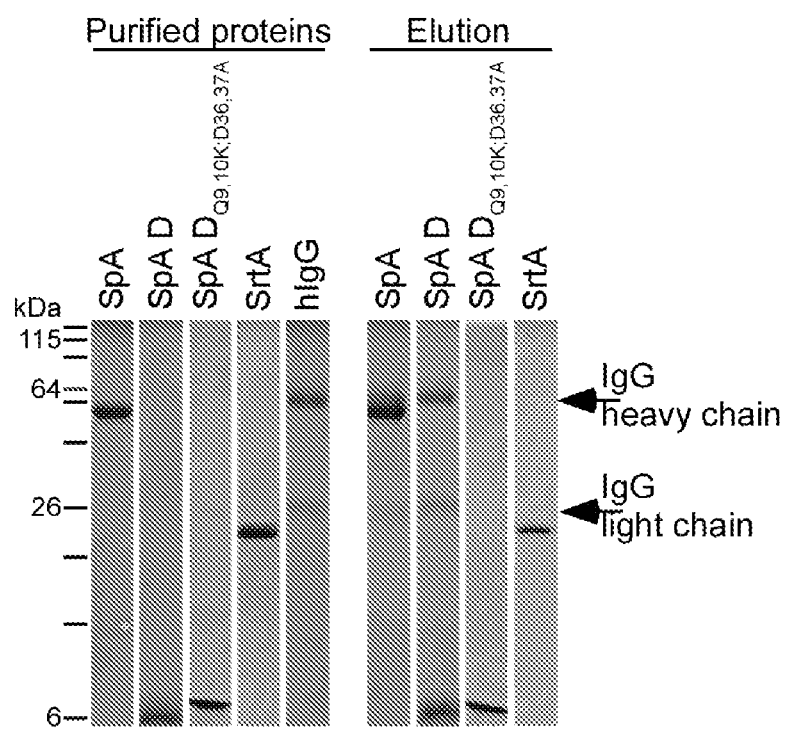
FIG. 3. Left panel—Coomassie Blue stained SDS-PAGE reveals the migrational position of purified His-tagged SpA, SpA-D, SpA-$D_{Q9,10K;D36,37A}$, human IgG, and sortase A (SrtA), a control protein. Right panel—Coomassie Blue stained SDS-PAGE to reveal the elution of Protein A immunoglobulin complexes eluted following affinity chromatography of human IgG on Ni-NTA columns pre-charged with His-tagged SpA, SpA-D, SpA-$D_{Q9,10K;D36,37A}$ or SrtA.

To measure binding of immunoglobulin to Protein A and its variants, 200 µg of purified protein was diluted into a 1 ml volume using column buffer (50 mM Tris-HCl, 150 mM NaCl, pH7.5) and then loaded onto a pre-equilibrated Ni-NTA column (1 ml bed volume). Columns were washed with 10 ml of column buffer. 200 µg of purified human IgG was diluted in a total volume of 1 ml column buffer and then applied to each of the columns charged with Protein A and its variants. The columns were subsequently washed with 5 ml wash buffer (10 mM imidazole in column buffer) and 5 ml column buffer. Protein samples were eluted with 2 ml elution buffer (500 mM imidazole in column buffer), fractions collected and aliquots subjected to SDS-PAGE gel electrophoresis, followed by Coomassie-Blue staining. As shown in FIG. 3, wild-type Protein A (SpA) and its SpA-domain D both retained immunogobulin during chromatography. In contrast, the SpA-D$_{Q9,10K;D36,37A}$ variant did not bind to immunoglobulin.

Figure 4:
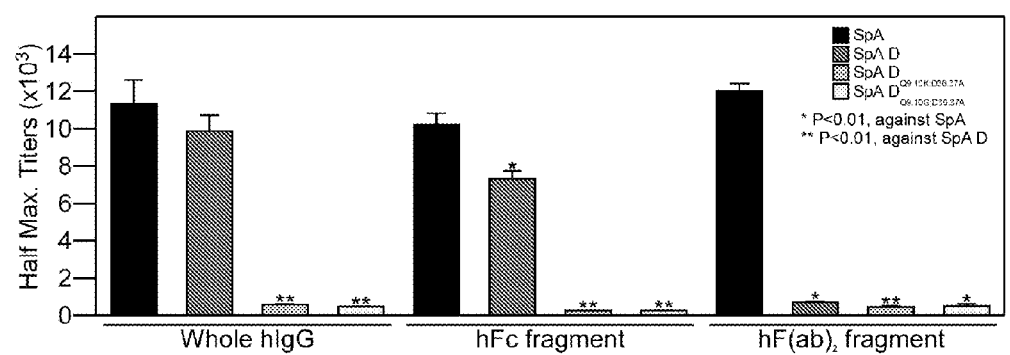
FIG. 4. ELISA assays to quantify human immunoglobulin (hIgG), human F(ab)$_2$ IgG fragments and human Fc fragments of immunoglobulin (hFc). Plates were coated with equal amounts of His-tagged SpA, SpA-D, SPA-$D_{Q9,10K;D36,37A}$ or SrtA. hIgG-HRP, F(ab)$_2$-HRP and hFc-HRP were added onto the plates and incubated for an hour. Absorbance at 450 nm was recorded and plotted to determine the half maximal titers.
Figure 5:
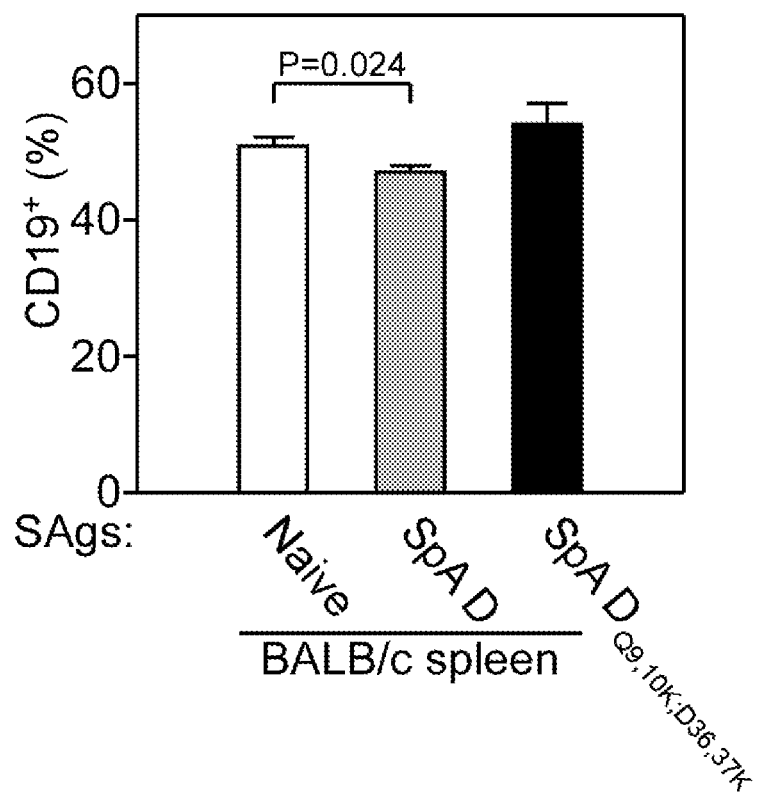
FIG. 5. Purified SpA-D, SpA-$D_{Q9,10K;D36,37A}$ or a PBS mock control were injected into the peritoneum of mice and analyzed for their ability to reduce the B cell population in the spleen of experimental BALB/c mice. Animals were killed 4 hours following injection, their spleen removed, tissue homogenized and stained with CD19 antibodies directed against B cells. The number of B cells was quantified by FACS sorting.
Figure 6:
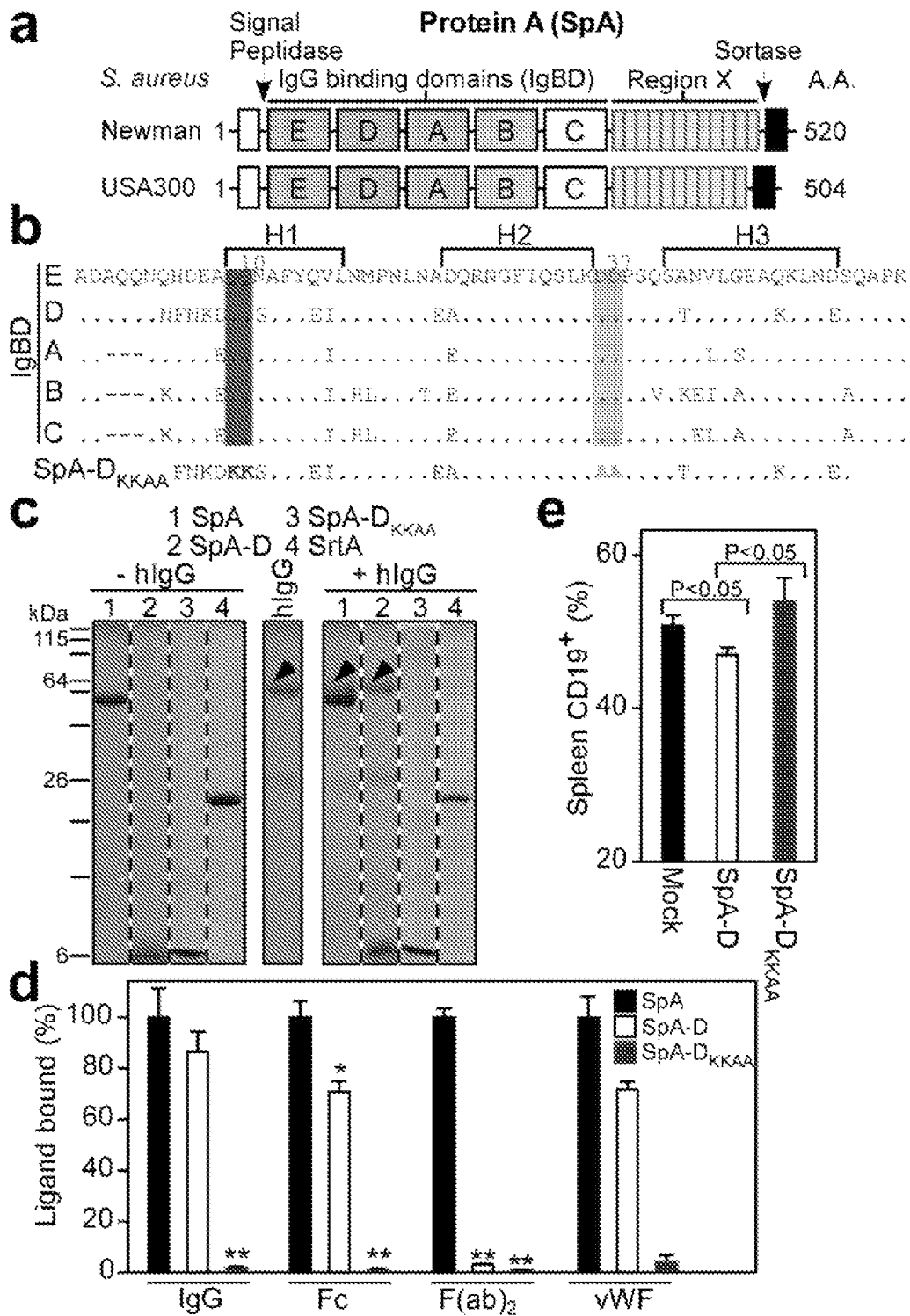
FIG. 6 Generation of a non-toxigenic protein A vaccine. a, Translational protein A (SpA) product of S. aureus Newman and USA300 LAC with an N-terminal signal peptide (white box), five immunoglobulin binding domains (IgBDs designated E, D, A, B and C), variable region X and C-terminal sorting signal (black box). b, Amino acid sequence of the five IgBDs as well as nontoxigenic SpA-$D_{KKAA}$, with the positions of triple α-helical bundles (H1, H2 and H3) as well as glutamine (Q) 9, 10 and aspartate (D) 36, 37 indicated. c, Coomassie Blue-stained SDS-PAGE of SpA, SpA-D, SpA-$D_{KKAA}$ or SrtA purified on Ni-NTA sepharose in the presence or absence of human immunoglobulin (hIgG). d, ELISA examining the association of immobilized SpA, SpA-D or SpA-$D_{KKAA}$ with human IgG as well as its Fc or F(ab)$_2$ fragments and von Willebrand factor (vWF). e, CD19+ B lymphocytes in splenic tissue of BALB/c mice that had been mock immunized or treated with SpA-D or SpA-$D_{KKAA}$ were quantified by FACS.
Figure 7:
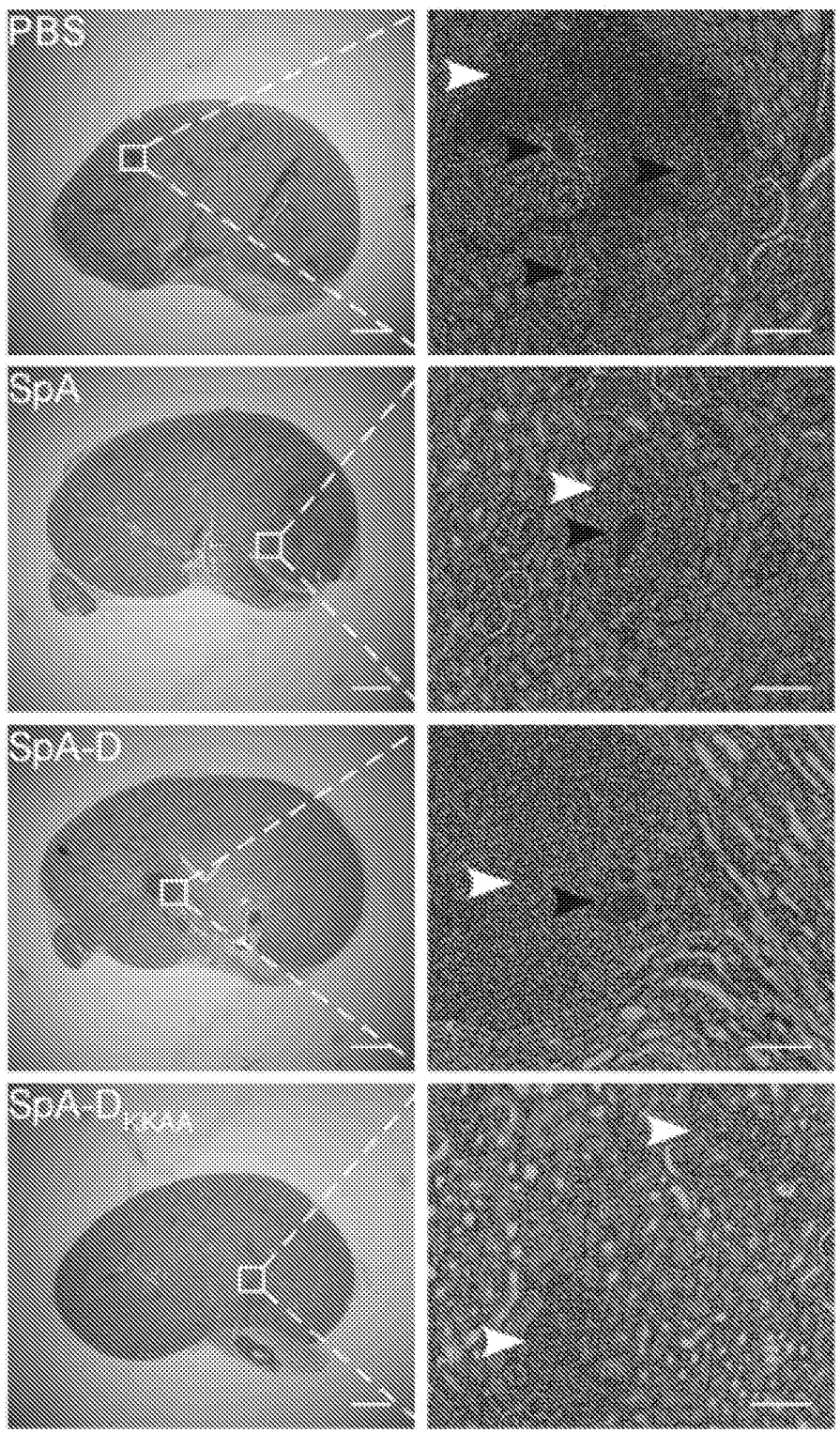
FIG. 7 Non-toxigenic protein A vaccine prevents abscess formation. Histopathology of renal tissue isolated during necropsy of BALB/c mice that had been mock immunized (PBS) or vaccinated with SpA, SpA-D as well as SpA-$D_{KKAA}$ and challenged with S. aureus Newman. Thin sectioned tissues were stained with hematoxylin-eosin. White arrows identify polymorphonuclear leukocyte (PMN) infiltrates. Dark arrows identify staphylococcal abscess communities.

To quantify the binding of Protein A and its variants to the Fc portion of immunoglobulin and the VH3 domain of Fab, HRP conjugated human immunoglobulin G [hIgG], the Fc portion of human IgG [hFc] and the F(ab)$_2$ portion of human IgG [hF(ab)$_2$] as well as ELISA assays were used to quantify the relative amount binding to Protein A and its variants. The data in FIG. 4 demonstrate the binding of SpA and SpA-D to hIgG and hFc, whereas SpA-D$_{Q9,10G;D36,37A}$ and SpA-D$_{Q9,10K;D36,37A}$ displayed only background binding activities. SpA bound similar amounts of hFc and hF(ab)$_2$, however the binding of SpA-D to hF(ab)$_2$ was reduced compared to full length SpA. This result suggests that the presence of multiple IgG binding domains may cooperatively increase the ability of Protein A to bind to the B cell receptor. When compared with the reduced binding power of SpA-D for hF(ab)$_2$, of the two variants only SpA-D$_{Q9,10K;D36,37A}$ displayed a significant reduction in the ability to bind the VH3 domain of immunoglobulin. To examine the toxigenic attributes of SpA-D and its variants, purified proteins were injected into mice, which were sacrificed after 4 hours to remove their spleens. Organ tissue was homogenized, capsular material removed and B cells stained with fluorescent CD19 antibodies. Following FACS analysis to quantify the abundance of B cells in splenic tissues, it was observed that SpA-D caused a 5% drop in the B cell count compared to a mock (PBS) control (FIG. 5). In contrast, SpA-D$_{Q9,10K;D36,37A}$ did not cause a reduction in B-cell counts, indicating that the mutant molecule had lost its toxigenic attributes of stimulating B cell proliferation and death (FIG. 5). In summary, amino acid substitutions in the SpA-D residues Q9, Q10, D36, and D37 abolished the ability of Protein A domains to bind immunoglobulins or exert toxigenic functions in human and animal tissues.

Non-toxigenic Protein A variants elicit vaccine protection. To test whether or not Protein A and its variants can function as vaccine antigens, SpA, SpA-D, SpA-$D_{Q9,10K;D36,37A}$, and SpA-$D_{Q9,10K;D36,37A}$ were emulsified with complete or incomplete Freund's adjuvant and immunized 4 week old BALB/c mice on day 1 and day 11 with 50 μg of purified protein. Cohort of animals (n=5) were analyzed for humoral immune responses to immunization by bleeding the animals before (day 0) and after the immunization schedule (day 21). Table 5 indicates that immunized mice generated only a modest humoral immune response directed at wild-type Protein A or its SpA-D module, whereas the amount of antibody raised following immunization with SPA-$D_{Q9,10K;D36,37A}$ or SpA-$D_{Q9,10K,D36,37A}$ was increased four to five fold. Following intravenous challenge with $1\times10^7$ CFU *S. aureus* Newman, animals were killed on day 4, their kidneys removed and either analyzed for staphylococcal load (by plating tissue homogenate on agar plates and enumerating colony forming units, CFU) or histopathology. As expected, mock (PBS) immunized mice (n=19) harbored 6.46 $\log_{10}$ (±0.25) CFU in kidney tissue and infectious lesions were organized into 3.7 (±1.2) abscesses per organ (n=10) (Table 5). Immunization of animals with SpA led to a 2.51 $\log_{10}$ CFU reduction on day 5 (P=0.0003) with 2.1 (±1.2) abscesses per organ. The latter data indicate that there was no significant reduction in abscess formation (P=0.35). Immunization with SpA-D generated similar results: a 2.03 $\log_{10}$ CFU reduction on day 5 (P=0.0001) with 1.5 (±0.8) abscesses per organ (P=0.15). In contrast, immunization with SpA-$D_{Q9,10K;D36,37A}$ or SpA-$D_{Q9,10G;D36,37A}$ created increased protection, with 3.07 $\log_{10}$ and 3.03 $\log_{10}$ CFU reduction on day 4, respectively (statistical significance P<0.0001 for both observations). Further, immunization with both SpA-$D_{Q9,10K,D36,37A}$ and SpA-$D_{Q9,10G,D36,37A}$ generated significant protection from staphylococcal abscess formation, as only 0.5 (±0.4) and 0.8 (±0.5) infectious lesions per organ (P=0.02 and P=0.04) were identified. Thus, immunization with non-toxigenic Protein A variants generates increased humoral immune responses for Protein A and provides protective immunity against staphylococcal challenge. These data indicate that Protein A is an ideal candidate for a human vaccine that prevents *S. aureus* disease.

These exciting results have several implications for the design of a human vaccine. First, the generation of substitution mutations that affect the ability of the immunoglobulin binding domains of Protein A, either alone or in combination of two or more domains, can generate non-toxigenic variants suitable for vaccine development. It seems likely that a combination of mutant IgG binding domains closely resembling the structure of Protein A can generate even better humoral immune responses as is reported here for the SpA-domain D alone. Further, a likely attribute of Protein A specific antibodies may be that the interaction of antigen binding sites with the microbial surface can neutralize the ability of staphylococci to capture immunoglobulins via their Fc portion or to stimulate the B cell receptor via the VH3 binding activities.

TABLE 5

Non-toxigenic Protein A variants as vaccine antigens that prevent *S. aureus* disease

| | Bacterial load in kidney (n = number of mice) | | | | | Abscess formation in mice (n = number of mice) | | | |
|---|---|---|---|---|---|---|---|---|---|
| Antigen | $^a\log_{10}$ CFU $g^{-1}$ | $^b$Reduction | $^c$P value | IgG titer | $^d$Surface abscess | Reduction | $^e$Histopathology | Reduction | $^f$P value |
| Mock | 6.46 ± 0.25 (n = 19) | — | — | <100 | 14/19 (70%) | — | 3.7 ± 1.2 (n = 10) | — | — |

TABLE 5-continued Non-toxigenic Protein A variants as vaccine antigens that prevent S. aureus disease

| Antigen | Bacterial load in kidney (n = number of mice) | | | | Abscess formation in mice (n = number of mice) | | | | |
|---|---|---|---|---|---|---|---|---|---|
| | [a]log$_{10}$ CFU g$^{-1}$ | [b]Reduction | [c]P value | IgG titer | [d]Surface abscess | Reduction | [e]Histopathology | Reduction | [f]P value |
| SpA | 3.95 ± 0.56 (n = 20) | 2.51 | 0.0003 | 1706 ± 370 | 10/20 (50%) | 32% | 2.1 ± 1.2 (n = 10) | 2.2 | 0.35 |
| SpA-D | 4.43 ± 0.41 (n = 18) | 2.03 | 0.0001 | 381 ± 27 | 10/18 (55%) | 25% | 1.5 ± 0.8 (n = 10) | 2.2 | 0.15 |
| SpA-D1 | 3.39 ± 0.50 (n = 19) | 3.07 | <0.0001 | 5600 ± 801 | 6/20 (30%) | 59% | 0.5 ± 0.4 (n = 10) | 3.2 | 0.02 |
| SpA-D2 | 3.43 ± 0.46 (n = 19) | 3.03 | <0.0001 | 3980 ± 676 | 6/19 (32%) | 57% | 0.8 ± 0.5 (n = 10) | 2.9 | 0.04 |

[a]Means of staphylococcal load calculated as log$_{10}$ CFU g$^{-1}$ in homogenized renal tissues 4 days following infection in cohorts of 18 to 20 BALB/c mice. Standard error of the means (±SEM) is indicated.
[c]Statistical significance was calculated with the Students t-test and P-values recorded; P-values <0.05 were deemed significant.
[b]Reduction in bacterial load calculated as log$_{10}$ CFU g$^{-1}$.
[d]Abscess formation in kidney tissues four days following infection was measured by macroscopic inspection (% positive)
[e]Histopathology of hematoxylin-eosin stained, thin sectioned kidneys from ten animals; the number of abscesses per kidney was recorded and averaged for the final mean (±SEM).
[f]Statistical significance was calculated with the Students t-test and P-values recorded; P-values <0.05 were deemed significant.
SpA-D1 and SpA-D2 represent SpA-D$_{Q9,10K;D36,37A}$ and SpA-D$_{Q9,10G;D36,37A}$, respectively.

Vaccine protection in murine abscess, murine lethal infection, and murine pneumonia models. Three animal models have been established for the study of S. aureus infectious disease. These models are used here to examine the level of protective immunity provided via the generation of Protein A specific antibodies.

Murine abscess—BALB/c mice (24-day-old female, 8-10 mice per group, Charles River Laboratories, Wilmington, Mass.) are immunized by intramuscular injection into the hind leg with purified protein (Chang et al., 2003; Schneewind et al., 1992). Purified SpA, SpA-D or SpA-DQ9,10K; D36,37A (50 µg protein) is administered on days 0 (emulsified 1:1 with complete Freund's adjuvant) and 11 (emulsified 1:1 with incomplete Freund's adjuvant). Blood samples are drawn by retroorbital bleeding on days 0, 11, and 20. Sera are examined by ELISA for IgG titers for specific SpA-D and SpA-DQ9,10K;D36,37A binding activity. Immunized animals are challenged on day 21 by retroorbital injection of 100 µl of S. aureus Newman or S. aureus USA300 suspension (1×10$^7$ cfu). For this, overnight cultures of S. aureus Newman are diluted 1:100 into fresh tryptic soy broth and grown for 3 h at 37° C. Staphylococci are centrifuged, washed twice, and diluted in PBS to yield an A$_{600}$ of 0.4 (1×10$^8$ cfu per ml). Dilutions are verified experimentally by agar plating and colony formation. Mice are anesthetized by intraperitoneal injection of 80-120 mg of ketamine and 3-6 mg of xylazine per kilogram of body weight and infected by retroorbital injection. On day 5 or 15 following challenge, mice are euthanized by compressed CO$_2$ inhalation. Kidneys are removed and homogenized in 1% Triton X-100. Aliquots are diluted and plated on agar medium for triplicate determination of cfu. For histology, kidney tissue is incubated at room temperature in 10% formalin for 24 h. Tissues are embedded in paraffin, thin-sectioned, stained with hematoxylinleosin, and examined by microscopy.

Murine lethal infection—BALB/c mice (24-day-old female, 8-10 mice per group, Charles River Laboratories, Wilmington, Mass.) are immunized by intramuscular injection into the hind leg with purified SpA, SpA-D or SpA-D$_{Q9,10K,D36,37A}$ (50 µg protein). Vaccine is administered on days 0 (emulsified 1:1 with complete Freund's adjuvant) and 11 (emulsified 1:1 with incomplete Freund's adjuvant). Blood samples are drawn by retroorbital bleeding on days 0, 11, and 20. Sera are examined by ELISA for IgG titers with specific SpA-D and SpA-D$_{QE,10K,D36,37A}$ binding activity. Immunized animals are challenged on day 21 by retroorbital injection of 100 µl of S. aureus Newman or S. aureus USA300 suspension (15×10$^7$ cfu) (34). For this, overnight cultures of S. aureus Newman are diluted 1:100 into fresh tryptic soy broth and grown for 3 h at 37° C. Staphylococci are centrifuged, washed twice, diluted in PBS to yield an A$_{600}$ of 0.4 (1×10$^8$ cfu per ml) and concentrated. Dilutions are verified experimentally by agar plating and colony formation. Mice are anesthetized by intraperitoneal injection of 80-120 mg of ketamine and 3-6 mg of xylazine per kilogram of body weight. Immunized animals are challenged on day 21 by intraperitoneal inject with 2×10$^{10}$ cfu of S. aureus Newman or 3–10×10$^9$ cfu of clinical S. aureus isolates. Animals are monitored for 14 days, and lethal disease is recorded.

Murine pneumonia model—S. aureus strains Newman or USA300 (LAC) are grown at 37° C. in tryptic soy broth/agar to OD$_{660}$ 0.5. 50-ml culture aliquots are centrifuged, washed in PBS, and suspended in 750 µl PBS for mortality studies (3-4×10$^8$ CFU per 30-µl volume), or 1,250 µl PBS (2×10$^8$ CFU per 30-µl volume) for bacterial load and histopathology experiments (2, 3). For lung infection, 7-wk-old C57BL/6J mice (The Jackson Laboratory) are anesthetized before inoculation of 30 µl of S. aureus suspension into the left nare. Animals are placed into the cage in a supine position for recovery and observed for 14 days. For active immunization, 4-wk-old mice receive 20 µg SpA-D or SpA-D$_{Q9,10K;D36,37A}$ in CFA on day 0 via the i.m. route, followed by a boost with 20 µg SpA-D or SpA-D$_{Q9,10K;D36,37A}$ in incomplete Freund's adjuvant (IFA) on day 10. Animals are challenged with S. aureus on day 21. Sera are collected before immunization and on day 20 to assess specific antibody production. For passive immunization studies, 7-wk-old mice receive 100 µl of either NRS (normal rabbit serum) or SpA-D-specific rabbit antisera via i.p. injection 24 h before challenge. To assess the pathological correlates of pneumonia, infected animals are killed via forced CO$_2$ inhalation before removal of both lungs. The right lung is homogenized for enumeration of lung bacterial load. The left lung is placed in 1% formalin and paraffin embedded, thin sectioned, stained with hematoxylin-eosin, and analyzed by microscopy.

Rabbit antibodies—Purified 200 μg SpA-D or SpA-$D_{Q9,10K;D36,37A}$ is used as an immunogen for the production of rabbit antisera. 200 μg protein is emulsified with CFA for injection at day 0, followed by booster injections with 200 μg protein emulsified with IFA on days 21 and 42. Rabbit antibody titers are determined by ELISA. Purified antibodies are obtained by affinity chromatography of rabbit serum on SpA-D or SpA-$D_{Q9,10K;D36,37A}$ sepharose. The concentration of eluted antibodies is measured by absorbance at $A_{280}$ and specific antibody titers are determined by ELISA.

Active immunization with SpA-domain D variants.—To determine vaccine efficacy, animals are actively immunized with purified SpA-D or $SpAD_{Q9,10K;D36,37A}$. As a control, animals are immunized with adjuvant alone. Antibody titers against Protein A preparations are determined using SpA-D or SpA-$D_{Q9,10K;D36,37A}$ as antigens; note that the SpA-$D_{Q9,10K;D36,37A}$ variant cannot bind the Fc or Fab portion of IgG. Using infectious disease models described above, any reduction in bacterial load (murine abscess and pneumonia), histopathology evidence of staphylococcal disease (murine abscess and pneumonia) and protection from lethal disease (murine lethal challenge and pneumonia) is measured.

Passive immunization with affinity purified rabbit polyclonal antibodies generated against SpA-domain D variants. To determine protective immunity of Protein A specific rabbit antibodies, mice are passively immunized with 5 mg/kg of purified SpA-D or SpA-$D_{Q9,10K,D36,37A}$ derived rabbit antibodies. Both of these antibody preparations are purified by affinity chromatography using immobilized SpA-D or SpA-$D_{Q9,10K;D36,37A}$. As a control, animals are passively immunized with rV 10 antibodies (a plague protective antigen that has no impact on the outcome of staphylococcal infections). Antibody titers against all Protein A preparations are determined using SpA-$D_{Q9,10k;D36,37A}$ as an antigen, as this variant cannot bind the Fc or Fab portion of IgG. Using the infectious disease models described above, the reduction in bacterial load (murine abscess and pneumonia), histopathology evidence of staphylococcal disease (murine abscess and pneumonia), and the protection from lethal disease (murine lethal challenge and pneumonia) is measured.

Example 2

Figure 8:
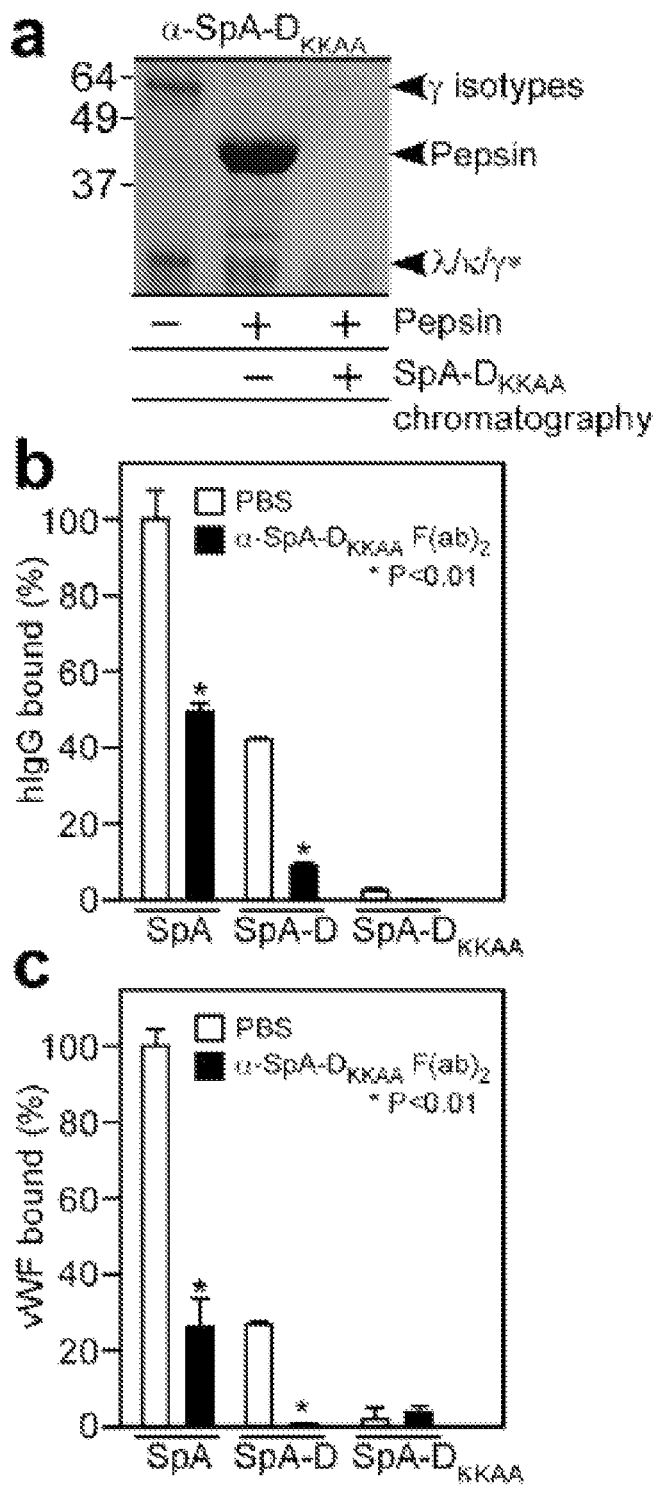
FIG. 8 Antibodies raised by the non-toxigenic protein A vaccine block the B cell superantigen function of SpA. a, Rabbit antibodies raised against SpA-$D_{KKAA}$ were purified on a matrix with immobilized antigen and analyzed by Coomassie Blue-stained SDS-PAGE. Antibodies were cleaved with pepsin and F(ab)2 fragments were purified by a second round of affinity chromatography on SpA-$D_{KKAA}$ matrix. b, SpA-$D_{KKAA}$ specific F(ab)2 interfere with the binding of SpA or SpA-D to human immunoglobulin (hIgG) or, c, to von Willebrand Factor (vWF).

Non-Toxigenic Protein A Vaccine for Methicillin-Resistant *Staphylococcus aureus* Infection Clinical isolates of *S. aureus* express protein A (Shopsin et al., 1999, whose primary translational product is comprised of an N-terminal signal peptide (DeDent et al., 2008), five Ig-BDs (designated E, D, A, B and C) (Sjodahl, 1977), region X with variable repeats of an eight residue peptide (Guss et al., 1984), and C-terminal sorting signal for the cell wall anchoring of SpA (Schneewind et al., 1992; Schneewind et al., 1995) (FIG. 6). Guided by amino acid homology (Uhlen et al., 1984), the triple α-helical bundle structure of IgBDs (Deisenhofer et al., 1978; Deisenhofer et al., 1981) and their atomic interactions with Fab $V_H3$ (Graille et al., 2000) or Fcγ (Gouda et al., 1998), glutamine 9 and 10 were selected as well as aspartate 36 and 37 as critical for the association of SpA with antibodies or B cell receptor, respectively. Substitutions Gln9Lys, Gln10Lys, Asp36Ala and Asp37Ala were introduced into the D domain to generate SpA-$D_{KKAA}$ (FIG. 6). The ability of isolated SpA-D or SpA-$D_{KKAA}$ to bind human IgG was analyzed by affinity chromatography (FIG. 6). Polyhistidine tagged SpA-D as well as full-length SpA retained human IgG on Ni-NTA, whereas SpA-$D_{KKAA}$ and a negative control (SrtA) did not (FIG. 6). A similar result was observed with von Willebrand factor (Hartleib et al., 2000), which, along with tumor necrosis factor receptor 1 (TNFR1)(Gomez et al., 2004), can also bind protein A via glutamine 9 and 10 (FIG. 6). Human immunoglobulin encompasses 60-70% $V_H3$-type IgG. The inventors distinguish between Fc domain and B cell receptor activation of Igs and measured association of human Fcγ and $F(ab)_2$ fragments, both of which bound to full-length SpA or SpA-D, but not to SpA-$D_{KKAA}$ (FIG. 6). Injection of SpA-D into the peritoneal cavity of mice resulted in B cell expansion followed by apoptotic collapse of CD 19+ lymphocytes in spleen tissue of BALB/c mice (Goodyear and Silverman, 2003)(FIG. 6). B cell superantigen activity was not observed following injection with SpA-$D_{KKAA}$, and TUNEL-staining of splenic tissue failed to detect the increase in apoptotic cells that follows injection of SpA or SpA-D (FIG. 6).

Naive six week old BALB/c mice were injected with 5014 each of purified SpA, SpA-D or SpA-$D_{KKAA}$ emulsified in CFA and boosted with the same antigen emulsified in IFA. In agreement with the hypothesis that SpA-D promotes the apoptotic collapse of activated clonal B cell populations, the inventors observed a ten-fold higher titer of SpA-$D_{KKAA}$ specific antibodies following immunization of mice with the non-toxigenic variant as compared to the B cell superantigen (Spa-D vs. SpA-$D_{KKAA}$ $P<0.0001$, Table 6). Antibody titers raised by immunization with full-length SpA were higher than those elicited by SpA-D ($P=0.0022$), which is likely due to the larger size and reiterative domain structure of this antigen (Table 6). Nevertheless, even SpA elicited lower antibody titers than SpA-$D_{KKAA}$ ($P=0.0003$), which encompasses only 50 amino acids of protein A (520 residues, SEQ ID NO:33). Immunized mice were challenged by intravenous inoculation with *S. aureus* Newman and the ability of staphylococci to seed abscesses in renal tissues was examined by necropsy four days after challenge. In homogenized renal tissue of mock (PBS/adjuvant) immunized mice, an average staphylococcal load of 6.46 $\log_{10}$ CFU $g^{-1}$ was enumerated (Table 6). Immunization of mice with SpA or SpA-D led to a reduction in staphylococcal load, however SpA-$D_{KKAA}$ vaccinated animals displayed an even greater, 3.07 $\log_{10}$ CFU $g^{-1}$ reduction of *S. aureus* Newman in renal tissues ($P<0.0001$, Table 6). Abscess formation in kidneys was analyzed by histopathology (FIG. 7). Mock immunized animals harbored an average of 3.7 (±1.2) abscesses per kidney (Table 6). Vaccination with SpA-$D_{KKAA}$ reduced the average number of abscesses to 0.5 (±0.4) ($P=0.0204$), whereas immunization with SpA or SpA-D did not cause a significant reduction in the number of abscess lesions (Table 6). Lesions from SpA-$D_{KKAA}$ vaccinated animals were smaller in size, with fewer infiltrating PMNs and characteristically lacked staphylococcal abscess communities (Cheng et al., 2009)(FIG. 7). Abscesses in animals that had been immunized with SpA or SpA-D displayed the same overall structure of lesions in mock immunized animals (FIG. 7).

The inventors examined whether SpA-$D_{KKAA}$ immunization can protect mice against MRSA strains and selected the USA300 LAC isolate for animal challenge (Diep et al., 2006). This highly virulent CA-MRSA strain spread rapidly throughout the United States, causing significant human morbidity and mortality (Kennedy et al., 2008). Compared to adjuvant control mice, SpA-$D_{KKAA}$ immunized animals harbored a 1.07 $\log_{10}$ CFU $g^{-1}$ reduction in bacterial load of infected kidney tissues. Histopathology examination of renal tissue following *S. aureus* USA300 challenge revealed that the average number of abscesses was reduced from 4.04 (±0.8) to 1.6 (±0.6) ($P=0.02774$). In contrast, SpA or SpA-D immunization did not cause a significant reduction in bacterial load or abscess formation (Table 6).

Rabbits were immunized with SpA-$D_{KKAA}$ and specific antibodies were purified on SpA-$D_{KKAA}$ affinity column followed by SDS-PAGE (FIG. 8). SpA-$D_{KKAA}$ specific IgG was cleaved with pepsin to generate Fcγ and $F(ab)_2$ fragments, the latter of which were purified by chromatography on SpA-D$_{KKAA}$ column (FIG. 8). Binding of human IgG or vWF to SpA or SpA-D was perturbed by SpA-D$_{KKAA}$ specific F(ab)$_2$, indicating that SpA-D$_{KKAA}$ derived antibodies neutralize the B cell superantigen function of protein A as well as its interactions with Ig (FIG. 8).

Figure 9:
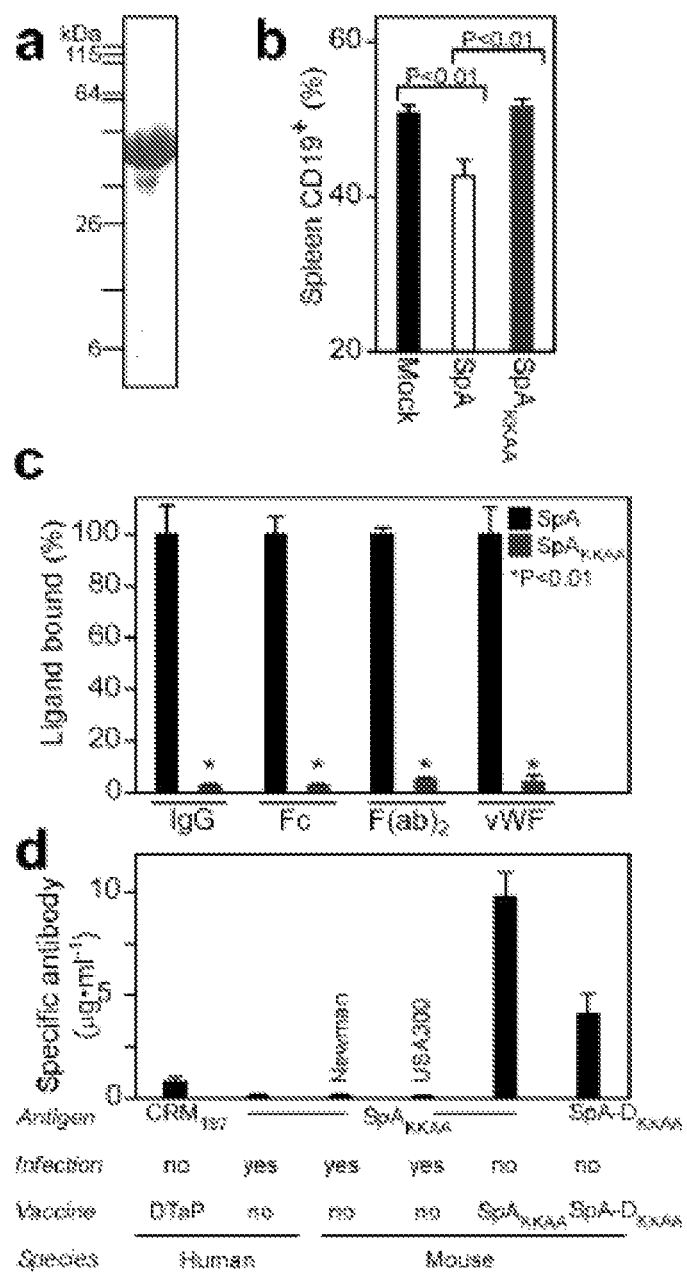
FIG. 9 Full-length non-toxigenic protein A generates improved immune responses. a, Full-length SpA$_{KKAA}$ was purified on Ni-NTA sepharose and analyzed by Coomassie-Blue stained SDS-PAGE. b, CD19+ B lymphocytes in splenic tissue of BALB/c mice that had been mock immunized or treated with SpA or SpA$_{KKAA}$ were quantified by FACS. c, ELISA examining the association of immobilized SpA or SpA$_{KKAA}$ with human IgG as well as its Fc or F(ab)2 fragments or von Willebrand factor (vWF). d, Human or mouse serum antibody titers to diphtheria toxoid (CRM197) and non-toxigenic SpA$_{KKAA}$ or SpA-$D_{KKAA}$. Human volunteers with a history of DTaP immunization and staphylococcal infection (n=16) as well as mice (n=20) that had been infected with S. aureus Newman or USA 300 LAC or immunized with SpA$_{KKAA}$ or SpA-$D_{KKAA}$ were examined by quantitative dot blot.
Figure 10:
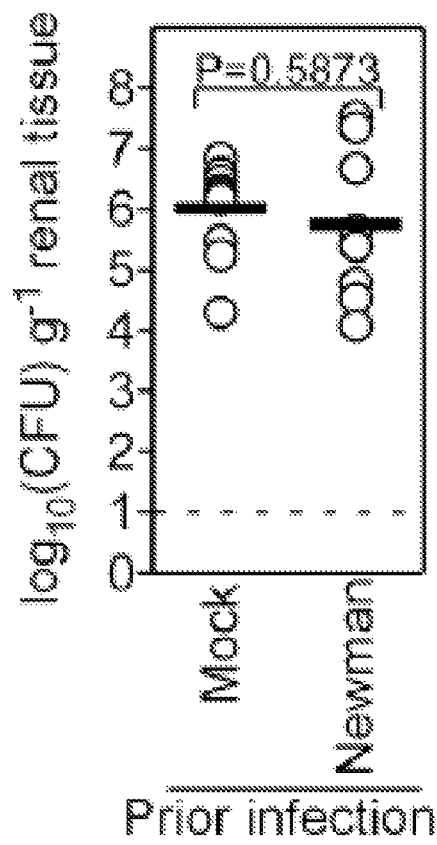
FIG. 10 Staphylococcal infection does not generate protective immunity. BALB/c mice (n=20) were infected with S. aureus Newman or mock challenged (PBS) for thirty days and infection cleared with chloramphenicol treatment. Both cohorts of animals were then challenged with S. aureus Newman and bacterial load (CFU) in kidney tissue homogenate analyzed following necropsy on day 4.
Figure 11:
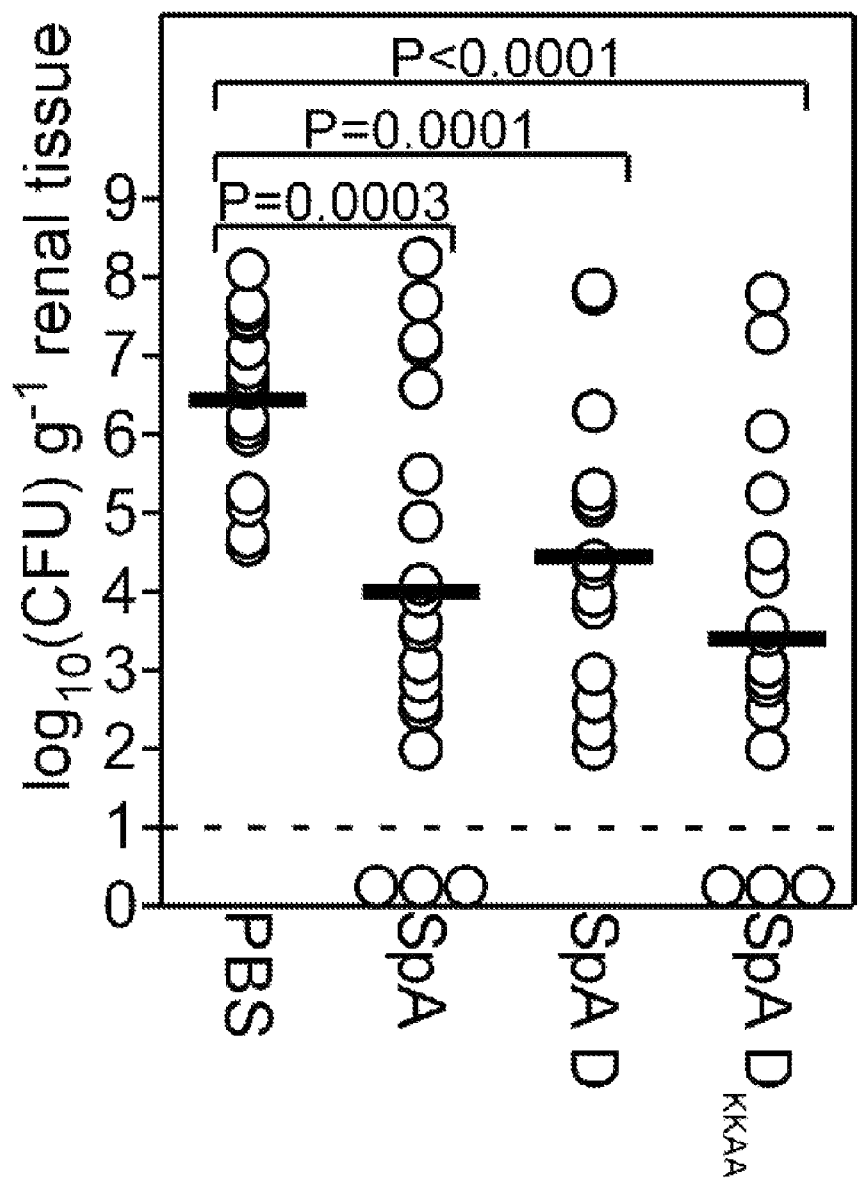
FIG. 11 Comparison of abscess formation in mice treated with PBS, SpA, SpA-D, and SpA-$D_{KKAA}$.
Figures 12A, 12B, 12C:
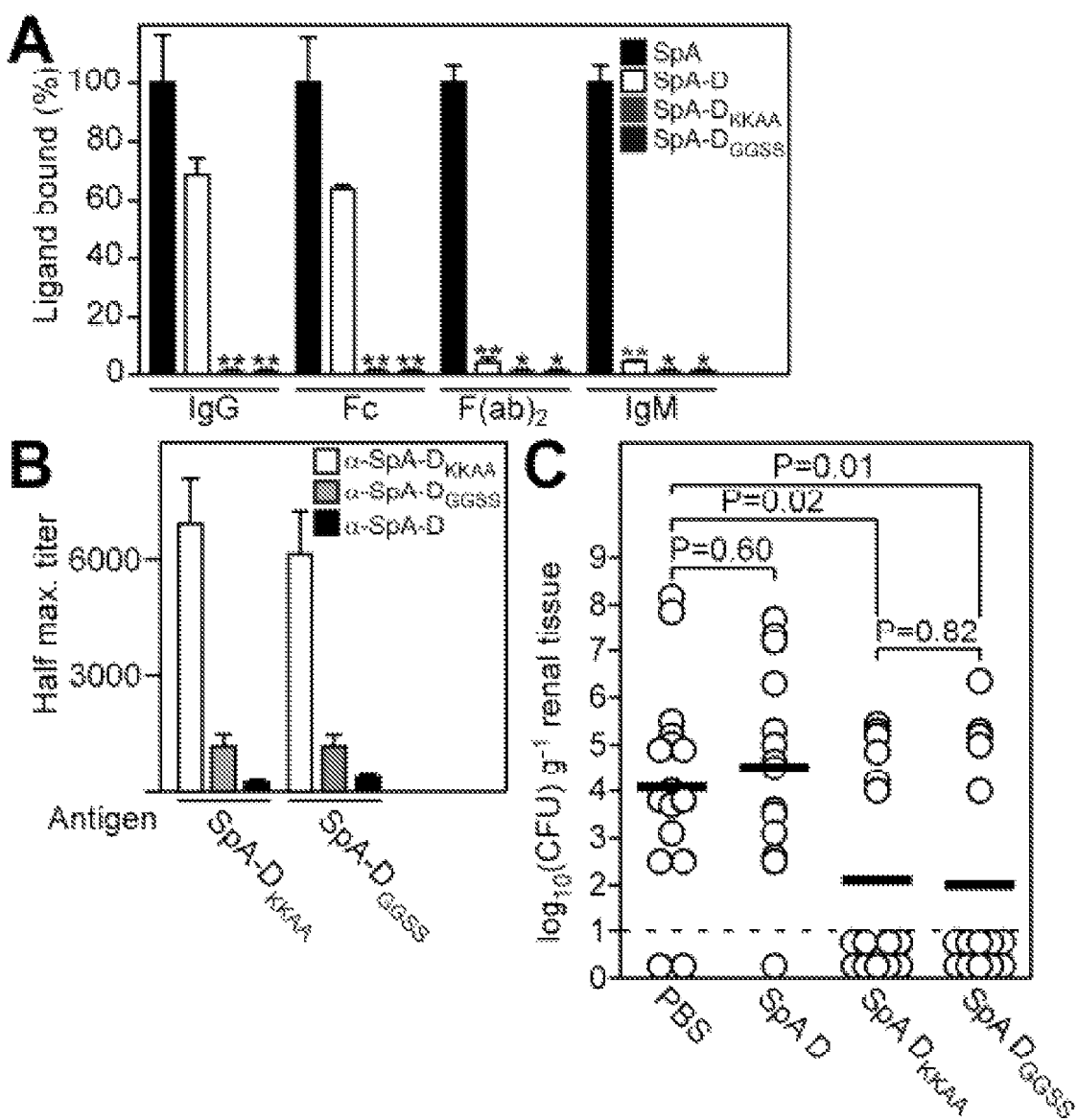
FIGS. 12A-12C (A) ELISA examining the association of immobilized SpA, SpA-D, SpA-DKKAA or SpA-DGGSS with human IgG as well as its Fc or F(ab)2 fragments and IgM. Statistical significance of SpA-DKKAA and SpA-DGGSS binding to each ligand was compared against SpA-D; SpA-D binding was compared against SpA (n=3); * signifies P<0.05; ** signifies P<0.01. (B) ELISA examining the level of cross-reactive antibodies of hyper-immune sera samples collected from actively immunized mice (n=5) with SpA-D, SpA-DKKAA and SpA-DGGSS. (C) Abscess formation in mice treated with PBS, SpA-D, SpA-$D_{KKAA}$ and SpA-$D_{GGSS}$.

To further improve the vaccine properties for non-toxigenic protein A, the inventors generated SpA$_{KKAA}$, which includes all five IgBDs with four amino acid substitutions—substitutions corresponding to Gln9Lys, Gln10Lys, Asp36Ala and Asp37Ala of domain D—in each of its five domains (E, D, A, B and C). Polyhistidine tagged $SpA_{KKAA}$ was purified by affinity chromatography and analyzed by Coomassie Blue-stained SDS-PAGE (FIG. 9). Unlike full-length SpA, $SpA_{KKAA}$ did not bind human IgG, Fe and $F(ab)_2$ or vWF (FIG. 9). $SpA_{KKAA}$ failed to display B cell superantigen activity, as injection of the variant into BALB/c mice did not cause a depletion of CD19+ B cells in splenic tissue (FIG. 9). $SpA_{KKAA}$ vaccination generated higher specific antibody titers than SpA-$D_{KKAA}$ immunization and provided mice with elevated protection against *S. aureus* USA300 challenge (Table 6). Four days following challenge, $SpA_{KKAA}$ vaccinated animals harbored 3.54 $\log_{10}$ CFU $g^{-1}$ fewer staphylococci in renal tissues (P=0.0001) and also caused a greater reduction in the number of abscess lesions (P=0.0109) (Table 6).

$SpA_{KKAA}$ was used to immunize rabbits. Rabbit antibodies specific for SpA-$D_{KKAA}$ or $SpA_{KKAA}$ were affinity purified on matrices with immobilized cognate antigen and injected at a concentration of 5 mg $kg^{-1}$ body weight into the peritoneal cavity of BALB/c mice (Table 7). Twenty-four hours later, specific antibody titers were determined in serum and animals challenged by intravenous inoculation with *S. aureus* Newman. Passive transfer reduced the staphylococcal load in kidney tissues for SpA-$D_{KKAA}$ (P=0.0016) or $SpA_{KKAA}$ (P=0.0005) specific antibodies. On histopathology examination, both antibodies reduced the abundance of abscess lesions in the kidneys of mice challenged with *S. aureus* Newman (Table 7). Together these data reveal that vaccine protection following immunization with SpA-$D_{KKAA}$ or $SpA_{KKAA}$ is conferred by antibodies that neutralize protein A.

TABLE 6

Immunization of mice with protein A vaccines.

| Antigen | Staphylococcal load and abscess formation in renal tissue: [a]$\log_{10}$ CFU $g^{-1}$ | [b]P-value | [c]Reduction ($\log_{10}$ CFU $g^{-1}$) | [d]IgG Titer | [e]Number of abscesses | [b]P-value |
|---|---|---|---|---|---|---|
| *S. aureus* Newman challenge | | | | | | |
| Mock | 6.46 ± 0.25 | — | — | <100 | 3.7 ± 1.2 | — |
| SpA | 3.95 ± 0.56 | 0.0003 | 2.51 | 1706 ± 370 | 2.1 ± 1.2 | 0.3581 |
| SpA-D | 4.43 ± 0.41 | 0.0001 | 2.03 | 381 ± 27 | 1.5 ± 0.8 | 0.1480 |
| SpA $D_{IXAA}$ | 3.39 ± 0.50 | <0.0001 | 3.07 | 5600 ± 801 | 0.5 ± 0.4 | 0.0204 |
| *S. aureus* USA300 (LAC) challenge | | | | | | |
| Mock | 7.20 ± 0.24 | — | — | <100 | 4.0 ± 0.8 | — |
| SpA | 6.81 ± 0.26 | 0.2819 | 0.39 | 476 ± 60 | 3.3 ± 1.0 | 0.5969 |
| SpA-D | 6.34 ± 0.52 | 0.1249 | 0.86 | 358 ± 19 | 2.2 ± 0.6 | 0.0912 |
| SpA-$D_{KKAA}$ | 6.00 ± 0.42 | 0.0189 | 1.20 | 3710 ± 1147 | 1.6 ± 0.6 | 0.0277 |
| $SpA_{KKAA}$ | 3.66 ± 0.76 | 0.0001 | 3.54 | 10200 ± 2476 | 1.2 ± 0.5 | 0.0109 |

[a]Means of staphylococcal load calculated as $\log_{10}$ CFU $g^{-1}$ in homogenized renal tissues 4 days following infection in cohorts of fifteen to twenty BALB/c mice per immunization. Representative of two independent and reproducible animal experiments is shown. Standard error of the means (±SEM) is indicated.
[b]Statistical significance was calculated with the unpaired two-tailed Students t-test and P-values recorded; P-values <0.05 were deemed significant.
[c]Reduction in bacterial load calculated as $\log_{10}$ CFU $g^{-1}$.
[d]Means of five randomly chosen serum IgG titers were measured prior to staphylococcal infection by ELISA
[e]Histopathology of hematoxylene-eosin stained, thin sectioned kidneys from ten animals; the average number of abscesses per kidney was recorded and averaged again for the final mean (±SEM).

TABLE 7

Passive immunization of mice with antibodies against protein A.

| [a]Antibody | Staphylococcal load and abscess formation in renal tissue: [b]$\log_{10}$ CFU $g^{-1}$ | [c]P-value | [d]Reduction ($\log_{10}$ CFU $g^{-1}$) | [e]IgG Titer | [f]Number of abscesses | [c]P-value |
|---|---|---|---|---|---|---|
| Mock | 7.10 ± 0.14 | — | — | <100 | 4.5 ± 0.8 | — |
| α-SpA-$D_{KKAA}$ | 5.53 ± 0.43 | 0.0016 | 1.57 | 466 ± 114 | 1.9 ± 0.7 | 0.0235 |
| α-$SpA_{KKAA}$ | 5.69 ± 0.34 | 0.0005 | 1.41 | 1575 ± 152 | 1.6 ± 0.5 | 0.0062 |

[a]Affinity purified antibodies were injected into the peritoneal cavity of BALB/c mice at a concentration of 5 mg · $kg^{-1}$ twenty-four hours prior to intravenous challenge with $1 \times 10^7$ CFU *S. aureus* Newman.
[b]Means of staphylococcal load calculated as $\log_{10}$ CFU $g^{-1}$ in homogenized renal tissues 4 days following infection in cohorts of fifteen BALB/c mice per immunization. Representative of two independent and reproducible animal experiments is shown. Standard error of the means (±SEM) is indicated.
[c]Statistical significance was calculated with the unpaired two-tailed Students t-test and P-values recorded; P-values <0.05 were deemed significant.
[d]Reduction in bacterial load calculated as $\log_{10}$ CFU $g^{-1}$.
[e]Means of five randomly chosen serum IgG titers were measured prior to staphylococcal infection by ELISA
[f]Histopathology of hematoxylene-eosin stained, thin sectioned kidneys from ten animals; the average number of abscesses per kidney was recorded and averaged again for the final mean (±SEM).

Following infection with virulent *S. aureus*, mice do not develop protective immunity against subsequent infection with the same strain (Burts et al., 2008) (FIG. 10). The average abundance of SpA-D$_{KKAA}$ specific IgG in these animals was determined by dot blot as 0.20 µg ml$^{-1}$ (±0.04) and 0.14 µg ml$^{-1}$ (±0.01) for strains Newman and USA300 LAC, respectively (FIG. 9). The minimal concentration of protein A-specific IgG required for disease protection in SpA$_{KKAA}$ or SpA-D$_{KAA}$ vaccinated animals (P .0.05 log$_{10}$ reduction in staphylococcal CFU g$^{-1}$ renal tissue) was calculated as 4.05 µg ml$^{-1}$ (±0.88). Average serum concentration of SpA-specific IgG in adult healthy human volunteers (n=16) was 0.21 µg ml$^{-1}$ (±0.02). Thus, *S. aureus* infections in mice or humans are not associated with immune responses that raise significant levels of neutralizing antibodies directed against protein A, which is likely due to the B cell superantigen attributes of this molecule. In contrast, the average serum concentration of IgG specific for diphtheria toxin in human volunteers, 0.068 ml$^{-1}$ (±0.20), was within range for protective immunity against diphtheria (Behring, 1890; Lagergard et al., 1992).

Clinical *S. aureus* isolates express protein A, an essential virulence factor whose B cell surperantigen activity and evasive attributes towards opsono-phagocytic clearance are absolutely required for staphylococcal abscess formation (Palmqvist et al., 2005; Cheng et al., 2009; Silverman and Goodyear, 2006). Protein A can thus be thought of as a toxin, essential for pathogenesis, whose molecular attributes must be neutralized in order to achieve protective immunity. By generating non-toxigenic variants unable to bind Igs via Fcγ or VH$_3$-Fab domains, the inventors measure here for the first time protein A neutralizing immune responses as a correlate for protective immunity against *S. aureus* infection. In contrast to many methicillin-sensitive strains, CA-MRSA isolate USA300 LAC is significantly more virulent (Cheng et al., 2009). For example, immunization of experimental animals with the surface protein IsdB (Kuklin et al., 2006; Stranger-Jones et al., 2006) raises antibodies that confer protection against *S. aureus* Newman (Stranger-Jones et al., 2009) but not against USA300 challenge.

The methods utilized include:

Bacterial strains and growth. *Staphylococcus aureus* strains Newman and USA300 were grown in tryptic soy broth (TSB) at 37° C. *Escherichia coli* strains DH5α and BL21 (DE3) were grown in Luria-Bertani (LB) broth with 100 µg mY$^1$ ampicillin at 37° C.

Rabbit antibodies. The coding sequence for SpA was PCR-amplified with two primers, gctgcacatatggcgcaacacgatgaagctcaac (SEQ ID NO:35) and agtggatccttatgcttgagattgttagcatctgc (SEQ ID NO:36) using *S. aureus* Newman template DNA. SpA-D was PCR-amplified with two primers, aacatatgttcaacaaagatcaacaaagc (SEQ ID NO:38) and aaggatccagattcgtttaatttttagc (SEQ ID NO:39). The sequence for SpA-D$_{KKAA}$ was mutagenized with two sets of primers catatgttcaacaaagataaaaaaagcgccttctatgaaatc (SEQ ID NO:42) and gatttcatagaaggcgcttttttatctttgttgaacatatg (SEQ ID NO:43) for Q9K, Q10K as well as cttcattcaaagtcttaaagccgccccaagccaaagcactaac (SEQ ID NO:40), and gttagtgattggcttggggcggattaagactttgaatgaag (SEQ ID NO:41) for D36A, D37A. The sequence of SpA$_{KKAA}$ was synthesized by Integrated DNA Technologies, Inc. PCR products were cloned into pET-15b generating N-terminal His$_6$ tagged recombinant protein. Plasmids were transformed into BL21 (DE3). Overnight cultures of transformants were diluted 1:100 into fresh media and grown at 37° C. to an OD$_{600}$ 0.5, at which point cultures were induced with 1 mM isopropyl β-D-1-thiogalatopyranoside (IPTG) and grown for an additional three hours. Bacterial cells were sedimented by centrifugation, suspended in column buffer (50 mM Tris-HCl, pH 7.5, 150 mM NaCl) and disrupted with a French pressure cell at 14,000 psi. Lysates were cleared of membrane and insoluble components by ultracentrifugation at 40,000×g. Proteins in the soluble lysate were subjected to nickel-nitrilotriacetic acid (Ni-NTA, Qiagen) affinity chromatography. Proteins were eluted in column buffer containing successively higher concentrations of imidazole (100-500 mM). Protein concentrations were determined by bicinchonic acid (BCA) assay (Thermo Scientific). For antibody generation, rabbits (6 month old New-Zealand white, female, Charles River Laboratories) were immunized with 500 µg protein emulsified in Complete Freund's Adjuvant (Difco) by subscapular injection. For booster immunizations, proteins emulsified in Incomplete Freund's Adjuvant and injected 24 or 48 days following the initial immunization. On day 60, rabbits were bled and serum recovered.

Purified antigen (5 mg protein) was covalently linked to HiTrap NHS-activated HP columns (GE Healthcare). Antigen-matrix was used for affinity chromatography of 10-20 ml of rabbit serum at 4° C. Charged matrix was washed with 50 column volumes of PBS, antibodies eluted with elution buffer (1 M glycine, pH 2.5, 0.5 M NaCl) and immediately neutralized with 1M Tris-HCl, pH 8.5. Purified antibodies were dialyzed overnight against PBS at 4° C.

F(ab)$_2$ fragments. Affinity purified antibodies were mixed with 3 mg of pepsin at 37° C. for 30 minutes. The reaction was quenched with 1 M Tris-HCl, pH 8.5 and F(ab)$_2$ fragments were affinity purified with specific antigen-conjugated HiTrap NHS-activated HP columns. Purified antibodies were dialyzed overnight against PBS at 4° C., loaded onto SDS-PAGE gel and visualized with Coomassie Blue staining.

Active and passive immunization. BALB/c mice (3 week old, female, Charles River Laboratories) were immunized with 50 µg protein emulsified in Complete Freund's Adjuvant (Difco) by intramuscular injection. For booster immunizations, proteins were emulsified in Incomplete Freund's Adjuvant and injected 11 days following the initial immunization. On day 20 following immunization, 5 mice were bled to obtain sera for specific antibody titers by enzyme-linked immunosorbent assay (ELISA).

Affinity purified antibodies in PBS were injected at a concentration 5 mg kg$^{-1}$ of experimental animal weight into the peritoneal cavity of BALB/c mice (6 week old, female, Charles River Laboratories) 24 hours prior to challenge with *S. aureus*. Animal blood was collected via periorbital vein puncture. Blood cells were removed with heparinized microhematocrit capillary tubes (Fisher) and Z-gel serum separation micro tubes (Sarstedt) were used to collect and measure antigen specific antibody titers by ELISA.

Mouse renal abscess. Overnight cultures of *S. aureus* Newman or USA300 (LAC) were diluted 1:100 into fresh TSB and grown for 2 hours at 37° C. Staphylococci were sedimented, washed and suspended PBS at OD$_{600}$ of 0.4 (~1×10$^8$ CFU ml$^{-1}$). Inocula were quantified by spreading sample aliquots on TSA and enumerating colonies formed. BALB/c mice (6 week old, female, Charles River Laboratories) were anesthetized via intraperitoneal injection with 100 mg ml$^-$ketamine and 20 mg ml$^{-1}$ xylazine per kilogram of body weight. Mice were infected by retro-obital injection with 1×10$^7$ CFU of *S. aureus* Newman or 5×10$^6$ CFU of *S. aureus* USA300. On day 4 following challenge, mice were killed by CO$_2$ inhalation. Both kidneys were removed, and the staphylococcal load in one organ was analyzed by homogenizing renal tissue with PBS, 1% Triton X-100. Serial dilutions of homogenate were spread on TSA and incubated for colony formation. The remaining organ was examined by histopathology. Briefly, kidneys were fixed in 10% formalin for 24 hours at room temperature. Tissues were embedded in paraffin, thin-sectioned, stained with hematoxylin-eosin, and inspected by light microscopy to enumerate abscess lesions. All mouse experiments were performed in accordance with the institutional guidelines following experimental protocol review and approval by the Institutional Biosafety Committee (IBC) and the Institutional Animal Care and Use Committee (IACUC) at the University of Chicago.

Protein A binding. For human IgG binding, Ni-NTA affinity columns were pre-charged with 200 μg of purified proteins (SpA, SpA-D, SpA-$D_{KKAA}$, and SrtA) in column buffer. After washing, 200 μg of human IgG (Sigma) was loaded onto the column. Protein samples were collected from washes and elutions and subjected to SDS-PAGE gel electrophoresis, followed by Coomassie Blue staining. Purified proteins (SpA, $SpA_{KKAA}$, SpA-D and SpA-$D_{KKAA}$) were coated onto MaxiSorp ELISA plates (NUNC) in 0.1M carbonate buffer (pH 9.5) at 1 μg ml$^{-1}$ concentration overnight at 4° C. Plates were next blocked with 5% whole milk followed by incubation with serial dilutions of peroxidase-conjugated human IgG, Fc or F(ab)$_2$ fragments for one hour. Plates were washed and developed using OptEIA ELISA reagents (BD). Reactions were quenched with 1 M phosphoric acid and $A_{450}$ readings were used to calculate half maximal titer and percent binding.

von Willebrand Factor (vWF) binding assays. Purified proteins (SpA, $SpA_{KKAA}$, SpA D and SpA-$D_{KKAA}$) were coated and blocked as described above. Plates were incubated with human vWF at 1 μg ml$^{-1}$ concentration for two hours, then washed and blocked with human IgG for another hour. After washing, plates were incubated with serial dilution of peroxidase-conjugated antibody directed against human vWF for one hour. Plates were washed and developed using OptEIA ELISA reagents (BD). Reactions were quenched with 1 M phosphoric acid and $A_{450}$ readings were used to calculate half maximal titer and percent binding. For inhibition assays, plates were incubated with affinity purified F(ab)$_2$ fragments specific for SpA-$D_{KKAA}$ at 10 μg ml$^{-1}$ concentration for one hour prior to ligand binding assays.

Splenocyte apoptosis. Affinity purified proteins (150 μg of SpA, SpA-D, $SpA_{KKAA}$, and SpA-$D_{KKAA}$) were injected into the peritoneal cavity of BALB/c mice (6 week old, female, Charles River Laboratories). Four hours following injection, animals were killed by $CO_2$ inhalation. Their spleens were removed and homogenized. Cell debris were removed using cell strainer and suspended cells were transferred to ACK lysis buffer (0.15 M NH$_4$Cl, 10 mM KHCO$_3$, 0.1 mM EDTA) to lyse red blood cells. White blood cells were sedimented by centrifugation, suspended in PBS and stained with 1:250 diluted R-PE conjugated anti-CD19 monoclonal antibody (Invitrogen) on ice and in the dark for one hour. Cells were washed with 1% FBS and fixed with 4% formalin overnight at 4° C. The following day, cells were diluted in PBS and analyzed by flow cytometry. The remaining organ was examined for histopathology. Briefly, spleens were fixed in 10% formalin for 24 hours at room temperature. Tissues were embedded in paraffin, thin-sectioned, stained with the Apoptosis detection kit (Millipore), and inspected by light microscopy.

Antibody quantification. Sera were collected from healthy human volunteers or BALB/c mice that had been either infected with *S. aureus* Newman or USA300 for 30 days or that had been immunized with SpA-$D_{KKAA}$/$SpA_{KKAA}$ as described above. Human/mouse IgG (Jackson Immunology Laboratory), $SpA_{KKAA}$, and $CRM_{197}$ were blotted onto nitrocellulose membrane. Membranes were blocked with 5% whole milk, followed by incubation with either human or mouse sera. IRDye 700DX conjugated affinity purified anti-human/mouse IgG (Rockland) was used to quantify signal intensities using the Odyssey™ infrared imaging system (Licor). Experiments with blood from human volunteers involved protocols that were reviewed, approved and performed under regulatory supervision of The University of Chicago's Institutional Review Board (IRB).

Statistical Analysis. Two tailed Student's t tests were performed to analyze the statistical significance of renal abscess, ELISA, and B cell superantigen data.

Example 3

Active Immunization Using Subunit Vaccine Including Multiple Antigens

Figures 13A, 13B:
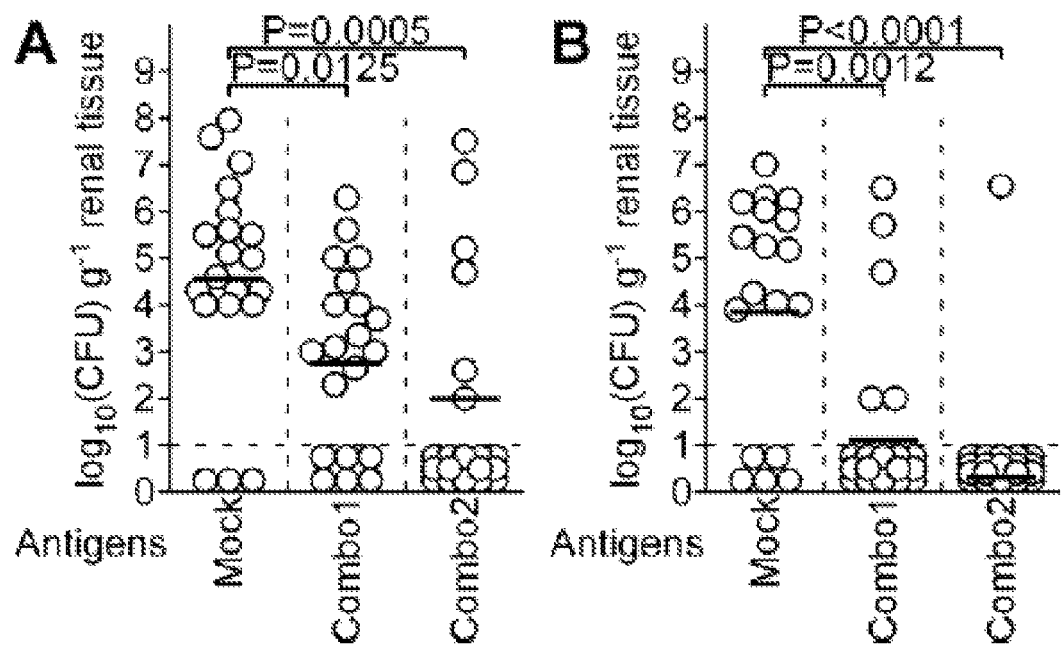
FIGS. 13A-13B BALB/c mice (n=18-20) were either mock immunized with PBS/adjuvant or injected with 25 µg of each antigen (Combo 1, ClfA+SdrD+FnBPB; Combo 2, Combo 1+SpA$_{KKAA}$). Immunized mice were challenged by intravenous inoculation with 1×107 CFU S. aureus Newman. Bacterial loads in kidney tissues were examined at A, day 4 and B, day 18 post challenge. Statistical significance was calculated with the unpaired two-tailed Students t-test and P-values recorded; P-values <0.05 were deemed significant.

BALB/c mice (n=18-20) were either mock immunized with PBS/adjuvant or injected with 25 μg of each antigen (Combo 1, ClfA+SdrD+FnBPB; Combo 2, Combo 1+SpA$_{KKAA}$). Immunized mice were challenged by intravenous inoculation with 1×10$^7$ CFU *S. aureus* Newman. Bacterial loads in kidney tissues were examined at day 4 (FIG. 13A) and day 18 (FIG. 13B) post challenge. Statistical significance was calculated with the unpaired two-tailed Students t-test and P-values recorded; P-values <0.05 were deemed significant. Combo 1 and Combo 2 showed significant reduction in bacterial load at 4 and 18 days post challenge.

Genetic Vaccinology Identifies Protective Antigens of *S. aureus*. The putative protective antigens identified by genetic vaccinology are sortase A-anchored surface proteins with C-terminal LPXTG sorting signals. Previous work assessed the contribution of surface proteins to disease pathogenesis and vaccine protection in the murine abscess model. Mutations in sdrD or clfA, but not fnbpB or sasF, reduced the staphylococcal load in infected renal tissues. When used as a single subunit vaccine antigen, purified SdrD or ClfA, not SasF or FnBPB, elicited IgG immune responses that conferred significant reduction in staphylococcal load. FnBPB is a homolog of FnBPA (60% sequence identity) and both polypeptides are known to bind fibronectin as well as fibrinogen. The contribution of both surface proteins to disease pathogens and protective immunity has not yet been assessed and this prompted the inclusion of FnBPB into a combination vaccine with ClfA and SdrD (Combo 1). Previous work identified non-toxigenic protein A ($SpA_{KKAA}$) as a protective antigen, which elicits neutralizing IgG responses for the Fcγ and Fab VH3 binding B cell superantigen attributes of SpA. The inventors included $SpA_{KKAA}$ to the antigen mixture with ClfA, FnBPB and SdrD (Combo 2).

Figures 14A, 14B, 14C, 14D, 14E, 14F, 14G, 14H:
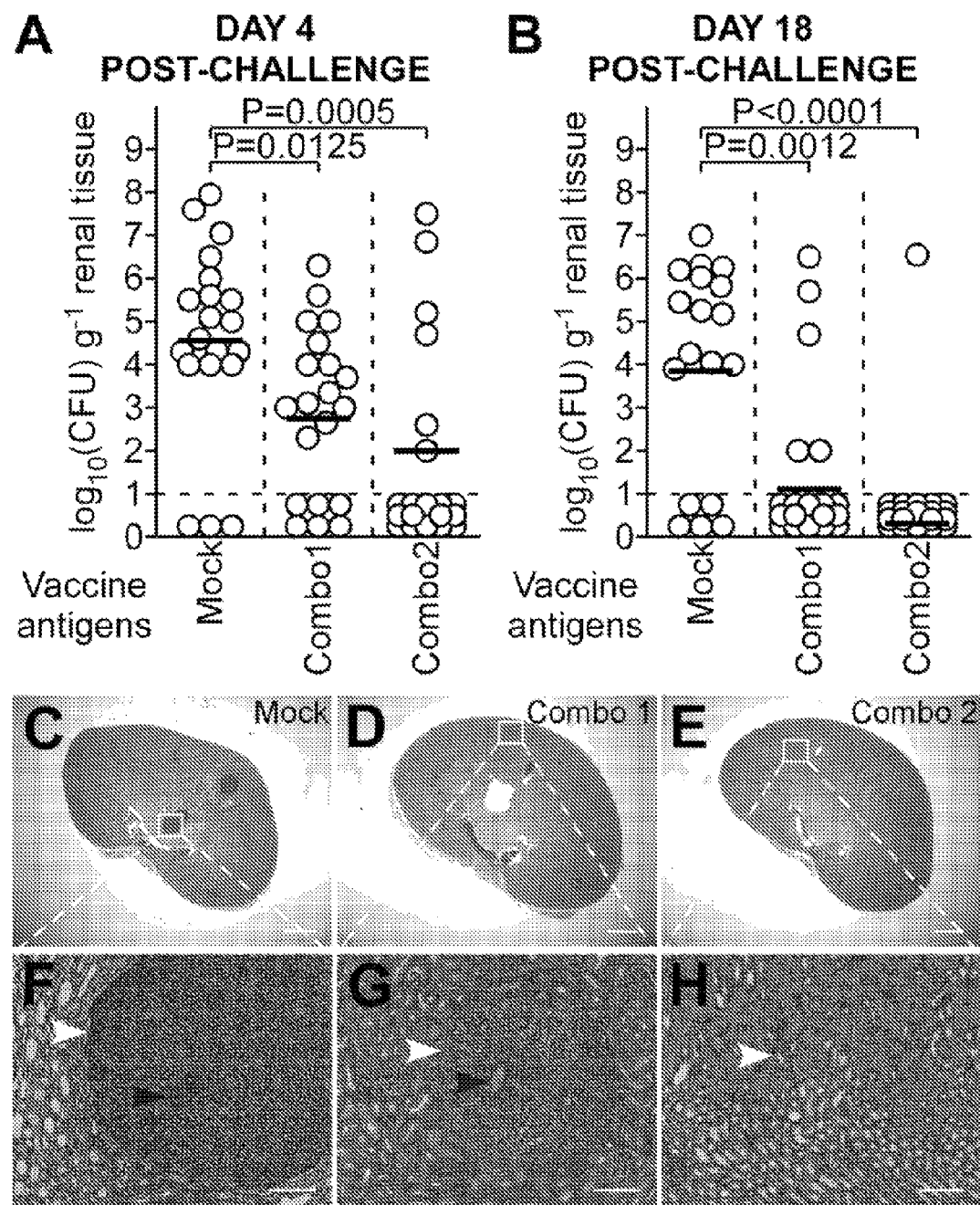
FIGS. 14A-14H. Active Immunization with Antigens Revealed by Genetic Vaccinology Elicits Protection in Mice against Staphylococcal Abscess Formation. Cohorts of BALB/c mice (n=18-20) were actively immunized with mock (PBS), Combo 1 (ClfA, FnBPB and SdrD) or Combo 2 (ClfA, FnBPB, SdrD and SpAKKAA) at day 0 and 11. On day 21, animals were challenged by retro-orbital injection with 1×10$^7$ CFU S. aureus Newman. On days 4 (A) and 18 (B) post challenge, animals were killed to enumerate staphylococcal burden in renal tissues. (C—H) Representative thin-sectioned, hematoxylin-eosin stained histopathology slides from each cohort (n=10, 4 days post challenge) are shown. White arrowheads identify polymorphonuclear leukocyte (PMN) infiltrates. Dark arrowheads identify staphylococcal abscess communities. Animal data are representative of two independent experiments.

Immunization of animals with Combo 1 or 2 emulsified in complete Freund adjuvant and boosted with the same antigen mixture emulsified in incomplete Freund adjuvant, raised specific IgG responses. Following intravenous challenge with *S. aureus* Newman, a significant reduction in bacterial load for both vaccines on day four after challenge with the wild-type strain *S. aureus* Newman was observed (FIG. 14; Table 8). To monitor the ability of vaccine formulations to prevent staphylococcal persistence, immunized animals were also analyzed eighteen days after challenge (FIG. 14; Table 8). Again, immunization with either Combo 1 or 2 conferred protection against persistent *S. aureus* Newman infection. Post vaccination antibody titers were also assessed and the results of these analyses are shown in Table 9 below.

TABLE 8

Active immunization with antigen combinations
prevents staphylococcal abscess formation Staphylococcal load and abscess formation in renal tissue

| Vaccine | [a]$\log_{10}$ CFU g$^{-1}$ | [b]P-value | [c]Reduction ($\log_{10}$ CFU g$^{-1}$) | [d]Number of abscesses | [b]P-value |
|---|---|---|---|---|---|
| *S. aureus* Newman challenge at day 4 | | | | | |
| Mock | 4.56 ± 0.51 (n = 20) | — | — | 2.1 ± 0.7 (n = 10) | — |
| Combo 1 | 2.74 ± 0.47 (n = 20) | 0.0125 | 1.82 | 0.4 ± 0.3 (n = 10) | 0.0471 |
| Combo 2 | 1.65 ± 0.59 (n = 20) | 0.0005 | 2.91 | 0.3 ± 0.3 (n = 10) | 0.0363 |
| *S. aureus* Newman challenge at day 18 | | | | | |
| Mock | 3.86 ± 0.58 (n = 18) | — | — | 1.9 ± 0.8 (n = 10) | — |
| Combo 1 | 1.10 ± 0.48 (n = 19) | 0.0012 | 2.76 | 0.1 ± 0.1 (n = 10) | 0.0404 |
| Combo 2 | 0.26 ± 0.26 (n = 20) | <0.0001 | 3.60 | 0.0 ± 0.0 (n = 10) | 0.0304 |

[a]Means of staphylococcal load calculated as $\log_{10}$ CFU g$^{-1}$ in homogenized renal tissues 4 or 18 days following infection in cohorts of twenty BALB/c mice per immunization. Combo 1 is composed of affinity-purified, recombinant ClfA, SdrD, and FnBPB. Combo 2 contains one additional antigen, SpA$_{KKAA}$. Representative data of two independent animal experiments are shown. Standard error of the means (±SEM) is indicated.
[b]Statistical significance was calculated with the unpaired two-tailed Students t-test and P-values recorded; P-values < 0.05 were deemed significant.
[c]Reduction in bacterial load calculated as $\log_{10}$ CFU g$^{-1}$.
[d]Histopathology of hematoxylin-eosin stained, thin sectioned kidneys; the average number of abscesses per kidney was recorded and averaged again for the final mean (±SEM).

TABLE 9

Humoral immune responses to staphylococcal subunit vaccines

| | Antigen specific IgG titer[a] | | | | |
|---|---|---|---|---|---|
| Vaccine | ClfA | FnbpB | SdrD | SdrE | SpA$_{KKAA}$ |
| Mock | <100 | <100 | <100 | <100 | <100 |
| Combo 1 | 2975 ± 396 | 6351 ± 1981 | 7569 ± 1405 | 2297 ± 538 | <100 |
| Combo 2 | 3457 ± 887 | 5539 ± 1292 | 4716 ± 870 | 3128 ± 1813 | 6667 ± 1980 |

[a]Means (±SEM) of five randomly chosen serum IgG titers were measured prior to staphylococcal infection by ELISA using individual antigens.

Figure 15:
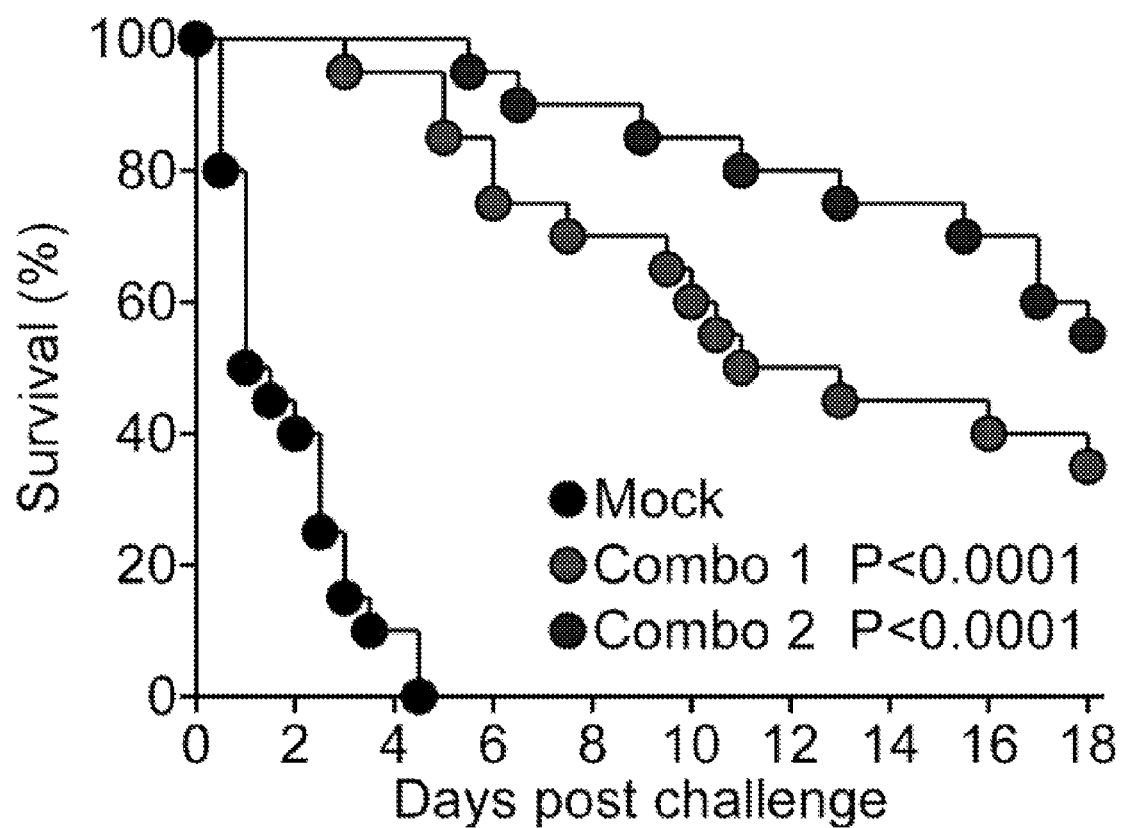
FIG. 15 Active Immunization with Antigens Revealed by Genetic Vaccinology Elicits Protection in Mice against Staphylococcal Sepsis. Cohorts of BALB/c mice (n=20) were actively immunized with mock (PBS), Combo 1 (ClfA, FnBPB and SdrD) or Combo 2 (ClfA, FnBPB, SdrD and SpA$_{KKAA}$) at day 0 and 11. On day 21, animals were challenged by retro-orbital injection with 1×10$^8$ CFU S. aureus Newman and monitored for survival. Animal data are representative of two independent experiments.

Vaccine Protection against Staphylococcal Sepsis. The mortality of *S. aureus* infections increases dramatically when the pathogen replicates in blood or on endocardial tissue. The inventors conducted studies to determine if combo 1 and 2 protect animals against lethal *S. aureus* Newman challenge. All of the mock immunized animals succumbed to challenge within four days (FIG. 15). In contrast, Combo 1 immunized mice displayed either a delayed time to death or survived the lethal challenge (FIG. 15). Mice immunized with Combo 2 displayed a further increase in protective immunity and delayed time-to-death (FIG. 15). Thus, the combination of antibodies against ClfA, FnBPA, SdrD and SpA generates significant protection from staphylococcal abscess formation and lethal challenge.

Bacterial Strains and Culturing Conditions. Staphylococci were cultured on tryptic soy agar or broth at 37° C. *E. coli* strains DH5α and BL21(DE3) (Studier et al., (1990) Methods Enzymol. 185, 60-89) were cultured on Luria agar or broth at 37° C. Ampicillin (100 μg erythromycin (200 μg ml$^{-1}$) and spectinomycin (200 μg ml$^{-1}$) were used for pET15b (Studier et al., (1990) Methods Enzymol. 185, 60-89), transposon mutant (Bae et al., (2004) Proc. Natl. Acad. Sci. USA 101, 12312-12317) and protein A mutant (Kim et al., J Exp Med 207, 1863-70) selection, respectively.

Mutagenesis. *Bursa aurealis* mini-transposon insertions from the *Phoenix* library were transduced into *S. aureus* Newman. The spa gene on the chromosome of *S. aureus* Newman was deleted by allelic replacement as described previously.

Cloning and Purification. Coding sequences for ClfA, SdrD, and FnBPB were PCR amplified using *S. aureus* Newman template DNA (Stranger-Jones et al., (2006) Proc. Nat. Acad. Sci. USA 103, 16942-16947). PCR products were cloned into pET15b to express recombinant proteins with N-terminal His$_6$-tag fusion. Cloning of non-toxigenic protein A was described previously (Kim et al., J Exp Med 207, 1863-70). Plasmids were transformed into BL21(DE3). Overnight cultures of transformants were diluted 1:100 into fresh media and grown at 37° C. to an OD$_{600}$ 0.5, at which point cultures were induced with 1 mM isopropyl β-D-1-thiogalatopyranoside (IPTG) and grown for an additional three hours. Bacterial cells were sedimented by centrifugation, suspended in column buffer (50 mM Tris-HCl, pH 7.5, 150 mM NaCl) and disrupted with a French pressure cell at 14,000 psi. Lysates were cleared of membrane and insoluble components by ultracentrifugation at 40,000×g. Proteins in the soluble lysate were subjected to nickel-nitrilotriacetic acid (Ni-NTA, Qiagen) affinity chromatography. Proteins were eluted in column buffer containing successively higher concentrations of imidazole (100-500 mM). Protein concentrations were determined by bicinchonic acid (BCA) assay (Thermo Scientific).

Live-Attenuated Vaccine and Renal Abscess Model. Overnight cultures of *S. aureus* Newman and its isogenic mutants were diluted 1:100 into fresh TSB and grown for 2 hours at 37° C. Staphylococci were sedimented, washed and suspended PBS at OD600 of 0.4 (~1×10$^8$ CFU ml-1). Inocula were quantified by spreading sample aliquots on TSA and enumerating colony formation. BALB/c mice (4 week old, female, Charles River Laboratories) were anesthetized via intraperitoneal injection with 100 mg ml-1 ketamine and 20 mg ml-1 xylazine per kilogram of body weight. Mice were infected with 100 µl of bacterial suspension ($1 \times 10^7$ CFU) by retro-orbital injection. On day 19 following infection, cohorts of mice were treated with antibiotics, a mixture of ampicillin (1 mg ml$^{-1}$) and chloramphenicol (1 mg ml$^{-1}$) in water for 3 days. On day 26, mice were challenged with 100 µl of S. aureus Newman ($1 \times 10^7$ CFU) by retro-orbital injection or bled to analyze adaptive immune response towards components of the antigen matrix. Animals were killed by CO2 inhalation on day 18 and 30 post initial infection. Both kidneys were removed, and the staphylococcal load in right kidney was analyzed by homogenizing renal tissue with PBS, 0.1% Triton X-100. Serial dilutions of homogenate were spread on TSA or TSA containing antibiotics and incubated for colony formation. The left kidney was examined by histopathology. Briefly, kidneys were fixed in 10% formalin for 24 hours at room temperature. Tissues were embedded in paraffin, thin-sectioned, stained with hematoxylin-eosin, and inspected by light microscopy to enumerate abscess lesions. Also, hyper-immune sera were collected via cardiac puncture and analyzed against components of the antigen matrix. All mouse experiments were performed in accordance with the institutional guidelines following experimental protocol review and approval by the Institutional Biosafety Committee (IBC) and the Institutional Animal Care and Use Committee (IACUC) at the University of Chicago.

Active Immunization. BALB/c mice (3 week old, female, Charles River Laboratories) were immunized with 25 µg protein emulsified in Complete Freund's Adjuvant (Difco) by intramuscular injection. For booster immunizations, proteins were emulsified in Incomplete Freund's Adjuvant and injected 11 days following the initial immunization. On day 20 following immunization, 5 mice were bled to obtain sera for specific antibody titers by enzyme-linked immunosorbent assay (ELISA). On day 21, all mice were challenged with $1 \times 10^7$ CFU S. aureus Newman. Four and eighteen days following challenge, kidneys were removed during necropsy, and renal tissue was analyzed for staphylococcal load or histopathology. Also, hyper-immune sera were collected via cardiac puncture and analyzed against components of the staphylococcal antigen matrix.

Antibody Quantification. For the antigen matrix, nitrocellulose membrane was blotted with 2 µg of a collection of Ni-NTA affinity purified recombinant His6 tagged staphylococcal proteins. Signal intensities in mouse sera were quantified and normalized using anti-His6 antibody with the Odyssey™.

Statistical Analysis. Unpaired two-tailed Student's t tests were performed to analyze the statistical significance. Linear regression analysis was performed using Graphpad Prism.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,338,298
U.S. Pat. No. 4,356,170
U.S. Pat. No. 4,367,110
U.S. Pat. No. 4,372,945
U.S. Pat. No. 4,452,901
U.S. Pat. No. 4,474,757
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,684,611
U.S. Pat. No. 4,690,915
U.S. Pat. No. 4,690,915
U.S. Pat. No. 4,748,018
U.S. Pat. No. 4,800,159
U.S. Pat. No. 4,879,236
U.S. Pat. No. 4,952,500
U.S. Pat. No. 5,084,269
U.S. Pat. No. 5,199,942
U.S. Pat. No. 5,221,605
U.S. Pat. No. 5,238,808
U.S. Pat. No. 5,302,523
U.S. Pat. No. 5,310,687
U.S. Pat. No. 5,322,783
U.S. Pat. No. 5,384,253
U.S. Pat. No. 5,464,765
U.S. Pat. No. 5,512,282
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,620,896
U.S. Pat. No. 5,648,240
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,801,234
U.S. Pat. No. 5,840,846
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,871,986
U.S. Pat. No. 5,916,776
U.S. Pat. No. 5,922,574
U.S. Pat. No. 5,925,565
U.S. Pat. No. 5,925,565
U.S. Pat. No. 5,928,905
U.S. Pat. No. 5,928,906
U.S. Pat. No. 5,932,451
U.S. Pat. No. 5,935,819
U.S. Pat. No. 5,935,825
U.S. Pat. No. 5,939,291

U.S. Pat. No. 5,942,391
U.S. Pat. No. 5,945,100
U.S. Pat. No. 5,958,895
U.S. Pat. No. 5,981,274
U.S. Pat. No. 5,994,624
U.S. Pat. No. 6,00,8341
U.S. Pat. No. 6,288,214
U.S. Pat. No. 6,294,177
U.S. Pat. No. 6,651,655
U.S. Pat. No. 6,656,462
U.S. Pat. No. 6,733,754
U.S. Pat. No. 6,756,361
U.S. Pat. No. 6,770,278
U.S. Pat. No. 6,793,923
U.S. Pat. No. 6,814,971
U.S. Pat. No. 6,936,258
U.S. Patent Appln. 2002/0169288
U.S. Patent Appln. 2003/0153022
Abdallah et al., *Mol. Microbiol.*, 62, 667-679, 2006.
Abdallah et al., *Nat. Rev. Microbiol.*, 5, 883-891, 2007.
Albus et al., *Infect. Immun.*, 59:1008-1014, 1991.
An, *J. Virol.*, 71(3):2292-302, 1997.
Anavi, Sc. thesis from the department of Molecular Microbiology and Biotechnology of the Tel-Aviv University, Israel, 1998.
Andersen et al., *J. Immunol.*, 154, 3359-3372, 1995.
Angel et al., *Cell*, 49:729, 1987b.
Angel et al., *Mol. Cell. Biol.*, 7:2256, 1987a.
Archer, *Clin. Infect. Dis.*, 26, 1179-1181, 1998.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Baba et al., *J. Bacteriol.* 190:300-310, 2007.
Bae and Schneewind, *Plasmid*, 55:58-63, 2006.
Bae et al., *Proc. Natl. Acad. Sci. USA*, 101, 12312-12317, 2004.
Banerji et al., *Cell*, 27(2 Pt 1):299-308, 1981.
Banerji et al., *Cell*, 33(3):729-740, 1983.
Barany and Merrifield, In: The Peptides, Gross and Meienhofer (Eds.), Academic Press, NY, 1-284, 1979.
Behring EA. Über das Zustandekommen der Diphtherie—Immunität bei Thieren. Deutsche Medzinische Wochenschrift, 16:1145-8, 1890.
Bellus, *J. Macromol. Sci. Pure Appl. Chem.*, A31(1): 1355-1376, 1994.
Berkhout et al., *Cell*, 59:273-282, 1989.
Birch-Hirschfeld, L. 1934. Über die Agglutination von Staphylokokken durch Bestandteile des Säugetierblutplasmas. Klinische Woschenschrift 13:331.
Bjerketorp et al., *FEMS Microbiol. Lett.*, 234:309-314, 2004.
Blanar et al., *EMBO J.*, 8:1139, 1989.
Bodine and Ley, *EMBO J*, 6:2997, 1987.
Borrebaeck, In: *Antibody Engineering—A Practical Guide*, W.H. Freeman and Co., 1992.
Boshart et al., *Cell*, 41:521, 1985.
Bosze et al., *EMBO* 1, 5(7):1615-1623, 1986.
Boucher and Corey. *Clin. Infect. Dis.* 46:S334-S349, 2008.
Braddock et al., *Cell*, 58:269, 1989.
Brown et al., *Biochemistry*, 37:4397-4406, 1998.
Bubeck Wardenburg and Schneewind. *J. Exp. Med.* 205:287-294, 2008.
Bubeck-Wardenburg et al., *Infect. Immun.* 74:1040-1044, 2007.
Bubeck-Wardenburg et al., *Proc. Natl. Acad. Sci. USA*, 103: 13831-13836, 2006.
Bulla and Siddiqui, *J. Virol.*, 62:1437, 1986.
Burke et al., *J. Inf. Dis.*, 170:1110-1119, 1994.
Burlak et al., *Cell Microbiol.*, 9:1172-1190, 2007.
Burts and Missiakas, *Mol. Microbiol.*, 69:736-46, 2008.
Burts et al., *Proc. Natl. Acad. Sci. USA*, 102:1169-1174, 2005.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75-82, 1999.
Cedergren et al., *Protein Eng.*, 6:441-448, 1993.
Celander and Haseltine, *J. Virology*, 61:269, 1987.
Celander et al., *J. Virology*, 62:1314, 1988.
Cespedes et al., *J. Infect. Dis.*, 191(3):444-52, 2005.
Champion et al., *Science*, 313:1632-1636, 2006.
Chandler et al., *Cell*, 33:489, 1983.
Chandler et al., *Proc. Natl. Acad. Sci. USA*, 94(8):3596-601, 1997.
Chang et al., *Lancet.*, 362(9381):362-369, 2003.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell. Biol.*, 7(8):2745-2752, 1987.
Cheng et al., *FASEB J.*, 23:1-12, 2009.
Cheng et al., *PLoS Pathog* 6.
Choi et al., *Cell*, 53:519, 1988.
Cocea, *Biotechniques*, 23(5):814-816, 1997.
Cohen et al., *J. Cell. Physiol.*, 5:75, 1987.
Cosgrove et al., *Infect. Control Hosp. Epidemiol.* 26:166-174, 2005.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Dalbey and Wickner, *J. Biol. Chem.*, 260:15925-15931, 1985.
Dandolo et al., *J. Virology*, 47:55-64, 1983.
De Villiers et al., *Nature*, 312(5991):242-246, 1984.
DeBord et al., *Infect. Immun.*, 74:4910-4914, 2006.
DeDent et al., *EMBO J.* 27:2656-2668, 2008.
DeDent et al., *J. Bacteriol.* 189:4473-4484, 2007.
Deisenhofer et al., *Hoppe-Seyh Zeitsch. Physiol. Chem.* 359: 975-985, 1978.
Deisenhofer, *Biochemistry* 20:2361-2370, 1981.
Deschamps et al., *Science*, 230:1174-1177, 1985.
Devereux et al., *Nucl. Acid Res.*, 12:387-395, 1984.
Diep et al., *J. Infect. Dis.*, 193:1495-1503, 2006a.
Diep et al., *Lancet.*, 367:731-739, 2006b.
Dinges et al., *Clin. Microbiol. Rev.*, 13:16-34, 2000.
Duthie and Lorenz, *J. Gen. Microbiol.*, 6:95-107, 1952.
Edbrooke et al., *Mol. Cell. Biol.*, 9:1908, 1989.
Edlund et al., *Science*, 230:912-916, 1985.
Ekstedt and Yotis, *Ann. N.Y. Acad. Sci.*, 80:496-500, 1960.
Emorl and Gaynes, *Clin. Microbiol. Rev.*, 6:428-442, 1993.
EP 0786519
EP 497524
EP 497525
Epitope Mapping Protocols In: *Methods in Molecular Biology*, Vol. 66, Morris (Ed.), 1996.
Fechheimer, et al., *Proc Natl. Acad. Sci. USA*, 84:8463-8467, 1987.
Feng and Holland, *Nature*, 334:6178, 1988.
Field and Smith, *J. Comp. Pathol.*, 55:63, 1945.
Firak and Subramanian, *Mol. Cell. Biol.*, 6:3667, 1986.
Foecking and Hofstetter, *Gene*, 45(1):101-105, 1986.
Fortune et al., *Proc Natl. Acad. Sci. USA*, 102:10676-10681, 2005.
Foster, *Nat. Rev. Microbiol.*, 3:948-958, 2005.
Fournier et al., *Infect. Immun.*, 45:87-93, 1984.
Fraley et al., *Proc. Natl. Acad. Sci. USA*, 76:3348-3352, 1979.
Friedrich et al., *Nature*, 425:535-539, 2003.

Fujita et al., *Cell*, 49:357, 1987.
GB Appln. 2 202 328
Gilles et al., *Cell*, 33:717, 1983.
Gloss et al., *EMBO J.*, 6:3735, 1987.
Godbout et al., *Mol. Cell. Biol.*, 8:1169, 1988.
Gomez et al., *EMBO J.* 26:701-709, 2007.
Gomez et al., *J. Biol. Chem.* 281:20190-20196, 2006.
Gomez et al., *Nature Med.* 10:842-8, 2004.
Goodbourn and Maniatis, *Proc. Natl. Acad. Sci. USA*, 85:1447, 1988.
Goodbourn et al., *Cell*, 45:601, 1986.
Goodyear and Silverman, *J. Exp. Med.*, 197:1125-1139, 2003.
Goodyear and Silverman, *Proc. Nat. Acad. Sci. USA*, 101: 11392-11397, 2004.
Gopal, *Mol. Cell. Biol.*, 5:1188-1190, 1985.
Gouda et al., *Biochemistry*, 31(40):9665-72, 1992.
Gouda et al., *Biochemistry*, 37:129-36, 1998.
Graham and Van Der Eb, *Virology*, 52:456-467, 1973.
Graille et al., *Proc. Nat. Acad. Sci. USA* 97:5399-5404, 2000.
Greene et al., *Immunology Today*, 10:272, 1989
Grosschedl and Baltimore, *Cell*, 41:885, 1985.
Guinn et al., *Mol. Microbiol.*, 51:359-370, 2004.
Guss et al., *Eur. J. Biochem.* 138:413-420, 1984.
Harland and Weintraub, *J. Cell Biol.*, 101(3):1094-1099, 1985.
Harlow et al., *Antibodies: A Laboratory Manual*, Cold Spring Harbor Laboratory, Cold Spring Harbor, N.Y., Chapter 8, 1988.
Hartleib et al., *Blood* 96:2149-2156, 2000.
Harvey et al., *Proc. Natl. Acad. Sci. USA*, 83:1084-1088, 1986.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Hsu et al., *Proc. Natl. Acad. Sci. USA*, 100:12420-12425, 2003.
Huang et al., *Cell*, 27:245, 1981.
Hug et al., *Mol. Cell. Biol.*, 8:3065, 1988.
Huston et al., In: *Methods in Enzymology*, Langone (Ed.), Academic Press, NY, 203:46-88, 1991.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc Natl Acad Sci USA*, 85(24):9436-9440, 1988.
Inouye and Inouye, *Nucleic Acids Res.*, 13: 3101-3109, 1985.
Jakobovits et al., *Mol. Cell. Biol.*, 8:2555, 1988.
Jameel and Siddiqui, *Mol. Cell. Biol.*, 6:710, 1986.
Jansson et al., *FEMS Immunol. Med. Microbiol.* 20:69-78 1998.
Jaynes et al., *Mol. Cell. Biol.*, 8:62, 1988.
Jensen, *Acta Path. Microbiol. Scandin.* 44:421-428, 1958.
Johnson et al., *Methods in Enzymol.*, 203:88-99, 1991.
Johnson et al., *Mol. Cell. Biol.*, 9:3393, 1989.
Jones, *Carb. Research*, 340:1097-1106, 2005.
Jonsson et al., *Oral Dis.*, 8(3):130-140, 2002.
Joyce et al., *Carbohydrate Research* 338:903-922 (2003
Kadesch and Berg, *Mol. Cell. Biol.*, 6:2593, 1986.
Kaeppler et al., *Plant Cell Rep.*, 8:415-418, 1990.
Kaneda et al., *Science*, 243:375-378, 1989.
Karin et al., *Mol. Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kennedy et al., *Proc. Natl. Acad. Sci. USA* 105:1327-1332, 2008.
Kiledjian et al., *Mol. Cell. Biol.*, 8:145, 1988.
Kim et al., *J Exp Med* 207, 1863-70, 2010.
Kinoshita, M., N. Kobayashi, S, Nagashima, M. Ishino, S. Otokozawa, K. Mise, A. Sumi, H. Tsutsumi, N. Uehara, N. Watanabe, and M. Endo. 2008. Diversity of staphylocoagulase and identification of novel variants of staphylocoagulase gene in *Staphylococcus aureus*. Microbiol. Immunols. 52:334-348.
Klamut et al., *Mol. Cell. Biol.*, 10:193, 1990.
Klevens et al., *Clin. Infect. Dis.*, 2008; 47:927-30, 2008.
Klevens et al., *JAMA*, 298:1763-1771, 2007.
Koch et al., *Mol. Cell. Biol.*, 9:303, 1989.
Kohler and Milstein, *Nature* 256:495-497 (1975
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kroh et al., *Proc. Natl. Acad. Sci. USA*, 106:7786-7791, 2009.
Kuhl et al., *Cell*, 50:1057, 1987.
Kuklin et al., *Infect. Immun.*, 74:2215-23, 2006.
Kunz et al., *Nucl. Acids Res.*, 17:1121, 1989.
Kuroda et al., *Lancet.*, 357:1225-1240, 2001.
Kyte and Doolittle, *J. Mol. Biol.*, 157(1):105-132, 1982.
Lagergard et al., *Eur. J. Clin. Microbiol. Infect. Dis.*, 11:341-5, 1992.
Lam et al., *J. Bacteriol.*, 86:87-91, 1963.
Larsen et al., *Proc Natl. Acad. Sci. USA.*, 83:8283, 1986, 1963.
Laspia et al., *Cell*, 59:283, 1989.
Latimer et al., *Mol. Cell. Biol.*, 10:760, 1990.
Lee et al., *Nature*, 294:228, 1981.
Lee et al., *Nucleic Acids Res.*, 12:4191-206, 1984.
Lee, *Trends Microbiol.* 4(4):162-166, 1996.
Levenson et al., *Hum. Gene Ther.*, 9(8):1233-1236, 1998.
Levinson et al., *Nature*, 295:79, 1982.
Lin et al., *Mol. Cell. Biol.*, 10:850, 1990.
Lowy, *New Engl. J. Med.*, 339:520-532, 1998.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
MacGum et al., *Mol. Microbiol.*, 57:1653-1663, 2005.
Maira-Litran et al., *Infect. Immun.*, 70:4433-4440, 2002.
Maira-Litran et al., *Vaccine*, 22:872-879, 2004.
Majors and Varmus, *Proc. Natl. Acad. Sci. USA*, 80:5866, 1983.
Markwardt, *Untersuchungen über Hirudin. Naturwissenschaften*, 41:537-538, 1955.
Mazmanian et al., *Mol. Microbiol.* 40, 1049-1057, 2001.
Mazmanian et al., *Mol. Microbiol.*, 40(5):1049-1057, 2001.
Mazmanian et al., *Proc. Natl. Acad. Sci. USA*, 97:5510-5515, 2000.

Mazmanian et al., *Science*, 285(5428):760-3, 1999.
McLaughlin et al., *PLoS Pathog.*, 3:e105, 2007.
McNeall et al., *Gene*, 76:81, 1989.
Memaugh et al., In: *Molecular Methods in Plant Pathology*, Singh et al. (Eds.), CRC Press Inc., Boca Raton, Fla., 359-365, 1995.
Merrifield, *Science*, 232(4748):341-347, 1986.
Miksicek et al., *Cell*, 46:203, 1986.
Mordacq and Linzer, *Genes and Dev.*, 3:760, 1989.
Moreau et al., *Carbohydrate Res.*, 201:285-297, 1990.
Moreau et al., *Nucl. Acids Res.*, 9:6047, 1981.
Moreillon et al., *Infect. Immun.*, 63:4738-4743, 1995.
Moreillon et al., *Infect. Immun.*, 63:4738-4743, 1995.
Mosmann and Coffman, *Ann. Rev. Immunol.*, 7:145-173, 1989.
Muesing et al., *Cell*, 48:691, 1987.
Musher et al., *Medicine (Baltimore)*, 73:186-208, 1994.
Navarre and Schneewind, *J. Biol. Chem.*, 274:15847-15856, 1999.
Needleman & Wunsch, *J. Mol. Biol.*, 48:443, 1970.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987.
Novick, *Mol. Microbiol.*, 48:1429-1449, 2003.
O'Brien et al., *Mol. Microbiol.* 44:1033-1044, 2002.
O'Seaghdha et al., *FEBS J.* 273:4831-4841, 2006.
Omirulleh et al., *Plant Mol. Biol.*, 21(3):415-28, 1993.
Ondek et al., *EMBO J.*, 6:1017, 1987.
Ornitz et al., *Mol. Cell. Biol.*, 7:3466, 1987.
Pallen, *Trends Microbiol.*, 10:209-212, 2002.
Palmiter et al., *Nature*, 300:611, 1982.
Palmqvist et al., *Microbes. Infect.*, 7:1501-11, 2005.
Panizzi et al., *J. Biol. Chem.*, 281:1179-1187, 2006.
PCT Appln. PCT/US89/01025
PCT Appln. WO 00/02523
PCT Appln. WO 00/12132
PCT Appln. WO 00/12689
PCT Appln. WO 00/15238
PCT Appln. WO 01/34809
PCT Appln. WO 01/60852
PCT Appln. WO 01/98499
PCT Appln. WO 02/059148
PCT Appln. WO 02/094868
PCT Appln. WO 03/53462
PCT Appln. WO 04/43407
PCT Appln. WO 06/032472
PCT Appln. WO 06/032475
PCT Appln. WO 06/032500
PCT Appln. WO 07/113,222
PCT Appln. WO 07/113,223
PCT Appln. WO 10/119,343
PCT Appln. WO 94/09699
PCT Appln. WO 95/06128
PCT Appln. WO 95/08348
PCT Appln. WO 98/57994
Pearson & Lipman, *Proc. Natl. Acad. Sci. USA*, 85:2444, 1988.
Pech et al., *Mol. Cell. Biol.*, 9:396, 1989.
Pelletier and Sonenberg, *Nature*, 334(6180):320-325, 1988.
Perez-Stable and Constantini, *Mol. Cell. Biol.*, 10:1116, 1990.
Phonimdaeng et al., *Mol. Microbiol.*, 4:393-404, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199(2):169-177, 1985.
Pugsley, *Microbiol. Rev.*, 57:50-108, 1993.
Pym et al., *Mol. Microbiol.*, 46;709-717, 2002.
Pym et al., *Nat. Med.*, 9:533-539, 2003.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Remington's Pharmaceutical Sciences, 18th Ed. Mack Printing Company, 1289-1329, 1990.
Resendez Jr. et al., *Mol. Cell. Biol.*, 8:4579, 1988.
Ripe et al., *Mol. Cell. Biol.*, 9:2224, 1989.
Rippe, et al., *Mol. Cell. Biol.*, 10:689-695, 1990.
Riffling et al., *Nuc. Acids Res.*, 17:1619, 1989.
Roben et al., *J. Immunol.* 154:6437-6445, 1995.
Rosen et al., *Cell*, 41:813, 1988.
Sakai et al., *Genes and Dev.*, 2:1144, 1988.
Salid-Salim et al., *Infect. Control Hosp. Epidemiol.* 24:451-455, 2003.
Sambrook et al., In: *Molecular cloning*, Cold Spring Harbor Laboratory Press, Cold Spring Harbor, N.Y., 2001.
Schaffner et al., *J. Mol. Biol.*, 201:81, 1988.
Schneewind et al., *Cell* 70:267-281, 1992.
Schneewind et al., *EMBO*, 12:4803-4811, 1993.
Schneewind et al., *Science*, 268:103-6, 1995.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Shaw et al., *Microbiology*, 150:217-228, 2004.
Sheagren, *N. Engl. J. Med.* 310:1368-1373, 1984.
Sherman et al., *Mol. Cell. Biol.*, 9:50, 1989.
Shopsin et al., *J. Clin. Microbiol.*, 37:3556-63, 1999.
Sibbald et al., *Microbiol. Mol. Biol. Rev.*, 70:755-788, 2006.
Silverman and Goodyear. *Nat. Rev. Immunol.*, 6:465-75, 2006.
Sjodahl, *Eur. J. Biochem.* 73:343-351, 1977.
Sjoquist et al., *Eur. J. Biochem.* 30:190-194, 1972.
Sleigh and Lockett, *J. EMBO*, 4:3831, 1985.
Smith & Waterman, *Adv. Appl. Math.*, 2:482, 1981.
Smith et al., *Brit. J. Exp. Pathol.*, 28:57, 1947.
Sorensen et al., *Infect. Immun.*, 63:1710-1717, 1995.
Spalholz et al., *Cell*, 42:183, 1985.
Spandau and Lee, *J. Virology*, 62:427, 1988.
Spandidos and Wilkie, *EMBO J.*, 2:1193, 1983.
Stanley et al., *Proc. Natl. Acad. Sci. USA*, 100:13001-13006, 2003.
Stephens and Hentschel, *Biochem. J.*, 248:1, 1987.
Stewart and Young, In: *Solid Phase Peptide Synthesis*, 2d. ed., Pierce Chemical Co., 1984.
Stranger-Jones et al., Proc. Nat. Acad. Sci. USA 103, 16942-16947, 2006.
Stranger-Jones et al., *Proc. Nat. Acad. Sci. USA*, 103:16942-16947, 2006.
Stuart et al., *Nature*, 317:828, 1985.
Studier et al., *Methods Enzymol.* 185, 60-89, 1990.
Studier et al., *Methods Enzymol.* 185:60-89 1990.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tam et al., *J. Am. Chem. Soc.*, 105:6442, 1983.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Thiesen et al., *J. Virology*, 62:614, 1988.
Thomson et al., *J. Immunol.*, 157(2):822-826, 1996.

Tigges et al., *J. Immunol.*, 156(10):3901-3910, 1996.
Tigges et al., *J. Immunol.*, 156(10):3901-3910, 1996.
Ton-That et al., *Proc. Natl. Acad. Sci. USA*, 96(22):12424-9, 1999.
Treisman, *Cell*, 42:889, 1985.
Tronche et al., *Mol. Biol. Med.*, 7:173, 1990.
Trudel and Constantini, *Genes and Dev.*, 6:954, 1987.
Tyndell et al., *Nuc. Acids. Res.*, 9:6231, 1981.
Uhlen et al., *J. Biol. Chem.* 259:1695-1702 and 13628 (Corr.) 1984.
van den Ent and Lowe, *FEBS Lett.*, 579:3837-3841, 2005.
van Wely et al., *FEMS Microbiol. Rev.*, 25:437-454, 2001.
Vannice and Levinson, *J. Virology*, 62:1305, 1988.
Vasseur et al., *Proc Natl. Acad. Sci. USA*, 77:1068, 1980.
Vaughan, et al., *Nat. Biotech.* 16; 535-539, 1998.
Wang and Calame, *Cell*, 47:241, 1986.
Weber et al., *Cell*, 36:983, 1984.
Weinberger et al. *Mol. Cell. Biol.*, 8:988, 1984.
Weiss et al., *J. Antimicrob. Chemother.*, 53(3):480-6, 2004.
Winoto and Baltimore, *Cell*, 59:649, 1989.
Wong et al., *Gene*, 10:87-94, 1980.
Xu et al., *J. Infect. Dis.*, 189:2323-2333, 2004.
Xu et al., *Mol. Microbiol.*, 66(3):787-800, 2007.
Yutzey et al. *Mol. Cell. Biol.*, 9:1397, 1989.

What is claimed is:

1. A composition comprising an isolated bacterial SdrD, ClfA, or FnbpB polypeptide and an isolated Protein A (SpA) variant having i) a lysine residue at amino acid positions corresponding to positions 9 and 10 of SEQ ID NO:2 and ii) an alanine residue at amino acid positions corresponding to positions 36 and 37 of SEQ ID NO:2.

2. The composition of claim 1, comprising isolated bacterial SdrD, ClfA, and FnbpB polypeptides.

3. A method for treating a staphylococcal infection in a subject comprising providing to a subject having, suspected of having or at risk of developing a staphylococcal infection the composition of claim 1.

4. The method of claim 3, wherein the composition comprises isolated bacterial SdrD, ClfA, and FnbpB polypeptide.

5. The method of claim 3, wherein the SdrD, ClfA, and FnbpB polypeptides are from *Staphylococcus aureus*.

6. The method of claims 4, wherein the composition is essentially free of other staphylococcal polypeptides.

7. The method of claims 4, wherein the composition is essentially free of other staphylococcal carbohydrates.

8. The method of claims 4, wherein the staphylococcal polypeptides in the composition consist essentially of the SpA variant and the isolated SdrD, ClfA, and FnbpB polypeptides.

9. The composition of claim 1, wherein the SdrD, ClfA, and FnbpB polypeptides are *Staphylococcus aureus* polypeptides.

10. The composition of claim 1, further comprising an adjuvant.

11. The composition of claim 2, wherein the composition is essentially free of other staphylococcal polypeptides.

12. The composition of claim 2, wherein the composition is essentially free of other staphylococcal carbohydrates.

13. The composition of claim 2, wherein the staphylococcal polypeptides in the composition consist essentially of the SpA variant and the isolated SdrD, ClfA, and FnbpB polypeptides.

14. The composition of claim 2, consisting essentially of the SpA variant, the isolated SdrD, ClfA, and FnbpB polypeptides and an adjuvant.

15. The composition of claim 1, wherein the lysine residue at amino acid positions corresponding to positions 9 and 10 of SEQ ID NO: 2 and the alanine residue at amino acid positions corresponding to positions 36 and 37 of SEQ ID NO: 2 are in the SpA D domain.

\* \* \* \* \*

UNITED STATES PATENT AND TRADEMARK OFFICE
CERTIFICATE OF CORRECTION

PATENT NO. : 9,095,540 B2
APPLICATION NO. : 13/821943
DATED : August 4, 2015
INVENTOR(S) : Olaf Schneewind et al.

Page 1 of 1

It is certified that error appears in the above-identified patent and that said Letters Patent is hereby corrected as shown below:

In the Claims

In Claim 6, on column 243, line 41, delete "claims" and insert --claim-- therefor.

In Claim 7, on column 243, line 43, delete "claims" and insert --claim-- therefor.

In Claim 8, on column 243, line 45, delete "claims" and insert --claim-- therefor.

Signed and Sealed this
Eighth Day of December, 2015

Michelle K. Lee
*Director of the United States Patent and Trademark Office*